(12) United States Patent
Kumar et al.

(10) Patent No.: US 11,976,111 B2
(45) Date of Patent: May 7, 2024

(54) ACTRIIA AND ALK4 POLYPEPTIDES FOR TREATING KIDNEY FIBROSIS, INFLAMMATION AND INJURY

(71) Applicant: Acceleron Pharma Inc., Cambridge, MA (US)

(72) Inventors: Ravindra Kumar, Acton, MA (US); Gang Li, Sudbury, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 1360 days.

(21) Appl. No.: 16/334,680

(22) PCT Filed: Oct. 4, 2017

(86) PCT No.: PCT/US2017/055199
§ 371 (c)(1),
(2) Date: Mar. 19, 2019

(87) PCT Pub. No.: WO2018/067740
PCT Pub. Date: Apr. 12, 2018

(65) Prior Publication Data
US 2022/0259297 A1    Aug. 18, 2022

Related U.S. Application Data

(60) Provisional application No. 62/404,603, filed on Oct. 5, 2016.

(51) Int. Cl.
| | | |
|---|---|---|
| *A61K 38/17* | (2006.01) | |
| *A61P 13/12* | (2006.01) | |
| *C07K 14/71* | (2006.01) | |
| *C07K 14/715* | (2006.01) | |
| *C07K 16/22* | (2006.01) | |
| *A61K 38/00* | (2006.01) | |

(52) U.S. Cl.
CPC .............. *C07K 16/22* (2013.01); *A61P 13/12* (2018.01); *C07K 14/71* (2013.01); *C07K 14/715* (2013.01); *A61K 38/00* (2013.01); *C07K 2317/76* (2013.01); *C07K 2317/92* (2013.01); *C07K 2319/00* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | | |
|---|---|---|---|
| 2010/0272734 A1* | 10/2010 | Berger .................... | A61P 13/02 435/69.6 |
| 2016/0297867 A1* | 10/2016 | Kumar .................... | A61P 35/00 |
| 2016/0298093 A1* | 10/2016 | Kumar .................... | A61P 19/00 |
| 2019/0375820 A1* | 12/2019 | Kumar .................... | A61P 37/02 |

FOREIGN PATENT DOCUMENTS

| | | |
|---|---|---|
| WO | WO-2014/071158 A1 | 5/2014 |
| WO | WO-2015/017576 A1 | 2/2015 |
| WO | WO-2015/161220 A1 | 10/2015 |
| WO | WO-2016/123454 A1 | 8/2016 |
| WO | WO-2016/164089 A2 | 10/2016 |
| WO | WO-2016164497 A1 | 10/2016 |

OTHER PUBLICATIONS

Maeshima et al. (Endocrine J. 55(1): 1-9, 2008).*
Agapova et al., "Ligand trap for the activin type IIA receptor protects against vascular disease and renal fibrosis in mice with chronic kidney disease," Kidney Int, 89(6):1231-1243 (2016).

* cited by examiner

*Primary Examiner* — Christine J Saoud
(74) *Attorney, Agent, or Firm* — Eric Greenwald; John C. Todaro

(57) ABSTRACT

In some aspects, the disclosure relates to activin and/or GDF antagonists and methods of using activin and/or GDF antagonists to treat, prevent, or reduce the progression rate and/or severity of kidney disease, particularly treating, preventing or reducing the progression rate and/or severity of one or more kidney disease-associated complications.

16 Claims, 62 Drawing Sheets
Specification includes a Sequence Listing.

```
ActRIIa  ILGRSETQEC LFFNANWEKD RTNQTGVEPC YGDKDKRRHC FATWKNISGS
ActRIIb  GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
         IELVKKGCWL DDFNCYDRQE CVATEENPQV YFCCCEGNFC NERFTHLPEA

EVTQPTSNPV TPKPP
         GGPEVTYEPP PTAPT
```

Figure 1

```
                 .........10        .........20        .........30        .........40        .........50
Human     ILGRSETQEC  LFFNANWEKD  RTNQTGVEPC  YGDKDKRRHC  FATWKNISGS
Sheep     ILGRSETQEC  IFYNANWERD  RTNRTGVESC  YGDKDKRRHC  FATWKNISGS
Mole      ILGRSETQEC  LFFNANWERD  RTNQTGVEPC  YGDKDKHRHC  FATWKNISGS
Mouse     ILGRSETQEC  LFFNANWERD  RTNQTGVEPC  YGDKDKRRHC  FATWKNISGS
Chicken   ILGRSETQEC  IYYNANWEKD  KTNRSGIEPC  YGDKDKRRHC  FATWKNISGS
Cow       ILGRSETQEC  IFYNANWERD  RTNRTGVESC  YGDKDKRRHC  FATWKNISGS
Owl       ILGRSETQEC  IYYNANWEKD  KTNRSGIEPC  YGDKDKRRHC  FATWKNISGS
Bat       ILGRSETQEC  IFYNANWERD  KTNRTGVELC  YGDKDKHRHC  FATWKNISGS .........60        .........70        .........80        .........90        ........100
Human     IEIVKQGCWL  DDINCYDRTD  CVEKKDSPEV  YFCCCEGNMC  NEKFSYFPEM
Sheep     IDIVKQGCWL  DDINCYDRTD  CIEKKDSPEV  YFCCCEGNMC  NERFSYFPEM
Mole      IEIVKQGCWL  DDINCYDRTD  CIEKKDSPEV  YFCCCEGNMC  NEKFSYFPEM
Mouse     IEIVKQGCWL  DDINCYDXTD  CIEKKDSPEV  YFCCCEGNMC  NEKFSYFPEM
Chicken   IEIVKQGCWL  DDINCYDRND  CIEKKDSPEV  FFCCCEGNMC  NERFFYFPEM
Cow       IEIVKQGCWL  DDINCYDRTD  CIEKKDSPEV  YFCCCEGNMC  NERFSYFPEM
Owl       IEIVKQGCWL  DDINCYDRND  CIEKKDSPEV  FFCCCEGNMC  NERFFYFPEM
Bat       IEIVKQGCWL  DDINCYDRTD  CIEKKDSPEV  YFCCCEGNMC  NERFSYFPEM ........110.....
Human     EVTQPTSNPV  TPKPP
Sheep     EVTQPTSNPV  TPKPP
Mole      EVTQPTSNPV  TPKAP
Mouse     EVTQPTSNPV  TPKPP
Chicken   EVTQPTSNPV  TPKPP
Cow       EVTQPTSNPV  TPKPP
Owl       EVTQPTSNPV  TPKPP
Bat       EVTQPTSNPV  TPKPP
```

Figure 3

```
IgG1  --------THTCPPCPAPELLGGPSVFLFPPKPKDTLMISRTPEVTCVVVDVSHEDPEVKF  63
IgG4  ----ESKYGPPCPSCPAPEFLGGPSVFLFPPKPKDTLMISRTPEVTCVVVDVSQEDPEVQF  57
IgG2  --------VECPPCPAPPVAG-PSVFLFPPKPKDTLMISRTPEVTCVVVDVSHEDPEVQF  51
IgG3  EPKSCDTPPPCPRCPAPELLGGPSVFLFPPKPKDTLMISRTPEVTCVVVDVSHEDPEVQF  60
              **  ****  *  ************************************:*****:*

IgG1  NWYVDGVEVHNAKTKPREEQYNSTYRVVSVLTVLHQDWLNGKEYKCKVSNKALPAPIEKT  113
IgG4  NWYVDGVEVHNAKTKPREEQFNSTYRVVSVLTVLHQDWLNGKEYKCKVSNKGLPSSIEKT  117
IgG2  NWYVDGVEVHNAKTKPREEQFNSTFRVVSVLTVVHQDWLNGKEYKCKVSNKGLPAPIEKT  111
IgG3  NWYVDGVEVHNAKTKPREEQYNSTFRVVSVLTVLHQDWLNGKEYKCKVSNKALPAPIEKT  120
      :********************:***:************:************.**:.****

IgG1  ISKAKGQPREPQVYTLPPSREEMTKNQVSLTCLVKGFYPSDIAVEWESNGQPENNYKTTP  173
IgG4  ISKAKGQPREPQVYTLPPSQEEMTKNQVSLTCLVKGFYPSDIAVEWESNGQPENNYKTTP  177
IgG2  ISKTKGQPREPQVYTLPPSREEMTKNQVSLTCLVKGFYPSDIAVEWESNGQPENNYKTTP  171
IgG3  ISKTKGQPREPQVYTLPPSREEMTKNQVSLTCLVKGFYPSDIAVEWESSGQPENNYNTTP  180
      ***:***************:*****************************..******.:***

IgG1  PVLDSDGSFFLYSKLTVDKSRWQQGNVFSCSVMHEALHNHYTQKSLSLSPGK  225
IgG4  PVLDSDGSFFLYSRLTVDKSRWQEGNVFSCSVMHEALHNHYTQKSLSLSLGK  229
IgG2  PMLDSDGSFFLYSKLTVDKSRWQQGNVFSCSVMHEALHNHYTQKSLSLSPGK  223
IgG3  PMLDSDGSFFLYSKLTVDKSRWQQGNIFSCSVMHEALHNRFTQKSLSLSPGK  232
      *:***********:********:****:*********** :********  **
```

Figure 4

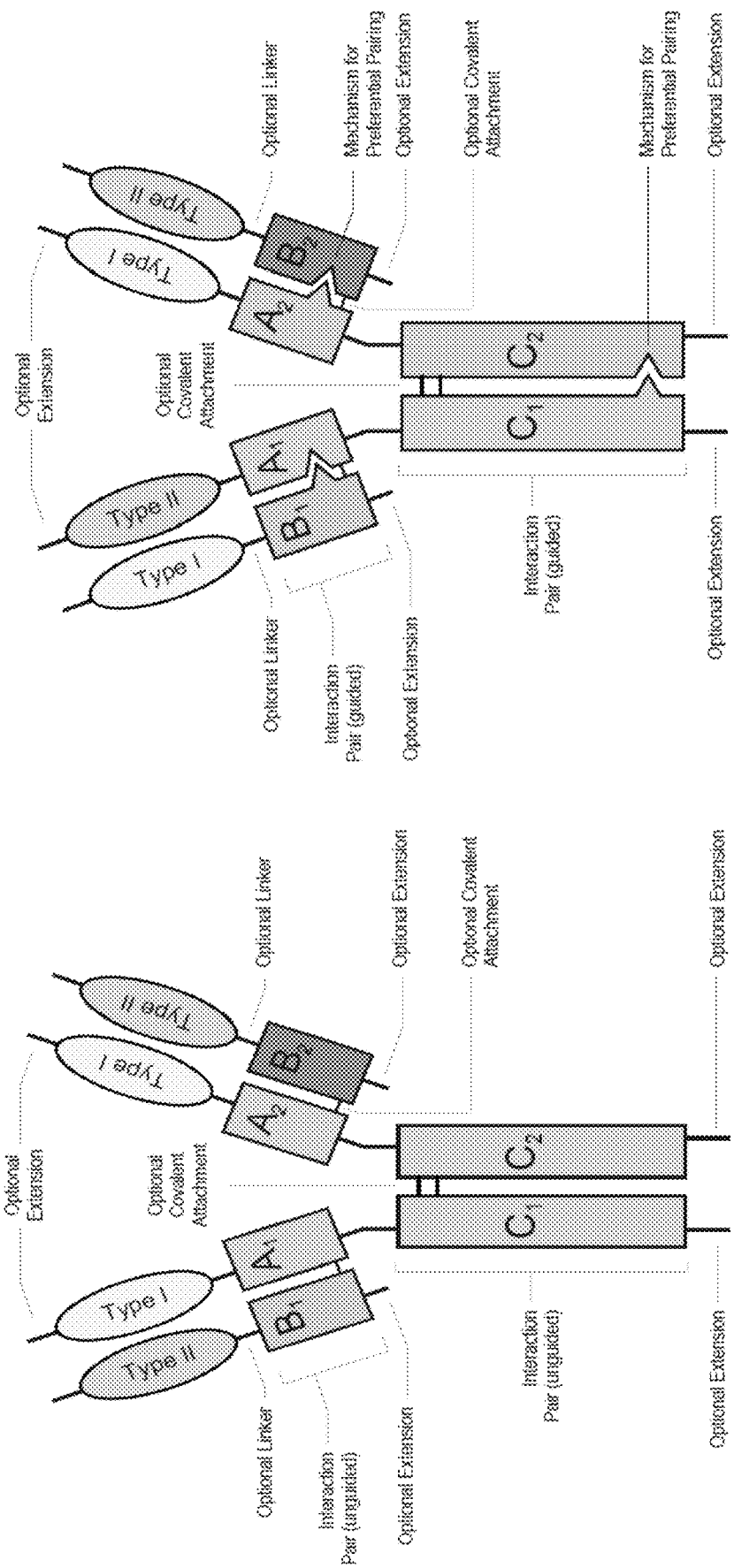

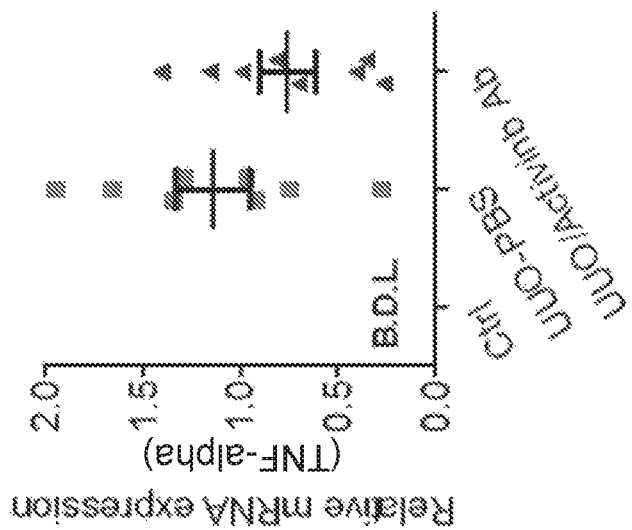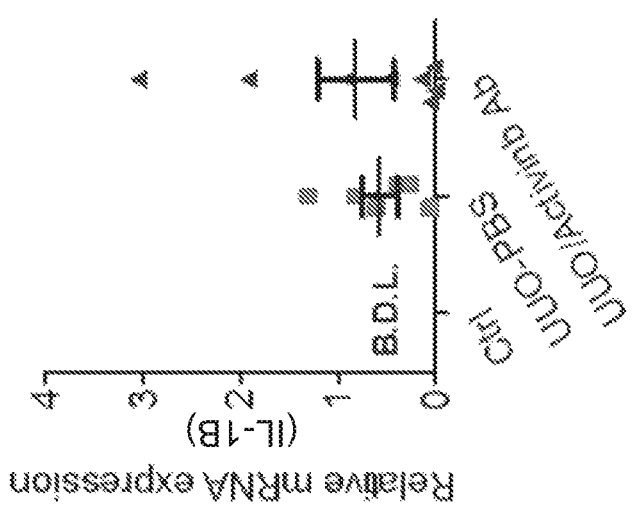
Figure 33

SEQUENCE LISTING

```
<160> NUMBER OF SEQ ID NOS: 225

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
                180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
```

His Val Ala Glu Thr Met Ser Arg Gly Leu Ser Tyr Leu His Glu Asp
    275                 280                 285
Val Pro Trp Cys Arg Gly Glu Gly His Lys Pro Ser Ile Ala His Arg
290                 295                 300
Asp Phe Lys Ser Lys Asn Val Leu Leu Lys Ser Asp Leu Thr Ala Val
305                 310                 315                 320
Leu Ala Asp Phe Gly Leu Ala Val Arg Phe Glu Pro Gly Lys Pro Pro
    325                 330                 335
Gly Asp Thr His Gly Gln Val Gly Thr Arg Arg Tyr Met Ala Pro Glu
        340                 345                 350
Val Leu Glu Gly Ala Ile Asn Phe Gln Arg Asp Ala Phe Leu Arg Ile
355                 360                 365
Asp Met Tyr Ala Met Gly Leu Val Leu Trp Glu Leu Val Ser Arg Cys
    370                 375                 380
Lys Ala Ala Asp Gly Pro Val Asp Glu Tyr Met Leu Pro Phe Glu Glu
385                 390                 395                 400
Glu Ile Gly Gln His Pro Ser Leu Glu Glu Leu Gln Glu Val Val Val
    405                 410                 415
His Lys Lys Met Arg Pro Thr Ile Lys Asp His Trp Leu Lys His Pro
        420                 425                 430
Gly Leu Ala Gln Leu Cys Val Thr Ile Glu Glu Cys Trp Asp His Asp
435                 440                 445
Ala Glu Ala Arg Leu Ser Ala Gly Cys Val Glu Glu Arg Val Ser Leu
    450                 455                 460
Ile Arg Arg Ser Val Asn Gly Thr Thr Ser Asp Cys Leu Val Ser Leu
465                 470                 475                 480
Val Thr Ser Val Thr Asn Val Asp Leu Pro Pro Lys Glu Ser Ser Ile
    485                 490                 495
        500                 505                 510

<210> SEQ ID NO 2
<211> LENGTH: 512
<212> TYPE: PRT
<213> ORGANISM: Homo sapiens

<400> SEQUENCE: 2

Met Thr Ala Pro Trp Val Ala Leu Ala Leu Leu Trp Gly Ser Leu Cys
1               5                   10                  15
Ala Gly Ser Gly Arg Gly Glu Ala Glu Thr Arg Glu Cys Ile Tyr Tyr
            20                  25                  30
Asn Ala Asn Trp Glu Leu Glu Arg Thr Asn Gln Ser Gly Leu Glu Arg
        35                  40                  45
Cys Glu Gly Glu Gln Asp Lys Arg Leu His Cys Tyr Ala Ser Trp Ala
    50                  55                  60
Asn Ser Ser Gly Thr Ile Glu Leu Val Lys Lys Gly Cys Trp Leu Asp
65                  70                  75                  80
Asp Phe Asn Cys Tyr Asp Arg Gln Glu Cys Val Ala Thr Glu Glu Asn
                85                  90                  95
Pro Gln Val Tyr Phe Cys Cys Cys Glu Gly Asn Phe Cys Asn Glu Arg
            100                 105                 110
Phe Thr His Leu Pro Glu Ala Gly Gly Pro Glu Val Thr Tyr Glu Pro
        115                 120                 125
Pro Pro Thr Ala Pro Thr Leu Leu Thr Val Leu Ala Tyr Ser Leu Leu
    130                 135                 140

```
Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
            165                 170                 175

Gly Pro Pro Pro Ser Pro Leu Val Gly Leu Lys Pro Leu Gln Leu
        180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
        210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
            245                 250                 255

Leu Glu Val Glu Leu Trp Leu Ile Thr Ala Phe His Asp Lys Gly Ser
        260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
        290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
            325                 330                 335

Leu Ala Asp Phe Gly Leu Ala Val Arg Phe Glu Pro Gly Lys Pro Pro
        340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
        370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
            405                 410                 415

Glu Ile Gly Gln His Pro Ser Leu Glu Glu Leu Gln Glu Val Val Val
        420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
        450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
            485                 490                 495

Val Thr Ser Val Thr Asn Val Asp Leu Pro Pro Lys Glu Ser Ser Ile
        500                 505                 510

<210> SEQ ID NO 3
<211> LENGTH: 115
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15
```

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 4
<211> LENGTH: 115
<212> TYPE: PRT
<213> ORGANISM: Homo sapiens

<400> SEQUENCE: 4

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 5
<211> LENGTH: 100
<212> TYPE: PRT
<213> ORGANISM: Homo sapiens

<400> SEQUENCE: 5

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                85                  90                  95

-continued

Leu Pro Glu Ala
         100

<210> SEQ ID NO 6
<211> LENGTH: 100
<212> TYPE: PRT
<213> ORGANISM: Homo sapiens

<400> SEQUENCE: 6

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
         100

<210> SEQ ID NO 7
<211> LENGTH: 1536
<212> TYPE: DNA
<213> ORGANISM: Homo sapiens

<400> SEQUENCE: 7
atgacggcgc cctgggtggc cctcgccctc ctctggggat cgctgtgcgc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggc gcaacagctc tggcaccatc gagctcgtga agaagggctg ctggctagat     240
gacttcaact gctacgatag gcaggagtgt gtggccactg aggagaaccc ccaggtgtac     300
ttctgctgct gtgaaggcaa cttctgcaac gaacgcttca ctcatttgcc agaggctggg     360
ggcccggaag tcacgtacga gccacccccg acagccccca ccctgctcac ggtgctggcc     420
tactcactgc tgcccatcgg ggccttttcc ctcatcgtcc tgctggcctt ttggatgtac     480
cggcatcgca agccccccta cggtcatgtg gacatccatg aggaccctgg gcctccacca     540
ccatcccctc tggtgggcct gaagccactg cagctgctgg agatcaaggc tcggggcgc     600 tttggctgtg tctggaaggc ccagctcatg aatgactttg tagctgtcaa gatcttccca     660
ctccaggaca gcagtcgtg gcagagtgaa cgggagatct tcagcacacc tggcatgaag     720
cacgagaacc tgctacagtt cattgctgcc gagaagcgag gctccaacct cgaagtagag     780
ctgtggctca tcacggcctt ccatgacaag ggctccctca ggattaccct caaggggaac     840
atcatcacat ggaacgaact gtgtcatgta gcagagacga tgtcacgagg cctctcatac     900
ctgcatgagg atgtgccctg gtgccgtggc gagggccaca gccgtctat tgcccacagg     960 gactttaaaa gtaagaatgt attgctgaag agcgacctca gccgtgctggctgactttt    1020 ggcttggctg ttcgatttga gccagggaaa cctccagggg acaccacgg acaggtaggc     1080 acgagacggt acatggctcc tgaggtgctc gagggagcca tcaacttcca gagagatgcc    1140

-continued

| | |
|---|---|
| ttcctgcgca ttgacatgta tgccatgggg ttggtgctgt gggagcttgt gtctcgctgc | 1200 |
| aaggctgcag acggacccgt ggatgagtac atgctgccct ttgaggaaga gattggccag | 1260 |
| caccctttcgt tggaggagct gcaggaggtg gtggtgcaca agaagatgag gcccaccatt | 1320 |
| aaagatcact ggttgaaaca cccgggcctg gcccagcttt gtgtgaccat cgaggagtgc | 1380 |
| tgggaccatg atgcagaggc tcgcttgtcc gcgggctgtg tggaggagcg ggtgtccctg | 1440 |
| attcggaggt cggtcaacgg cactacctcg gactgtctcg tttccctggt gacctctgtc | 1500 |
| accaatgtgg acctgccccc taaagagtca agcatc | 1536 |

<210> SEQ ID NO 8
<211> LENGTH: 345
<212> TYPE: DNA
<213> ORGANISM: Homo sapiens

<400> SEQUENCE: 8

| | |
|---|---|
| gggcgtgggg aggctgagac acgggagtgc atctactaca acgccaactg ggagctggag | 60 |
| cgcaccaacc agagcggcct ggagcgctgc gaaggcgagc aggacaagcg gctgcactgc | 120 |
| tacgcctcct ggcgcaacag ctctggcacc atcgagctcg tgaagaaggg ctgctggcta | 180 |
| gatgacttca actgctacga taggcaggag tgtgtggcca ctgaggagaa ccccccaggtg | 240 |
| tacttctgct gctgtgaagg caacttctgc aacgaacgct tcactcattt gccagaggct | 300 |
| gggggcccgg aagtcacgta cgagccaccc ccgacagccc ccacc | 345 |

<210> SEQ ID NO 9
<211> LENGTH: 513
<212> TYPE: PRT
<213> ORGANISM: Homo sapiens

<400> SEQUENCE: 9

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys

```
                    195                 200                 205
Ala Gln Leu Leu Asn Glu Tyr Val Ala Val Lys Ile Phe Pro Ile Gln
            210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
        290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
                340                 345                 350

Ala Gly Asp Thr His Gly Gln Val Gly Thr Arg Arg Tyr Met Ala Pro
            355                 360                 365

Glu Val Leu Glu Gly Ala Ile Asn Phe Gln Arg Asp Ala Phe Leu Arg
370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 10
<211> LENGTH: 405
<212> TYPE: PRT
<213> ORGANISM: Homo sapiens

<400> SEQUENCE: 10

Met Cys Asn Glu Lys Phe Ser Tyr Phe Pro Glu Met Glu Val Thr Gln
1               5                   10                  15

Pro Thr Ser Asn Pro Val Thr Pro Lys Pro Pro Tyr Tyr Asn Ile Leu
            20                  25                  30

Leu Tyr Ser Leu Val Pro Leu Met Leu Ile Ala Gly Ile Val Ile Cys
        35                  40                  45

Ala Phe Trp Val Tyr Arg His His Lys Met Ala Tyr Pro Pro Val Leu
```

```
                        50                  55                  60
Val Pro Thr Gln Asp Pro Gly Pro Pro Pro Ser Pro Leu Leu Gly
 65                  70                  75                  80

Leu Lys Pro Leu Gln Leu Leu Glu Val Lys Ala Arg Gly Arg Phe Gly
                     85                  90                  95

Cys Val Trp Lys Ala Gln Leu Leu Asn Glu Tyr Val Ala Val Lys Ile
                    100                 105                 110

Phe Pro Ile Gln Asp Lys Gln Ser Trp Gln Asn Glu Tyr Glu Val Tyr
                    115                 120                 125

Ser Leu Pro Gly Met Lys His Glu Asn Ile Leu Gln Phe Ile Gly Ala
                    130                 135                 140

Glu Lys Arg Gly Thr Ser Val Asp Val Asp Leu Trp Leu Ile Thr Ala
145                 150                 155                 160

Phe His Glu Lys Gly Ser Leu Ser Asp Phe Leu Lys Ala Asn Val Val
                    165                 170                 175

Ser Trp Asn Glu Leu Cys His Ile Ala Glu Thr Met Ala Arg Gly Leu
                    180                 185                 190

Ala Tyr Leu His Glu Asp Ile Pro Gly Leu Lys Asp Gly His Lys Pro
                    195                 200                 205

Ala Ile Ser His Arg Asp Ile Lys Ser Lys Asn Val Leu Leu Lys Asn
                    210                 215                 220

Asn Leu Thr Ala Cys Ile Ala Asp Phe Gly Leu Ala Leu Lys Phe Glu
225                 230                 235                 240

Ala Gly Lys Ser Ala Gly Asp Thr His Gly Gln Val Gly Thr Arg Arg
                    245                 250                 255

Tyr Met Ala Pro Glu Val Leu Glu Gly Ala Ile Asn Phe Gln Arg Asp
                    260                 265                 270

Ala Phe Leu Arg Ile Asp Met Tyr Ala Met Gly Leu Val Leu Trp Glu
                    275                 280                 285

Leu Ala Ser Arg Cys Thr Ala Ala Asp Gly Pro Val Asp Glu Tyr Met
                    290                 295                 300

Leu Pro Phe Glu Glu Glu Ile Gly Gln His Pro Ser Leu Glu Asp Met
305                 310                 315                 320

Gln Glu Val Val Val His Lys Lys Arg Pro Val Leu Arg Asp Tyr
                    325                 330                 335

Trp Gln Lys His Ala Gly Met Ala Met Leu Cys Glu Thr Ile Glu Glu
                    340                 345                 350

Cys Trp Asp His Asp Ala Glu Ala Arg Leu Ser Ala Gly Cys Val Gly
                    355                 360                 365

Glu Arg Ile Thr Gln Met Gln Arg Leu Thr Asn Ile Ile Thr Thr Glu
                    370                 375                 380

Asp Ile Val Thr Val Val Thr Met Val Thr Asn Val Asp Phe Pro Pro
385                 390                 395                 400

Lys Glu Ser Ser Leu
                405

<210> SEQ ID NO 11
<211> LENGTH: 115
<212> TYPE: PRT
<213> ORGANISM: Homo sapiens

<400> SEQUENCE: 11

Ile Leu Gly Arg Ser Glu Thr Gln Glu Cys Leu Phe Phe Asn Ala Asn
 1                   5                  10                  15
```

```
Trp Glu Lys Asp Arg Thr Asn Gln Thr Gly Val Glu Pro Cys Tyr Gly
         20                  25                  30

Asp Lys Asp Lys Arg Arg His Cys Phe Ala Thr Trp Lys Asn Ile Ser
             35                  40                  45

Gly Ser Ile Glu Ile Val Lys Gln Gly Cys Trp Leu Asp Asp Ile Asn
         50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
             85                  90                  95

Phe Pro Glu Met Glu Val Thr Gln Pro Thr Ser Asn Pro Val Thr Pro
            100                 105                 110

Lys Pro Pro
        115

<210> SEQ ID NO 12
<211> LENGTH: 100
<212> TYPE: PRT
<213> ORGANISM: Homo sapiens

<400> SEQUENCE: 12

Ile Leu Gly Arg Ser Glu Thr Gln Glu Cys Leu Phe Phe Asn Ala Asn
 1               5                  10                  15

Trp Glu Lys Asp Arg Thr Asn Gln Thr Gly Val Glu Pro Cys Tyr Gly
         20                  25                  30

Asp Lys Asp Lys Arg Arg His Cys Phe Ala Thr Trp Lys Asn Ile Ser
             35                  40                  45

Gly Ser Ile Glu Ile Val Lys Gln Gly Cys Trp Leu Asp Asp Ile Asn
         50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
             85                  90                  95

Phe Pro Glu Met
            100

<210> SEQ ID NO 13
<211> LENGTH: 1539
<212> TYPE: DNA
<213> ORGANISM: Homo sapiens

<400> SEQUENCE: 13
atgggagctg ctgcaaagtt ggcgtttgcc gtctttctta tctcctgttc ttcaggtgct      60
atacttggta gatcagaaac tcaggagtgt cttttcttta tgctaattg ggaaaaagac     120 agaaccaatc aaactggtgt tgaaccgtgt tatggtgaca agataaacg gcggcattgt     180 tttgctacct ggaagaatat ttctggttcc attgaaatag tgaaacaagg ttgttggctg     240
gatgatatca actgctatga caggactgat tgtgtagaaa aaaagacag ccctgaagta     300 tattttttgtt gctgtgaggg caatatgtgt aatgaaaagt tttcttattt tccggagatg     360
gaagtcacac agcccacttc aaatccagtt acacctaagc cacccctatta caacatcctg     420 ctctattcct tggtgccact tatgttaatt gcggggattg tcatttgtgc attttgggtg     480
tacaggcatc acaagatggc ctaccctcct gtacttgttc aactcaaga cccaggacca     540 cccccacctt ctccattact aggtttgaaa ccactgcagt tattagaagt gaaagcaagg     600
ggaagatttg gttgtgtctg gaaagcccag ttgcttaacg aatatgtggc tgtcaaaata     660
```

```
tttccaatac aggacaaaca gtcatggcaa aatgaatacg aagtctacag tttgcctgga    720
atgaagcatg agaacatatt acagttcatt ggtgcagaaa aacgaggcac cagtgttgat    780
gtggatcttt ggctgatcac agcatttcat gaaaagggtt cactatcaga ctttcttaag    840
gctaatgtgg tctcttggaa tgaactgtgt catattgcag aaaccatggc tagaggattg    900
gcatatttac atgaggatat acctggccta aaagatggcc acaaacctgc catatctcac    960
agggacatca aaagtaaaaa tgtgctgttg aaaaacaacc tgacagcttg cattgctgac   1020
tttgggttgg ccttaaaatt tgaggctggc aagtctgcag gcgataccca tggacaggtt   1080
ggtacccgga ggtacatggc tccagaggta ttagagggtg ctataaactt ccaaagggat   1140 gcattttga ggatagatat gtatgccatg ggattagtcc tatgggaact ggcttctcgc    1200
tgtactgctg cagatggacc tgtagatgaa tacatgttgc catttgagga ggaaattggc   1260
cagcatccat ctcttgaaga catgcaggaa gttgttgtgc ataaaaaaaa gaggcctgtt   1320
ttaagagatt attggcagaa acatgctgga atggcaatgc tctgtgaaac cattgaagaa   1380
tgttgggatc acgacgcaga agccaggtta tcagctggat gtgtaggtga agaattacc    1440 cagatgcaga gactaacaaa tattattacc acagaggaca ttgtaacagt ggtcacaatg   1500
gtgacaaatg ttgactttcc tcccaaagaa tctagtcta                         1539
```

```
<210> SEQ ID NO 14
<211> LENGTH: 345
<212> TYPE: DNA
<213> ORGANISM: Homo sapiens

<400> SEQUENCE: 14
```

```
atacttggta gatcagaaac tcaggagtgt cttttcttta atgctaattg ggaaaaagac     60
agaaccaatc aaactggtgt tgaaccgtgt tatggtgaca agataaacg gcggcattgt    120 tttgctacct ggaagaatat ttctggttcc attgaaatag tgaaacaagg ttgttggctg    180
gatgatatca actgctatga caggactgat tgtgtagaaa aaaaagacag ccctgaagta    240 tattttttgtt gctgtgaggg caatatgtgt aatgaaaagt tttcttatt tccggagatg     300 gaagtcacac agcccacttc aaatccagtt acacctaagc caccc                    345
```

```
<210> SEQ ID NO 15
<211> LENGTH: 150
<212> TYPE: PRT
<213> ORGANISM: Homo sapiens

<400> SEQUENCE: 15
```

```
Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
        50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
                100                 105                 110
```

-continued

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
            130                 135                 140

Val Pro Leu Met Leu Ile
145                 150

<210> SEQ ID NO 16
<211> LENGTH: 150
<212> TYPE: PRT
<213> ORGANISM: Homo sapiens

<400> SEQUENCE: 16

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 17
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Thr, Ala or absent
<220> FEATURE:
<221> NAME/KEY: MOD_RES
<222> LOCATION: (121)..(121)
<223> OTHER INFORMATION: Pro, Ala, Val or Met

<400> SEQUENCE: 17

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
50                  55                  60

```
Trp Arg Asn Ser Ser Gly Thr Ile Glu Leu Val Lys Lys Gly Cys Trp
 65                  70                  75                  80

Leu Asp Asp Phe Asn Cys Tyr Asp Arg Gln Glu Cys Val Ala Thr Glu
                 85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150
```

<210> SEQ ID NO 18
<211> LENGTH: 115
<212> TYPE: PRT
<213> ORGANISM: Ovis aries

<400> SEQUENCE: 18

```
Ile Leu Gly Arg Ser Glu Thr Gln Glu Cys Ile Phe Tyr Asn Ala Asn
 1               5                  10                  15

Trp Glu Arg Asp Arg Thr Asn Arg Thr Gly Val Glu Ser Cys Tyr Gly
                 20                  25                  30

Asp Lys Asp Lys Arg Arg His Cys Phe Ala Thr Trp Lys Asn Ile Ser
             35                  40                  45

Gly Ser Ile Asp Ile Val Lys Gln Gly Cys Trp Leu Asp Asp Ile Asn
     50                  55                  60

Cys Tyr Asp Arg Thr Asp Cys Ile Glu Lys Lys Asp Ser Pro Glu Val
 65                  70                  75                  80

Tyr Phe Cys Cys Cys Glu Gly Asn Met Cys Asn Glu Arg Phe Ser Tyr
                 85                  90                  95

Phe Pro Glu Met Glu Val Thr Gln Pro Thr Ser Asn Pro Val Thr Pro
            100                 105                 110

Lys Pro Pro
        115
```

<210> SEQ ID NO 19
<211> LENGTH: 115
<212> TYPE: PRT
<213> ORGANISM: Condylura cristata

<400> SEQUENCE: 19

```
Ile Leu Gly Arg Ser Glu Thr Gln Glu Cys Leu Phe Phe Asn Ala Asn
 1               5                  10                  15

Trp Glu Arg Asp Arg Thr Asn Gln Thr Gly Val Glu Pro Cys Tyr Gly
                 20                  25                  30

Asp Lys Asp Lys Arg Arg His Cys Phe Ala Thr Trp Lys Asn Ile Ser
             35                  40                  45

Gly Ser Ile Glu Ile Val Lys Gln Gly Cys Trp Leu Asp Asp Ile Asn
     50                  55                  60

Cys Tyr Asp Arg Thr Asp Cys Ile Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met Glu Val Thr Gln Pro Thr Ser Asn Pro Val Thr Pro
            100                 105                 110
```

```
Lys Ala Pro
        115

<210> SEQ ID NO 20
<211> LENGTH: 115
<212> TYPE: PRT
<213> ORGANISM: Mus musculus

<400> SEQUENCE: 20

Ile Leu Gly Arg Ser Glu Thr Gln Glu Cys Leu Phe Phe Asn Ala Asn
1               5                   10                  15

Trp Glu Arg Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Ile Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 21
<211> LENGTH: 115
<212> TYPE: PRT
<213> ORGANISM: Gallus gallus

<400> SEQUENCE: 21

Ile Leu Gly Arg Ser Glu Thr Gln Glu Cys Ile Tyr Tyr Asn Ala Asn
1               5                   10                  15

Trp Glu Lys Asp Lys Thr Asn Arg Ser Gly Ile Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Asn Asp Cys Ile Glu Lys Lys Asp Ser Pro Glu Val
65                  70                  75                  80

Phe Phe Cys Cys Cys Glu Gly Asn Met Cys Asn Glu Arg Phe Phe Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 22
<211> LENGTH: 115
<212> TYPE: PRT
<213> ORGANISM: Bos taurus

<400> SEQUENCE: 22

Ile Leu Gly Arg Ser Glu Thr Gln Glu Cys Ile Phe Tyr Asn Ala Asn
1               5                   10                  15

Trp Glu Arg Asp Arg Thr Asn Arg Thr Gly Val Glu Ser Cys Tyr Gly
```

```
                    20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Ile Glu Lys Lys Asp Ser Pro Glu Val
 65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 23
<211> LENGTH: 115
<212> TYPE: PRT
<213> ORGANISM: Tyto alba

<400> SEQUENCE: 23

Ile Leu Gly Arg Ser Glu Thr Gln Glu Cys Ile Tyr Tyr Asn Ala Asn
 1               5                  10                  15

Trp Glu Lys Asp Lys Thr Asn Arg Ser Gly Ile Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Asn Asp Cys Ile Glu Lys Lys Asp Ser Pro Glu Val
 65                  70                  75                  80

Phe Phe Cys Cys Cys Glu Gly Asn Met Cys Asn Glu Arg Phe Phe Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 24
<211> LENGTH: 115
<212> TYPE: PRT
<213> ORGANISM: Myotis davidii

<400> SEQUENCE: 24

Ile Leu Gly Arg Ser Glu Thr Gln Glu Cys Ile Phe Tyr Asn Ala Asn
 1               5                  10                  15

Trp Glu Arg Asp Lys Thr Asn Arg Thr Gly Val Glu Leu Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Ile Glu Lys Lys Asp Ser Pro Glu Val
 65                  70                  75                  80

Tyr Phe Cys Cys Cys Glu Gly Asn Met Cys Asn Glu Arg Phe Ser Tyr
                85                  90                  95

Phe Pro Glu Met Glu Val Thr Gln Pro Thr Ser Asn Pro Val Thr Pro
```

```
                    100                 105                 110

Lys Pro Pro
        115

<210> SEQ ID NO 25
<211> LENGTH: 150
<212> TYPE: PRT
<213> ORGANISM: Rattus norvegicus

<400> SEQUENCE: 25

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 26
<211> LENGTH: 150
<212> TYPE: PRT
<213> ORGANISM: Sus scrofa

<400> SEQUENCE: 26

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
```

```
145                     150

<210> SEQ ID NO 27
<211> LENGTH: 150
<212> TYPE: PRT
<213> ORGANISM: Mus musculus

<400> SEQUENCE: 27

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 28
<211> LENGTH: 150
<212> TYPE: PRT
<213> ORGANISM: Bos taurus

<400> SEQUENCE: 28

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150
```

<210> SEQ ID NO 29
<211> LENGTH: 150
<212> TYPE: PRT
<213> ORGANISM: Xenopus sp.

<400> SEQUENCE: 29

Met Gly Ala Ser Val Ala Leu Thr Phe Leu Leu Leu Ala Thr Phe
1               5                   10                  15

Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
        35                  40                  45

Arg Leu Val Glu Gly Lys Lys Asp Lys Arg Leu His Cys Tyr Ala Ser
    50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
        115                 120                 125

Gln Pro Ser Ala Ser Val Leu Asn Ile Leu Ile Tyr Ser Leu Leu Pro
    130                 135                 140

Ile Val Gly Leu Ser Met
145                 150

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34
<211> LENGTH: 1038
<212> TYPE: PRT
<213> ORGANISM: Homo sapiens

<400> SEQUENCE: 34

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

```
Leu Cys Ala Phe Lys Asp Pro Tyr Gln Gln Asp Leu Gly Ile Gly Glu
             35                  40                  45

Ser Arg Ile Ser His Glu Asn Gly Thr Ile Leu Cys Ser Lys Gly Ser
 50                  55                  60

Thr Cys Tyr Gly Leu Trp Glu Lys Ser Lys Gly Asp Ile Asn Leu Val
 65                  70                  75                  80

Lys Gln Gly Cys Trp Ser His Ile Gly Asp Pro Gln Glu Cys His Tyr
                 85                  90                  95

Glu Glu Cys Val Val Thr Thr Thr Pro Pro Ser Ile Gln Asn Gly Thr
                100                 105                 110

Tyr Arg Phe Cys Cys Cys Ser Thr Asp Leu Cys Asn Val Asn Phe Thr
                115                 120                 125

Glu Asn Phe Pro Pro Pro Asp Thr Thr Pro Leu Ser Pro Pro His Ser
            130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
            195                 200                 205

Ile Gly Arg Gly Arg Tyr Gly Ala Val Tyr Lys Gly Ser Leu Asp Glu
            210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
                260                 265                 270

Met Glu Tyr Leu Leu Val Met Glu Tyr Tyr Pro Asn Gly Ser Leu Cys
            275                 280                 285

Lys Tyr Leu Ser Leu His Thr Ser Asp Trp Val Ser Ser Cys Arg Leu
            290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
            355                 360                 365

Glu Asp Asn Ala Ala Ile Ser Glu Val Gly Thr Ile Arg Tyr Met Ala
            370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
                420                 425                 430

Gln Met Ala Phe Gln Thr Glu Val Gly Asn His Pro Thr Phe Glu Asp
            435                 440                 445

Met Gln Val Leu Val Ser Arg Glu Lys Gln Arg Pro Lys Phe Pro Glu
```

```
            450                 455                 460
Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
                500                 505                 510

Ser Val Ser Pro Thr Val Asn Pro Met Ser Thr Ala Met Gln Asn Glu
                515                 520                 525

Arg Asn Leu Ser His Asn Arg Arg Val Pro Lys Ile Gly Pro Tyr Pro
                530                 535                 540

Asp Tyr Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
                580                 585                 590

Gln Ala Gln Ala Arg Ile Pro Ser Pro Glu Thr Ser Val Thr Ser Leu
                595                 600                 605

Ser Thr Asn Thr Thr Thr Asn Thr Thr Gly Leu Thr Pro Ser Thr
                610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
                660                 665                 670

Val Asp Lys Asn Leu Lys Glu Ser Ser Asp Glu Asn Leu Met Glu His
                675                 680                 685

Ser Leu Lys Gln Phe Ser Gly Pro Asp Pro Leu Ser Ser Thr Ser Ser
                690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
                740                 745                 750

Lys Arg Pro Thr Ser Leu Pro Leu Asn Thr Lys Asn Ser Thr Lys Glu
                755                 760                 765

Pro Arg Leu Lys Phe Gly Ser Lys His Lys Ser Asn Leu Lys Gln Val
                770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
                820                 825                 830

Gly Gln Thr Thr Asn Ile Val Thr His Arg Ala Gln Glu Met Leu Gln
                835                 840                 845

Asn Gln Phe Ile Gly Glu Asp Thr Arg Leu Asn Ile Asn Ser Ser Pro
                850                 855                 860

Asp Glu His Glu Pro Leu Leu Arg Arg Glu Gln Gln Ala Gly His Asp
865                 870                 875                 880
```

```
Glu Gly Val Leu Asp Arg Leu Val Asp Arg Arg Gly Arg Pro Leu Glu
                885                 890                 895
Gly Gly Arg Thr Asn Ser Asn Asn Asn Ser Asn Pro Cys Ser Glu
            900                 905                 910
Gln Asp Val Leu Ala Gln Gly Val Pro Ser Thr Ala Ala Asp Pro Gly
            915                 920                 925
Pro Ser Lys Pro Arg Arg Ala Gln Arg Pro Asn Ser Leu Asp Leu Ser
        930                 935                 940
Ala Thr Asn Val Leu Asp Gly Ser Ser Ile Gln Ile Gly Glu Ser Thr
945                 950                 955                 960
Gln Asp Gly Lys Ser Gly Ser Gly Glu Lys Ile Lys Lys Arg Val Lys
                965                 970                 975
Thr Pro Tyr Ser Leu Lys Arg Trp Arg Pro Ser Thr Trp Val Ile Ser
            980                 985                 990
Thr Glu Ser Leu Asp Cys Glu Val  Asn Asn Asn Gly Ser  Asn Arg Ala
            995                 1000                1005
Val His  Ser Lys Ser Ser Thr  Ala Val Tyr Leu Ala  Glu Gly Gly
    1010                1015                1020
Thr Ala  Thr Thr Met Val Ser  Lys Asp Ile Gly Met  Asn Cys Leu
    1025                1030                1035

<210> SEQ ID NO 35
<211> LENGTH: 3114
<212> TYPE: DNA
<213> ORGANISM: Homo sapiens

<400> SEQUENCE: 35
atgacttcct cgctgcagcg gccctggcgg gtgccctggc taccatggac catcctgctg      60
gtcagcactg cggctgcttc gcagaatcaa gaacggctat gtgcgtttaa agatccgtat     120
cagcaagacc ttgggatagg tgagagtaga atctctcatg aaaatgggac aatattatgc     180
tcgaaaggta gcacctgcta tggcctttgg gagaaatcaa aagggacat aaatcttgta      240 aaacaaggat gttggtctca cattggagat ccccaagagt gtcactatga agaatgtgta     300
gtaactacca ctcctcccct aattcagaat ggaacatacc gtttctgctg ttgtagcaca     360
gatttatgta atgtcaactt tactgagaat tttccaccct ctgacacaac accactcagt     420
ccacctcatt catttaaccg agatgagaca ataatcattg ctttggcatc agtctctgta     480
ttagctgttt tgatagttgc cttatgcttt ggatacagaa tgttgacagg agaccgtaaa     540
caaggtcttc acagtatgaa catgatggag gcagcagcat ccgaaccctc tcttgatcta     600
gataatctga aactgttgga gctgattggc cgaggtcgat atggagcagt atataaaggc     660
tccttggatg agcgtccagt tgctgtaaaa gtgttttcct ttgcaaaccg tcagaatttt     720
atcaacgaaa agaacattta cagagtgcct tgatggaaac atgacaacat tgcccgcttt     780
atagttggag atgagagagt cactgcagat ggacgcatgg aatatttgct tgtgatggag     840
tactatccca atggatcttt atgcaagtat ttaagtctcc acacaagtga ctgggtaagc     900
tcttgccgtc ttgctcattc tgttactaga ggactggctt atcttcacac agaattacca     960
cgaggagatc attataaacc tgcaatttcc catcgagatt aaacagcag aaatgtccta    1020 gtgaaaaatg atggaacctg tgttattagt gactttggac tgtccatgag gctgactgga    1080
aatagactgg tgcgcccagg ggaggaagat aatgcagcca taagcgaggt tggcactatc    1140
agatatatgg caccagaagt gctagaagga gctgtgaact tgagggactg tgaatcagct    1200
```

| | |
|---|---|
| ttgaaacaag tagacatgta tgctcttgga ctaatctatt gggagatatt tatgagatgt | 1260 |
| acagacctct tcccagggga atccgtacca gagtaccaga tggcttttca gacagaggtt | 1320 |
| ggaaaccatc ccacttttga ggatatgcag gttctcgtgt ctagggaaaa acagagaccc | 1380 |
| aagttcccag aagcctggaa agaaaatagc ctggcagtga ggtcactcaa ggagacaatc | 1440 |
| gaagactgtt gggaccagga tgcagaggct cggcttactg cacagtgtgc tgaggaaagg | 1500 |
| atggctgaac ttatgatgat ttgggaaaga aacaaatctg tgagcccaac agtcaatcca | 1560 |
| atgtctactg ctatgcagaa tgaacgcaac ctgtcacata taggcgtgt gccaaaaatt | 1620 |
| ggtccttatc cagattattc ttcctcctca tacattgaag actctatcca tcatactgac | 1680 |
| agcatcgtga agaatatttc ctctgagcat tctatgtcca gcacaccttt gactataggg | 1740 |
| gaaaaaaacc gaaattcaat taactatgaa cgacagcaag cacaagctcg aatccccagc | 1800 |
| cctgaaacaa gtgtcaccag cctctccacc aacacaacaa ccacaaacac cacaggactc | 1860 |
| acgccaagta ctggcatgac tactatatct gagatgccat acccagatga aacaaatctg | 1920 |
| cataccacaa atgttgcaca gtcaattggg ccaacccctg tctgcttaca gctgacagaa | 1980 |
| gaagacttgg aaaccaacaa gctagaccca aaagaagttg ataagaacct caaggaaagc | 2040 |
| tctgatgaga atctcatgga gcactctctt aaacagttca gtggcccaga cccactgagc | 2100 |
| agtactagtt ctagcttgct ttacccactc ataaaacttg cagtagaagc aactggacag | 2160 |
| caggacttca cacagactgc aaatggccaa gcatgtttga ttcctgatgt tctgcctact | 2220 |
| cagatctatc ctctccccaa gcagcagaac cttcccaaga gacctactag tttgcctttg | 2280 |
| aacaccaaaa attcaacaaa agagcccgg ctaaatttg gcagcaagca caaatcaaac | 2340 |
| ttgaaacaag tcgaaactgg agttgccaag atgaatacaa tcaatgcagc agaacctcat | 2400 |
| gtggtgacag tcaccatgaa tggtgtggca ggtagaaacc acagtgttaa ctcccatgct | 2460 |
| gccacaaccc aatatgccaa tgggacagta ctatctggcc aaacaaccaa catagtgaca | 2520 |
| catagggccc aagaaatgtt gcagaatcag tttattggtg aggacacccg gctgaatatt | 2580 |
| aattccagtc ctgatgagca tgagccttta ctgagacgag agcaacaagc tggccatgat | 2640 |
| gaaggtgttc tggatcgtct tgtggacagg agggaacggc cactagaagg tggccgaact | 2700 |
| aattccaata caacaacag caatccatgt tcagaacaag atgttcttgc acagggtgtt | 2760 |
| ccaagcacag cagcagatcc tgggccatca aagcccagaa gagcacagag gcctaattct | 2820 |
| ctggatcttt cagccacaaa tgtcctggat ggcagcagta tacagatagg tgagtcaaca | 2880 |
| caagatggca aatcaggatc aggtgaaaag atcaagaaac gtgtgaaaac tccctattct | 2940 |
| cttaagcggt ggcgccccta cacctgggtc atctccactg aatcgctgga ctgtgaagtc | 3000 |
| aacaataatg gcagtaacag ggcagttcat tccaaatcca gcactgctgt ttaccttgca | 3060 |
| gaaggaggca ctgctacaac catggtgtct aaagatatag gaatgaactg tctg | 3114 |

<210> SEQ ID NO 36
<211> LENGTH: 124
<212> TYPE: PRT
<213> ORGANISM: Homo sapiens

<400> SEQUENCE: 36

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys

-continued

```
                 35                  40                  45
Gly Asp Ile Asn Leu Val Lys Gln Gly Cys Trp Ser His Ile Gly Asp
         50                  55                  60
Pro Gln Glu Cys His Tyr Glu Glu Cys Val Val Thr Thr Thr Pro Pro
 65                  70                  75                  80
Ser Ile Gln Asn Gly Thr Tyr Arg Phe Cys Cys Ser Thr Asp Leu
                 85                  90                  95
Cys Asn Val Asn Phe Thr Glu Asn Phe Pro Pro Pro Asp Thr Thr Pro
                100                 105                 110
Leu Ser Pro Pro His Ser Phe Asn Arg Asp Glu Thr
                115                 120

<210> SEQ ID NO 37
<211> LENGTH: 372
<212> TYPE: DNA
<213> ORGANISM: Homo sapiens

<400> SEQUENCE: 37
tcgcagaatc aagaacggct atgtgcgttt aaagatccgt atcagcaaga ccttgggata    60
ggtgagagta gaatctctca tgaaaatggg acaatattat gctcgaaagg tagcacctgc   120
tatggccttt gggagaaatc aaaaggggac ataaatcttg taaaacaagg atgttggtct   180
cacattggag atccccaaga gtgtcactat gaagaatgtg tagtaactac cactcctccc   240
tcaattcaga atggaacata ccgtttctgc tgttgtagca cagatttatg taatgtcaac   300
tttactgaga attttccacc tcctgacaca acaccactca gtccacctca ttcatttaac   360
cgagatgaga ca                                                        372

<210> SEQ ID NO 38
<211> LENGTH: 530
<212> TYPE: PRT
<213> ORGANISM: Homo sapiens

<400> SEQUENCE: 38

Met Thr Ser Ser Leu Gln Arg Pro Trp Arg Val Pro Trp Leu Pro Trp
  1               5                  10                  15
Thr Ile Leu Leu Val Ser Thr Ala Ala Ala Ser Gln Asn Gln Glu Arg
                 20                  25                  30
Leu Cys Ala Phe Lys Asp Pro Tyr Gln Gln Asp Leu Gly Ile Gly Glu
                 35                  40                  45
Ser Arg Ile Ser His Glu Asn Gly Thr Ile Leu Cys Ser Lys Gly Ser
         50                  55                  60
Thr Cys Tyr Gly Leu Trp Glu Lys Ser Lys Gly Asp Ile Asn Leu Val
 65                  70                  75                  80
Lys Gln Gly Cys Trp Ser His Ile Gly Asp Pro Gln Glu Cys His Tyr
                 85                  90                  95
Glu Glu Cys Val Val Thr Thr Thr Pro Pro Ser Ile Gln Asn Gly Thr
                100                 105                 110
Tyr Arg Phe Cys Cys Cys Ser Thr Asp Leu Cys Asn Val Asn Phe Thr
                115                 120                 125
Glu Asn Phe Pro Pro Pro Asp Thr Thr Pro Leu Ser Pro Pro His Ser
            130                 135                 140
Phe Asn Arg Asp Glu Thr Ile Ile Ile Ala Leu Ala Ser Val Ser Val
145                 150                 155                 160
Leu Ala Val Leu Ile Val Ala Leu Cys Phe Gly Tyr Arg Met Leu Thr
                165                 170                 175
```

```
Gly Asp Arg Lys Gln Gly Leu His Ser Met Asn Met Glu Ala Ala
            180                 185                 190
Ala Ser Glu Pro Ser Leu Asp Leu Asp Asn Leu Lys Leu Leu Glu Leu
        195                 200                 205
Ile Gly Arg Gly Arg Tyr Gly Ala Val Tyr Lys Gly Ser Leu Asp Glu
    210                 215                 220
Arg Pro Val Ala Val Lys Val Phe Ser Phe Ala Asn Arg Gln Asn Phe
225                 230                 235                 240
Ile Asn Glu Lys Asn Ile Tyr Arg Val Pro Leu Met Glu His Asp Asn
                245                 250                 255
Ile Ala Arg Phe Ile Val Gly Asp Glu Arg Val Thr Ala Asp Gly Arg
            260                 265                 270
Met Glu Tyr Leu Leu Val Met Glu Tyr Tyr Pro Asn Gly Ser Leu Cys
        275                 280                 285
Lys Tyr Leu Ser Leu His Thr Ser Asp Trp Val Ser Ser Cys Arg Leu
    290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
            340                 345                 350
Gly Leu Ser Met Arg Leu Thr Gly Asn Arg Leu Val Arg Pro Gly Glu
        355                 360                 365
Glu Asp Asn Ala Ala Ile Ser Glu Val Gly Thr Ile Arg Tyr Met Ala
    370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
                405                 410                 415
Phe Met Arg Cys Thr Asp Leu Phe Pro Gly Glu Ser Val Pro Glu Tyr
            420                 425                 430
Gln Met Ala Phe Gln Thr Glu Val Gly Asn His Pro Thr Phe Glu Asp
        435                 440                 445
Met Gln Val Leu Val Ser Arg Glu Lys Gln Arg Pro Lys Phe Pro Glu
    450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Gly Arg Asn Lys
            500                 505                 510
Ser Val Ser Pro Thr Val Asn Pro Met Ser Thr Ala Met Gln Asn Glu
        515                 520                 525
Arg Arg
    530

<210> SEQ ID NO 39
<211> LENGTH: 1590
<212> TYPE: DNA
<213> ORGANISM: Homo sapiens

<400> SEQUENCE: 39
atgacttcct cgctgcagcg gccctggcgg gtgccctggc taccatggac catcctgctg    60
```

```
gtcagcactg cggctgcttc gcagaatcaa gaacggctat gtgcgtttaa agatccgtat      120
cagcaagacc ttgggatagg tgagagtaga atctctcatg aaaatgggac aatattatgc      180
tcgaaaggta gcacctgcta tggcctttgg gagaaatcaa aaggggacat aaatcttgta      240
aaacaaggat gttggtctca cattggagat ccccaagagt gtcactatga gaatgtgta       300 gtaactacca ctcctccctc aattcagaat ggaacatacc gtttctgctg ttgtagcaca      360
gatttatgta atgtcaactt tactgagaat tttccacctc ctgacacaac accactcagt      420
ccacctcatt catttaaccg agatgagaca ataatcattg ctttggcatc agtctctgta      480
ttagctgttt tgatagttgc cttatgcttt ggatacagaa tgttgacagg agaccgtaaa      540
caaggtcttc acagtatgaa catgatggag gcagcagcat ccgaaccctc tcttgatcta      600
gataatctga actgttgga gctgattggc cgaggtcgat atggagcagt atataaaggc       660
tccttggatg agcgtccagt tgctgtaaaa gtgttttcct ttgcaaaccg tcagaatttt      720
atcaacgaaa agaacattta cagagtgcct ttgatggaac atgacaacat tgcccgcttt      780
atagttggag atgagagagt cactgcagat ggacgcatgg aatatttgct tgtgatggag      840
tactatccca atggatcttt atgcaagtat ttaagtctcc acacaagtga ctgggtaagc      900
tcttgccgtc ttgctcattc tgttactaga ggactggctt atcttcacac agaattacca      960
cgaggagatc attataaacc tgcaatttcc catcgagatt taaacagcag aaatgtccta     1020
gtgaaaaatg atggaacctg tgttattagt gactttggac tgtccatgag gctgactgga     1080
aatagactgg tgcgcccagg ggaggaagat aatgcagcca taagcgaggt tggcactatc     1140
agatatatgg caccagaagt gctagaagga gctgtgaact tgagggactg tgaatcagct     1200
ttgaaacaag tagacatgta tgctcttgga ctaatctatt gggagatatt tatgagatgt     1260
acagacctct tcccagggga atccgtacca gagtaccaga tggcttttca gacagaggtt     1320
ggaaaccatc ccacttttga ggatatgcag gttctcgtgt ctagggaaaa acagagaccc     1380
aagttcccag aagcctggaa agaaaatagc ctggcagtga ggtcactcaa ggagacaatc     1440
gaagactgtt gggaccagga tgcagaggct cggcttactg cacagtgtgc tgaggaaagg     1500
atggctgaac ttatgatgat ttgggaaaga aacaaatctg tgagcccaac agtcaatcca     1560
atgtctactg ctatgcagaa tgaacgtagg                                      1590
```

<210> SEQ ID NO 40
<211> LENGTH: 124
<212> TYPE: PRT
<213> ORGANISM: Homo sapiens

<400> SEQUENCE: 40

```
Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95
```

```
Cys Asn Val Asn Phe Thr Glu Asn Phe Pro Pro Asp Thr Thr Pro
            100                 105                 110

Leu Ser Pro Pro His Ser Phe Asn Arg Asp Glu Thr
        115                 120
```

<210> SEQ ID NO 41
<211> LENGTH: 372
<212> TYPE: DNA
<213> ORGANISM: Homo sapiens

<400> SEQUENCE: 41

```
tcgcagaatc aagaacggct atgtgcgttt aaagatccgt atcagcaaga ccttgggata    60
ggtgagagta gaatctctca tgaaaatggg acaatattat gctcgaaagg tagcacctgc   120
tatggccttt gggagaaatc aaagggac ataaatcttg taaaacaagg atgttggtct    180
cacattggag atccccaaga gtgtcactat gaagaatgtg tagtaactac cactcctccc   240
tcaattcaga atggaacata ccgtttctgc tgttgtagca cagatttatg taatgtcaac   300
tttactgaga attttccacc tcctgacaca acaccactca gtccacctca ttcatttaac   360
cgagatgaga ca                                                      372
```

<210> SEQ ID NO 42
<211> LENGTH: 573
<212> TYPE: PRT
<213> ORGANISM: Homo sapiens

<400> SEQUENCE: 42

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
```

|     |     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- | --- |

Gln Ala Glu Arg Ala Leu Tyr Glu Leu Pro Gly Leu Gln His Asp His
        245       250      255

Ile Val Arg Phe Ile Thr Ala Ser Arg Gly Gly Pro Gly Arg Leu Leu
     260       265      270

Ser Gly Pro Leu Leu Val Leu Glu Leu His Pro Lys Gly Ser Leu Cys
     275       280      285

His Tyr Leu Thr Gln Tyr Thr Ser Asp Trp Gly Ser Ser Leu Arg Met
   290       295      300

Ala Leu Ser Leu Ala Gln Gly Leu Ala Phe Leu His Glu Glu Arg Trp
305       310       315      320

Gln Asn Gly Gln Tyr Lys Pro Gly Ile Ala His Arg Asp Leu Ser Ser
       325       330      335

Gln Asn Val Leu Ile Arg Glu Asp Gly Ser Cys Ala Ile Gly Asp Leu
     340       345      350

Gly Leu Ala Leu Val Leu Pro Gly Leu Thr Gln Pro Pro Ala Trp Thr
   355       360      365

Pro Thr Gln Pro Gln Gly Pro Ala Ala Ile Met Glu Ala Gly Thr Gln
 370       375       380

Arg Tyr Met Ala Pro Glu Leu Leu Asp Lys Thr Leu Asp Leu Gln Asp
385       390       395      400

Trp Gly Met Ala Leu Arg Arg Ala Asp Ile Tyr Ser Leu Ala Leu Leu
     405       410      415

Leu Trp Glu Ile Leu Ser Arg Cys Pro Asp Leu Arg Pro Asp Ser Ser
   420       425      430

Pro Pro Pro Phe Gln Leu Ala Tyr Glu Ala Glu Leu Gly Asn Thr Pro
     435       440      445

Thr Ser Asp Glu Leu Trp Ala Leu Ala Val Gln Glu Arg Arg Arg Pro
   450       455      460

Tyr Ile Pro Ser Thr Trp Arg Cys Phe Ala Thr Asp Pro Asp Gly Leu
465       470       475      480

Arg Glu Leu Leu Glu Asp Cys Trp Asp Ala Asp Pro Glu Ala Arg Leu
     485       490      495

Thr Ala Glu Cys Val Gln Gln Arg Leu Ala Ala Leu Ala His Pro Gln
     500       505      510

Glu Ser His Pro Phe Pro Glu Ser Cys Pro Arg Gly Cys Pro Pro Leu
   515       520      525

Cys Pro Glu Asp Cys Thr Ser Ile Pro Ala Pro Thr Ile Leu Pro Cys
 530       535       540

Arg Pro Gln Arg Ser Ala Cys His Phe Ser Val Gln Gln Gly Pro Cys
545       550       555      560

Ser Arg Asn Pro Gln Pro Ala Cys Thr Leu Ser Pro Val
     565       570

<210> SEQ ID NO 43
<211> LENGTH: 1719
<212> TYPE: DNA
<213> ORGANISM: Homo sapiens

<400> SEQUENCE: 43

```
atgctagggt cttggggct ttgggcatta cttcccacag ctgtggaagc acccccaaac      60
aggcgaacct gtgtgttctt tgaggcccct ggagtgcggg aagcacaaa gacactggga     120 gagctgctag atacaggcac agagctcccc agagctatcc gctgcctcta cagccgctgc     180
```

```
tgctttggga tctggaacct gacccaagac cgggcacagg tggaaatgca aggatgccga    240
gacagtgatg agccaggctg tgagtccctc cactgtgacc caagtccccg agcccacccc    300
agccctggct ccactctctt cacctgctcc tgtggcactg acttctgcaa tgccaattac    360
agccatctgc ctcctccagg gagccctggg actcctggct cccagggtcc ccaggctgcc    420
ccaggtgagt ccatctggat ggcactggtg ctgctggggc tgttcctcct cctcctgctg    480
ctgctgggca gcatcatctt ggccctgcta gcgcgaaaga actacagagt gcgaggtgag    540
ccagtgccag agccaaggcc agactcaggc agggactgga gtgtggagct gcaggagctg    600
cctgagctgt gtttctccca ggtaatccgg aaggaggtc atgcagtggt ttgggccggg     660
cagctgcaag gaaaactggt tgccatcaag gccttcccac cgaggtctgt ggctcagttc    720
caagctgaga gagcattgta cgaacttcca ggcctacagc acgaccacat tgtccgattt    780
atcactgcca gccggggggg tcctggccgc ctgctctctg ggcccctgct ggtactggaa    840
ctgcatccca agggctccct gtgccactac ttgacccagt acaccagtga ctggggaagt    900
tccctgcgga tggcactgtc cctggcccag ggcctggcat ttctccatga ggagcgctgg    960
cagaatggcc aatataaacc aggtattgcc caccgagatc tgagcagcca aatgtgctc   1020
attcgggaag atggatcgtg tgccattgga gacctgggcc ttgccttggt gctccctggc   1080
ctcactcagc cccctgcctg gacccctact caaccacaag gcccagctgc catcatggaa   1140
gctggcaccc agaggtacat ggcaccgag ctcttggaca agactctgga cctacaggat   1200
tggggcatgg ccctccgacg agctgatatt tactctttgg ctctgctcct gtgggagata   1260
ctgagccgct gccagatttt gaggcctgac agcagtccac cacccttcca actggcctat   1320
gaggcagaac tggcaatac ccctacctct gatgagctat gggccttggc agtgcaggag    1380
aggaggcgtc cctacatccc atccacctgg cgctgctttg ccacagaccc tgatgggctg   1440
agggagctcc tagaagactg ttgggatgca gacccagaag cacggctgac agctgagtgt   1500
gtacagcagc gcctggctgc cttggcccat cctcaagaga gccacccctt ccagagagc    1560
tgtccacgtg gctgcccacc tctctgccca gaagactgta cttcaattcc tgcccctacc   1620
atcctccct gtaggcctca gcggagtgcc tgccacttca gcgttcagca aggcccttgt    1680
tccaggaatc ctcagcctgc ctgtacccct tctcctgtg                         1719
```

<210> SEQ ID NO 44  
<211> LENGTH: 132  
<212> TYPE: PRT  
<213> ORGANISM: Homo sapiens

<400> SEQUENCE: 44

```
Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Gly Ser Pro
```

```
                        100                 105                 110
Gly Thr Pro Gly Ser Gln Gly Pro Gln Ala Ala Pro Gly Glu Ser Ile
            115                 120                 125

Trp Met Ala Leu
    130

<210> SEQ ID NO 45
<211> LENGTH: 396
<212> TYPE: DNA
<213> ORGANISM: Homo sapiens

<400> SEQUENCE: 45
cccccaaaca ggcgaacctg tgtgttcttt gaggcccctg gagtgcgggg aagcacaaag      60
acactgggag agctgctaga tacaggcaca gagctcccca gagctatccg ctgcctctac     120
agccgctgct gctttgggat ctggaacctg acccaagacc gggcacaggt ggaaatgcaa     180
ggatgccgag acagtgatga gccaggctgt gagtccctcc actgtgaccc aagtccccga     240
gcccacccca gccctggctc cactctcttc acctgctcct gtggcactga cttctgcaat     300
gccaattaca gccatctgcc tcctccaggg agccctggga ctcctggctc ccagggtccc     360
caggctgccc caggtgagtc catctggatg gcactg                               396

<210> SEQ ID NO 46
<211> LENGTH: 478
<212> TYPE: PRT
<213> ORGANISM: Homo sapiens

<400> SEQUENCE: 46

Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220
```

```
Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
            245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
        290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
            325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Ala Gly Thr Gln
370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
            405                 410                 415

Leu Trp Glu Ile Leu Ser Arg Cys Pro Asp Leu Arg Pro Ala Val His
            420                 425                 430

His Pro Ser Asn Trp Pro Met Arg Gln Asn Trp Ala Ile Pro Leu Pro
        435                 440                 445

Leu Met Ser Tyr Gly Pro Trp Gln Cys Arg Arg Gly Gly Val Pro Thr
450                 455                 460

Ser His Pro Pro Gly Ala Ala Leu Pro Gln Thr Leu Met Gly
465                 470                 475

<210> SEQ ID NO 47
<211> LENGTH: 1434
<212> TYPE: DNA
<213> ORGANISM: Homo sapiens

<400> SEQUENCE: 47
atgctagggt cttttgggct ttgggcatta cttcccacag ctgtggaagc accccccaaac      60 aggcgaacct gtgtgttctt tgaggcccct ggagtgcggg gaagcacaaa gacactggga     120
gagctgctag atacaggcac agagctcccc agagctatcc gctgcctcta cagccgctgc     180
tgctttggga tctggaacct gacccaagac cgggcacagg tggaaatgca aggatgccga     240
gacagtgatg agccaggctg tgagtccctc cactgtgacc caagtcccccg agcccacccc     300 agccctggct ccactctctt cacctgctcc tgtggcactg acttctgcaa tgccaattac     360
agccatctgc ctcctccagg gagccctggg actcctggct cccagggtcc ccaggctgcc     420
ccaggtgagt ccatctggat ggcactggtg ctgctggggc tgttcctcct cctcctgctg     480
ctgctgggca gcatcatctc ggccctgcta cagcgaaaga actacagagt gcgaggtgag     540
ccagtgccag agccaaggcc agactcaggc agggactgga gtgtggagct gcaggagctg     600
cctgagctgt gtttctccca ggtaatccgg gaaggaggtc atgcagtggt ttgggccggg     660
```

| | |
|---|---|
| cagctgcaag gaaaactggt tgccatcaag gccttcccac cgaggtctgt ggctcagttc | 720 |
| caagctgaga gagcattgta cgaacttcca ggcctacagc acgaccacat tgtccgattt | 780 |
| atcactgcca gccgggggg tcctggccgc ctgctctctg ggcccctgct ggtactggaa | 840 |
| ctgcatccca agggctccct gtgccactac ttgacccagt acaccagtga ctggggaagt | 900 |
| tccctgcgga tggcactgtc cctggcccag ggcctggcat ttctccatga ggagcgctgg | 960 |
| cagaatggcc aatataaacc aggtattgcc caccgagatc tgagcagcca gaatgtgctc | 1020 |
| attcgggaag atggatcgtg tgccattgga gacctgggcc ttgccttggt gctccctggc | 1080 |
| ctcactcagc ccctgcctg accctact caaccacaag cccagctgc atcatggaa | 1140 |
| gctggcaccc agaggtacat ggcaccagag ctcttggaca agactctgga cctacaggat | 1200 |
| tggggcatgg ccctccgacg agctgatatt tactctttgg ctctgctcct gtgggagata | 1260 |
| ctgagccgct gcccagattt gaggcctgca gtccaccacc cttccaactg gcctatgagg | 1320 |
| cagaactggg caatacccct acctctgatg agctatgggc cttggcagtg caggagagga | 1380 |
| ggcgtcccta catcccatcc acctggcgct gctttgccac agaccctgat gggc | 1434 |

<210> SEQ ID NO 48
<211> LENGTH: 478
<212> TYPE: PRT
<213> ORGANISM: Homo sapiens

<400> SEQUENCE: 48

Met Leu Gly Ser Leu Gly Leu Trp Ala Leu Leu Pro Thr Ala Val Glu
1               5                   10                  15

Ala Pro Pro Asn Arg Arg Thr Cys Val Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Gly Ser
        115                 120                 125

Pro Gly Thr Pro Gly Ser Gln Gly Pro Gln Ala Pro Gly Glu Ser
    130                 135                 140

Ile Trp Met Ala Leu Val Leu Leu Gly Leu Phe Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Asp Pro Asp Gly
    370                 375                 380

Leu Arg Glu Leu Leu Glu Asp Cys Trp Asp Ala Asp Pro Glu Ala Arg
385                 390                 395                 400

Leu Thr Ala Glu Cys Val Gln Gln Arg Leu Ala Ala Leu Ala His Pro
                405                 410                 415

Gln Glu Ser His Pro Phe Pro Glu Ser Cys Pro Arg Gly Cys Pro Pro
            420                 425                 430

Leu Cys Pro Glu Asp Cys Thr Ser Ile Pro Ala Pro Thr Ile Leu Pro
        435                 440                 445

Cys Arg Pro Gln Arg Ser Ala Cys His Phe Ser Val Gln Gln Gly Pro
    450                 455                 460

Cys Ser Arg Asn Pro Gln Pro Ala Cys Thr Leu Ser Pro Val
465                 470                 475

<210> SEQ ID NO 49
<211> LENGTH: 1434
<212> TYPE: DNA
<213> ORGANISM: Homo sapiens

<400> SEQUENCE: 49
atgctagggt cttttgggct ttgggcatta cttcccacag ctgtggaagc accccccaaac    60 aggcgaacct gtgtgttctt tgaggcccct ggagtgcggg gaagcacaaa gacactggga   120
gagctgctag atacaggcac agagctcccc agagctatcc gctgcctcta cagccgctgc   180
tgctttggga tctggaacct gacccaagac cgggcacagg tggaaatgca aggatgccga   240
gacagtgatg agccaggctg tgagtccctc cactgtgacc caagtccccg agcccacccc   300
agccctggct ccactctctt cacctgctcc tgtggcactg acttctgcaa tgccaattac   360
agccatctgc ctcctccagg gagccctggg actcctggct cccagggtcc ccaggctgcc   420
ccaggtgagt ccatctggat ggcactggtg ctgctgggc tgttcctcct cctcctgctg   480
ctgctgggca gcatcatctt ggccctgcta cagcgaaaga actacagagt gcgaggtgag   540
ccagtgccag agccaaggcc agactcaggc agggactgga gtgtggagct gcaggagctg   600
cctgagctgt gtttctccca ggtaatccgg gaaggaggtc atgcagtggt ttgggccggg   660
cagctgcaag gaaaactggt tgccatcaag gccttccacc gaggtctgt ggctcagttc   720 caagctgaga gagcattgta cgaacttcca ggcctacagc acgaccacat tgtccgattt   780

-continued

| | |
|---|---|
| atcactgcca gccgggggggg tcctggccgc ctgctctctg ggcccctgct ggtactggaa | 840 |
| ctgcatccca agggctccct gtgccactac ttgacccagt acaccagtga ctggggaagt | 900 |
| tccctgcgga tggcactgtc cctggcccag ggcctggcat ttctccatga ggagcgctgg | 960 |
| cagaatggcc aatataaacc aggtattgcc caccgagatc tgagcagcca gaatgtgctc | 1020 |
| attcgggaag atggatcgtg tgccattgga gacctgggcc ttgccttggt gctccctggc | 1080 |
| ctcactcagc cccctgcctg gaccccctact caaccacaag cccagctgc catcatggaa | 1140 |
| gaccctgatg ggctgaggga gctcctagaa gactgttggg atgcagaccc agaagcacgg | 1200 |
| ctgacagctg agtgtgtaca gcagcgcctg gctgccttgg cccatcctca agagagccac | 1260 |
| cccttccag agagctgtcc acgtggctgc ccacctctct gcccagaaga ctgtacttca | 1320 |
| attcctgccc ctaccatcct cccctgtagg cctcagcgga gtgcctgcca cttcagcgtt | 1380 |
| cagcaaggcc cttgttccag gaatcctcag cctgcctgta ccctttctcc tgtg | 1434 |

<210> SEQ ID NO 50
<211> LENGTH: 9
<212> TYPE: PRT
<213> ORGANISM: Homo sapiens

<400> SEQUENCE: 50

Ile Leu Gly Arg Ser Glu Thr Gln Glu
1               5

<210> SEQ ID NO 51
<211> LENGTH: 6
<212> TYPE: PRT
<213> ORGANISM: Homo sapiens

<400> SEQUENCE: 51

Gly Arg Gly Glu Ala Glu
1               5

<210> SEQ ID NO 52
<211> LENGTH: 503
<212> TYPE: PRT
<213> ORGANISM: Homo sapiens

<400> SEQUENCE: 52

Met Thr Leu Gly Ser Pro Arg Lys Gly Leu Leu Met Leu Met Ala
1               5                   10                  15

Leu Val Thr Gln Gly Asp Pro Val Lys Pro Ser Arg Gly Pro Leu Val
                20                  25                  30

Thr Cys Thr Cys Glu Ser Pro His Cys Lys Gly Pro Thr Cys Arg Gly
            35                  40                  45

Ala Trp Cys Thr Val Val Leu Val Arg Glu Gly Arg His Pro Gln
        50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95

His Asn Val Ser Leu Val Leu Glu Ala Thr Gln Pro Pro Ser Glu Gln
                100                 105                 110

Pro Gly Thr Asp Gly Gln Leu Ala Leu Ile Leu Gly Pro Val Leu Ala
            115                 120                 125

Leu Leu Ala Leu Val Ala Leu Gly Val Leu Gly Leu Trp His Val Arg
        130                 135                 140

```
Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Ser Met Leu Gly Asp
            165                 170                 175

Leu Leu Asp Ser Asp Cys Thr Thr Gly Ser Gly Ser Gly Leu Pro Phe
        180                 185                 190

Leu Val Gln Arg Thr Val Ala Arg Gln Val Ala Leu Val Glu Cys Val
            195                 200                 205

Gly Lys Gly Arg Tyr Gly Glu Val Trp Arg Gly Leu Trp His Gly Glu
210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
            245                 250                 255

Leu Gly Phe Ile Ala Ser Asp Met Thr Ser Arg Asn Ser Ser Thr Gln
        260                 265                 270

Leu Trp Leu Ile Thr His Tyr His Glu His Gly Ser Leu Tyr Asp Phe
    275                 280                 285

Leu Gln Arg Gln Thr Leu Glu Pro His Leu Ala Leu Arg Leu Ala Val
290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
            325                 330                 335

Leu Val Lys Ser Asn Leu Gln Cys Cys Ile Ala Asp Leu Gly Leu Ala
        340                 345                 350

Val Met His Ser Gln Gly Ser Asp Tyr Leu Asp Ile Gly Asn Asn Pro
    355                 360                 365

Arg Val Gly Thr Lys Arg Tyr Met Ala Pro Glu Val Leu Asp Glu Gln
370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
            405                 410                 415

Ile Val Glu Asp Tyr Arg Pro Pro Phe Tyr Asp Val Val Pro Asn Asp
        420                 425                 430

Pro Ser Phe Glu Asp Met Lys Lys Val Val Cys Val Asp Gln Gln Thr
    435                 440                 445

Pro Thr Ile Pro Asn Arg Leu Ala Ala Asp Pro Val Leu Ser Gly Leu
450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
            485                 490                 495

Glu Lys Pro Lys Val Ile Gln
            500

<210> SEQ ID NO 53
<211> LENGTH: 1509
<212> TYPE: DNA
<213> ORGANISM: Homo sapiens

<400> SEQUENCE: 53
atgaccttgg gctcccccag gaaaggcctt ctgatgctgc tgatggcctt ggtgacccag    60
```

```
ggagaccctg tgaagccgtc tcggggcccg ctggtgacct gcacgtgtga gagcccacat    120 tgcaagggc ctacctgccg gggggcctgg tgcacagtag tgctggtgcg ggaggagggg    180 aggcacccccc aggaacatcg gggctgcggg aacttgcaca gggagctctg caggggcgc    240 cccaccgagt tcgtcaacca ctactgctgc gacagccacc tctgcaacca caacgtgtcc    300
ctggtgctgg aggccaccca acctccttcg gagcagccgg aacagatgg ccagctggcc    360 ctgatcctgg ccccgtgct ggccttgctg ccctggtgg ccctgggtgt cctgggcctg    420
tggcatgtcc gacggaggca ggagaagcag cgtggcctgc acagcgagct gggagagtcc    480
agtctcatcc tgaaagcatc tgagcagggc gacagcatgt ggggacct cctggacagt    540 gactgcacca cagggagtgg ctcagggctc cccttcctgg tgcagaggac agtggcacgg    600
caggttgcct tggtggagtg tgtgggaaaa ggccgctatg gcgaagtgtg gcggggcttg    660
tggcacggtg agagtgtggc cgtcaagatc ttctcctcga gggatgaaca gtcctggttc    720
cgggagactg agatctataa cacagtgttg ctcagacacg acaacatcct aggcttcatc    780
gcctcagaca tgacctcccg caactcgagc acgcagctgt ggctcatcac gcactaccac    840
gagcacggct ccctctacga cttttctgcag agacagacgc tggagcccca tctggctctg    900
aggctagctg tgtccgcggc atgcggcctg cgcacctgc acgtggagat cttcggtaca    960
cagggcaaac cagccattgc ccaccgcgac ttcaagagcc gcaatgtgct ggtcaagagc   1020
aacctgcagt gttgcatcgc cgacctgggc ctggctgtga tgcactcaca gggcagcgat   1080
tacctggaca tcggcaacaa cccgagagtg ggcaccaagc ggtacatggc acccgaggtg   1140
ctggacgagc agatccgcac ggactgcttt gagtcctaca gtggactga catctgggcc   1200 tttggcctgg tgctgtggga gattgcccgc cggaccatcg tgaatggcat cgtggaggac   1260
tatagaccac cctttctatga tgtggtgccc aatgacccca gctttgagga catgaagaag   1320
gtggtgtgtg tggatcagca gaccccaccac atccctaacc ggctggctgc agacccggtc   1380
ctctcaggcc tagctcagat gatgcgggag tgctggtacc aaaccccctc tgcccgactc   1440
accgcgctgc ggatcaagaa gacactacaa aaaattagca acagtccaga gaagcctaaa   1500
gtgattcaa                                                          1509
```

<210> SEQ ID NO 54
<211> LENGTH: 97
<212> TYPE: PRT
<213> ORGANISM: Homo sapiens

<400> SEQUENCE: 54

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln

<210> SEQ ID NO 55
<211> LENGTH: 291
<212> TYPE: DNA
<213> ORGANISM: Homo sapiens

<400> SEQUENCE: 55

```
gaccctgtga agccgtctcg gggcccgctg gtgacctgca cgtgtgagag cccacattgc      60
aaggggccta cctgccgggg ggcctggtgc acagtagtgc tggtgcggga ggaggggagg     120
cacccccagg aacatcgggg ctgcgggaac ttgcacaggg agctctgcag ggggcgcccc     180
accgagttcg tcaaccacta ctgctgcgac agccacctct gcaaccacaa cgtgtccctg     240
gtgctggagg ccacccaacc tccttcggag cagccgggaa cagatggcca g              291
```

<210> SEQ ID NO 56
<211> LENGTH: 505
<212> TYPE: PRT
<213> ORGANISM: Homo sapiens

<400> SEQUENCE: 56

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285
```

```
Ser Leu Phe Asp Tyr Leu Asn Arg Tyr Thr Val Thr Ile Glu Gly Met
    290                 295                 300
Ile Lys Leu Ala Leu Ser Ala Ala Ser Gly Leu Ala His Leu His Met
305                 310                 315                 320
Glu Ile Val Gly Thr Gln Gly Lys Pro Gly Ile Ala His Arg Asp Leu
                325                 330                 335
Lys Ser Lys Asn Ile Leu Val Lys Lys Asn Gly Met Cys Ala Ile Ala
            340                 345                 350
Asp Leu Gly Leu Ala Val Arg His Asp Ala Val Thr Asp Thr Ile Asp
        355                 360                 365
Ile Ala Pro Asn Gln Arg Val Gly Thr Lys Arg Tyr Met Ala Pro Glu
    370                 375                 380
Val Leu Asp Glu Thr Ile Asn Met Lys His Phe Asp Ser Phe Lys Cys
385                 390                 395                 400
Ala Asp Ile Tyr Ala Leu Gly Leu Val Tyr Trp Glu Ile Ala Arg Arg
                405                 410                 415
Cys Asn Ser Gly Gly Val His Glu Glu Tyr Gln Leu Pro Tyr Tyr Asp
            420                 425                 430
Leu Val Pro Ser Asp Pro Ser Ile Glu Glu Met Arg Lys Val Val Cys
        435                 440                 445
Asp Gln Lys Leu Arg Pro Asn Ile Pro Asn Trp Trp Gln Ser Tyr Glu
    450                 455                 460
Ala Leu Arg Val Met Gly Lys Met Met Arg Glu Cys Trp Tyr Ala Asn
465                 470                 475                 480
Gly Ala Ala Arg Leu Thr Ala Leu Arg Ile Lys Lys Thr Leu Ser Gln
                485                 490                 495
Leu Ser Val Gln Glu Asp Val Lys Ile
        500                 505

<210> SEQ ID NO 57
<211> LENGTH: 1515
<212> TYPE: DNA
<213> ORGANISM: Homo sapiens

<400> SEQUENCE: 57
atggcggagt cggccggagc ctcctccttc ttccccttg ttgtcctcct gctcgccggc      60
agcggcgggt ccgggccccg gggggtccag gctctgctgt gtgcgtgcac cagctgcctc    120
caggccaact acacgtgtga cagatgggg gcctgcatgg tttccatttt caatctggat     180
gggatggagc accatgtgcg cacctgcatc cccaaagtgg agctggtccc tgccggggag    240
cccttctact gcctgagctc ggaggacctg cgcaacaccc actgctgcta cactgactac    300
tgcaacagga tcgacttgag ggtgcccagt ggtcacctca aggagcctga gcacccgtcc    360
atgtggggcc cggtggagct ggtaggcatc atcgccggcc cggtgttcct cctgttcctc    420
atcatcatca ttgttttcct tgtcattaac tatcatcagc gtgtctatca aaccgccag     480 agactggaca tggaagatcc ctcatgtgag atgtgtctct ccaaagacaa gacgctccag    540
gatcttgtct acgatctctc cacctcaggg tctggctcag ggttaccct ctttgtccag     600 cgcacagtgg cccgaaccat cgttttacaa gagattattg caagggtcg gtttggggaa     660 gtatggcggg gccgctggag gggtggtgat gtggctgtga aaatattctc ttctcgtgaa    720
gaacggtctt ggtcaggga agcagagata taccagacgg tcatgctgcg ccatgaaaac    780
atccttggat ttattgctgc tgacaataaa gataatggca cctggacaca gctgtggctt    840
gtttctgact atcatgagca cgggtccctg tttgattatc tgaaccggta cacagtgaca    900
```

-continued

```
attgagggga tgattaagct ggccttgtct gctgctagtg ggctggcaca cctgcacatg    960
gagatcgtgg gcacccaagg gaagcctgga attgctcatc gagacttaaa gtcaaagaac   1020
attctggtga agaaaaatgg catgtgtgcc atagcagacc tgggcctggc tgtccgtcat   1080
gatgcagtca ctgacaccat tgacattgcc ccgaatcaga gggtggggac caaacgatac   1140
atggcccctg aagtacttga tgaaaccatt aatatgaaac actttgactc ctttaaatgt   1200
gctgatattt atgccctcgg gcttgtatat tgggagattg ctcgaagatg caattctgga   1260
ggagtccatg aagaatatca gctgccatat tacgacttag tgccctctga cccttccatt   1320
gaggaaatgc gaaaggttgt atgtgatcag aagctgcgtc ccaacatccc caactggtgg   1380
cagagttatg aggcactgcg ggtgatgggg aagatgatgc gagagtgttg gtatgccaac   1440
ggcgcagccc gcctgacggc cctgcgcatc aagaagaccc tctcccagct cagcgtgcag   1500
gaagacgtga agatc                                                   1515
```

<210> SEQ ID NO 58
<211> LENGTH: 103
<212> TYPE: PRT
<213> ORGANISM: Homo sapiens

<400> SEQUENCE: 58

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100

<210> SEQ ID NO 59
<211> LENGTH: 309
<212> TYPE: DNA
<213> ORGANISM: Homo sapiens

<400> SEQUENCE: 59

```
tccgggcccc gggggtccca ggctctgctg tgtgcgtgca ccagctgcct ccaggccaac    60
tacacgtgtg agacagatgg ggcctgcatg gtttccattt tcaatctgga tgggatggag   120
caccatgtgc gcacctgcat ccccaaagtg gagctggtcc ctgccgggaa gcccttctac   180
tgcctgagct cggaggacct gcgcaacacc cactgctgct acactgacta ctgcaacagg   240
atcgacttga gggtgcccag tggtcacctc aaggagcctg agcacccgtc catgtggggc   300
ccggtggag                                                           309
```

<210> SEQ ID NO 60
<211> LENGTH: 546
<212> TYPE: PRT
<213> ORGANISM: Homo sapiens

<400> SEQUENCE: 60

```
Met Ala Glu Ser Ala Gly Ala Ser Ser Phe Phe Pro Leu Val Val Leu
1               5                   10                  15

Leu Leu Ala Gly Ser Gly Ser Gly Pro Arg Gly Val Gln Ala Leu
            20              25                  30

Leu Cys Ala Cys Thr Ser Cys Leu Gln Ala Asn Tyr Thr Cys Glu Thr
        35              40                  45

Asp Gly Ala Cys Met Val Ser Ile Phe Asn Leu Asp Gly Met Glu His
    50              55                  60

His Val Arg Thr Cys Ile Pro Lys Val Glu Leu Val Pro Ala Gly Lys
65              70              75                  80

Pro Phe Tyr Cys Leu Ser Ser Glu Asp Leu Arg Asn Thr His Cys Cys
                85              90                  95

Tyr Thr Asp Tyr Cys Asn Arg Ile Asp Leu Arg Val Pro Ser Gly His
            100             105                 110

Leu Lys Glu Pro Glu His Pro Ser Met Trp Gly Pro Val Glu Leu Val
        115             120                 125

Gly Ile Ile Ala Gly Pro Val Phe Leu Leu Phe Leu Ile Ile Ile Ile
    130             135                 140

Val Phe Leu Val Ile Asn Tyr His Gln Arg Val Tyr His Asn Arg Gln
145             150                 155                 160

Arg Leu Asp Met Glu Asp Pro Ser Cys Glu Met Cys Leu Ser Lys Asp
                165             170                 175

Lys Thr Leu Gln Asp Leu Val Tyr Asp Leu Ser Thr Ser Gly Ser Gly
            180             185                 190

Ser Gly Leu Pro Leu Phe Val Gln Arg Thr Val Ala Arg Thr Ile Val
        195             200                 205

Leu Gln Glu Ile Ile Gly Lys Gly Arg Phe Gly Glu Val Trp Arg Gly
    210             215                 220

Arg Trp Arg Gly Gly Asp Val Ala Val Lys Ile Phe Ser Ser Arg Glu
225             230                 235                 240

Glu Arg Ser Trp Phe Arg Glu Ala Glu Ile Tyr Gln Thr Val Met Leu
                245             250                 255

Arg His Glu Asn Ile Leu Gly Phe Ile Ala Ala Asp Asn Lys Ala Asp
            260             265                 270

Cys Ser Phe Leu Thr Leu Pro Trp Glu Val Val Met Val Ser Ala Ala
        275             280                 285

Pro Lys Leu Arg Ser Leu Arg Leu Gln Tyr Lys Gly Gly Arg Gly Arg
    290             295                 300

Ala Arg Phe Leu Phe Pro Leu Asn Asn Gly Thr Trp Thr Gln Leu Trp
305             310                 315                 320

Leu Val Ser Asp Tyr His Glu His Gly Ser Leu Phe Asp Tyr Leu Asn
                325             330                 335

Arg Tyr Thr Val Thr Ile Glu Gly Met Ile Lys Leu Ala Leu Ser Ala
            340             345                 350

Ala Ser Gly Leu Ala His Leu His Met Glu Ile Val Gly Thr Gln Gly
        355             360                 365

Lys Pro Gly Ile Ala His Arg Asp Leu Lys Ser Lys Asn Ile Leu Val
    370             375                 380

Lys Lys Asn Gly Met Cys Ala Ile Ala Asp Leu Gly Leu Ala Val Arg
385             390                 395                 400

His Asp Ala Val Thr Asp Thr Ile Asp Ile Ala Pro Asn Gln Arg Val
                405             410                 415
```

Gly Thr Lys Arg Tyr Met Ala Pro Glu Val Leu Asp Glu Thr Ile Asn
            420                 425                 430

Met Lys His Phe Asp Ser Phe Lys Cys Ala Asp Ile Tyr Ala Leu Gly
            435                 440                 445

Leu Val Tyr Trp Glu Ile Ala Arg Arg Cys Asn Ser Gly Gly Val His
        450                 455                 460

Glu Glu Tyr Gln Leu Pro Tyr Tyr Asp Leu Val Pro Ser Asp Pro Ser
465                 470                 475                 480

Ile Glu Glu Met Arg Lys Val Val Cys Asp Gln Lys Leu Arg Pro Asn
                485                 490                 495

Ile Pro Asn Trp Trp Gln Ser Tyr Glu Ala Leu Arg Val Met Gly Lys
            500                 505                 510

Met Met Arg Glu Cys Trp Tyr Ala Asn Gly Ala Ala Arg Leu Thr Ala
            515                 520                 525

Leu Arg Ile Lys Lys Thr Leu Ser Gln Leu Ser Val Gln Glu Asp Val
        530                 535                 540

Lys Ile
545

<210> SEQ ID NO 61
<211> LENGTH: 1638
<212> TYPE: DNA
<213> ORGANISM: Homo sapiens

<400> SEQUENCE: 61

| | | |  |
|---|---|---|---|
| atggcggagt cggccggagc ctcctccttc ttccccttg ttgtcctcct gctcgccggc | 60 |
| agcggcgggt ccgggccccg ggggtccag gctctgctgt gtgcgtgcac cagctgcctc | 120 |
| caggccaact acacgtgtga cacagatggg gcctgcatgg tttccatttt caatctggat | 180 |
| gggatggagc accatgtgcg cacctgcatc cccaaagtgg agctggtccc tgccgggaag | 240 |
| cccttctact gcctgagctc ggaggacctg cgcaacaccc actgctgcta cactgactac | 300 |
| tgcaacagga tcgacttgag ggtgcccagt ggtcacctca aggagcctga gcacccgtcc | 360 |
| atgtggggcc cggtggagct ggtaggcatc atcgccggcc cggtgttcct cctgttcctc | 420 |
| atcatcatca ttgttttcct tgtcattaac tatcatcagc gtgtctatca aaccgccag | 480 |
| agactggaca tggaagatcc ctcatgtgag atgtgtctct ccaaagacaa gacgctccag | 540 |
| gatcttgtct acgatctctc cacctcaggg tctggctcag ggttacccct ctttgtccag | 600 |
| cgcacagtgg cccgaaccat cgttttacaa gagattattg caagggtcg gtttggggaa | 660 |
| gtatggcggg gccgctggag gggtggtgat gtggctgtga aaatattctc ttctcgtgaa | 720 |
| gaacggtctt ggttcaggga agcagagata taccagacgg tcatgctgcg ccatgaaaac | 780 |
| atccttggat ttattgctgc tgacaataaa gcagactgct cattcctcac attgccatgg | 840 |
| gaagttgtaa tggtctctgc tgcccccaag ctgaggagcc ttagactcca atacaaggga | 900 |
| ggaaggggaa gagcaagatt tttattccca ctgaataatg gcacctggac acagctgtgg | 960 |
| cttgtttctg actatcatga gcacgggtcc ctgtttgatt atctgaaccg gtacacagtg | 1020 |
| acaattgagg ggatgattaa gctggccttg tctgctgcta gtgggctggc acacctgcac | 1080 |
| atggagatcg tgggcaccca aggaagcct ggaattgctc atcgagactt aaagtcaaag | 1140 |
| aacattctgg tgaagaaaaa tggcatgtgt gccatagcag acctgggcct ggctgtccgt | 1200 |
| catgatgcag tcactgacac cattgacatt gccccgaatc agagggtggg gaccaaacga | 1260 |
| tacatggccc ctgaagtact tgatgaaacc attaatatga acactttga ctccttaaa | 1320 |

-continued

```
tgtgctgata tttatgccct cgggcttgta tattgggaga ttgctcgaag atgcaattct    1380
ggaggagtcc atgaagaata tcagctgcca tattacgact tagtgccctc tgacccttcc    1440
attgaggaaa tgcgaaaggt tgtatgtgat cagaagctgc gtcccaacat ccccaactgg    1500
tggcagagtt atgaggcact gcgggtgatg gggaagatga tgcgagagtg ttggtatgcc    1560
aacggcgcag cccgcctgac ggccctgcgc atcaagaaga ccctctccca gctcagcgtg    1620
caggaagacg tgaagatc                                                  1638
```

<210> SEQ ID NO 62
<211> LENGTH: 503
<212> TYPE: PRT
<213> ORGANISM: Homo sapiens

<400> SEQUENCE: 62

```
Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
    210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
305                 310                 315                 320
```

```
Val Gly Thr Gln Gly Lys Pro Ala Ile Ala His Arg Asp Leu Lys Ser
            325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
            370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
            405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
            435                 440                 445

Lys Leu Arg Pro Asn Ile Pro Asn Arg Trp Gln Ser Cys Glu Ala Leu
            450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
            485                 490                 495

Gln Gln Glu Gly Ile Lys Met
            500
```

<210> SEQ ID NO 63
<211> LENGTH: 1509
<212> TYPE: DNA
<213> ORGANISM: Homo sapiens

<400> SEQUENCE: 63

| | | | | | |
|---|---|---|---|---|---|
| atggaggcgg | cggtcgctgc | tccgcgtccc | cggctgctcc | tcctcgtgct | ggcggcggcg | 60 |
| gcggcggcgg | cggcggcgct | gctcccgggg | gcgacggcgt | acagtgtttt | ctgccacctc | 120 |
| tgtacaaaag | acaattttac | ttgtgtgaca | gatgggctct | gctttgtctc | tgtcacagag | 180 |
| accacagaca | agttatataca | caacagcatg | tgtatagctg | aaattgactt | aattcctcga | 240 |
| gataggccgt | ttgtatgtgc | accctcttca | aaaactgggt | ctgtgactac | aacatattgc | 300 |
| tgcaatcagg | accattgcaa | taaaatagaa | cttccaacta | ctgtaaagtc | atcacctggc | 360 |
| cttggtcctg | tggaactggc | agctgtcatt | gctggaccag | tgtgcttcgt | ctgcatctca | 420 |
| ctcatgttga | tggtctatat | ctgccacaac | cgcactgtca | ttcaccatcg | agtgccaaat | 480 |
| gaagaggacc | cttcattaga | tcgccctttt | atttcagagg | gtactacgtt | gaaagactta | 540 |
| atttatgata | tgacaacgtc | aggttctggc | tcaggtttac | cattgcttgt | tcagagaaca | 600 |
| attgcgagaa | ctattgtgtt | acaagaaagc | attggcaaag | gtcgatttgg | agaagtttgg | 660 |
| agaggaaagt | ggcgggggaga | agaagttgct | gttaagatat | tctcctctag | agaagaacgt | 720 |
| tcgtggttcc | gtgaggcaga | gatttatcaa | actgtaatgt | tacgtcatga | aaacatcctg | 780 |
| ggatttatag | cagcagacaa | taaagacaat | ggtacttgga | ctcagctctg | gttggtgtca | 840 |
| gattatcatg | agcatggatc | ccttttttgat | tacttaaaca | gatacacagt | tactgtggaa | 900 |
| ggaatgataa | aacttgctct | gtccacggcg | agcggtcttg | cccatcttca | catggagatt | 960 |
| gttggtaccc | aaggaaagcc | agccattgct | catagagatt | tgaaatcaaa | gaatatcttg | 1020 |

```
gtaaagaaga atggaacttg ctgtattgca gacttaggac tggcagtaag acatgattca    1080
gccacagata ccattgatat tgctccaaac cacagagtgg gaacaaaaag gtacatggcc    1140
cctgaagttc tcgatgattc cataaatatg aaacattttg aatccttcaa acgtgctgac    1200
atctatgcaa tgggcttagt attctgggaa attgctcgac gatgttccat tggtggaatt    1260
catgaagatt accaactgcc ttattatgat cttgtacctt ctgacccatc agttgaagaa    1320
atgagaaaag ttgtttgtga acagaagtta aggccaaata tcccaaacag atggcagagc    1380
tgtgaagcct tgagagtaat ggctaaaatt atgagagaat gttggtatgc caatggagca    1440
gctaggctta cagcattgcg gattaagaaa acattatcgc aactcagtca acaggaaggc    1500
atcaaaatg                                                            1509
```

<210> SEQ ID NO 64
<211> LENGTH: 102
<212> TYPE: PRT
<213> ORGANISM: Homo sapiens

<400> SEQUENCE: 64

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Leu Gly Pro Val Glu Leu
            100
```

<210> SEQ ID NO 65
<211> LENGTH: 306
<212> TYPE: DNA
<213> ORGANISM: Homo sapiens

<400> SEQUENCE: 65

```
gcggcgctgc tcccgggggc gacggcgtta cagtgtttct gccacctctg tacaaaagac    60 aatttttactt gtgtgacaga tgggctctgc tttgtctctg tcacagagac cacagacaaa   120
gttatacaca acagcatgtg tatagctgaa attgacttaa ttcctcgaga taggccgttt    180
gtatgtgcac cctcttcaaa aactgggtct gtgactacaa catattgctg caatcaggac    240
cattgcaata aaatagaact tccaactact gtaaagtcat cacctggcct tggtcctgtg    300
gaactg                                                                306
```

<210> SEQ ID NO 66
<211> LENGTH: 507
<212> TYPE: PRT
<213> ORGANISM: Homo sapiens

<400> SEQUENCE: 66

```
Met Glu Ala Ala Val Ala Ala Pro Arg Pro Arg Leu Leu Leu Leu Val
1               5                   10                  15

Leu Ala Ala Ala Ala Ala Ala Ala Ala Ala Leu Leu Pro Gly Ala Thr
```

```
                20                  25                  30
Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
 50                  55                  60

Val Ile His Asn Ser Met Cys Ile Ala Glu Ile Asp Leu Ile Pro Arg
 65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Pro Phe Ser Val Lys Ser Ser Pro Gly Leu Gly Pro Val
            115                 120                 125

Glu Leu Ala Ala Val Ile Ala Gly Pro Val Cys Phe Val Cys Ile Ser
            130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                165                 170                 175

Glu Gly Thr Thr Leu Lys Asp Leu Ile Tyr Asp Met Thr Thr Ser Gly
            180                 185                 190

Ser Gly Ser Gly Leu Pro Leu Leu Val Gln Arg Thr Ile Ala Arg Thr
            195                 200                 205

Ile Val Leu Gln Glu Ser Ile Gly Lys Gly Arg Phe Gly Glu Val Trp
            210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                245                 250                 255

Met Leu Arg His Glu Asn Ile Leu Gly Phe Ile Ala Ala Asp Asn Lys
            260                 265                 270

Asp Asn Gly Thr Trp Thr Gln Leu Trp Leu Val Ser Asp Tyr His Glu
            275                 280                 285

His Gly Ser Leu Phe Asp Tyr Leu Asn Arg Tyr Thr Val Thr Val Glu
            290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
            340                 345                 350

Ile Ala Asp Leu Gly Leu Ala Val Arg His Asp Ser Ala Thr Asp Thr
            355                 360                 365

Ile Asp Ile Ala Pro Asn His Arg Val Gly Thr Lys Arg Tyr Met Ala
            370                 375                 380

Pro Glu Val Leu Asp Asp Ser Ile Asn Met Lys His Phe Glu Ser Phe
385                 390                 395                 400

Lys Arg Ala Asp Ile Tyr Ala Met Gly Leu Val Phe Trp Glu Ile Ala
                405                 410                 415

Arg Arg Cys Ser Ile Gly Gly Ile His Glu Asp Tyr Gln Leu Pro Tyr
            420                 425                 430

Tyr Asp Leu Val Pro Ser Asp Pro Ser Val Glu Glu Met Arg Lys Val
            435                 440                 445
```

```
Val Cys Glu Gln Lys Leu Arg Pro Asn Ile Pro Asn Arg Trp Gln Ser
    450                 455                 460
Cys Glu Ala Leu Arg Val Met Ala Lys Ile Met Arg Glu Cys Trp Tyr
465                 470                 475                 480
Ala Asn Gly Ala Ala Arg Leu Thr Ala Leu Arg Ile Lys Lys Thr Leu
                485                 490                 495
Ser Gln Leu Ser Gln Gln Glu Gly Ile Lys Met
                500                 505
```

<210> SEQ ID NO 67
<211> LENGTH: 1521
<212> TYPE: DNA
<213> ORGANISM: Homo sapiens

<400> SEQUENCE: 67

```
atggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc     120
tgtacaaaag acaattttac ttgtgtgaca gatgggctct gctttgtctc tgtcacagag     180
accacagaca agttatacaa acagcatgtg tatagctgaa attgacttaa ttcctcga      240
gataggccgt tgtatgtgc accctcttca aaaactgggt ctgtgactac aacatattgc     300
tgcaatcagg accattgcaa taaaatagaa cttccaacta ctggcccttt ttcagtaaag     360
tcatcacctg gccttggtcc tgtggaactg gcagctgtca ttgctggacc agtgtgcttc     420
gtctgcatct cactcatgtt gatggtctat atctgccaca accgcactgt cattcaccat     480
cgagtgccaa atgaagagga cccttcatta gatcgcccct ttatttcaga gggtactacg     540
ttgaaagact taatttatga tatgacaacg tcaggttctg gctcaggttt accattgctt     600
gttcagagaa caattgcgag aactattgtg ttacaagaaa gcattggcaa aggtcgattt     660
ggagaagttt ggagaggaaa gtggcgggga agaagttg ctgttaagat attctcctct     720
agagaagaac gttcgtggtt ccgtgaggca gagatttatc aaactgtaat gttacgtcat     780
gaaaacatcc tggatttat agcagcagac aataaagaca atggtacttg gactcagctc     840
tggttggtgt cagattatca tgagcatgga tcccttttg attacttaaa cagatacaca     900
gttactgtgg aaggaatgat aaaacttgct ctgtccacgg cgagcggtct tgcccatctt     960
cacatggaga ttgttggtac ccaaggaaag ccagccattg ctcatagaga tttgaaatca    1020
aagaatatct tggtaaagaa gaatggaact tgctgtattg cagacttagg actggcagta    1080
agacatgatt cagccacaga taccattgat attgctccaa accacagtg gggaacaaaa    1140
aggtacatgg cccctgaagt tctcgatgat tccataaata tgaaacattt tgaatccttc    1200
aaacgtgctg acatctatgc aatgggctta gtattctggg aaattgctcg acgatgttcc    1260
attggtggaa ttcatgaaga ttaccaactg ccttattatg atcttgtacc ttctgaccca    1320
tcagttgaag aaatgagaaa agttgtttgt gaacagaagt taaggccaaa tatcccaaac    1380
agatggcaga gctgtgaagc cttgagagta atggctaaaa ttatgagaga atgttggtat    1440
gccaatggag cagctaggct tacagcattg cggattaaga aacattatc gcaactcagt    1500
caacaggaag gcatcaaaat g                                              1521
```

<210> SEQ ID NO 68
<211> LENGTH: 106
<212> TYPE: PRT
<213> ORGANISM: Homo sapiens

<400> SEQUENCE: 68

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Gly Pro Phe Ser Val Lys
                85                  90                  95

Ser Ser Pro Gly Leu Gly Pro Val Glu Leu
            100                 105

<210> SEQ ID NO 69
<211> LENGTH: 318
<212> TYPE: DNA
<213> ORGANISM: Homo sapiens

<400> SEQUENCE: 69
gcggcgctgc tcccgggggc gacggcgtta cagtgtttct gccacctctg tacaaaagac     60
aattttactt gtgtgacaga tgggctctgc tttgtctctg tcacagagac cacagacaaa    120
gttatacaca acagcatgtg tatagctgaa attgacttaa ttcctcgaga taggccgttt    180
gtatgtgcac cctcttcaaa aactgggtct gtgactacaa catattgctg caatcaggac    240
cattgcaata aaatagaact tccaactact ggcccttttt cagtaaagtc atcacctggc    300
cttggtcctg tggaactg                                                  318

<210> SEQ ID NO 70
<211> LENGTH: 493
<212> TYPE: PRT
<213> ORGANISM: Homo sapiens

<400> SEQUENCE: 70

Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Leu Ala Ile Ile Ile Thr Val Pro Val Cys Leu Leu Ser Ile Ala
        115                 120                 125

Ala Met Leu Thr Val Trp Ala Cys Gln Gly Arg Gln Cys Ser Tyr Arg
    130                 135                 140

Lys Lys Lys Arg Pro Asn Val Glu Glu Pro Leu Ser Glu Cys Asn Leu

```
                145                 150                 155                 160
Val Asn Ala Gly Lys Thr Leu Lys Asp Leu Ile Tyr Asp Val Thr Ala
                    165                 170                 175
Ser Gly Ser Gly Ser Gly Leu Pro Leu Leu Val Gln Arg Thr Ile Ala
                    180                 185                 190
Arg Thr Ile Val Leu Gln Glu Ile Val Gly Lys Gly Arg Phe Gly Glu
                    195                 200                 205
Val Trp His Gly Arg Trp Cys Gly Glu Asp Val Ala Val Lys Ile Phe
                    210                 215                 220
Ser Ser Arg Asp Glu Arg Ser Trp Phe Arg Glu Ala Glu Ile Tyr Gln
225                 230                 235                 240
Thr Val Met Leu Arg His Glu Asn Ile Leu Gly Phe Ile Ala Ala Asp
                    245                 250                 255
Asn Lys Asp Asn Gly Thr Trp Thr Gln Leu Trp Leu Val Ser Glu Tyr
                    260                 265                 270
His Glu Gln Gly Ser Leu Tyr Asp Tyr Leu Asn Arg Asn Ile Val Thr
                    275                 280                 285
Val Ala Gly Met Ile Lys Leu Ala Leu Ser Ile Ala Ser Gly Leu Ala
                    290                 295                 300
His Leu His Met Glu Ile Val Gly Thr Gln Gly Lys Pro Ala Ile Ala
305                 310                 315                 320
His Arg Asp Ile Lys Ser Lys Asn Ile Leu Val Lys Lys Cys Glu Thr
                    325                 330                 335
Cys Ala Ile Ala Asp Leu Gly Leu Ala Val Lys His Asp Ser Ile Leu
                    340                 345                 350
Asn Thr Ile Asp Ile Pro Gln Asn Pro Lys Val Gly Thr Lys Arg Tyr
                    355                 360                 365
Met Ala Pro Glu Met Leu Asp Asp Thr Met Asn Val Asn Ile Phe Glu
                    370                 375                 380
Ser Phe Lys Arg Ala Asp Ile Tyr Ser Val Gly Leu Val Tyr Trp Glu
385                 390                 395                 400
Ile Ala Arg Arg Cys Ser Val Gly Gly Ile Val Glu Glu Tyr Gln Leu
                    405                 410                 415
Pro Tyr Tyr Asp Met Val Pro Ser Asp Pro Ser Ile Glu Glu Met Arg
                    420                 425                 430
Lys Val Val Cys Asp Gln Lys Phe Arg Pro Ser Ile Pro Asn Gln Trp
                    435                 440                 445
Gln Ser Cys Glu Ala Leu Arg Val Met Gly Arg Ile Met Arg Glu Cys
                    450                 455                 460
Trp Tyr Ala Asn Gly Ala Ala Arg Leu Thr Ala Leu Arg Ile Lys Lys
465                 470                 475                 480
Thr Ile Ser Gln Leu Cys Val Lys Glu Asp Cys Lys Ala
                    485                 490

<210> SEQ ID NO 71
<211> LENGTH: 1479
<212> TYPE: DNA
<213> ORGANISM: Homo sapiens

<400> SEQUENCE: 71
atgacccggg cgctctgctc agcgctccgc caggctctcc tgctgctcgc agcggccgcc    60
gagctctcgc caggactgaa gtgtgtatgt cttttgtgtg attcttcaaa ctttacctgc   120
caaacagaag gagcatgttg gcatcagtc atgctaacca atggaaaaga gcaggtgatc   180
```

```
aaatcctgtg tctcccttcc agaactgaat gctcaagtct tctgtcatag ttccaacaat    240
gttaccaaaa ccgaatgctg cttcacagat ttttgcaaca acataacact gcaccttcca    300
acagcatcac caaatgcccc aaaacttgga cccatggagc tggccatcat tattactgtg    360
cctgtttgcc tcctgtccat agctgcgatg ctgacagtat gggcatgcca gggtcgacag    420
tgctcctaca ggaagaaaaa gagaccaaat gtggaggaac cactctctga gtgcaatctg    480
gtaaatgctg gaaaaactct gaaagatctg atttatgatg tgaccgcctc tggatctggc    540
tctggtctac ctctgttggt tcaaaggaca attgcaagga cgattgtgct tcaggaaata    600
gtaggaaaag gtagatttgg tgaggtgtgg catggaagat ggtgtgggga agatgtggct    660
gtgaaaatat tctcctccag agatgaaaga tcttggtttc gtgaggcaga aatttaccag    720
acggtcatgc tgcgacatga aacatccctt ggtttcattg ctgctgacaa caaagataat    780
ggaacttgga ctcaactttg ctggtatctg aatatcatg aacagggctc cttatatgac    840
tatttgaata gaaatatagt gaccgtggct ggaatgatca agctggcgct ctcaattgct    900
agtggtctgg cacaccttca tatggagatt gttggtacac aaggtaaacc tgctattgct    960
catcgagaca taaaatcaaa gaatatctta gtgaaaaagt gtgaaacttg tgccatagcg   1020
gacttaggggt tggctgtgaa gcatgattca atactgaaca ctatcgacat acctcagaat   1080
cctaaagtgg gaaccaagag gtatatggct cctgaaatgc ttgatgatac aatgaatgtg   1140
aatatctttg agtccttcaa acgagctgac atctattctg ttggtctggt ttactgggaa   1200
atagcccgga ggtgttcagt cggaggaatt gttgaggagt accaattgcc ttattatgac   1260
atggtgcctt cagatccctc gatagaggaa atgagaaagg ttgtttgtga ccagaagttt   1320
cgaccaagta tcccaaacca gtggcaaagt tgtgaagcac tccgagtcat ggggagaata   1380
atgcgtgagt gttggtatgc caacggagcg gcccgcctaa ctgctcttcg tattaagaag   1440
actatatctc aactttgtgt caaagaagac tgcaaagcc                          1479

<210> SEQ ID NO 72
<211> LENGTH: 93
<212> TYPE: PRT
<213> ORGANISM: Homo sapiens

<400> SEQUENCE: 72

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Val Thr Lys Thr
    50                  55                  60

Glu Cys Cys Phe Thr Asp Phe Cys Asn Asn Ile Thr Leu His Leu Pro
65                  70                  75                  80

Thr Ala Ser Pro Asn Ala Pro Lys Leu Gly Pro Met Glu
                85                  90

<210> SEQ ID NO 73
<211> LENGTH: 279
<212> TYPE: DNA
<213> ORGANISM: Homo sapiens

<400> SEQUENCE: 73
gagctctcgc caggactgaa gtgtgtatgt cttttgtgtg attcttcaaa ctttacctgc    60
```

```
caaacagaag gagcatgttg ggcatcagtc atgctaacca atggaaaaga gcaggtgatc    120
aaatcctgtg tctcccttcc agaactgaat gctcaagtct tctgtcatag ttccaacaat    180
gttaccaaaa ccgaatgctg cttcacagat ttttgcaaca acataacact gcaccttcca    240
acagcatcac caaatgcccc aaaacttgga cccatggag                           279
```

```
<210> SEQ ID NO 74
<211> LENGTH: 443
<212> TYPE: PRT
<213> ORGANISM: Homo sapiens

<400> SEQUENCE: 74
```

```
Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
            20                  25                  30

Lys Thr Glu Cys Cys Phe Thr Asp Phe Cys Asn Asn Ile Thr Leu His
        35                  40                  45

Leu Pro Thr Ala Ser Pro Asn Ala Pro Lys Leu Gly Pro Met Glu Leu
    50                  55                  60

Ala Ile Ile Ile Thr Val Pro Val Cys Leu Leu Ser Ile Ala Ala Met
65                  70                  75                  80

Leu Thr Val Trp Ala Cys Gln Gly Arg Gln Cys Ser Tyr Arg Lys Lys
                85                  90                  95

Lys Arg Pro Asn Val Glu Glu Pro Leu Ser Glu Cys Asn Leu Val Asn
            100                 105                 110

Ala Gly Lys Thr Leu Lys Asp Leu Ile Tyr Asp Val Thr Ala Ser Gly
        115                 120                 125

Ser Gly Ser Gly Leu Pro Leu Leu Val Gln Arg Thr Ile Ala Arg Thr
    130                 135                 140

Ile Val Leu Gln Glu Ile Val Gly Lys Gly Arg Phe Gly Glu Val Trp
145                 150                 155                 160

His Gly Arg Trp Cys Gly Glu Asp Val Ala Val Lys Ile Phe Ser Ser
                165                 170                 175

Arg Asp Glu Arg Ser Trp Phe Arg Glu Ala Glu Ile Tyr Gln Thr Val
            180                 185                 190

Met Leu Arg His Glu Asn Ile Leu Gly Phe Ile Ala Ala Asp Asn Lys
        195                 200                 205

Asp Asn Gly Thr Trp Thr Gln Leu Trp Leu Val Ser Glu Tyr His Glu
    210                 215                 220

Gln Gly Ser Leu Tyr Asp Tyr Leu Asn Arg Asn Ile Val Thr Val Ala
225                 230                 235                 240

Gly Met Ile Lys Leu Ala Leu Ser Ile Ala Ser Gly Leu Ala His Leu
                245                 250                 255

His Met Glu Ile Val Gly Thr Gln Gly Lys Pro Ala Ile Ala His Arg
            260                 265                 270

Asp Ile Lys Ser Lys Asn Ile Leu Val Lys Lys Cys Glu Thr Cys Ala
        275                 280                 285

Ile Ala Asp Leu Gly Leu Ala Val Lys His Asp Ser Ile Leu Asn Thr
    290                 295                 300

Ile Asp Ile Pro Gln Asn Pro Lys Val Gly Thr Lys Arg Tyr Met Ala
305                 310                 315                 320

Pro Glu Met Leu Asp Asp Thr Met Asn Val Asn Ile Phe Glu Ser Phe
                325                 330                 335
```

```
Lys Arg Ala Asp Ile Tyr Ser Val Gly Leu Val Tyr Trp Glu Ile Ala
                340                 345                 350
Arg Arg Cys Ser Val Gly Gly Ile Val Glu Glu Tyr Gln Leu Pro Tyr
            355                 360                 365
Tyr Asp Met Val Pro Ser Asp Pro Ser Ile Glu Met Arg Lys Val
370                 375                 380
Val Cys Asp Gln Lys Phe Arg Pro Ser Ile Pro Asn Gln Trp Gln Ser
385                 390                 395                 400
Cys Glu Ala Leu Arg Val Met Gly Arg Ile Met Arg Glu Cys Trp Tyr
                405                 410                 415
Ala Asn Gly Ala Ala Arg Leu Thr Ala Leu Arg Ile Lys Lys Thr Ile
            420                 425                 430
Ser Gln Leu Cys Val Lys Glu Asp Cys Lys Ala
            435                 440

<210> SEQ ID NO 75
<211> LENGTH: 1329
<212> TYPE: DNA
<213> ORGANISM: Homo sapiens

<400> SEQUENCE: 75
atgctaacca atggaaaaga gcaggtgatc aaatcctgtg tctcccttcc agaactgaat      60
gctcaagtct tctgtcatag ttccaacaat gttaccaaaa ccgaatgctg cttcacagat     120
ttttgcaaca acataacact gcaccttcca acagcatcac caaatgcccc aaaacttgga     180
cccatggagc tggccatcat tattactgtg cctgtttgcc tcctgtccat agctgcgatg     240
ctgacagtat gggcatgcca gggtcgacag tgctcctaca ggaagaaaaa gagaccaaat     300
gtggaggaac cactctctga gtgcaatctg gtaaatgctg aaaaactct gaaagatctg     360
atttatgatg tgaccgcctc tggatctggc tctggtctac ctctgttggt tcaaaggaca     420
attgcaagga cgattgtgct tcaggaaata gtaggaaaag gtagatttgg tgaggtgtgg     480
catggaagat ggtgtgggga agatgtggct gtgaaaatat tctcctccag agatgaaaga     540
tcttggtttc gtgaggcaga aatttaccag acggtcatgc tgcgacatga aaacatcctt     600
ggtttcattg ctgctgacaa caaagataat ggaacttgga ctcaactttg ctggtatct      660
gaatatcatg aacagggctc cttatatgac tatttgaata aaatatagt gaccgtggct     720
ggaatgatca agctggcgct ctcaattgct agtggtctgg cacaccttca tatggagatt     780
gttggtacac aagtaaaacc tgctattgct catcgagaca aaatcaaa gaatatctta     840
gtgaaaaagt gtgaaacttg tgccatagcg gacttagggt tggctgtgaa gcatgattca     900
atactgaaca ctatcgacat acctcagaat cctaaagtgg aaccaagag gtatatggct     960
cctgaaatgc ttgatgatac aatgaatgtg aatatctttg agtccttcaa acgagctgac    1020
atctattctg ttggtctggt ttactgggaa atagcccgga ggtgttcagt cggaggaatt    1080
gttgaggagt accaattgcc ttattatgac atggtgcctt cagatccctc gatagaggaa    1140
atgagaaagg ttgtttgtga ccagaagttt cgaccaagta tcccaaacca gtggcaaagt    1200
tgtgaagcac tccgagtcat ggggagaata atgcgtgagt gttggtatgc aacggagcg    1260
gcccgcctaa ctgctcttcg tattaagaag actatatctc aactttgtgt caagaagac    1320
tgcaaagcc                                                            1329

<210> SEQ ID NO 76
<211> LENGTH: 63
```

<212> TYPE: PRT
<213> ORGANISM: Homo sapiens

<400> SEQUENCE: 76

```
Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
            20                  25                  30

Lys Thr Glu Cys Cys Phe Thr Asp Phe Cys Asn Asn Ile Thr Leu His
        35                  40                  45

Leu Pro Thr Ala Ser Pro Asn Ala Pro Lys Leu Gly Pro Met Glu
    50                  55                  60
```

<210> SEQ ID NO 77
<211> LENGTH: 189
<212> TYPE: DNA
<213> ORGANISM: Homo sapiens

<400> SEQUENCE: 77

```
atgctaacca atggaaaaga gcaggtgatc aaatcctgtg tctcccttcc agaactgaat      60
gctcaagtct tctgtcatag ttccaacaat gttaccaaaa ccgaatgctg cttcacagat     120
ttttgcaaca acataacact gcaccttcca acagcatcac caaatgcccc aaaacttgga     180
cccatggag                                                             189
```

<210> SEQ ID NO 78
<211> LENGTH: 413
<212> TYPE: PRT
<213> ORGANISM: Homo sapiens

<400> SEQUENCE: 78

```
Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Gly Leu Pro Leu Leu Val Gln Arg Thr Ile Ala
            100                 105                 110

Arg Thr Ile Val Leu Gln Glu Ile Val Gly Lys Gly Arg Phe Gly Glu
        115                 120                 125

Val Trp His Gly Arg Trp Cys Gly Glu Asp Val Ala Val Lys Ile Phe
    130                 135                 140

Ser Ser Arg Asp Glu Arg Ser Trp Phe Arg Glu Ala Glu Ile Tyr Gln
145                 150                 155                 160

Thr Val Met Leu Arg His Glu Asn Ile Leu Gly Phe Ile Ala Ala Asp
                165                 170                 175

Asn Lys Asp Asn Gly Thr Trp Thr Gln Leu Trp Leu Val Ser Glu Tyr
            180                 185                 190

His Glu Gln Gly Ser Leu Tyr Asp Tyr Leu Asn Arg Asn Ile Val Thr
        195                 200                 205
```

Val Ala Gly Met Ile Lys Leu Ala Leu Ser Ile Ala Ser Gly Leu Ala
    210                 215                 220

His Leu His Met Glu Ile Val Gly Thr Gln Gly Lys Pro Ala Ile Ala
225                 230                 235                 240

His Arg Asp Ile Lys Ser Lys Asn Ile Leu Val Lys Lys Cys Glu Thr
                245                 250                 255

Cys Ala Ile Ala Asp Leu Gly Leu Ala Val Lys His Asp Ser Ile Leu
                260                 265                 270

Asn Thr Ile Asp Ile Pro Gln Asn Pro Lys Val Gly Thr Lys Arg Tyr
            275                 280                 285

Met Ala Pro Glu Met Leu Asp Asp Thr Met Asn Val Asn Ile Phe Glu
    290                 295                 300

Ser Phe Lys Arg Ala Asp Ile Tyr Ser Val Gly Leu Val Tyr Trp Glu
305                 310                 315                 320

Ile Ala Arg Arg Cys Ser Val Gly Gly Ile Val Glu Glu Tyr Gln Leu
                325                 330                 335

Pro Tyr Tyr Asp Met Val Pro Ser Asp Pro Ser Ile Glu Glu Met Arg
                340                 345                 350

Lys Val Val Cys Asp Gln Lys Phe Arg Pro Ser Ile Pro Asn Gln Trp
            355                 360                 365

Gln Ser Cys Glu Ala Leu Arg Val Met Gly Arg Ile Met Arg Glu Cys
    370                 375                 380

Trp Tyr Ala Asn Gly Ala Ala Arg Leu Thr Ala Leu Arg Ile Lys Lys
385                 390                 395                 400

Thr Ile Ser Gln Leu Cys Val Lys Glu Asp Cys Lys Ala
                405                 410

<210> SEQ ID NO 79
<211> LENGTH: 1239
<212> TYPE: DNA
<213> ORGANISM: Homo sapiens

<400> SEQUENCE: 79
atgacccggg cgctctgctc agcgctccgc caggctctcc tgctgctcgc agcggccgcc        60
gagctctcgc caggactgaa gtgtgtatgt cttttgtgtg attcttcaaa ctttacctgc       120
caaacagaag gagcatgttg gcatcagtc atgctaacca atggaaaaga gcaggtgatc        180
aaatcctgtg tctcccttcc agaactgaat gctcaagtct tctgtcatag ttccaacaat       240
gttaccaaaa ccgaatgctg cttcacagat ttttgcaaca acataacact gcaccttcca       300
acaggtctac ctctgttggt tcaaaggaca attgcaagga cgattgtgct tcaggaaata       360
gtaggaaaag gtagatttgg tgaggtgtgg catggaagat ggtgtgggga agatgtggct       420
gtgaaaatat tctcctccag agatgaaaga tcttggtttc gtgaggcaga aatttaccag       480
acggtcatgc tgcgacatga aaacatcctt ggtttcattg ctgctgacaa caaagataat       540
ggaacttgga ctcaactttg gctggtatct gaatatcatg aacagggctc cttatatgac       600
tatttgaata gaaatatagt gaccgtggct ggaatgatca agctggcgct ctcaattgct       660
agtggtctgg cacaccttca tatggagatt gttggtacac aagtaaaacc tgctattgct       720
catcgagaca taaatcaaa gaatatctta gtgaaaaagt gtgaaacttg tgccatagcg       780
gacttagggt tggctgtgaa gcatgattca atactgaaca ctatcgacat acctcagaat       840
cctaaagtgg gaaccaagag gtatatggct cctgaaatgc ttgatgatac aatgaatgtg       900
aatatctttg agtccttcaa acgagctgac atctattctg ttggtctggt ttactgggaa       960

```
atagcccgga ggtgttcagt cggaggaatt gttgaggagt accaattgcc ttattatgac    1020
atggtgcctt cagatccctc gatagaggaa atgagaaagg ttgtttgtga ccagaagttt    1080
cgaccaagta tcccaaacca gtggcaaagt tgtgaagcac tccgagtcat ggggagaata    1140
atgcgtgagt gttggtatgc caacggagcg gcccgcctaa ctgctcttcg tattaagaag    1200
actatatctc aactttgtgt caaagaagac tgcaaagcc                            1239
```

<210> SEQ ID NO 80
<211> LENGTH: 393
<212> TYPE: PRT
<213> ORGANISM: Homo sapiens

<400> SEQUENCE: 80

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Gly Leu Pro Leu Leu Val Gln Arg Thr Ile Ala Arg Thr Ile Val
                85                  90                  95

Leu Gln Glu Ile Val Gly Lys Gly Arg Phe Gly Glu Val Trp His Gly
            100                 105                 110

Arg Trp Cys Gly Glu Asp Val Ala Val Lys Ile Phe Ser Ser Arg Asp
        115                 120                 125

Glu Arg Ser Trp Phe Arg Glu Ala Glu Ile Tyr Gln Thr Val Met Leu
    130                 135                 140

Arg His Glu Asn Ile Leu Gly Phe Ile Ala Ala Asp Asn Lys Asp Asn
145                 150                 155                 160

Gly Thr Trp Thr Gln Leu Trp Leu Val Ser Glu Tyr His Glu Gln Gly
                165                 170                 175

Ser Leu Tyr Asp Tyr Leu Asn Arg Asn Ile Val Thr Val Ala Gly Met
            180                 185                 190

Ile Lys Leu Ala Leu Ser Ile Ala Ser Gly Leu Ala His Leu His Met
        195                 200                 205

Glu Ile Val Gly Thr Gln Gly Lys Pro Ala Ile Ala His Arg Asp Ile
    210                 215                 220

Lys Ser Lys Asn Ile Leu Val Lys Lys Cys Glu Thr Cys Ala Ile Ala
225                 230                 235                 240

Asp Leu Gly Leu Ala Val Lys His Asp Ser Ile Leu Asn Thr Ile Asp
                245                 250                 255

Ile Pro Gln Asn Pro Lys Val Gly Thr Lys Arg Tyr Met Ala Pro Glu
            260                 265                 270

Met Leu Asp Asp Thr Met Asn Val Asn Ile Phe Glu Ser Phe Lys Arg
        275                 280                 285

Ala Asp Ile Tyr Ser Val Gly Leu Val Tyr Trp Glu Ile Ala Arg Arg
    290                 295                 300

Cys Ser Val Gly Gly Ile Val Glu Glu Tyr Gln Leu Pro Tyr Tyr Asp
305                 310                 315                 320

Met Val Pro Ser Asp Pro Ser Ile Glu Glu Met Arg Lys Val Cys
            325                 330                 335

Asp Gln Lys Phe Arg Pro Ser Ile Pro Asn Gln Trp Gln Ser Cys Glu
        340                 345                 350

Ala Leu Arg Val Met Gly Arg Ile Met Arg Glu Cys Trp Tyr Ala Asn
    355                 360                 365

Gly Ala Ala Arg Leu Thr Ala Leu Arg Ile Lys Lys Thr Ile Ser Gln
370                 375                 380

Leu Cys Val Lys Glu Asp Cys Lys Ala
385                 390

<210> SEQ ID NO 81
<211> LENGTH: 1179
<212> TYPE: DNA
<213> ORGANISM: Homo sapiens

<400> SEQUENCE: 81

| | | | | | |
|---|---|---|---|---|---|
| gagctctcgc | caggactgaa | gtgtgtatgt | cttttgtgtg | attcttcaaa | ctttacctgc | 60 |
| caaacagaag | gagcatgttg | ggcatcagtc | atgctaacca | atggaaaaga | gcaggtgatc | 120 |
| aaatcctgtg | tctcccttcc | agaactgaat | gctcaagtct | tctgtcatag | ttccaacaat | 180 |
| gttaccaaaa | ccgaatgctg | cttcacagat | ttttgcaaca | cataacact | gcaccttcca | 240 |
| acaggtctac | ctctgttggt | tcaaaggaca | attgcaagga | cgattgtgct | tcaggaaata | 300 |
| gtaggaaaag | gtagatttgg | tgaggtgtgg | catggaagat | ggtgtgggga | agatgtggct | 360 |
| gtgaaaatat | tctcctccag | agatgaaaga | tcttggtttc | gtgaggcaga | aatttaccag | 420 |
| acggtcatgc | tgcgacatga | aacatccttg | gtttcattg | ctgctgacaa | caaagataat | 480 |
| ggaacttgga | ctcaactttg | gctggtatct | gaatatcatg | aacagggctc | cttatatgac | 540 |
| tatttgaata | gaaatatagt | gaccgtggct | ggaatgatca | agctggcgct | ctcaattgct | 600 |
| agtggtctgg | cacaccttca | tatggagatt | gttggtacac | aagtaaaacc | tgctattgct | 660 |
| catcgagaca | taaaatcaaa | gaatatctta | gtgaaaaagt | gtgaaacttg | tgccatagcg | 720 |
| gacttagggt | tggctgtgaa | gcatgattca | atactgaaca | ctatcgacat | acctcagaat | 780 |
| cctaaagtgg | gaaccaagag | gtatatggct | cctgaaatgc | ttgatgatac | aatgaatgtg | 840 |
| aatatctttg | agtccttcaa | acgagctgac | atctattctg | ttggtctggt | ttactgggaa | 900 |
| atagcccgga | ggtgttcagt | cggaggaatt | gttgaggagt | accaattgcc | ttattatgac | 960 |
| atggtgcctt | cagatccctc | gatagaggaa | atgagaaagg | ttgtttgtga | ccagaagttt | 1020 |
| cgaccaagta | tcccaaacca | gtggcaaagt | tgtgaagcac | tccgagtcat | ggggagaata | 1080 |
| atgcgtgagt | gttggtatgc | caacggagcg | gcccgcctaa | ctgctcttcg | tattaagaag | 1140 |
| actatatctc | aactttgtgt | caaagaagac | tgcaaagcc | | | 1179 |

<210> SEQ ID NO 82
<211> LENGTH: 336
<212> TYPE: PRT
<213> ORGANISM: Homo sapiens

<400> SEQUENCE: 82

Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

```
Ser Val Met Leu Thr Asn Gly Lys Glu Gln Val Ile Lys Ser Cys Val
 50                  55                  60

Ser Leu Pro Glu Leu Asn Ala Gln Val Phe Cys His Ser Ser Asn Asn
 65                  70                  75                  80

Val Thr Lys Thr Glu Cys Cys Phe Thr Asp Phe Cys Asn Asn Ile Thr
                 85                  90                  95

Leu His Leu Pro Thr Asp Asn Gly Thr Trp Thr Gln Leu Trp Leu Val
                100                 105                 110

Ser Glu Tyr His Glu Gln Gly Ser Leu Tyr Asp Tyr Leu Asn Arg Asn
                115                 120                 125

Ile Val Thr Val Ala Gly Met Ile Lys Leu Ala Leu Ser Ile Ala Ser
130                 135                 140

Gly Leu Ala His Leu His Met Glu Ile Val Gly Thr Gln Gly Lys Pro
145                 150                 155                 160

Ala Ile Ala His Arg Asp Ile Lys Ser Lys Asn Ile Leu Val Lys Lys
                165                 170                 175

Cys Glu Thr Cys Ala Ile Ala Asp Leu Gly Leu Ala Val Lys His Asp
                180                 185                 190

Ser Ile Leu Asn Thr Ile Asp Ile Pro Gln Asn Pro Lys Val Gly Thr
                195                 200                 205

Lys Arg Tyr Met Ala Pro Glu Met Leu Asp Asp Thr Met Asn Val Asn
210                 215                 220

Ile Phe Glu Ser Phe Lys Arg Ala Asp Ile Tyr Ser Val Gly Leu Val
225                 230                 235                 240

Tyr Trp Glu Ile Ala Arg Arg Cys Ser Val Gly Gly Ile Val Glu Glu
                245                 250                 255

Tyr Gln Leu Pro Tyr Tyr Asp Met Val Pro Ser Asp Pro Ser Ile Glu
                260                 265                 270

Glu Met Arg Lys Val Val Cys Asp Gln Lys Phe Arg Pro Ser Ile Pro
                275                 280                 285

Asn Gln Trp Gln Ser Cys Glu Ala Leu Arg Val Met Gly Arg Ile Met
                290                 295                 300

Arg Glu Cys Trp Tyr Ala Asn Gly Ala Ala Arg Leu Thr Ala Leu Arg
305                 310                 315                 320

Ile Lys Lys Thr Ile Ser Gln Leu Cys Val Lys Glu Asp Cys Lys Ala
                325                 330                 335

<210> SEQ ID NO 83
<211> LENGTH: 1011
<212> TYPE: DNA
<213> ORGANISM: Homo sapiens

<400> SEQUENCE: 83
atgacccggg cgctctgctc agcgctccgc caggctctcc tgctgctcgc agcggccgcc    60
gagctctcgc caggactgaa gtgtgtatgt cttttgtgtg attcttcaaa ctttacctgc   120
caaacagaag gagcatgttg ggcatcagtc atgctaacca atggaaaaga gcaggtgatc   180
aaatcctgtg tctcccttcc agaactgaat gctcaagtct tctgtcatag ttccaacaat   240
gttaccaaaa ccgaatgctg cttcacagat ttttgcaaca cataacact gcaccttcca   300 acagataatg gaacttggac tcaactttgg ctggtatctg aatatcatga cagggctcc   360 ttatatgact atttgaatag aaatatagtg accgtggctg gaatgatcaa gctggcgctc   420
tcaattgcta gtggtctggc acaccttcat atggagattg ttggtacaca aggtaaacct   480
```

-continued

```
gctattgctc atcgagacat aaaatcaaag aatatcttag tgaaaagtg tgaaacttgt    540 gccatagcgg acttagggtt ggctgtgaag catgattcaa tactgaacac tatcgacata    600
cctcagaatc ctaaagtggg aaccaagagg tatatggctc ctgaaatgct tgatgataca    660
atgaatgtga atatctttga gtccttcaaa cgagctgaca tctattctgt tggtctggtt    720
tactgggaaa tagcccggag gtgttcagtc ggaggaattg ttgaggagta ccaattgcct    780
tattatgaca tggtgccttc agatccctcg atagaggaaa tgagaaaggt tgtttgtgac    840
cagaagtttc gaccaagtat cccaaaccag tggcaaagtt gtgaagcact ccgagtcatg    900
gggagaataa tgcgtgagtg ttggtatgcc aacggagcgg cccgcctaac tgctcttcgt    960
attaagaaga ctatatctca actttgtgtc aaagaagact gcaaagccta a            1011
```

<210> SEQ ID NO 84
<211> LENGTH: 316
<212> TYPE: PRT
<213> ORGANISM: Homo sapiens

<400> SEQUENCE: 84

```
Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Asp Asn Gly Thr Trp Thr Gln Leu Trp Leu Val Ser Glu Tyr His
                85                  90                  95

Glu Gln Gly Ser Leu Tyr Asp Tyr Leu Asn Arg Asn Ile Val Thr Val
            100                 105                 110

Ala Gly Met Ile Lys Leu Ala Leu Ser Ile Ala Ser Gly Leu Ala His
        115                 120                 125

Leu His Met Glu Ile Val Gly Thr Gln Gly Lys Pro Ala Ile Ala His
    130                 135                 140

Arg Asp Ile Lys Ser Lys Asn Ile Leu Val Lys Lys Cys Glu Thr Cys
145                 150                 155                 160

Ala Ile Ala Asp Leu Gly Leu Ala Val Lys His Asp Ser Ile Leu Asn
                165                 170                 175

Thr Ile Asp Ile Pro Gln Asn Pro Lys Val Gly Thr Lys Arg Tyr Met
            180                 185                 190

Ala Pro Glu Met Leu Asp Asp Thr Met Asn Val Asn Ile Phe Glu Ser
        195                 200                 205

Phe Lys Arg Ala Asp Ile Tyr Ser Val Gly Leu Val Tyr Trp Glu Ile
    210                 215                 220

Ala Arg Arg Cys Ser Val Gly Gly Ile Val Glu Glu Tyr Gln Leu Pro
225                 230                 235                 240

Tyr Tyr Asp Met Val Pro Ser Asp Pro Ser Ile Glu Glu Met Arg Lys
                245                 250                 255

Val Val Cys Asp Gln Lys Phe Arg Pro Ser Ile Pro Asn Gln Trp Gln
            260                 265                 270

Ser Cys Glu Ala Leu Arg Val Met Gly Arg Ile Met Arg Glu Cys Trp
        275                 280                 285
```

Tyr Ala Asn Gly Ala Ala Arg Leu Thr Ala Leu Arg Ile Lys Lys Thr
            290                 295                 300

Ile Ser Gln Leu Cys Val Lys Glu Asp Cys Lys Ala
305                 310                 315

<210> SEQ ID NO 85
<211> LENGTH: 951
<212> TYPE: DNA
<213> ORGANISM: Homo sapiens

<400> SEQUENCE: 85

| | | | | | |
|---|---|---|---|---|---|
| gagctctcgc | caggactgaa | gtgtgtatgt | cttttgtgtg | attcttcaaa | ctttacctgc | 60 |
| caaacagaag | gagcatgttg | ggcatcagtc | atgctaacca | atggaaaaga | gcaggtgatc | 120 |
| aaatcctgtg | tctcccttcc | agaactgaat | gctcaagtct | tctgtcatag | ttccaacaat | 180 |
| gttaccaaaa | ccgaatgctg | cttcacagat | ttttgcaaca | acataacact | gcaccttcca | 240 |
| acagataatg | gaacttggac | tcaactttgg | ctggtatctg | aatatcatga | acagggctcc | 300 |
| ttatatgact | atttgaatag | aaatatagtg | accgtggctg | gaatgatcaa | gctggcgctc | 360 |
| tcaattgcta | gtggtctggc | acaccttcat | atggagattt | ttggtacaca | aggtaaacct | 420 |
| gctattgctc | atcgagacat | aaaatcaaag | aatatcttag | tgaaaagtg | tgaaacttgt | 480 |
| gccatagcgg | acttagggtt | ggctgtgaag | catgattcaa | tactgaacac | tatcgacata | 540 |
| cctcagaatc | ctaaagtggg | aaccaagagg | tatatggctc | ctgaaatgct | tgatgataca | 600 |
| atgaatgtga | atatctttga | gtccttcaaa | cgagctgaca | tctattctgt | tggtctggtt | 660 |
| tactgggaaa | tagcccggag | gtgttcagtc | ggaggaattg | ttgaggagta | ccaattgcct | 720 |
| tattatgaca | tggtgccttc | agatccctcg | atagaggaaa | tgagaaaggt | tgtttgtgac | 780 |
| cagaagtttc | gaccaagtat | cccaaaccag | tggcaaagtt | gtgaagcact | ccgagtcatg | 840 |
| gggagaataa | tgcgtgagtg | ttggtatgcc | aacggagcgg | cccgcctaac | tgctcttcgt | 900 |
| attaagaaga | ctatatctca | actttgtgtc | aaagaagact | gcaaagccta | a | 951 |

<210> SEQ ID NO 86
<211> LENGTH: 88
<212> TYPE: PRT
<213> ORGANISM: Homo sapiens

<400> SEQUENCE: 86

Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro Thr Ala Ser Pro Asn
65                  70                  75                  80

Ala Pro Lys Leu Gly Pro Met Glu
                85

<210> SEQ ID NO 87
<211> LENGTH: 188
<212> TYPE: PRT
<213> ORGANISM: Homo sapiens

<400> SEQUENCE: 87

Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185

<210> SEQ ID NO 88
<211> LENGTH: 564
<212> TYPE: DNA
<213> ORGANISM: Homo sapiens

<400> SEQUENCE: 88
atggactgca ggaagatggc ccgcttctct tacagtgtga tttggatcat ggccatttct     60
aaagtctttg aactgggatt agttgccggg ctgggccatc aggaatttgc tcgtccatct    120
cggggatacc tggccttcag agatgacagc atttggcccc aggaggagcc tgcaattcgg    180
cctcggtctt cccagcgtgt gccgcccatg gggatacagc acagtaagga gctaaacaga    240
acctgctgcc tgaatggggg aacctgcatg ctggggtcct tttgtgcctg ccctcccctcc    300 ttctacggac ggaactgtga gcacgatgtg cgcaaagaga actgtgggtc tgtgccccat    360
gacacctggc tgcccaagaa gtgttccctg tgtaaatgct ggcacggtca gctccgctgc    420
tttcctcagg catttctacc cggctgtgat ggccttgtga tggatgagca cctcgtggct    480
tccaggactc cagaactacc accgtctgca cgtactacca cttttatgct agttggcatc    540
tgcctttcta tacaaagcta ctat                                           564

<210> SEQ ID NO 89
<211> LENGTH: 131
<212> TYPE: PRT
<213> ORGANISM: Homo sapiens

<400> SEQUENCE: 89

Leu Gly His Gln Glu Phe Ala Arg Pro Ser Arg Gly Tyr Leu Ala Phe
1               5                   10                  15

Arg Asp Asp Ser Ile Trp Pro Gln Glu Glu Pro Ala Ile Arg Pro Arg
            20                  25                  30

Ser Ser Gln Arg Val Pro Pro Met Gly Ile Gln His Ser Lys Glu Leu
        35                  40                  45

Asn Arg Thr Cys Cys Leu Asn Gly Gly Thr Cys Met Leu Gly Ser Phe
 50                  55                  60

Cys Ala Cys Pro Pro Ser Phe Tyr Gly Arg Asn Cys Glu His Asp Val
 65                  70                  75                  80

Arg Lys Glu Asn Cys Gly Ser Val Pro His Asp Thr Trp Leu Pro Lys
                 85                  90                  95

Lys Cys Ser Leu Cys Lys Cys Trp His Gly Gln Leu Arg Cys Phe Pro
                100                 105                 110

Gln Ala Phe Leu Pro Gly Cys Asp Gly Leu Val Met Asp Glu His Leu
            115                 120                 125

Val Ala Ser
    130

<210> SEQ ID NO 90
<211> LENGTH: 393
<212> TYPE: DNA
<213> ORGANISM: Homo sapiens

<400> SEQUENCE: 90
ctgggccatc aggaatttgc tcgtccatct cggggatacc tggccttcag agatgacagc    60
atttggcccc aggaggagcc tgcaattcgg cctcggtctt cccagcgtgt gccgcccatg   120
gggatacagc acagtaagga gctaaacaga acctgctgcc tgaatggggg aacctgcatg   180
ctggggtcct ttgtgcctg ccctccctcc ttctacggac ggaactgtga gcacgatgtg   240
cgcaaagaga actgtgggtc tgtgccccat gacacctggc tgcccaagaa gtgttccctg   300
tgtaaatgct ggcacggtca gctccgctgc tttcctcagg catttctacc cggctgtgat   360
ggccttgtga tggatgagca cctcgtggct tcc                                393

<210> SEQ ID NO 91
<211> LENGTH: 172
<212> TYPE: PRT
<213> ORGANISM: Homo sapiens

<400> SEQUENCE: 91

Met Ala Ile Ser Lys Val Phe Glu Leu Gly Leu Val Ala Gly Leu Gly
 1               5                  10                  15

His Gln Glu Phe Ala Arg Pro Ser Arg Gly Tyr Leu Ala Phe Arg Asp
            20                  25                  30

Asp Ser Ile Trp Pro Gln Glu Pro Ala Ile Arg Pro Arg Ser Ser
        35                  40                  45

Gln Arg Val Pro Pro Met Gly Ile Gln His Ser Lys Glu Leu Asn Arg
 50                  55                  60

Thr Cys Cys Leu Asn Gly Gly Thr Cys Met Leu Gly Ser Phe Cys Ala
 65                  70                  75                  80

Cys Pro Pro Ser Phe Tyr Gly Arg Asn Cys Glu His Asp Val Arg Lys
                 85                  90                  95

Glu Asn Cys Gly Ser Val Pro His Asp Thr Trp Leu Pro Lys Lys Cys
            100                 105                 110

Ser Leu Cys Lys Cys Trp His Gly Gln Leu Arg Cys Phe Pro Gln Ala
        115                 120                 125

Phe Leu Pro Gly Cys Asp Gly Leu Val Met Asp Glu His Leu Val Ala
    130                 135                 140

Ser Arg Thr Pro Glu Leu Pro Pro Ser Ala Arg Thr Thr Thr Phe Met
145                 150                 155                 160

Leu Val Gly Ile Cys Leu Ser Ile Gln Ser Tyr Tyr
                165                 170

<210> SEQ ID NO 92
<211> LENGTH: 516
<212> TYPE: DNA
<213> ORGANISM: Homo sapiens

<400> SEQUENCE: 92
atggccattt ctaaagtctt tgaactggga ttagttgccg ggctgggcca tcaggaattt      60
gctcgtccat ctcggggata cctggccttc agagatgaca gcatttggcc ccaggaggag     120
cctgcaattc ggcctcggtc ttcccagcgt gtgccgccca tggggataca gcacagtaag     180
gagctaaaca gaacctgctg cctgaatggg ggaacctgca tgctggggtc cttttgtgcc     240
tgccctccct ccttctacgg acggaactgt gagcacgatg tgcgcaaaga aactgtgggg     300
tctgtgcccc atgacacctg ctgcccaag aagtgttccc tgtgtaaatg ctggcacggt     360
cagctccgct gctttcctca ggcatttcta cccggctgtg atggccttgt gatggatgag     420
cacctcgtgg cttccaggac tccagaacta ccaccgtctg cacgtactac cactttatg     480 ctagttggca tctgcctttc tatacaaagc tactat                                 516

<210> SEQ ID NO 93
<211> LENGTH: 145
<212> TYPE: PRT
<213> ORGANISM: Homo sapiens

<400> SEQUENCE: 93

Met Ala Ile Ser Lys Val Phe Glu Leu Gly Leu Val Ala Gly Leu Gly
1               5                   10                  15

His Gln Glu Phe Ala Arg Pro Ser Arg Gly Tyr Leu Ala Phe Arg Asp
            20                  25                  30

Asp Ser Ile Trp Pro Gln Glu Pro Ala Ile Arg Pro Arg Ser Ser
        35                  40                  45

Gln Arg Val Pro Pro Met Gly Ile Gln His Ser Lys Glu Leu Asn Arg
    50                  55                  60

Thr Cys Cys Leu Asn Gly Gly Thr Cys Met Leu Gly Ser Phe Cys Ala
65                  70                  75                  80

Cys Pro Pro Ser Phe Tyr Gly Arg Asn Cys Glu His Asp Val Arg Lys
                85                  90                  95

Glu Asn Cys Gly Ser Val Pro His Asp Thr Trp Leu Pro Lys Lys Cys
            100                 105                 110

Ser Leu Cys Lys Cys Trp His Gly Gln Leu Arg Cys Phe Pro Gln Ala
        115                 120                 125

Phe Leu Pro Gly Cys Asp Gly Leu Val Met Asp Glu His Leu Val Ala
    130                 135                 140

Ser
145

<210> SEQ ID NO 94
<211> LENGTH: 435
<212> TYPE: DNA
<213> ORGANISM: Homo sapiens

<400> SEQUENCE: 94
atggccattt ctaaagtctt tgaactggga ttagttgccg ggctgggcca tcaggaattt      60

```
gctcgtccat ctcggggata cctggccttc agagatgaca gcatttggcc ccaggaggag    120
cctgcaattc ggcctcggtc ttcccagcgt gtgccgccca tggggataca gcacagtaag    180
gagctaaaca gaacctgctg cctgaatggg ggaacctgca tgctggggtc cttttgtgcc    240
tgccctccct ccttctacgg acggaactgt gagcacgatg tgcgcaaaga aactgtgggg    300
tctgtgcccc atgacacctg gctgcccaag aagtgttccc tgtgtaaatg ctggcacggt    360
cagctccgct gctttcctca ggcatttcta cccggctgtg atggccttgt gatggatgag    420
cacctcgtgg cttcc                                                     435
```

```
<210> SEQ ID NO 95
<211> LENGTH: 223
<212> TYPE: PRT
<213> ORGANISM: Homo sapiens

<400> SEQUENCE: 95
```

Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
            20                  25                  30

Gly Gly Arg Glu Glu Val Thr Lys Val Ala Thr Gln Lys His Arg Gln
        35                  40                  45

Ser Pro Leu Asn Trp Thr Ser Ser His Phe Gly Glu Val Thr Gly Ser
    50                  55                  60

Ala Glu Gly Trp Gly Pro Glu Pro Leu Pro Tyr Ser Arg Ala Phe
65                  70                  75                  80

Gly Glu Gly Ala Ser Ala Arg Pro Arg Cys Cys Arg Asn Gly Gly Thr
                85                  90                  95

Cys Val Leu Gly Ser Phe Cys Val Cys Pro Ala His Phe Thr Gly Arg
            100                 105                 110

Tyr Cys Glu His Asp Gln Arg Arg Ser Glu Cys Gly Ala Leu Glu His
        115                 120                 125

Gly Ala Trp Thr Leu Arg Ala Cys His Leu Cys Arg Cys Ile Phe Gly
    130                 135                 140

Ala Leu His Cys Leu Pro Leu Gln Thr Pro Asp Arg Cys Asp Pro Lys
145                 150                 155                 160

Asp Phe Leu Ala Ser His Ala His Gly Pro Ser Ala Gly Gly Ala Pro
                165                 170                 175

Ser Leu Leu Leu Leu Pro Cys Ala Leu Leu His Arg Leu Leu Arg
            180                 185                 190

Pro Asp Ala Pro Ala His Pro Arg Ser Leu Val Pro Ser Val Leu Gln
        195                 200                 205

Arg Glu Arg Arg Pro Cys Gly Arg Pro Gly Leu Gly His Arg Leu
    210                 215                 220

```
<210> SEQ ID NO 96
<211> LENGTH: 669
<212> TYPE: DNA
<213> ORGANISM: Homo sapiens

<400> SEQUENCE: 96
atgacctgga ggcaccatgt caggcttctg tttacggtca gtttggcatt acagatcatc     60
aatttgggaa acagctatca agagagaaa cataacggcg gtagagagga agtcaccaag    120
gttgccactc agaagcaccg acagtcaccg ctcaactgga cctccagtca tttcggagag    180
```

-continued

```
gtgactggga gcgccgaggg ctgggggccg gaggagccgc tcccctactc ccgggctttc    240
ggagagggtg cgtccgcgcg gccgcgctgc tgcaggaacg gcggtacctg cgtgctgggc    300
agcttctgcg tgtgcccggc ccacttcacc ggccgctact gcgagcatga ccagaggcgc    360
agtgaatgcg gcgccctgga gcacggagcc tggaccctcc gcgcctgcca cctctgcagg    420
tgcatcttcg gggccctgca ctgcctcccc ctccagacgc ctgaccgctg tgacccgaaa    480
gacttcctgg cctcccacgc tcacgggccg agcgccgggg gcgcgcccag cctgctactc    540
ttgctgccct gcgcactcct gcaccgcctc ctgcgcccgg atgcgcccgc gcaccctcgg    600
tccctggtcc cttccgtcct ccagcgggag cggcgcccct gcggaaggcc gggacttggg    660
catcgcctt                                                             669
```

<210> SEQ ID NO 97
<211> LENGTH: 144
<212> TYPE: PRT
<213> ORGANISM: Homo sapiens
<400> SEQUENCE: 97

```
Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
                20                  25                  30

Phe Gly Glu Val Thr Gly Ser Ala Glu Gly Trp Gly Pro Glu Glu Pro
        35                  40                  45

Leu Pro Tyr Ser Arg Ala Phe Gly Gly Ala Ser Ala Arg Pro Arg
    50                  55                  60

Cys Cys Arg Asn Gly Gly Thr Cys Val Leu Gly Ser Phe Cys Val Cys
65                  70                  75                  80

Pro Ala His Phe Thr Gly Arg Tyr Cys Glu His Asp Gln Arg Arg Ser
                85                  90                  95

Glu Cys Gly Ala Leu Glu His Gly Ala Trp Thr Leu Arg Ala Cys His
            100                 105                 110

Leu Cys Arg Cys Ile Phe Gly Ala Leu His Cys Leu Pro Leu Gln Thr
        115                 120                 125

Pro Asp Arg Cys Asp Pro Lys Asp Phe Leu Ala Ser His Ala His Gly
    130                 135                 140
```

<210> SEQ ID NO 98
<211> LENGTH: 432
<212> TYPE: DNA
<213> ORGANISM: Homo sapiens
<400> SEQUENCE: 98

```
tatcaaagag agaaacataa cggcggtaga gaggaagtca ccaaggttgc cactcagaag     60
caccgacagt caccgctcaa ctggacctcc agtcatttcg agaggtgac tgggagcgcc    120 gagggctggg gccggagga ccgctcccc tactcccggg ctttcggaga gggtgcgtcc    180
gcgcggccgc gctgctgcag gaacggcggt acctgcgtgc tgggcagctt ctgcgtgtgc    240
ccggcccact tcaccggccg ctactgcgag catgaccaga ggcgcagtga atgcggcgcc    300
ctggagcacg gagcctggac cctccgcgcc tgccacctct gcaggtgcat cttcggggcc    360
ctgcactgcc tccccctcca gacgcctgac cgctgtgacc cgaaagactt cctggcctcc    420
cacgctcacg gg                                                        432
```

<210> SEQ ID NO 99

<211> LENGTH: 191
<212> TYPE: PRT
<213> ORGANISM: Homo sapiens

<400> SEQUENCE: 99

```
Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
            20                  25                  30

Gly Gly Arg Glu Glu Val Thr Lys Val Ala Thr Gln Lys His Arg Gln
        35                  40                  45

Ser Pro Leu Asn Trp Thr Ser His Phe Gly Glu Val Thr Gly Ser
    50                  55                  60

Ala Glu Gly Trp Gly Pro Glu Pro Leu Pro Tyr Ser Arg Ala Phe
65              70                  75                  80

Gly Glu Val Asn Ala Ala Pro Trp Ser Thr Glu Pro Gly Pro Ser Ala
                85                  90                  95

Pro Ala Thr Ser Ala Gly Ala Ser Ser Gly Pro Cys Thr Ala Ser Pro
            100                 105                 110

Ser Arg Arg Leu Thr Ala Val Thr Arg Lys Thr Ser Trp Pro Pro Thr
        115                 120                 125

Leu Thr Gly Arg Ala Pro Gly Ala Arg Pro Ala Cys Tyr Ser Cys Cys
    130                 135                 140

Pro Ala His Ser Cys Thr Ala Ser Cys Ala Arg Met Arg Pro Arg Thr
145                 150                 155                 160

Leu Gly Pro Trp Ser Leu Pro Ser Ser Gly Ser Gly Ala Pro Ala
                165                 170                 175

Glu Gly Arg Asp Leu Gly Ile Ala Phe Asn Phe Leu Cys Cys Lys
            180                 185                 190
```

<210> SEQ ID NO 100
<211> LENGTH: 573
<212> TYPE: DNA
<213> ORGANISM: Homo sapiens

<400> SEQUENCE: 100

```
atgacctgga ggcaccatgt caggcttctg tttacggtca gtttggcatt acagatcatc      60
aatttgggaa acagctatca agagagaaa cataacggcg gtagagagga agtcaccaag      120
gttgccactc agaagcaccg acagtcaccg ctcaactgga cctccagtca tttcggagag      180
gtgactggga gcgccgaggg ctggggggcc gaggagccgc tccctactc ccgggctttc       240
ggagaggtga atgcggcgcc ctggagcacg agcctggac cctccgcgcc tgccacctct       300
gcaggtgcat cttcggggcc ctgcactgcc tcccctcca gacgcctgac cgctgtgacc       360
cgaaagactt cctggcctcc cacgctcacg ggccgagcgc cggggcgcg cccagcctgc       420
tactcttgct gccctgcgca ctcctgcacc gcctcctgcg cccggatgcg cccgcgcacc      480
ctcggtccct ggtcccttcc gtcctccagc gggagcggcg cccctgcgga aggccgggac      540
ttgggcatcg cctttaattt tctatgttgt aaa                                   573
```

<210> SEQ ID NO 101
<211> LENGTH: 166
<212> TYPE: PRT
<213> ORGANISM: Homo sapiens

<400> SEQUENCE: 101

```
Tyr Gln Arg Glu Lys His Asn Gly Gly Arg Glu Glu Val Thr Lys Val
```

```
              1               5              10              15
            Ala Thr Gln Lys His Arg Gln Ser Pro Leu Asn Trp Thr Ser His
                             20              25              30
            Phe Gly Glu Val Thr Gly Ser Ala Glu Gly Trp Gly Pro Glu Pro
                             35              40              45
            Leu Pro Tyr Ser Arg Ala Phe Gly Glu Val Asn Ala Ala Pro Trp Ser
                50                      55              60
            Thr Glu Pro Gly Pro Ser Ala Pro Ala Thr Ser Ala Gly Ala Ser Ser
             65                      70              75                      80
            Gly Pro Cys Thr Ala Ser Pro Ser Arg Arg Leu Thr Ala Val Thr Arg
                             85              90              95
            Lys Thr Ser Trp Pro Pro Thr Leu Thr Gly Arg Ala Pro Gly Ala Arg
                            100             105             110
            Pro Ala Cys Tyr Ser Cys Cys Pro Ala His Ser Cys Thr Ala Ser Cys
                            115             120             125
            Ala Arg Met Arg Pro Arg Thr Leu Gly Pro Trp Ser Leu Pro Ser Ser
                            130             135             140
            Ser Gly Ser Gly Ala Pro Ala Glu Gly Arg Asp Leu Gly Ile Ala Phe
            145                     150             155                     160
            Asn Phe Leu Cys Cys Lys
                            165
```

<210> SEQ ID NO 102
<211> LENGTH: 498
<212> TYPE: DNA
<213> ORGANISM: Homo sapiens

<400> SEQUENCE: 102

```
tatcaaagag agaaacataa cggcggtaga gaggaagtca ccaaggttgc cactcagaag      60
caccgacagt caccgctcaa ctggacctcc agtcatttcg gagaggtgac tgggagcgcc     120
gagggctggg ggccggagga gccgctcccc tactcccggg cttcggaga ggtgaatgcg      180
gcgccctgga gcacggagcc tggaccctcc gcgcctgcca cctctgcagg tgcatcttcg     240
gggcccgca ctgcctcccc ctccagacgc ctgaccgctg tgacccgaaa gacttcctgg     300
cctcccacgc tcacgggccg agcgccgggg gcgcgcccag cctgctactc ttgctgccct     360
gcgcactcct gcaccgcctc ctgcgcccgg atgcgcccgc gcaccctcgg tccctggtcc     420
cttccgtcct ccagcgggag cggcgcccct gcggaaggcc gggacttggg catcgccttt     480
aattttctat gttgtaaa                                                   498
```

<210> SEQ ID NO 103
<211> LENGTH: 148
<212> TYPE: PRT
<213> ORGANISM: Homo sapiens

<400> SEQUENCE: 103

```
            Met Thr Trp Arg His His Val Arg Leu Leu Phe Thr Val Ser Leu Ala
             1               5              10              15
            Leu Gln Ile Ile Asn Leu Gly Asn Ser Tyr Gln Arg Glu Lys His Asn
                             20              25              30
            Gly Gly Arg Glu Glu Val Thr Lys Val Ala Thr Gln Lys His Arg Gln
                             35              40              45
            Ser Pro Leu Asn Trp Thr Ser Ser His Phe Gly Glu Val Thr Gly Ser
                50                      55              60
            Ala Glu Gly Trp Gly Pro Glu Glu Pro Leu Pro Tyr Ser Arg Ala Phe
```

Gly Glu Asp Pro Lys Asp Phe Leu Ala Ser His Ala His Gly Pro Ser
            65                  70                  75                  80

Ala Gly Gly Ala Pro Ser Leu Leu Leu Leu Leu Pro Cys Ala Leu Leu
            85                  90                  95

His Arg Leu Leu Arg Pro Asp Ala Pro Ala His Pro Arg Ser Leu Val
        100                 105                 110

Pro Ser Val Leu Gln Arg Glu Arg Arg Pro Cys Gly Arg Pro Gly Leu
    115                 120                 125

Gly His Arg Leu
        130                 135                 140

145

<210> SEQ ID NO 104
<211> LENGTH: 444
<212> TYPE: DNA
<213> ORGANISM: Homo sapiens

<400> SEQUENCE: 104
atgacctgga ggcaccatgt caggcttctg tttacggtca gtttggcatt acagatcatc      60
aatttgggaa acagctatca agagagaaa cataacggcg gtagagagga agtcaccaag      120
gttgccactc agaagcaccg acagtcaccg ctcaactgga cctccagtca tttcggagag     180
gtgactggga cgccgagggc tggggggccg gaggagccgc tccctactc ccggggctttc    240 ggagaggacc cgaaagactt cctggcctcc cacgctcacg gccgagcgc cggggcgcg     300 cccagcctgc tactcttgct gccctgcgca ctcctgcacc gctcctgcg cccggatgcg      360 cccgcgcacc ctcggtccct ggtccccttcc gtcctccagc gggagcggcg cccctgcgga   420
aggccgggac ttgggcatcg cctt                                          444

<210> SEQ ID NO 105
<211> LENGTH: 69
<212> TYPE: PRT
<213> ORGANISM: Homo sapiens

<400> SEQUENCE: 105

Tyr Gln Arg Glu Lys His Asn Gly Gly Arg Glu Glu Val Thr Lys Val
1               5                   10                  15

Ala Thr Gln Lys His Arg Gln Ser Pro Leu Asn Trp Thr Ser Ser His
            20                  25                  30

Phe Gly Glu Val Thr Gly Ser Ala Glu Gly Trp Gly Pro Glu Glu Pro
        35                  40                  45

Leu Pro Tyr Ser Arg Ala Phe Gly Glu Asp Pro Lys Asp Phe Leu Ala
    50                  55                  60

Ser His Ala His Gly
65

<210> SEQ ID NO 106
<211> LENGTH: 207
<212> TYPE: DNA
<213> ORGANISM: Homo sapiens

<400> SEQUENCE: 106
tatcaaagag agaaacataa cggcggtaga gaggaagtca ccaaggttgc cactcagaag     60
caccgacagt caccgctcaa ctggacctcc agtcatttcg gagaggtgac tgggagcgcc    120
gagggctggg gccgaggaga gccgctcccc tactcccggg ctttcggaga ggaccccgaaa   180 gacttcctgg cctcccacgc tcacggg                                        207

<210> SEQ ID NO 107
<211> LENGTH: 223
<212> TYPE: PRT
<213> ORGANISM: Homo sapiens

<400> SEQUENCE: 107

```
Met Thr Trp Arg His His Val Arg Leu Leu Phe Thr Val Ser Leu Ala
1               5                   10                  15
Leu Gln Ile Ile Asn Leu Gly Asn Ser Tyr Gln Arg Glu Lys His Asn
            20                  25                  30
Gly Gly Arg Glu Glu Val Thr Lys Val Ala Thr Gln Lys His Arg Gln
        35                  40                  45
Ser Pro Leu Asn Trp Thr Ser Ser His Phe Gly Glu Val Thr Gly Ser
    50                  55                  60
Ala Glu Gly Trp Gly Pro Glu Glu Pro Leu Pro Tyr Ser Trp Ala Phe
65                  70                  75                  80
Gly Glu Gly Ala Ser Ala Arg Pro Arg Cys Cys Arg Asn Gly Gly Thr
                85                  90                  95
Cys Val Leu Gly Ser Phe Cys Val Cys Pro Ala His Phe Thr Gly Arg
            100                 105                 110
Tyr Cys Glu His Asp Gln Arg Ser Glu Cys Gly Ala Leu Glu His
        115                 120                 125
Gly Ala Trp Thr Leu Arg Ala Cys His Leu Cys Arg Cys Ile Phe Gly
    130                 135                 140
Ala Leu His Cys Leu Pro Leu Gln Thr Pro Asp Arg Cys Asp Pro Lys
145                 150                 155                 160
Asp Phe Leu Ala Ser His Ala His Gly Pro Ser Ala Gly Gly Ala Pro
                165                 170                 175
Ser Leu Leu Leu Leu Pro Cys Ala Leu Leu His Arg Leu Leu Arg
            180                 185                 190
Pro Asp Ala Pro Ala His Pro Arg Ser Leu Val Pro Ser Val Leu Gln
        195                 200                 205
Arg Glu Arg Arg Pro Cys Gly Arg Pro Gly Leu Gly His Arg Leu
    210                 215                 220
```

<210> SEQ ID NO 108
<211> LENGTH: 669
<212> TYPE: DNA
<213> ORGANISM: Homo sapiens

<400> SEQUENCE: 108

```
atgacctgga ggcaccatgt caggcttctg tttacggtca gtttggcatt acagatcatc      60
aatttgggaa acagctatca agagagaaa cataacggcg gtagagagga agtcaccaag      120
gttgccactc agaagcaccg acagtcaccg ctcaactgga cctccagtca tttcggagag      180
gtgactggga gcgccgaggg ctggggccg gaggagccgc tcccatactc ctgggctttc      240
ggagagggtg cgtccgcgcg gccgcgctgc tgcaggaacg gcggtacctg cgtgctgggc      300
agcttctgcg tgtgcccggc ccacttcacc ggccgctact gcgagcatga ccagaggcgc      360
agtgaatgcg gcgccctgga gcacggagcc tggaccctcc gcgcctgcca cctctgcagg      420
tgcatcttcg gggccctgca ctgcctcccc ctccagacgc ctgaccgctg tgacccgaaa      480
gacttcctgg cctcccacgc tcacgggccg agcgccgggg gcgcgcccag cctgctactc      540
ttgctgcccct gcgcactcct gcaccgcctc ctgcgcccgg atgcgcccgc gcaccctcgg      600
```

```
tccctggtcc cttccgtcct ccagcgggag cggcgcccct gcggaaggcc gggacttggg    660
catcgcctt                                                            669
```

<210> SEQ ID NO 109
<211> LENGTH: 144
<212> TYPE: PRT
<213> ORGANISM: Homo sapiens

<400> SEQUENCE: 109

```
Tyr Gln Arg Glu Lys His Asn Gly Gly Arg Glu Val Thr Lys Val
1               5                   10                  15

Ala Thr Gln Lys His Arg Gln Ser Pro Leu Asn Trp Thr Ser His
                20                  25                  30

Phe Gly Glu Val Thr Gly Ser Ala Glu Gly Trp Gly Pro Glu Pro
            35                  40                  45

Leu Pro Tyr Ser Trp Ala Phe Gly Glu Gly Ala Ser Ala Arg Pro Arg
    50                  55                  60

Cys Cys Arg Asn Gly Gly Thr Cys Val Leu Gly Ser Pro Cys Val Cys
65                  70                  75                  80

Pro Ala His Phe Thr Gly Arg Tyr Cys Glu His Asp Gln Arg Arg Ser
                85                  90                  95

Glu Cys Gly Ala Leu Glu His Gly Ala Trp Thr Leu Arg Ala Cys His
            100                 105                 110

Leu Cys Arg Cys Ile Phe Gly Ala Leu His Cys Leu Pro Leu Gln Thr
        115                 120                 125

Pro Asp Arg Cys Asp Pro Lys Asp Phe Leu Ala Ser His Ala His Gly
    130                 135                 140
```

<210> SEQ ID NO 110
<211> LENGTH: 432
<212> TYPE: DNA
<213> ORGANISM: Homo sapiens

<400> SEQUENCE: 110

```
tatcaaagag agaaacataa cggcggtaga gaggaagtca ccaaggttgc cactcagaag     60
caccgacagt caccgctcaa ctggacctcc agtcatttcg gagaggtgac tgggagcgcc    120
gagggctggg ggccggagga gccgctccca tactcctggg cttttcggaga gggtgcgtcc   180 gcgcggccgc gctgctgcag gaacggcggt acctgcgtgc tgggcagctt ctgcgtgtgc    240
ccggcccact tcaccggccg ctactgcgag catgaccaga ggcgcagtga atgcggcgcc    300
ctggagcacg gagcctggac cctccgcgcc tgccacctct gcaggtgcat cttcggggcc    360
ctgcactgcc tccccctcca gacgcctgac cgctgtgacc cgaaagactt cctggcctcc    420
cacgctcacg gg                                                        432
```

<210> SEQ ID NO 111

<400> SEQUENCE: 111

000

<210> SEQ ID NO 112

<400> SEQUENCE: 112

000

<210> SEQ ID NO 113

```
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
```

000

<210> SEQ ID NO 125
<400> SEQUENCE: 125
000

<210> SEQ ID NO 126
<400> SEQUENCE: 126
000

<210> SEQ ID NO 127
<400> SEQUENCE: 127
000

<210> SEQ ID NO 128
<400> SEQUENCE: 128
000

<210> SEQ ID NO 129
<400> SEQUENCE: 129
000

<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<211> LENGTH: 225
<212> TYPE: PRT
<213> ORGANISM: Homo sapiens

<400> SEQUENCE: 135

```
Thr His Thr Cys Pro Pro Cys Pro Ala Pro Glu Leu Leu Gly Gly Pro
 1               5                  10                  15
Ser Val Phe Leu Phe Pro Pro Lys Pro Lys Asp Thr Leu Met Ile Ser
             20                  25                  30
Arg Thr Pro Glu Val Thr Cys Val Val Val Asp Val Ser His Glu Asp
         35                  40                  45
Pro Glu Val Lys Phe Asn Trp Tyr Val Asp Gly Val Glu Val His Asn
     50                  55                  60
Ala Lys Thr Lys Pro Arg Glu Glu Gln Tyr Asn Ser Thr Tyr Arg Val
 65                  70                  75                  80
Val Ser Val Leu Thr Val Leu His Gln Asp Trp Leu Asn Gly Lys Glu
                 85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Ser Arg Glu Glu Met Thr Lys Asn Gln Val Ser Leu Thr
    130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225
```

<210> SEQ ID NO 136
<211> LENGTH: 223
<212> TYPE: PRT
<213> ORGANISM: Homo sapiens

<400> SEQUENCE: 136

```
Val Glu Cys Pro Pro Cys Pro Ala Pro Pro Val Ala Gly Pro Ser Val
 1               5                  10                  15
Phe Leu Phe Pro Pro Lys Pro Lys Asp Thr Leu Met Ile Ser Arg Thr
             20                  25                  30
Pro Glu Val Thr Cys Val Val Val Asp Val Ser His Glu Asp Pro Glu
         35                  40                  45
Val Gln Phe Asn Trp Tyr Val Asp Gly Val Glu Val His Asn Ala Lys
     50                  55                  60
Thr Lys Pro Arg Glu Glu Gln Phe Asn Ser Thr Phe Arg Val Val Ser
 65                  70                  75                  80
Val Leu Thr Val Val His Gln Asp Trp Leu Asn Gly Lys Glu Tyr Lys
                 85                  90                  95
Cys Lys Val Ser Asn Lys Gly Leu Pro Ala Pro Ile Glu Lys Thr Ile
            100                 105                 110
Ser Lys Thr Lys Gly Gln Pro Arg Glu Pro Gln Val Tyr Thr Leu Pro
        115                 120                 125
```

```
Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 137
<211> LENGTH: 232
<212> TYPE: PRT
<213> ORGANISM: Homo sapiens

<400> SEQUENCE: 137

```
Glu Pro Lys Ser Cys Asp Thr Pro Pro Cys Pro Arg Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Lys Trp Tyr Val
50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230
```

<210> SEQ ID NO 138
<211> LENGTH: 279
<212> TYPE: PRT
<213> ORGANISM: Homo sapiens

<400> SEQUENCE: 138

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
        130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
                260                 265                 270

Leu Ser Leu Ser Pro Gly Lys
        275

<210> SEQ ID NO 139
<211> LENGTH: 229
<212> TYPE: PRT
<213> ORGANISM: Homo sapiens

<400> SEQUENCE: 139

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95
```

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 140
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Lys Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Lys Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly

Lys
225

<210> SEQ ID NO 141
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Asp Thr Thr Pro Pro Val Leu
                165                 170                 175

Asp Ser Asp Gly Ser Phe Phe Leu Tyr Ser Asp Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 142
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp

```
            35                  40                  45
Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Tyr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 143
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Thr His Thr Cys Pro Pro Cys Pro Ala Pro Glu Leu Leu Gly Gly Pro
 1               5                  10                  15

Ser Val Phe Leu Phe Pro Pro Lys Pro Lys Asp Thr Leu Met Ile Ser
                 20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160
```

Ser Asn Gly Gln Pro Glu Asn Asn Tyr Lys Thr Thr Pro Pro Val Leu
         165                 170                 175

Asp Ser Asp Gly Ser Phe Phe Leu Thr Ser Lys Leu Thr Val Asp Lys
         180                 185                 190

Ser Arg Trp Gln Gln Gly Asn Val Phe Ser Cys Ser Val Met His Glu
     195                 200                 205

Ala Leu His Asn His Tyr Thr Gln Lys Ser Leu Ser Leu Ser Pro Gly
 210                 215                 220

Lys
225

<210> SEQ ID NO 144
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
             20                  25                  30

Arg Thr Pro Glu Val Thr Cys Val Val Val Asp Val Ser His Glu Asp
         35                  40                  45

Pro Glu Val Lys Phe Asn Trp Tyr Val Asp Gly Val Glu Val His Asn
     50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
             100                 105                 110

Thr Ile Ser Lys Ala Lys Gly Gln Pro Arg Glu Pro Gln Val Tyr Thr
         115                 120                 125

Leu Pro Pro Cys Arg Glu Glu Met Thr Lys Asn Gln Val Ser Leu Trp
     130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                 165                 170                 175

Asp Ser Asp Gly Ser Phe Phe Leu Tyr Ser Lys Leu Thr Val Asp Lys
             180                 185                 190

Ser Arg Trp Gln Gln Gly Asn Val Phe Ser Cys Ser Val Met His Glu
         195                 200                 205

Ala Leu His Asn His Tyr Thr Gln Lys Ser Leu Ser Leu Ser Pro Gly
 210                 215                 220

Lys
225

<210> SEQ ID NO 145
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
            115                 120                 125

Leu Pro Pro Ser Arg Glu Glu Met Thr Lys Asn Gln Val Ser Leu Ser
130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 146
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
            100                 105                 110

```
Thr Ile Ser Lys Ala Lys Gly Gln Pro Phe Arg Pro Glu Val His Leu
            115                 120                 125

Leu Pro Pro Ser Arg Glu Glu Met Thr Lys Asn Gln Val Ser Leu Thr
        130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
210                 215                 220

Ser Pro Gly Lys
225

<210> SEQ ID NO 147
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Glu Glu Leu Ala Leu Asn Glu Leu Val Thr Leu
        130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
            180                 185                 190

Val Ala Ala Glu Asp Trp Lys Lys Gly Asp Thr Phe Ser Cys Ser Val
        195                 200                 205

Met His Glu Ala Leu His Asn His Tyr Thr Gln Lys Ser Leu Asp Arg
210                 215                 220

Ser Pro Gly Lys
```

<210> SEQ ID NO 148
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
                245                 250                 255

Ala Gln Gly Ala Thr
            260

<210> SEQ ID NO 149
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser

```
                 20                  25                  30
Arg Thr Pro Glu Val Thr Cys Val Val Asp Val Ser His Glu Asp
             35                  40                  45
Pro Glu Val Lys Phe Asn Trp Tyr Val Asp Gly Val Glu Val His Asn
 50                  55                  60
Ala Lys Thr Lys Pro Arg Glu Glu Gln Tyr Asn Ser Thr Tyr Arg Val
 65                  70                  75                  80
Val Ser Val Leu Thr Val Leu His Gln Asp Trp Leu Asn Gly Lys Glu
                 85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
            115                 120                 125
Leu Pro Pro Ser Arg Glu Glu Met Thr Lys Asn Gln Val Ser Leu Thr
            130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
            195                 200                 205
Ala Leu His Asn His Tyr Thr Gln Lys Ser Leu Ser Leu Ser Pro Gly
            210                 215                 220
Lys Gly Gly Ser Ala Gln Leu Lys Lys Leu Gln Ala Leu Lys Lys
225                 230                 235                 240
Lys Asn Ala Gln Leu Lys Trp Lys Leu Gln Ala Leu Lys Lys Leu
                245                 250                 255
Ala Gln Gly Ala Thr
            260

<210> SEQ ID NO 150
<211> LENGTH: 317
<212> TYPE: PRT
<213> ORGANISM: Homo sapiens

<400> SEQUENCE: 150

Met Val Arg Ala Arg His Gln Pro Gly Gly Leu Cys Leu Leu Leu
 1               5                  10                  15
Leu Leu Cys Gln Phe Met Glu Asp Arg Ser Ala Gln Ala Gly Asn Cys
                 20                  25                  30
Trp Leu Arg Gln Ala Lys Asn Gly Arg Cys Gln Val Leu Tyr Lys Thr
             35                  40                  45
Glu Leu Ser Lys Glu Glu Cys Cys Ser Thr Gly Arg Leu Ser Thr Ser
 50                  55                  60
Trp Thr Glu Glu Asp Val Asn Asp Asn Thr Leu Phe Lys Trp Met Ile
 65                  70                  75                  80
Phe Asn Gly Gly Ala Pro Asn Cys Ile Pro Cys Lys Glu Thr Cys Glu
                 85                  90                  95
Asn Val Asp Cys Gly Pro Gly Lys Lys Cys Arg Met Asn Lys Lys Asn
            100                 105                 110
Lys Pro Arg Cys Val Cys Ala Pro Asp Cys Ser Asn Ile Thr Trp Lys
            115                 120                 125
```

```
Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn
305                 310                 315

<210> SEQ ID NO 151
<211> LENGTH: 344
<212> TYPE: PRT
<213> ORGANISM: Homo sapiens

<400> SEQUENCE: 151

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190
```

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
        290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 152
<211> LENGTH: 288
<212> TYPE: PRT
<213> ORGANISM: Homo sapiens

<400> SEQUENCE: 152

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly

```
              210                 215                 220
Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
            275                 280                 285

<210> SEQ ID NO 153
<211> LENGTH: 315
<212> TYPE: PRT
<213> ORGANISM: Homo sapiens

<400> SEQUENCE: 153

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
            275                 280                 285

Ser Ile Ser Glu Asp Thr Glu Glu Glu Glu Asp Glu Asp Gln Asp
            290                 295                 300
```

Tyr Ser Phe Pro Ile Ser Ser Ile Leu Glu Trp
305                 310                 315

<210> SEQ ID NO 154
<211> LENGTH: 133
<212> TYPE: PRT
<213> ORGANISM: Homo sapiens

<400> SEQUENCE: 154

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys
    130

<210> SEQ ID NO 155
<211> LENGTH: 203
<212> TYPE: PRT
<213> ORGANISM: Homo sapiens

<400> SEQUENCE: 155

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Cys Glu Asn Val Asp Cys Gly Pro Gly Lys Lys
    130                 135                 140

Cys Arg Met Asn Lys Lys Asn Lys Pro Arg Cys Val Cys Ala Pro Asp
145                 150                 155                 160

Cys Ser Asn Ile Thr Trp Lys Gly Pro Val Cys Gly Leu Asp Gly Lys
                165                 170                 175

Thr Tyr Arg Asn Glu Cys Ala Leu Leu Lys Ala Arg Cys Lys Glu Gln
            180                 185                 190

Pro Glu Leu Glu Val Gln Tyr Gln Gly Arg Cys
        195                 200

<210> SEQ ID NO 156
<211> LENGTH: 142
<212> TYPE: PRT
<213> ORGANISM: Homo sapiens

<400> SEQUENCE: 156

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
50                  55                  60

Gln Tyr Gln Gly Arg Cys Cys Arg Asp Val Phe Cys Pro Gly Ser Ser
65                  70                  75                  80

Thr Cys Val Val Asp Gln Thr Asn Asn Ala Tyr Cys Val Thr Cys Asn
                85                  90                  95

Arg Ile Cys Pro Glu Pro Ala Ser Ser Glu Gln Tyr Leu Cys Gly Asn
            100                 105                 110

Asp Gly Val Thr Tyr Ser Ser Ala Cys His Leu Arg Lys Ala Thr Cys
        115                 120                 125

Leu Leu Gly Arg Ser Ile Gly Leu Ala Tyr Glu Gly Lys Cys
130                 135                 140

<210> SEQ ID NO 157
<211> LENGTH: 214
<212> TYPE: PRT
<213> ORGANISM: Homo sapiens

<400> SEQUENCE: 157

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
50                  55                  60

Gln Tyr Gln Gly Arg Cys Cys Arg Asp Val Phe Cys Pro Gly Ser Ser
65                  70                  75                  80

Thr Cys Val Val Asp Gln Thr Asn Asn Ala Tyr Cys Val Thr Cys Asn
                85                  90                  95

Arg Ile Cys Pro Glu Pro Ala Ser Ser Glu Gln Tyr Leu Cys Gly Asn
            100                 105                 110

Asp Gly Val Thr Tyr Ser Ser Ala Cys His Leu Arg Lys Ala Thr Cys
        115                 120                 125

Leu Leu Gly Arg Ser Ile Gly Leu Ala Tyr Glu Gly Lys Cys Cys Glu
            130                 135                 140

Asp Ile Gln Cys Thr Gly Gly Lys Lys Cys Leu Trp Asp Phe Lys Val
145                 150                 155                 160

Gly Arg Gly Arg Cys Ser Leu Cys Asp Glu Leu Cys Pro Asp Ser Lys
              165                 170                 175

Ser Asp Glu Pro Val Cys Ala Ser Asp Asn Ala Thr Tyr Ala Ser Glu
            180                 185                 190

Cys Ala Met Lys Glu Ala Ala Cys Ser Ser Gly Val Leu Leu Glu Val
                195                 200                 205

Lys His Ser Gly Ser Cys
    210

<210> SEQ ID NO 158
<211> LENGTH: 205
<212> TYPE: PRT
<213> ORGANISM: Homo sapiens

<400> SEQUENCE: 158

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Cys Arg Asp Val Phe Cys Pro Gly Ser Ser Thr
    130                 135                 140

Cys Val Val Asp Gln Thr Asn Asn Ala Tyr Cys Val Thr Cys Asn Arg
145                 150                 155                 160

Ile Cys Pro Glu Pro Ala Ser Ser Glu Gln Tyr Leu Cys Gly Asn Asp
                165                 170                 175

Gly Val Thr Tyr Ser Ser Ala Cys His Leu Arg Lys Ala Thr Cys Leu
            180                 185                 190

Leu Gly Arg Ser Ile Gly Leu Ala Tyr Glu Gly Lys Cys
        195                 200                 205

<210> SEQ ID NO 159
<211> LENGTH: 320
<212> TYPE: PRT
<213> ORGANISM: Homo sapiens

<400> SEQUENCE: 159

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

```
Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                 85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Lys Lys Cys
                245                 250                 255

Leu Trp Asp Phe Lys Val Gly Arg Gly Arg Cys Ser Leu Cys Asp Glu
                260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

<210> SEQ ID NO 160
<211> LENGTH: 291
<212> TYPE: PRT
<213> ORGANISM: Homo sapiens

<400> SEQUENCE: 160

Gly Asn Cys Trp Leu Arg Gln Ala Lys Asn Gly Arg Cys Gln Val Leu
  1               5                  10                  15

Tyr Lys Thr Glu Leu Ser Lys Glu Glu Cys Cys Ser Thr Gly Arg Leu
                 20                  25                  30

Ser Thr Ser Trp Thr Glu Glu Asp Val Asn Asp Asn Thr Leu Phe Lys
             35                  40                  45

Trp Met Ile Phe Asn Gly Gly Ala Pro Asn Cys Ile Pro Cys Lys Glu
         50                  55                  60

Thr Cys Glu Asn Val Asp Cys Gly Pro Gly Lys Lys Cys Arg Met Asn
 65                  70                  75                  80

Lys Lys Asn Lys Pro Arg Cys Val Cys Ala Pro Asp Cys Ser Asn Ile
                 85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125
```

```
Val Gln Tyr Gln Gly Arg Cys Lys Lys Thr Cys Arg Asp Val Phe Cys
            130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser
    290

<210> SEQ ID NO 161
<211> LENGTH: 263
<212> TYPE: PRT
<213> ORGANISM: Homo sapiens

<400> SEQUENCE: 161

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
```

```
                195                 200                 205
Glu Leu Cys Gly Asn Asn Val Thr Tyr Ile Ser Ser Cys His Met
        210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
                245                 250                 255

Glu Glu Glu Glu Asn Phe Val
            260
```

<210> SEQ ID NO 162
<211> LENGTH: 226
<212> TYPE: PRT
<213> ORGANISM: Homo sapiens

<400> SEQUENCE: 162

```
Cys Trp Leu Gln Gln Gly Gln Glu Ala Thr Cys Ser Leu Val Leu Gln
1               5                   10                  15

Thr Asp Val Thr Arg Ala Glu Cys Cys Ala Ser Gly Asn Ile Asp Thr
                20                  25                  30

Ala Trp Ser Asn Leu Thr His Pro Gly Asn Lys Ile Asn Leu Leu Gly
            35                  40                  45

Phe Leu Gly Leu Val His Cys Leu Pro Cys Lys Asp Ser Cys Asp Gly
    50                  55                  60

Val Glu Cys Gly Pro Gly Lys Ala Cys Arg Met Leu Gly Gly Arg Pro
65                  70                  75                  80

Arg Cys Glu Cys Ala Pro Asp Cys Ser Gly Leu Pro Ala Arg Leu Gln
                85                  90                  95

Val Cys Gly Ser Asp Gly Ala Thr Tyr Arg Asp Glu Cys Glu Leu Arg
            100                 105                 110

Ala Ala Arg Cys Arg Gly His Pro Asp Leu Ser Val Met Tyr Arg Gly
        115                 120                 125

Arg Cys Arg Lys Ser Cys Glu His Val Val Cys Pro Arg Pro Gln Ser
    130                 135                 140

Cys Val Val Asp Gln Thr Gly Ser Ala His Cys Val Val Cys Arg Ala
145                 150                 155                 160

Ala Pro Cys Pro Val Pro Ser Ser Pro Gly Gln Glu Leu Cys Gly Asn
                165                 170                 175

Asn Asn Val Thr Tyr Ile Ser Ser Cys His Met Arg Gln Ala Thr Cys
            180                 185                 190

Phe Leu Gly Arg Ser Ile Gly Val Arg His Ala Gly Ser Cys Ala Gly
        195                 200                 205

Thr Pro Glu Glu Pro Pro Gly Gly Glu Ser Ala Glu Glu Glu Glu Asn
    210                 215                 220

Phe Val
225
```

<210> SEQ ID NO 163
<211> LENGTH: 130
<212> TYPE: PRT
<213> ORGANISM: Homo sapiens

<400> SEQUENCE: 163

```
Gly Val Cys Trp Leu Gln Gln Gly Gln Glu Ala Thr Cys Ser Leu Val
1               5                   10                  15

Leu Gln Thr Asp Val Thr Arg Ala Glu Cys Cys Ala Ser Gly Asn Ile
```

```
                20                  25                  30

Asp Thr Ala Trp Ser Asn Leu Thr His Pro Gly Asn Lys Ile Asn Leu
            35                  40                  45

Leu Gly Phe Leu Gly Leu Val His Cys Leu Pro Cys Lys Cys Asp Gly
        50                  55                  60

Val Glu Cys Gly Pro Gly Lys Ala Cys Arg Met Leu Gly Gly Arg Pro
65                  70                  75                  80

Arg Cys Glu Cys Ala Pro Asp Cys Ser Gly Leu Pro Ala Arg Leu Gln
                85                  90                  95

Val Cys Gly Ser Asp Gly Ala Thr Tyr Arg Asp Glu Cys Glu Leu Arg
            100                 105                 110

Ala Ala Arg Cys Arg Gly His Pro Asp Leu Ser Val Met Tyr Arg Gly
        115                 120                 125

Arg Cys
    130

<210> SEQ ID NO 164
<211> LENGTH: 203
<212> TYPE: PRT
<213> ORGANISM: Homo sapiens

<400> SEQUENCE: 164

Gly Val Cys Trp Leu Gln Gln Gly Gln Glu Ala Thr Cys Ser Leu Val
1               5                   10                  15

Leu Gln Thr Asp Val Thr Arg Ala Glu Cys Cys Ala Ser Gly Asn Ile
            20                  25                  30

Asp Thr Ala Trp Ser Asn Leu Thr His Pro Gly Asn Lys Ile Asn Leu
        35                  40                  45

Leu Gly Phe Leu Gly Leu Val His Cys Leu Pro Cys Lys Cys Asp Gly
    50                  55                  60

Val Glu Cys Gly Pro Gly Lys Ala Cys Arg Met Leu Gly Gly Arg Pro
65                  70                  75                  80

Arg Cys Glu Cys Ala Pro Asp Cys Ser Gly Leu Pro Ala Arg Leu Gln
                85                  90                  95

Val Cys Gly Ser Asp Gly Ala Thr Tyr Arg Asp Glu Cys Glu Leu Arg
            100                 105                 110

Ala Ala Arg Cys Arg Gly His Pro Asp Leu Ser Val Met Tyr Arg Gly
        115                 120                 125

Arg Cys Cys Glu His Val Val Cys Pro Arg Pro Gln Ser Cys Val Val
    130                 135                 140

Asp Gln Thr Gly Ser Ala His Cys Val Val Cys Arg Ala Ala Pro Cys
145                 150                 155                 160

Pro Val Pro Ser Ser Pro Gly Gln Glu Leu Cys Gly Asn Asn Asn Val
                165                 170                 175

Thr Tyr Ile Ser Ser Cys His Met Arg Gln Ala Thr Cys Phe Leu Gly
            180                 185                 190

Arg Ser Ile Gly Val Arg His Ala Gly Ser Cys
        195                 200

<210> SEQ ID NO 165
<211> LENGTH: 548
<212> TYPE: PRT
<213> ORGANISM: Homo sapiens

<400> SEQUENCE: 165

Met Pro Ala Leu Arg Pro Leu Leu Pro Leu Leu Leu Leu Leu Arg Leu
```

-continued

```
1               5                   10                  15
Thr Ser Gly Ala Gly Leu Leu Pro Gly Leu Gly Ser His Pro Gly Val
                20                  25                  30
Cys Pro Asn Gln Leu Ser Pro Asn Leu Trp Val Asp Ala Gln Ser Thr
                35                  40                  45
Cys Glu Arg Glu Cys Ser Arg Asp Gln Asp Cys Ala Ala Ala Glu Lys
    50                  55                  60
Cys Cys Ile Asn Val Cys Gly Leu His Ser Cys Val Ala Ala Arg Phe
65                  70                  75                  80
Pro Gly Ser Pro Ala Ala Pro Thr Thr Ala Ala Ser Cys Glu Gly Phe
                85                  90                  95
Val Cys Pro Gln Gln Gly Ser Asp Cys Asp Ile Trp Asp Gly Gln Pro
                100                 105                 110
Val Cys Arg Cys Arg Asp Arg Cys Glu Lys Glu Pro Ser Phe Thr Cys
                115                 120                 125
Ala Ser Asp Gly Leu Thr Tyr Tyr Asn Arg Cys Tyr Met Asp Ala Glu
            130                 135                 140
Ala Cys Leu Arg Gly Leu His Leu His Ile Val Pro Cys Lys His Val
145                 150                 155                 160
Leu Ser Trp Pro Pro Ser Ser Pro Gly Pro Pro Glu Thr Thr Ala Arg
                165                 170                 175
Pro Thr Pro Gly Ala Ala Pro Val Pro Pro Ala Leu Tyr Ser Ser Pro
                180                 185                 190
Ser Pro Gln Ala Val Gln Val Gly Gly Thr Ala Ser Leu His Cys Asp
                195                 200                 205
Val Ser Gly Arg Pro Pro Pro Ala Val Thr Trp Glu Lys Gln Ser His
            210                 215                 220
Gln Arg Glu Asn Leu Ile Met Arg Pro Asp Gln Met Tyr Gly Asn Val
225                 230                 235                 240
Val Val Thr Ser Ile Gly Gln Leu Val Leu Tyr Asn Ala Arg Pro Glu
                245                 250                 255
Asp Ala Gly Leu Tyr Thr Cys Thr Ala Arg Asn Ala Ala Gly Leu Leu
                260                 265                 270
Arg Ala Asp Phe Pro Leu Ser Val Val Gln Arg Glu Pro Ala Arg Asp
                275                 280                 285
Ala Ala Pro Ser Ile Pro Ala Pro Ala Glu Cys Leu Pro Asp Val Gln
            290                 295                 300
Ala Cys Thr Gly Pro Thr Ser Pro His Leu Val Leu Trp His Tyr Asp
305                 310                 315                 320
Pro Gln Arg Gly Gly Cys Met Thr Phe Pro Ala Arg Gly Cys Asp Gly
                325                 330                 335
Ala Ala Arg Gly Phe Glu Thr Tyr Glu Ala Cys Gln Gln Ala Cys Ala
                340                 345                 350
Arg Gly Pro Gly Asp Ala Cys Val Leu Pro Ala Val Gln Gly Pro Cys
                355                 360                 365
Arg Gly Trp Glu Pro Arg Trp Ala Tyr Ser Pro Leu Leu Gln Gln Cys
                370                 375                 380
His Pro Phe Val Tyr Gly Gly Cys Glu Gly Asn Gly Asn Asn Phe His
385                 390                 395                 400
Ser Arg Glu Ser Cys Glu Asp Ala Cys Pro Val Pro Arg Thr Pro Pro
                405                 410                 415
Cys Arg Ala Cys Arg Leu Arg Ser Lys Leu Ala Leu Ser Leu Cys Arg
                420                 425                 430
```

```
Ser Asp Phe Ala Ile Val Gly Arg Leu Thr Glu Val Leu Glu Glu Pro
            435                 440                 445

Glu Ala Ala Gly Gly Ile Ala Arg Val Ala Leu Glu Asp Val Leu Lys
    450                 455                 460

Asp Asp Lys Met Gly Leu Lys Phe Leu Gly Thr Lys Tyr Leu Glu Val
465                 470                 475                 480

Thr Leu Ser Gly Met Asp Trp Ala Cys Pro Cys Pro Asn Met Thr Ala
                485                 490                 495

Gly Asp Gly Pro Leu Val Ile Met Gly Glu Val Arg Asp Gly Val Ala
                500                 505                 510

Val Leu Asp Ala Gly Ser Tyr Val Arg Ala Ala Ser Glu Lys Arg Val
                515                 520                 525

Lys Lys Ile Leu Glu Leu Leu Glu Lys Gln Ala Cys Glu Leu Leu Asn
                530                 535                 540

Arg Phe Gln Asp
545

<210> SEQ ID NO 166
<211> LENGTH: 529
<212> TYPE: PRT
<213> ORGANISM: Homo sapiens

<400> SEQUENCE: 166

Ala Gly Leu Leu Pro Gly Leu Gly Ser His Pro Gly Val Cys Pro Asn
1               5                   10                  15

Gln Leu Ser Pro Asn Leu Trp Val Asp Ala Gln Ser Thr Cys Glu Arg
            20                  25                  30

Glu Cys Ser Arg Asp Gln Asp Cys Ala Ala Glu Lys Cys Cys Ile
            35                  40                  45

Asn Val Cys Gly Leu His Ser Cys Val Ala Ala Arg Phe Pro Gly Ser
    50                  55                  60

Pro Ala Ala Pro Thr Thr Ala Ala Ser Cys Glu Gly Phe Val Cys Pro
65                  70                  75                  80

Gln Gln Gly Ser Asp Cys Asp Ile Trp Asp Gly Gln Pro Val Cys Arg
                85                  90                  95

Cys Arg Asp Arg Cys Glu Lys Glu Pro Ser Phe Thr Cys Ala Ser Asp
            100                 105                 110

Gly Leu Thr Tyr Tyr Asn Arg Cys Tyr Met Asp Ala Glu Ala Cys Leu
        115                 120                 125

Arg Gly Leu His Leu His Ile Val Pro Cys Lys His Val Leu Ser Trp
    130                 135                 140

Pro Pro Ser Ser Pro Gly Pro Pro Glu Thr Thr Ala Arg Pro Thr Pro
145                 150                 155                 160

Gly Ala Ala Pro Val Pro Pro Ala Leu Tyr Ser Ser Pro Ser Pro Gln
                165                 170                 175

Ala Val Gln Val Gly Gly Thr Ala Ser Leu His Cys Asp Val Ser Gly
                180                 185                 190

Arg Pro Pro Pro Ala Val Thr Trp Glu Lys Gln Ser His Gln Arg Glu
            195                 200                 205

Asn Leu Ile Met Arg Pro Asp Gln Met Tyr Gly Asn Val Val Val Thr
    210                 215                 220

Ser Ile Gly Gln Leu Val Leu Tyr Asn Ala Arg Pro Glu Asp Ala Gly
225                 230                 235                 240

Leu Tyr Thr Cys Thr Ala Arg Asn Ala Ala Gly Leu Leu Arg Ala Asp
```

```
                245                 250                 255
Phe Pro Leu Ser Val Gln Arg Glu Pro Ala Arg Asp Ala Ala Pro
            260                 265                 270
Ser Ile Pro Ala Pro Ala Glu Cys Leu Pro Asp Val Gln Ala Cys Thr
        275                 280                 285
Gly Pro Thr Ser Pro His Leu Val Leu Trp His Tyr Asp Pro Gln Arg
    290                 295                 300
Gly Gly Cys Met Thr Phe Pro Ala Arg Gly Cys Asp Gly Ala Ala Arg
305                 310                 315                 320
Gly Phe Glu Thr Tyr Glu Ala Cys Gln Gln Ala Cys Ala Arg Gly Pro
            325                 330                 335
Gly Asp Ala Cys Val Leu Pro Ala Val Gln Gly Pro Cys Arg Gly Trp
            340                 345                 350
Glu Pro Arg Trp Ala Tyr Ser Pro Leu Leu Gln Gln Cys His Pro Phe
            355                 360                 365
Val Tyr Gly Gly Cys Glu Gly Asn Gly Asn Asn Phe His Ser Arg Glu
    370                 375                 380
Ser Cys Glu Asp Ala Cys Pro Val Pro Arg Thr Pro Pro Cys Arg Ala
385                 390                 395                 400
Cys Arg Leu Arg Ser Lys Leu Ala Leu Ser Leu Cys Arg Ser Asp Phe
            405                 410                 415
Ala Ile Val Gly Arg Leu Thr Glu Val Leu Glu Glu Pro Glu Ala Ala
            420                 425                 430
Gly Gly Ile Ala Arg Val Ala Leu Glu Asp Val Leu Lys Asp Asp Lys
            435                 440                 445
Met Gly Leu Lys Phe Leu Gly Thr Lys Tyr Leu Glu Val Thr Leu Ser
    450                 455                 460
Gly Met Asp Trp Ala Cys Pro Cys Pro Asn Met Thr Ala Gly Asp Gly
465                 470                 475                 480
Pro Leu Val Ile Met Gly Glu Val Arg Asp Gly Val Ala Val Leu Asp
            485                 490                 495
Ala Gly Ser Tyr Val Arg Ala Ala Ser Glu Lys Arg Val Lys Lys Ile
            500                 505                 510
Leu Glu Leu Leu Glu Lys Gln Ala Cys Glu Leu Leu Asn Arg Phe Gln
            515                 520                 525
Asp

<210> SEQ ID NO 167
<211> LENGTH: 65
<212> TYPE: PRT
<213> ORGANISM: Homo sapiens

<400> SEQUENCE: 167

Cys Glu Gly Phe Val Cys Pro Gln Gln Gly Ser Asp Cys Asp Ile Trp
1               5                   10                  15
Asp Gly Gln Pro Val Cys Arg Cys Arg Asp Arg Cys Glu Lys Glu Pro
            20                  25                  30
Ser Phe Thr Cys Ala Ser Asp Gly Leu Thr Tyr Tyr Asn Arg Cys Tyr
        35                  40                  45
Met Asp Ala Glu Ala Cys Leu Arg Gly Leu His Leu His Ile Val Pro
    50                  55                  60
Cys
65
```

```
<210> SEQ ID NO 168
<211> LENGTH: 576
<212> TYPE: PRT
<213> ORGANISM: Homo sapiens

<400> SEQUENCE: 168

Met Trp Ala Pro Arg Cys Arg Arg Phe Trp Ser Arg Trp Glu Gln Val
1               5                   10                  15

Ala Ala Leu Leu Leu Leu Leu Leu Leu Gly Val Pro Pro Arg Ser
            20                  25                  30

Leu Ala Leu Pro Pro Ile Arg Tyr Ser His Ala Gly Ile Cys Pro Asn
            35                  40                  45

Asp Met Asn Pro Asn Leu Trp Val Asp Ala Gln Ser Thr Cys Arg Arg
    50                  55                  60

Glu Cys Glu Thr Asp Gln Glu Cys Glu Thr Tyr Glu Lys Cys Cys Pro
65                  70                  75                  80

Asn Val Cys Gly Thr Lys Ser Cys Val Ala Ala Arg Tyr Met Asp Val
                85                  90                  95

Lys Gly Lys Lys Gly Pro Val Gly Met Pro Lys Glu Ala Thr Cys Asp
            100                 105                 110

His Phe Met Cys Leu Gln Gln Gly Ser Glu Cys Asp Ile Trp Asp Gly
            115                 120                 125

Gln Pro Val Cys Lys Cys Lys Asp Arg Cys Glu Lys Glu Pro Ser Phe
    130                 135                 140

Thr Cys Ala Ser Asp Gly Leu Thr Tyr Tyr Asn Arg Cys Tyr Met Asp
145                 150                 155                 160

Ala Glu Ala Cys Ser Lys Gly Ile Thr Leu Ala Val Val Thr Cys Arg
                165                 170                 175

Tyr His Phe Thr Trp Pro Asn Thr Ser Pro Pro Pro Glu Thr Thr
            180                 185                 190

Met His Pro Thr Thr Ala Ser Pro Glu Thr Pro Glu Leu Asp Met Ala
            195                 200                 205

Ala Pro Ala Leu Leu Asn Asn Pro Val His Gln Ser Val Thr Met Gly
    210                 215                 220

Glu Thr Val Ser Phe Leu Cys Asp Val Val Gly Arg Pro Arg Pro Glu
225                 230                 235                 240

Ile Thr Trp Glu Lys Gln Leu Glu Asp Arg Glu Asn Val Val Met Arg
                245                 250                 255

Pro Asn His Val Arg Gly Asn Val Val Thr Asn Ile Ala Gln Leu
            260                 265                 270

Val Ile Tyr Asn Ala Gln Leu Gln Asp Ala Gly Ile Tyr Thr Cys Thr
    275                 280                 285

Ala Arg Asn Val Ala Gly Val Leu Arg Ala Asp Phe Pro Leu Ser Val
290                 295                 300

Val Arg Gly His Gln Ala Ala Thr Ser Glu Ser Ser Pro Asn Gly
305                 310                 315                 320

Thr Ala Phe Pro Ala Ala Glu Cys Leu Lys Pro Pro Asp Ser Glu Asp
            325                 330                 335

Cys Gly Glu Glu Gln Thr Arg Trp His Phe Asp Ala Gln Ala Asn Asn
            340                 345                 350

Cys Leu Thr Phe Thr Phe Gly His Cys His Arg Asn Leu Asn His Phe
            355                 360                 365

Glu Thr Tyr Glu Ala Cys Met Leu Ala Cys Met Ser Gly Pro Leu Ala
            370                 375                 380
```

-continued

```
Ala Cys Ser Leu Pro Ala Leu Gln Gly Pro Cys Lys Ala Tyr Ala Pro
385                 390                 395                 400

Arg Trp Ala Tyr Asn Ser Gln Thr Gly Gln Cys Gln Ser Phe Val Tyr
            405                 410                 415

Gly Gly Cys Glu Gly Asn Gly Asn Asn Phe Glu Ser Arg Glu Ala Cys
        420                 425                 430

Glu Glu Ser Cys Pro Phe Pro Arg Gly Asn Gln Arg Cys Arg Ala Cys
    435                 440                 445

Lys Pro Arg Gln Lys Leu Val Thr Ser Phe Cys Arg Ser Asp Phe Val
450                 455                 460

Ile Leu Gly Arg Val Ser Glu Leu Thr Glu Glu Pro Asp Ser Gly Arg
465                 470                 475                 480

Ala Leu Val Thr Val Asp Glu Val Leu Lys Asp Glu Lys Met Gly Leu
            485                 490                 495

Lys Phe Leu Gly Gln Glu Pro Leu Glu Val Thr Leu Leu His Val Asp
        500                 505                 510

Trp Ala Cys Pro Cys Pro Asn Val Thr Val Ser Glu Met Pro Leu Ile
    515                 520                 525

Ile Met Gly Glu Val Asp Gly Gly Met Ala Met Leu Arg Pro Asp Ser
530                 535                 540

Phe Val Gly Ala Ser Ser Ala Arg Arg Val Arg Lys Leu Arg Glu Val
545                 550                 555                 560

Met His Lys Lys Thr Cys Asp Val Leu Lys Glu Phe Leu Gly Leu His
            565                 570                 575

<210> SEQ ID NO 169
<211> LENGTH: 542
<212> TYPE: PRT
<213> ORGANISM: Homo sapiens

<400> SEQUENCE: 169

Leu Pro Pro Ile Arg Tyr Ser His Ala Gly Ile Cys Pro Asn Asp Met
1               5                   10                  15

Asn Pro Asn Leu Trp Val Asp Ala Gln Ser Thr Cys Arg Arg Glu Cys
            20                  25                  30

Glu Thr Asp Gln Glu Cys Glu Thr Tyr Glu Lys Cys Cys Pro Asn Val
        35                  40                  45

Cys Gly Thr Lys Ser Cys Val Ala Ala Arg Tyr Met Asp Val Lys Gly
    50                  55                  60

Lys Lys Gly Pro Val Gly Met Pro Lys Glu Ala Thr Cys Asp His Phe
65                  70                  75                  80

Met Cys Leu Gln Gln Gly Ser Glu Cys Asp Ile Trp Asp Gly Gln Pro
            85                  90                  95

Val Cys Lys Cys Lys Asp Arg Cys Glu Lys Glu Pro Ser Phe Thr Cys
        100                 105                 110

Ala Ser Asp Gly Leu Thr Tyr Tyr Asn Arg Cys Tyr Met Asp Ala Glu
    115                 120                 125

Ala Cys Ser Lys Gly Ile Thr Leu Ala Val Val Thr Cys Arg Tyr His
130                 135                 140

Phe Thr Trp Pro Asn Thr Ser Pro Pro Pro Glu Thr Thr Met His
145                 150                 155                 160

Pro Thr Thr Ala Ser Pro Glu Thr Pro Glu Leu Asp Met Ala Ala Pro
            165                 170                 175

Ala Leu Leu Asn Asn Pro Val His Gln Ser Val Thr Met Gly Glu Thr
        180                 185                 190
```

Val Ser Phe Leu Cys Asp Val Gly Arg Pro Arg Pro Glu Ile Thr
        195                 200                 205

Trp Glu Lys Gln Leu Glu Asp Arg Glu Asn Val Val Met Arg Pro Asn
    210                 215                 220

His Val Arg Gly Asn Val Val Thr Asn Ile Ala Gln Leu Val Ile
225                 230                 235                 240

Tyr Asn Ala Gln Leu Gln Asp Ala Gly Ile Tyr Thr Cys Thr Ala Arg
                245                 250                 255

Asn Val Ala Gly Val Leu Arg Ala Asp Phe Pro Leu Ser Val Val Arg
                260                 265                 270

Gly His Gln Ala Ala Thr Ser Glu Ser Pro Asn Gly Thr Ala
                275                 280                 285

Phe Pro Ala Ala Glu Cys Leu Lys Pro Pro Asp Ser Glu Asp Cys Gly
            290                 295                 300

Glu Glu Gln Thr Arg Trp His Phe Asp Ala Gln Ala Asn Asn Cys Leu
305                 310                 315                 320

Thr Phe Thr Phe Gly His Cys His Arg Asn Leu Asn His Phe Glu Thr
                325                 330                 335

Tyr Glu Ala Cys Met Leu Ala Cys Met Ser Gly Pro Leu Ala Ala Cys
                340                 345                 350

Ser Leu Pro Ala Leu Gln Gly Pro Cys Lys Ala Tyr Ala Pro Arg Trp
            355                 360                 365

Ala Tyr Asn Ser Gln Thr Gly Gln Cys Gln Ser Phe Val Tyr Gly Gly
    370                 375                 380

Cys Glu Gly Asn Gly Asn Asn Phe Glu Ser Arg Glu Ala Cys Glu Glu
385                 390                 395                 400

Ser Cys Pro Phe Pro Arg Gly Asn Gln Arg Cys Arg Ala Cys Lys Pro
                405                 410                 415

Arg Gln Lys Leu Val Thr Ser Phe Cys Arg Ser Asp Phe Val Ile Leu
                420                 425                 430

Gly Arg Val Ser Glu Leu Thr Glu Glu Pro Asp Ser Gly Arg Ala Leu
            435                 440                 445

Val Thr Val Asp Glu Val Leu Lys Asp Glu Lys Met Gly Leu Lys Phe
    450                 455                 460

Leu Gly Gln Glu Pro Leu Glu Val Thr Leu Leu His Val Asp Trp Ala
465                 470                 475                 480

Cys Pro Cys Pro Asn Val Thr Val Ser Glu Met Pro Leu Ile Ile Met
                485                 490                 495

Gly Glu Val Asp Gly Met Ala Met Leu Arg Pro Asp Ser Phe Val
            500                 505                 510

Gly Ala Ser Ser Ala Arg Arg Val Arg Lys Leu Arg Glu Val Met His
            515                 520                 525

Lys Lys Thr Cys Asp Val Leu Lys Glu Phe Leu Gly Leu His
    530                 535                 540

<210> SEQ ID NO 170
<211> LENGTH: 65
<212> TYPE: PRT
<213> ORGANISM: Homo sapiens

<400> SEQUENCE: 170

Cys Asp His Phe Met Cys Leu Gln Gln Gly Ser Glu Cys Asp Ile Trp
1               5                   10                  15

Asp Gly Gln Pro Val Cys Lys Cys Lys Asp Arg Cys Glu Lys Glu Pro

Ser Phe Thr Cys Ala Ser Asp Gly Leu Thr Tyr Tyr Asn Arg Cys Tyr
                35                  40                  45

Met Asp Ala Glu Ala Cys Ser Lys Gly Ile Thr Leu Ala Val Val Thr
        50                  55                  60

Cys
65

<210> SEQ ID NO 171
<211> LENGTH: 571
<212> TYPE: PRT
<213> ORGANISM: Mus musculus

<400> SEQUENCE: 171

Met Cys Ala Pro Gly Tyr His Arg Phe Trp Phe His Trp Gly Leu Leu
1               5                   10                  15

Leu Leu Leu Leu Leu Glu Ala Pro Leu Arg Gly Leu Ala Leu Pro Pro
                20                  25                  30

Ile Arg Tyr Ser His Ala Gly Ile Cys Pro Asn Asp Met Asn Pro Asn
                35                  40                  45

Leu Trp Val Asp Ala Gln Ser Thr Cys Lys Arg Glu Cys Glu Thr Asp
        50                  55                  60

Gln Glu Cys Glu Thr Tyr Glu Lys Cys Cys Pro Asn Val Cys Gly Thr
65                  70                  75                  80

Lys Ser Cys Val Ala Ala Arg Tyr Met Asp Val Lys Gly Lys Lys Gly
                85                  90                  95

Pro Val Gly Met Pro Lys Glu Ala Thr Cys Asp His Phe Met Cys Leu
                100                 105                 110

Gln Gln Gly Ser Glu Cys Asp Ile Trp Asp Gly Gln Pro Val Cys Lys
            115                 120                 125

Cys Lys Asp Arg Cys Glu Lys Glu Pro Ser Phe Thr Cys Ala Ser Asp
        130                 135                 140

Gly Leu Thr Tyr Tyr Asn Arg Cys Phe Met Asp Ala Glu Ala Cys Ser
145                 150                 155                 160

Lys Gly Ile Thr Leu Ser Val Val Thr Cys Arg Tyr His Phe Thr Trp
                165                 170                 175

Pro Asn Thr Ser Pro Pro Pro Glu Thr Thr Val His Pro Thr Thr
                180                 185                 190

Ala Ser Pro Glu Thr Leu Gly Leu Asp Met Ala Ala Pro Ala Leu Leu
            195                 200                 205

Asn His Pro Val His Gln Ser Val Thr Val Gly Glu Thr Val Ser Phe
        210                 215                 220

Leu Cys Asp Val Val Gly Arg Pro Arg Pro Glu Leu Thr Trp Glu Lys
225                 230                 235                 240

Gln Leu Glu Asp Arg Glu Asn Val Val Met Arg Pro Asn His Val Arg
                245                 250                 255

Gly Asn Val Val Val Thr Asn Ile Ala Gln Leu Val Ile Tyr Asn Val
                260                 265                 270

Gln Pro Gln Asp Ala Gly Ile Tyr Thr Cys Thr Ala Arg Asn Val Ala
            275                 280                 285

Gly Val Leu Arg Ala Asp Phe Pro Leu Ser Val Val Arg Gly Gly Gln
        290                 295                 300

Ala Arg Ala Thr Ser Glu Ser Ser Leu Asn Gly Thr Ala Phe Pro Ala
305                 310                 315                 320

-continued

Thr Glu Cys Leu Lys Pro Pro Asp Ser Glu Asp Cys Gly Glu Glu Gln
                325                 330                 335

Thr Arg Trp His Phe Asp Ala Gln Ala Asn Asn Cys Leu Thr Phe Thr
            340                 345                 350

Phe Gly His Cys His His Asn Leu Asn His Phe Glu Thr Tyr Glu Ala
        355                 360                 365

Cys Met Leu Ala Cys Met Ser Gly Pro Leu Ala Ile Cys Ser Leu Pro
    370                 375                 380

Ala Leu Gln Gly Pro Cys Lys Ala Tyr Val Pro Arg Trp Ala Tyr Asn
385                 390                 395                 400

Ser Gln Thr Gly Leu Cys Gln Ser Phe Val Tyr Gly Gly Cys Glu Gly
                405                 410                 415

Asn Gly Asn Asn Phe Glu Ser Arg Glu Ala Cys Glu Glu Ser Cys Pro
            420                 425                 430

Phe Pro Arg Gly Asn Gln His Cys Arg Ala Cys Lys Pro Arg Gln Lys
        435                 440                 445

Leu Val Thr Ser Phe Cys Arg Ser Asp Phe Val Ile Leu Gly Arg Val
    450                 455                 460

Ser Glu Leu Thr Glu Glu Gln Asp Ser Gly Arg Ala Leu Val Thr Val
465                 470                 475                 480

Asp Glu Val Leu Lys Asp Glu Lys Met Gly Leu Lys Phe Leu Gly Arg
                485                 490                 495

Glu Pro Leu Glu Val Thr Leu Leu His Val Asp Trp Thr Cys Pro Cys
            500                 505                 510

Pro Asn Val Thr Val Gly Glu Thr Pro Leu Ile Ile Met Gly Glu Val
        515                 520                 525

Asp Gly Gly Met Ala Met Leu Arg Pro Asp Ser Phe Val Gly Ala Ser
    530                 535                 540

Ser Thr Arg Arg Val Arg Lys Leu Arg Glu Val Met Tyr Lys Lys Thr
545                 550                 555                 560

Cys Asp Val Leu Lys Asp Phe Leu Gly Leu Gln
                565                 570

<210> SEQ ID NO 172
<211> LENGTH: 542
<212> TYPE: PRT
<213> ORGANISM: > Mus musculus

<400> SEQUENCE: 172

Leu Pro Pro Ile Arg Tyr Ser His Ala Gly Ile Cys Pro Asn Asp Met
1               5                   10                  15

Asn Pro Asn Leu Trp Val Asp Ala Gln Ser Thr Cys Lys Arg Glu Cys
            20                  25                  30

Glu Thr Asp Gln Glu Cys Glu Thr Tyr Glu Lys Cys Cys Pro Asn Val
        35                  40                  45

Cys Gly Thr Lys Ser Cys Val Ala Ala Arg Tyr Met Asp Val Lys Gly
    50                  55                  60

Lys Lys Gly Pro Val Gly Met Pro Lys Glu Ala Thr Cys Asp His Phe
65                  70                  75                  80

Met Cys Leu Gln Gln Gly Ser Glu Cys Asp Ile Trp Asp Gly Gln Pro
                85                  90                  95

Val Cys Lys Cys Lys Asp Arg Cys Glu Lys Glu Pro Ser Phe Thr Cys
            100                 105                 110

Ala Ser Asp Gly Leu Thr Tyr Tyr Asn Arg Cys Phe Met Asp Ala Glu
        115                 120                 125

```
Ala Cys Ser Lys Gly Ile Thr Leu Ser Val Val Thr Cys Arg Tyr His
    130                 135                 140

Phe Thr Trp Pro Asn Thr Ser Pro Pro Pro Glu Thr Val His
145                 150                 155                 160

Pro Thr Thr Ala Ser Pro Glu Thr Leu Gly Leu Asp Met Ala Ala Pro
                165                 170                 175

Ala Leu Leu Asn His Pro Val His Gln Ser Val Thr Val Gly Glu Thr
                180                 185                 190

Val Ser Phe Leu Cys Asp Val Val Gly Arg Pro Arg Pro Glu Leu Thr
            195                 200                 205

Trp Glu Lys Gln Leu Glu Asp Arg Glu Asn Val Val Met Arg Pro Asn
    210                 215                 220

His Val Arg Gly Asn Val Val Thr Asn Ile Ala Gln Leu Val Ile
225                 230                 235                 240

Tyr Asn Val Gln Pro Gln Asp Ala Gly Ile Tyr Thr Cys Thr Ala Arg
                245                 250                 255

Asn Val Ala Gly Val Leu Arg Ala Asp Phe Pro Leu Ser Val Val Arg
                260                 265                 270

Gly Gly Gln Ala Arg Ala Thr Ser Glu Ser Ser Leu Asn Gly Thr Ala
            275                 280                 285

Phe Pro Ala Thr Glu Cys Leu Lys Pro Pro Asp Ser Glu Asp Cys Gly
    290                 295                 300

Glu Glu Gln Thr Arg Trp His Phe Asp Ala Gln Ala Asn Asn Cys Leu
305                 310                 315                 320

Thr Phe Thr Phe Gly His Cys His His Asn Leu Asn His Phe Glu Thr
                325                 330                 335

Tyr Glu Ala Cys Met Leu Ala Cys Met Ser Gly Pro Leu Ala Ile Cys
            340                 345                 350

Ser Leu Pro Ala Leu Gln Gly Pro Cys Lys Ala Tyr Val Pro Arg Trp
    355                 360                 365

Ala Tyr Asn Ser Gln Thr Gly Leu Cys Gln Ser Phe Val Tyr Gly Gly
                370                 375                 380

Cys Glu Gly Asn Gly Asn Asn Phe Glu Ser Arg Glu Ala Cys Glu Glu
385                 390                 395                 400

Ser Cys Pro Phe Pro Arg Gly Asn Gln His Cys Arg Ala Cys Lys Pro
                405                 410                 415

Arg Gln Lys Leu Val Thr Ser Phe Cys Arg Ser Asp Phe Val Ile Leu
                420                 425                 430

Gly Arg Val Ser Glu Leu Thr Glu Glu Gln Asp Ser Gly Arg Ala Leu
            435                 440                 445

Val Thr Val Asp Glu Val Leu Lys Asp Glu Lys Met Gly Leu Lys Phe
    450                 455                 460

Leu Gly Arg Glu Pro Leu Glu Val Thr Leu Leu His Val Asp Trp Thr
465                 470                 475                 480

Cys Pro Cys Pro Asn Val Thr Val Gly Glu Thr Pro Leu Ile Ile Met
                485                 490                 495

Gly Glu Val Asp Gly Gly Met Ala Met Leu Arg Pro Asp Ser Phe Val
            500                 505                 510

Gly Ala Ser Ser Thr Arg Arg Val Arg Lys Leu Arg Glu Val Met Tyr
            515                 520                 525

Lys Lys Thr Cys Asp Val Leu Lys Asp Phe Leu Gly Leu Gln
    530                 535                 540
```

<210> SEQ ID NO 173
<211> LENGTH: 366
<212> TYPE: PRT
<213> ORGANISM: Homo sapiens

<400> SEQUENCE: 173

Met Trp Pro Leu Trp Leu Cys Trp Ala Leu Trp Val Leu Pro Leu Ala
1               5                   10                  15

Gly Pro Gly Ala Ala Leu Thr Glu Glu Gln Leu Leu Gly Ser Leu Leu
            20                  25                  30

Arg Gln Leu Gln Leu Ser Glu Val Pro Val Leu Asp Arg Ala Asp Met
        35                  40                  45

Glu Lys Leu Val Ile Pro Ala His Val Arg Ala Gln Tyr Val Val Leu
    50                  55                  60

Leu Arg Arg Ser His Gly Asp Arg Ser Arg Gly Lys Arg Phe Ser Gln
65                  70                  75                  80

Ser Phe Arg Glu Val Ala Gly Arg Phe Leu Ala Ser Glu Ala Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Pro Arg Ser Ala Gln Ala Arg
    130                 135                 140

Val Thr Val Glu Trp Leu Arg Val Arg Asp Asp Gly Ser Asn Arg Thr
145                 150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Leu Ala Ser Gly Ala His Lys Leu Val Arg Phe Ala Ser Gln
    210                 215                 220

Gly Ala Pro Ala Gly Leu Gly Glu Pro Gln Leu Glu Leu His Thr Leu
225                 230                 235                 240

Asp Leu Arg Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
            260                 265                 270

Gln Gly Met Lys Trp Ala Lys Asn Trp Val Leu Glu Pro Pro Gly Phe
        275                 280                 285

Leu Ala Tyr Glu Cys Val Gly Thr Cys Gln Gln Pro Pro Glu Ala Leu
    290                 295                 300

Ala Phe Asn Trp Pro Phe Leu Gly Pro Arg Gln Cys Ile Ala Ser Glu
305                 310                 315                 320

Thr Ala Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
            340                 345                 350

Cys Ala Ser Asp Gly Ala Leu Val Pro Arg Arg Leu Gln Pro
        355                 360                 365

<210> SEQ ID NO 174

```
<211> LENGTH: 366
<212> TYPE: PRT
<213> ORGANISM: Homo sapiens

<400> SEQUENCE: 174

Met Gln Pro Leu Trp Leu Cys Trp Ala Leu Trp Val Leu Pro Leu Ala
1               5                   10                  15

Ser Pro Gly Ala Ala Leu Thr Gly Glu Gln Leu Leu Gly Ser Leu Leu
            20                  25                  30

Arg Gln Leu Gln Leu Lys Glu Val Pro Thr Leu Asp Arg Ala Asp Met
        35                  40                  45

Glu Glu Leu Val Ile Pro Thr His Val Arg Ala Gln Tyr Val Ala Leu
50                  55                  60

Leu Gln Arg Ser His Gly Asp Arg Ser Arg Gly Lys Arg Phe Ser Gln
65                  70                  75                  80

Ser Phe Arg Glu Val Ala Gly Arg Phe Leu Ala Leu Glu Ala Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Pro Arg Ser Ala Arg Ala Arg
130                 135                 140

Val Thr Val Glu Trp Leu Arg Val Arg Asp Asp Gly Ser Asn Arg Thr
145                 150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Leu Ala Ser Gly Ala His Lys Leu Val Arg Phe Ala Ser Gln
210                 215                 220

Gly Ala Pro Ala Gly Leu Gly Glu Pro Gln Leu Glu Leu His Thr Leu
225                 230                 235                 240

Asp Leu Gly Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
            260                 265                 270

Gln Gly Met Lys Trp Ala Glu Asn Trp Val Leu Glu Pro Pro Gly Phe
        275                 280                 285

Leu Ala Tyr Glu Cys Val Gly Thr Cys Arg Gln Pro Pro Glu Ala Leu
        290                 295                 300

Ala Phe Lys Trp Pro Phe Leu Gly Pro Arg Gln Cys Ile Ala Ser Glu
305                 310                 315                 320

Thr Asp Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
            340                 345                 350

Cys Ala Ser Asp Gly Ala Leu Val Pro Arg Arg Leu Gln Pro
        355                 360                 365

<210> SEQ ID NO 175
<211> LENGTH: 267
<212> TYPE: PRT
```

<213> ORGANISM: Homo sapiens

<400> SEQUENCE: 175

```
Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
            20                  25                  30

Val Leu Leu Pro Arg Asn Gln Arg Glu Leu Pro Thr Gly Asn His Glu
        35                  40                  45

Glu Ala Glu Glu Lys Pro Asp Leu Phe Val Ala Val Pro His Leu Val
50                  55                  60

Ala Thr Ser Pro Ala Gly Glu Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
            100                 105                 110

Ile Gln Pro Ile Asp Gly Met Lys Met Glu Lys Ser Pro Leu Arg Glu
        115                 120                 125

Glu Ala Lys Lys Phe Trp His His Phe Met Phe Arg Lys Thr Pro Ala
130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205

Cys Leu Pro Ala Lys Phe Thr Thr Met His Leu Pro Leu Asn Cys Thr
210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala
            260                 265
```

<210> SEQ ID NO 176
<211> LENGTH: 189
<212> TYPE: PRT
<213> ORGANISM: Homo sapiens

<400> SEQUENCE: 176

```
Met Leu Leu Gly Gln Leu Ser Thr Leu Leu Cys Leu Leu Ser Gly Ala
1               5                   10                  15

Leu Pro Thr Gly Ser Gly Arg Pro Glu Pro Gln Ser Pro Arg Pro Gln
            20                  25                  30

Ser Trp Ala Ala Ala Asn Gln Thr Trp Ala Leu Gly Pro Gly Ala Leu
        35                  40                  45

Pro Pro Leu Val Pro Ala Ser Ala Leu Gly Ser Trp Lys Ala Phe Leu
50                  55                  60

Gly Leu Gln Lys Ala Arg Gln Leu Gly Met Gly Arg Leu Gln Arg Gly
65                  70                  75                  80

Gln Asp Glu Val Ala Ala Val Thr Leu Pro Leu Asn Pro Gln Glu Val
```

```
            85                  90                  95
Ile Gln Gly Met Cys Lys Ala Val Pro Phe Val Gln Val Phe Ser Arg
            100                 105                 110

Pro Gly Cys Ser Ala Ile Arg Leu Arg Asn His Leu Cys Phe Gly His
            115                 120                 125

Cys Ser Ser Leu Tyr Ile Pro Gly Ser Asp Pro Thr Pro Leu Val Leu
            130                 135                 140

Cys Asn Ser Cys Met Pro Ala Arg Lys Arg Trp Ala Pro Val Val Leu
145                 150                 155                 160

Trp Cys Leu Thr Gly Ser Ser Ala Ser Arg Arg Val Lys Ile Ser
                165                 170                 175

Thr Met Leu Ile Glu Gly Cys His Cys Ser Pro Lys Ala
            180                 185

<210> SEQ ID NO 177
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
            115                 120                 125

Pro Glu Leu Leu Gly Gly Pro Ser Val Phe Leu Phe Pro Pro Lys Pro
            130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Ala
            210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255
```

```
Lys Asn Gln Val Ser Leu Thr Cys Leu Val Lys Gly Phe Tyr Pro Ser
                260                 265                 270

Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr
        290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
                340

<210> SEQ ID NO 178
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                245                 250                 255

Thr Ile Ser Lys Ala Lys Gly Gln Pro Arg Glu Pro Gln Val Tyr Thr
            260                 265                 270
```

```
Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 179
<211> LENGTH: 1114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta     120
attgggaaaa agacagaacc aatcaaactg gtgttgaacc gttatggt gacaaagata      180 aacggcggca ttgttttgct acctggaaga atatttctgg ttccattgaa tagtgaaaca     240
aggttgttgg ctggatgata tcaactgcta tgacaggact gattgtgtag aaaaaaaaga     300
cagccctgaa gtatatttct gttgctgtga gggcaatatg tgtaatgaaa gttttctta     360 ttttccggag atggaagtca cacagcccac ttcaaatcca gttacaccta agccacccac     420
cggtggtgga actcacacat gcccaccgtg cccagcacct gaactcctgg ggggaccgtc     480
agtcttcctc ttccccccaa aacccaagga caccctcatg atctcccgga cccctgaggt     540
cacatgcgtg gtggtggacg tgagccacga agaccctgag gtcaagttca actggtacgt     600
ggacggcgtg gaggtgcata atgccaagac aaagccgcgg gaggagcagt acaacagcac     660
gtaccgtgtg gtcagcgtcc tcaccgtcct gcaccaggac tggctgaatg caaggagta     720 caagtgcaag gtctccaaca aagccctccc agtccccatc gagaaaacca tctccaaagc     780
caaagggcag ccccgagaac cacaggtgta caccctgccc ccatcccggg aggagatgac     840
caagaaccag gtcagcctga cctgcctggt caaaggcttc tatcccagcg atcgccgt      900 ggagtgggag agcaatgggc agccggagaa caactacaag accacgcctc ccgtgctgga     960
ctccgacggc tccttcttcc tctatagcaa gctcaccgtg gacaagagca ggtggcagca    1020
ggggaacgtc ttctcatgct ccgtgatgca tgaggctctg cacaaccact acacgcagaa    1080
gagcctctcc ctgtctccgg gtaaatgaga attc                              1114

<210> SEQ ID NO 180
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 180

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
                100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 181
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

```
Gly Arg Gly Glu Ala Glu Thr Arg Glu Cys Ile Tyr Tyr Asn Ala Asn
1               5                   10                  15
```

Trp Glu Leu Glu Arg Thr Asn Gln Ser Gly Leu Glu Arg Cys Gly Glu
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 182
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
            210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
            290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 183
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120

-continued

```
aactgggagc tggagcgcac caaccagagc ggcctggagc gctgcgaagg cgagcaggac    180 agcggctgc actgctacgc ctcctggcgc aacagctctg gcaccatcga gctcgtgaag    240
aagggctgct ggctagatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc caccccgac agcccccacc     420 ggtggtggaa ctcacacatg cccaccgtgc ccagcacctg aactcctggg ggaccgtca     480 gtcttcctct cccccaaa acccaaggac accctcatga tctcccggac ccctgaggtc      540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gtccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107
```

<210> SEQ ID NO 184
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

```
Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Leu
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
```

```
                180                 185                 190
Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
            210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 185
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
atggatgcaa tgaagagagg ctctgctgt gtgctgctgc tgtgtggagc agtcttcgtt      60
tcgcccggcg ccgctgagac acgggagtgc atctactaca cgccaactg ggagctggag    120 cgcaccaacc agagcggcct ggagcgctgc gaaggcgagc aggacaagcg gctgcactgc    180
tacgcctcct ggcgcaacag ctctggcacc atcgagctcg tgaagaaggg ctgctggcta    240
gatgacttca actgctacga taggcaggag tgtgtggcca ctgaggagaa ccccccaggtg    300 tacttctgct gctgtgaagg caacttctgc aacgagcgct tcactcattt gccagaggct    360
gggggcccgg aagtcacgta cgagccaccc ccgacaggtg gtggaactca cacatgccca    420
ccgtgcccag cacctgaact cctgggggga ccgtcagtct tcctcttccc cccaaaaccc    480
aaggacaccc tcatgatctc ccggacccct gaggtcacat gcgtggtggt ggacgtgagc    540
cacgaagacc ctgaggtcaa gttcaactgg tacgtggacg gcgtggaggt gcataatgcc    600
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag gcagccccg agaaccacag    780 gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga acgtcttctc atgctccgtg   1020
```

-continued

| | |
|---|---|
| atgcatgagg ctctgcacaa ccactacacg cagaagagcc tctccctgtc cccgggtaaa | 1080 |
| tga | 1083 |

<210> SEQ ID NO 186
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 186

| | |
|---|---|
| atggatgcaa tgaagagagg ctctgctgt gtgctgctgc tgtgtggagc agtcttcgtt | 60 |
| tcgcccggcg ccgccgaaac ccgcgaatgt atttattaca atgctaattg ggaactcgaa | 120 |
| cggacgaacc aatccgggct cgaacggtgt gaggggaac aggataaacg cctccattgc | 180 |
| tatgcgtcgt ggaggaactc ctccgggacg attgaactgg tcaagaaagg gtgctggctg | 240 |
| gacgatttca attgttatga ccgccaggaa tgtgtcgcga ccgaagagaa tccgcaggtc | 300 |
| tatttctgtt gttgcgaggg gaatttctgt aatgaacggt ttacccacct ccccgaagcc | 360 |
| ggcgggcccg aggtgaccta tgaaccccg cccaccggtg gtggaactca cacatgccca | 420 |
| ccgtgcccag cacctgaact cctgggggga ccgtcagtct tcctcttccc cccaaaaccc | 480 |
| aaggacaccc tcatgatctc ccggacccct gaggtcacat gcgtggtggt ggacgtgagc | 540 |
| cacgaagacc ctgaggtcaa gttcaactgg tacgtggacg gcgtggaggt gcataatgcc | 600 |
| aagacaaagc cgcggggagga gcagtacaac agcacgtacc gtgtggtcag cgtcctcacc | 660 |
| gtcctgcacc aggactggct gaatggcaag gagtacaagt gcaaggtctc caacaaagcc | 720 |
| ctcccagccc ccatcgagaa aaccatctcc aaagccaaag gcagccccg agaaccacag | 780 |
| gtgtacaccc tgcccccatc ccgggaggag atgaccaaga accaggtcag cctgacctgc | 840 |
| ctggtcaaag gcttctatcc cagcgacatc gccgtggagt gggagagcaa tgggcagccg | 900 |
| gagaacaact acaagaccac gcctcccgtg ctggactccg acggctcctt cttcctctat | 960 |
| agcaagctca ccgtggacaa gagcaggtgg cagcagggga acgtcttctc atgctccgtg | 1020 |
| atgcatgagg ctctgcacaa ccactacacg cagaagagcc tctccctgtc cccgggtaaa | 1080 |
| tga | 1083 |

<210> SEQ ID NO 187
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

```
Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
        100                 105                 110

Thr Cys Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
        210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 188
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
```

```
                    100                 105                 110

Ala Pro Thr Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
        130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
            165                 170                 175

Gly Val Glu Val His Asn Ala Lys Thr Lys Pro Arg Glu Glu Gln Tyr
        180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
        210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
        290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 189
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110
```

Ala Pro Thr
        115

<210> SEQ ID NO 190
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

```
Leu His Asn His Tyr Thr Gln Lys Ser Leu Ser Leu Ser Pro Gly Lys
        355                 360                 365
```

<210> SEQ ID NO 191
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

```
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct gggacgatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc acccccgac agcccccacc      420
ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gtccccatcg agaaaaccat ctccaaagcc     780
aaagggcagc cccgagaacc acaggtgtac accctgcccc catcccggga ggagatgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctggac     960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaatga                                         1107
```

<210> SEQ ID NO 192
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

```
Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Asp
65                  70                  75                  80
```

Asp Asp Phe Asn Cys Tyr Asp Arg Gln Glu Cys Val Ala Thr Glu Glu
                85                  90                  95

Asn Pro Gln Val Tyr Phe Cys Cys Glu Gly Asn Phe Cys Asn Glu
            100                 105                 110

Arg Phe Thr His Leu Pro Glu Ala Gly Gly Pro Glu Val Thr Tyr Glu
            115                 120                 125

Pro Pro Pro Thr Gly Gly Thr His Thr Cys Pro Pro Cys Pro Ala
130             135                 140

Pro Glu Leu Leu Gly Gly Pro Ser Val Phe Leu Phe Pro Pro Lys Pro
145             150                 155                 160

Lys Asp Thr Leu Met Ile Ser Arg Thr Pro Glu Val Thr Cys Val Val
            165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
            210                 215                 220

Asp Trp Leu Asn Gly Lys Glu Tyr Lys Cys Lys Val Ser Asn Lys Ala
225             230                 235                 240

Leu Pro Ala Pro Ile Glu Lys Thr Ile Ser Lys Ala Lys Gly Gln Pro
            245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
290             295                 300

Lys Thr Thr Pro Pro Val Leu Asp Ser Asp Gly Ser Phe Phe Leu Tyr
305             310                 315                 320

Ser Lys Leu Thr Val Asp Lys Ser Arg Trp Gln Gln Gly Asn Val Phe
            325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 193
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
            35                  40                  45

Val Lys Lys Gly Cys Trp Asp Asp Asp Phe Asn Cys Tyr Asp Arg Gln
            50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
        210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 194
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
atggatgcaa tgaagagagg gctctgctgt gtgctgctgc tgtgtggagc agtcttcgtt    60
tcgcccggcg ccgctgagac acgggagtgc atctactaca acgccaactg ggagctggag   120
cgcaccaacc agagcggcct ggagcgctgc gaaggcgagc aggacaagcg gctgcactgc   180
tacgcctcct ggcgcaacag ctctggcacc atcgagctcg tgaagaaggg ctgctgggac   240
gatgacttca actgctacga taggcaggag tgtgtggcca ctgaggagaa cccccaggtg   300
tacttctgct gctgtgaagg caacttctgc aacgagcgct tcactcattt gccagaggct   360
gggggcccgg aagtcacgta cgagccaccc ccgacaggtg gtggaactca cacatgccca   420
ccgtgcccag cacctgaact cctgggggga ccgtcagtct tcctcttccc cccaaaaccc   480
aaggacaccc tcatgatctc ccggacccct gaggtcacat gcgtggtggt ggacgtgagc   540
cacgaagacc ctgaggtcaa gttcaactgg tacgtggacg gcgtggaggt gcataatgcc   600

```
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag gcagccccg agaaccacag     780 gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga cgtcttctc atgctccgtg    1020 atgcatgagg ctctgcacaa ccactacacg cagaagagcc tctccctgtc cccgggtaaa   1080
tga                                                                 1083

<210> SEQ ID NO 195
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
atggatgcaa tgaagagagg gctctgctgt gtgctgctgc tgtgtggagc agtcttcgtt     60
tcgcccggcg ccgccgaaac ccgcgaatgt atttattaca atgctaattg ggaactcgaa    120
cggacgaacc aatccgggct cgaacggtgt gaggggggaac aggataaacg cctccattgc   180
tatgcgtcgt ggaggaactc ctccgggacg attgaactgg tcaagaaagg gtgctgggac    240
gacgatttca attgttatga ccgccaggaa tgtgtcgcga ccgaagagaa tccgcaggtc    300
tatttctgtt gttgcgaggg gaatttctgt aatgaacggt ttacccacct ccccgaagcc    360
ggcgggcccg aggtgaccta tgaaccccg cccaccggtg gtggaactca cacatgccca    420
ccgtgcccag cacctgaact cctgggggga ccgtcagtct tcctcttccc cccaaaaccc    480
aaggacaccc tcatgatctc ccggacccct gaggtcacat gcgtggtggt ggacgtgagc    540
cacgaagacc ctgaggtcaa gttcaactgg tacgtgacg gcgtggaggt gcataatgcc     600
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag gcagccccg agaaccacag     780 gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga cgtcttctc atgctccgtg    1020 atgcatgagg ctctgcacaa ccactacacg cagaagagcc tctccctgtc cccgggtaaa   1080
tga                                                                 1083

<210> SEQ ID NO 196
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196
```

-continued

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Asn Pro Gln Val
65                  70                  75                  80

Tyr Phe Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 197
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Asp Asp Phe Asn
        50                  55                  60

Cys Tyr Asp Arg Gln Glu Cys Val Ala Thr Glu Asn Pro Gln Val
65                  70                  75                  80

Tyr Phe Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 198
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Gly Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Ala Gly Asp Gln Gly Ser
        115                 120                 125

Gly Ala Leu Trp Leu Cys Leu Glu Gly Pro Ala His Glu Thr Gly Gly
130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 199
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Asp Ala Met Lys Arg Gly Leu Cys Cys Val Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Lys Glu Met Thr Lys Asn Gln Val Ser Leu Thr Cys
        275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Lys
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 200
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide -continued

```
<400> SEQUENCE: 200
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc   120
aactgggagc tggagcgcac caaccagagc ggcctggagc gctgcgaagg cgagcaggac   180
aagcggctgc actgctacgc ctcctggcgc aacagctctg gcaccatcga gctcgtgaag   240
aagggctgct ggctagatga cttcaactgc tacgataggc aggagtgtgt ggccactgag   300
gagaaccccc aggtgtactt ctgctgctgt gaaggcaact tctgcaacga gcgcttcact   360
catttgccag aggctggggg cccggaagtc acgtacgagc cccccgac agccccacc     420 ggtggtggaa ctcacacatg cccaccgtgc ccagcacctg aactcctggg gggaccgtca   480
gtcttcctct tccccccaaa acccaaggac accctcatga tctcccggac ccctgaggtc   540
acatgcgtgg tggtggacgt gagccacgaa gaccctgagg tcaagttcaa ctggtacgtg   600
gacggcgtgg aggtgcataa tgccaagaca aagccgcggg aggagcagta caacagcacg   660
taccgtgtgg tcagcgtcct caccgtcctg caccaggact ggctgaatgg caaggagtac   720
aagtgcaagg tctccaacaa agccctccca gcccccatcg agaaaaccat ctccaaagcc   780
aaagggcagc cccgagaacc acaggtgtac accctgcccc catcccggaa ggagatgacc   840
aagaaccagg tcagcctgac ctgcctggtc aaaggcttct atcccagcga catcgccgtg   900
gagtgggaga gcaatgggca gccggagaac aactacaaga ccacgcctcc cgtgctgaag   960
tccgacggct ccttcttcct ctatagcaag ctcaccgtgg acaagagcag gtggcagcag  1020
gggaacgtct tctcatgctc cgtgatgcat gaggctctgc acaaccacta cacgcagaag  1080
agcctctccc tgtctccggg taaa                                          1104

<210> SEQ ID NO 201
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Gly Asn Phe Cys Asn Glu Arg Phe Thr His
                85                  90                  95

Leu Pro Glu Ala Gly Gly Pro Glu Val Thr Tyr Glu Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
```

```
                145                 150                 155                 160
Asp Val Ser His Glu Asp Pro Glu Val Lys Phe Asn Trp Tyr Val Asp
            165                 170                 175

Gly Val Glu Val His Asn Ala Lys Thr Lys Pro Arg Glu Glu Gln Tyr
        180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Lys Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Lys Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 202
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160
```

Met Ile Ser Arg Thr Pro Glu Val Thr Cys Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly
        355

<210> SEQ ID NO 203
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
atggatgcaa tgaagagagg gctctgctgt gtgctgctgc tgtgtggagc agtcttcgtt      60
tcgcccggcg cctccgggcc ccgggggtc caggctctgc tgtgtgcgtg caccagctgc     120
ctccaggcca actacacgtg tgagacagat ggggcctgca tggtttccat tttcaatctg    180
gatgggatgg agcaccatgt gcgcacctgc atccccaaag tggagctggt ccctgccggg    240
aagcccttct actgcctgag ctcggaggac ctgcgcaaca cccactgctg ctacactgac    300
tactgcaaca ggatcgactt gagggtgccc agtggtcacc tcaaggagcc tgagcacccg    360
tccatgtggg gcccggtgga gaccggtggt ggaactcaca catgcccacc gtgcccagca    420
cctgaactcc tggggggacc gtcagtcttc ctcttccccc caaaacccaa ggacaccctc    480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtacaccctg    780
cccccatccc gggaggagat gaccaagaac caggtcagcc tgacctgcct ggtcaaaggc    840
ttctatccca gcgacatcgc cgtggagtgg gagagcaatg ggcagccgga gaacaactac    900

```
gacaccacgc ctcccgtgct ggactccgac ggctccttct tcctctatag cgacctcacc    960
gtggacaaga gcaggtggca gcaggggaac gtcttctcat gctccgtgat gcatgaggct   1020
ctgcacaacc actacacgca gaagagcctc tccctgtctc cgggt                   1065
```

<210> SEQ ID NO 204
<211> LENGTH: 331
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 204

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Asp Thr Thr Pro Pro Val Leu Asp Ser Asp Gly Ser
        275                 280                 285

Phe Phe Leu Tyr Ser Asp Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
```

<210> SEQ ID NO 205
<211> LENGTH: 368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Cys Arg Glu Glu Met Thr Lys Asn Gln Val Ser Leu Trp Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
             355                 360                 365

<210> SEQ ID NO 206
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

```
<210> SEQ ID NO 207
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
```

<210> SEQ ID NO 208
<211> LENGTH: 332
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 208

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 209
<211> LENGTH: 341

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Asp Thr
        275                 280                 285

Thr Pro Pro Val Leu Asp Ser Asp Gly Ser Phe Phe Leu Tyr Ser Asp
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
            340

<210> SEQ ID NO 210
<211> LENGTH: 1023
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210

```
atggatgcaa tgaagagagg gctctgctgt gtgctgctgc tgtgtggagc agtcttcgtt    60
tcgcccggcg ccggactgaa gtgtgtatgt cttttgtgtg attcttcaaa ctttacctgc   120
caaacagaag gagcatgttg ggcatcagtc atgctaacca atggaaaaga gcaggtgatc   180
aaatcctgtg tctcccttcc agaactgaat gctcaagtct tctgtcatag ttccaacaat   240
gttaccaaaa ccgaatgctg cttcacagat ttttgcaaca acataacact gcaccttcca   300
acagcatcac caaatgcccc aaaacttgga cccatggaga ccggtggtgg aactcacaca   360
tgcccaccgt gcccagcacc tgaactcctg ggggaccgt cagtcttcct cttccccca    420
aaacccaagg acaccctcat gatctcccgg acccctgagg tcacatgcgt ggtggtggac   480
gtgagccacg aagaccctga ggtcaagttc aactggtacg tggacggcgt ggaggtgcat   540
aatgccaaga caaagccgcg ggaggagcag tacaacagca cgtaccgtgt ggtcagcgtc   600
ctcaccgtcc tgcaccagga ctggctgaat ggcaaggagt acaagtgcaa ggtctccaac   660
aaagccctcc cagcccccat cgagaaaacc atctccaaag ccaagggca gccccgagaa   720
ccacaggtgt acaccctgcc cccatcccgg gaggagatga ccaagaacca ggtcagcctg   780
acctgcctgg tcaaaggctt ctatcccagc gacatcgccg tggagtggga gagcaatggg   840
cagccggaga acaactacga caccacgcct cccgtgctgg actccgacgg ctccttcttc   900
ctctatagcg acctcaccgt ggacaagagc aggtggcagc aggggaacgt cttctcatgc   960
tccgtgatgc atgaggctct gcacaaccac tacacgcaga agagcctctc cctgtctccg  1020
ggt                                                                1023
```

<210> SEQ ID NO 211
<211> LENGTH: 317
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

```
Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Thr His Thr
            85                  90                  95

Cys Pro Pro Cys Pro Ala Pro Glu Leu Leu Gly Gly Pro Ser Val Phe
        100                 105                 110

Leu Phe Pro Pro Lys Pro Lys Asp Thr Leu Met Ile Ser Arg Thr Pro
    115                 120                 125

Glu Val Thr Cys Val Val Val Asp Val Ser His Glu Asp Pro Glu Val
        130                 135                 140
```

```
Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Tyr Thr Leu Pro Pro
    210                 215                 220

Ser Arg Glu Glu Met Thr Lys Asn Gln Val Ser Leu Thr Cys Leu Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Asp Thr Thr Pro Pro Val Leu Asp Ser Asp
                260                 265                 270

Gly Ser Phe Phe Leu Tyr Ser Asp Leu Thr Val Asp Lys Ser Arg Trp
            275                 280                 285

Gln Gln Gly Asn Val Phe Ser Cys Ser Val Met His Glu Ala Leu His
    290                 295                 300

Asn His Tyr Thr Gln Lys Ser Leu Ser Leu Ser Pro Gly
305                 310                 315

<210> SEQ ID NO 212
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
```

```
            180                 185                 190
Ser Thr Tyr Arg Val Val Ser Val Leu Thr Val Leu His Gln Asp Trp
            195                 200                 205
Leu Asn Gly Lys Glu Tyr Lys Cys Lys Val Ser Asn Lys Ala Leu Pro
            210                 215                 220
Ala Pro Ile Glu Lys Thr Ile Ser Lys Ala Lys Gly Gln Pro Arg Glu
225                 230                 235                 240
Pro Gln Val Cys Thr Leu Pro Pro Ser Arg Glu Glu Met Thr Lys Asn
                245                 250                 255
Gln Val Ser Leu Ser Cys Ala Val Lys Gly Phe Tyr Pro Ser Asp Ile
                260                 265                 270
Ala Val Glu Trp Glu Ser Asn Gly Gln Pro Glu Asn Asn Tyr Lys Thr
                275                 280                 285
Thr Pro Pro Val Leu Asp Ser Asp Gly Ser Phe Phe Leu Val Ser Lys
            290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly Lys
            340

<210> SEQ ID NO 213
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Leu Lys Cys Val Cys Leu Leu Cys Asp Ser Ser Asn Phe Thr Cys
1               5                   10                  15
Gln Thr Glu Gly Ala Cys Trp Ala Ser Val Met Leu Thr Asn Gly Lys
                20                  25                  30
Glu Gln Val Ile Lys Ser Cys Val Ser Leu Pro Glu Leu Asn Ala Gln
            35                  40                  45
Val Phe Cys His Ser Ser Asn Asn Val Thr Lys Thr Glu Cys Cys Phe
        50                  55                  60
Thr Asp Phe Cys Asn Asn Ile Thr Leu His Leu Pro Thr Ala Ser Pro
65                  70                  75                  80
Asn Ala Pro Lys Leu Gly Pro Met Glu Thr Gly Gly Thr His Thr
                85                  90                  95
Cys Pro Pro Cys Pro Ala Pro Glu Leu Leu Gly Gly Pro Ser Val Phe
            100                 105                 110
Leu Phe Pro Pro Lys Pro Lys Asp Thr Leu Met Ile Ser Arg Thr Pro
        115                 120                 125
Glu Val Thr Cys Val Val Val Asp Val Ser His Glu Asp Pro Glu Val
    130                 135                 140
Lys Phe Asn Trp Tyr Val Asp Gly Val Glu Val His Asn Ala Lys Thr
145                 150                 155                 160
Lys Pro Arg Glu Glu Gln Tyr Asn Ser Thr Tyr Arg Val Val Ser Val
                165                 170                 175
Leu Thr Val Leu His Gln Asp Trp Leu Asn Gly Lys Glu Tyr Lys Cys
            180                 185                 190
```

-continued

```
Lys Val Ser Asn Lys Ala Leu Pro Ala Pro Ile Glu Lys Thr Ile Ser
            195                 200                 205
Lys Ala Lys Gly Gln Pro Arg Glu Pro Gln Val Cys Thr Leu Pro Pro
        210                 215                 220
Ser Arg Glu Glu Met Thr Lys Asn Gln Val Ser Leu Ser Cys Ala Val
225                 230                 235                 240
Lys Gly Phe Tyr Pro Ser Asp Ile Ala Val Glu Trp Glu Ser Asn Gly
                245                 250                 255
Gln Pro Glu Asn Asn Tyr Lys Thr Thr Pro Pro Val Leu Asp Ser Asp
            260                 265                 270
Gly Ser Phe Phe Leu Val Ser Lys Leu Thr Val Asp Lys Ser Arg Trp
        275                 280                 285
Gln Gln Gly Asn Val Phe Ser Cys Ser Val Met His Glu Ala Leu His
    290                 295                 300
Asn His Tyr Thr Gln Lys Ser Leu Ser Leu Ser Pro Gly Lys
305                 310                 315

<210> SEQ ID NO 214
<211> LENGTH: 21
<212> TYPE: PRT
<213> ORGANISM: Apis mellifera

<400> SEQUENCE: 214

Met Lys Phe Leu Val Asn Val Ala Leu Val Phe Met Val Val Tyr Ile
1               5                   10                  15
Ser Tyr Ile Tyr Ala
            20

<210> SEQ ID NO 215
<211> LENGTH: 22
<212> TYPE: PRT
<213> ORGANISM: Unknown
<220> FEATURE:
<223> OTHER INFORMATION: Description of Unknown:
      TPA leader sequence

<400> SEQUENCE: 215

Met Asp Ala Met Lys Arg Gly Leu Cys Cys Val Leu Leu Leu Cys Gly
1               5                   10                  15
Ala Val Phe Val Ser Pro
            20

<210> SEQ ID NO 216
<211> LENGTH: 20
<212> TYPE: PRT
<213> ORGANISM: Unknown
<220> FEATURE:
<223> OTHER INFORMATION: Description of Unknown:
      Native leader sequence

<400> SEQUENCE: 216

Met Gly Ala Ala Ala Lys Leu Ala Phe Ala Val Phe Leu Ile Ser Cys
1               5                   10                  15
Ser Ser Gly Ala
            20

<210> SEQ ID NO 217
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 217

Thr Gly Gly Gly
1

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Gly Gly Gly
1

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Thr Gly Gly Gly Gly
1               5

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Gly Gly Gly Gly
1               5

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Gly Gly Ser
1               5

<210> SEQ ID NO 222
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Gly Gly Gly
1

<210> SEQ ID NO 223
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Gly Gly
1

<210> SEQ ID NO 224
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Gly Gly Ser
1

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 225

His His His His His His
1               5
```

ACTRIIA AND ALK4 POLYPEPTIDES FOR TREATING KIDNEY FIBROSIS, INFLAMMATION AND INJURY

CROSS-REFERENCE TO RELATED APPLICATIONS

This application is a national-stage application of International Application No. PCT/US2017/055199, filed Oct. 4, 2017, which claims the benefit of U.S. Provisional Application No. 62/404,603, filed on Oct. 5, 2016. The entire contents of these applications are hereby incorporated herein by this reference in their entireties.

SEQUENCE LISTING

The instant application contains a Sequence Listing which has been submitted electronically in ASCII format and is hereby incorporated by reference in its entirety. Said ASCII copy, created on Oct. 19, 2017, is named APH_002_01_SL.txt and is 391,809 bytes in size.

BACKGROUND OF THE INVENTION

Kidney diseases include a range of conditions that can lead to loss of kidney function, and, in some cases, can be fatal. Normally-functioning kidneys filter wastes and excess fluids from the blood, which are then excreted in urine. When chronic kidney disease reaches an advanced stage, dangerous levels of fluid, electrolytes and wastes can build up in the bloodstream. If left untreated, kidney disease can progress to end-stage kidney failure, which is fatal without artificial filtering (dialysis) or a kidney transplant. Thus, there is a high, unmet need for effective therapies for treating kidney disease.

SUMMARY OF THE INVENTION

In part, the present disclosure relates to methods of treating kidney diseases or kidney-related disease or disorders, comprising administering to a patient in need thereof an effective amount of an activin and/or GDF antagonist (inhibitor), or combination of activin and/or GDF antagonists (inhibitors). In certain aspects, the disclosure relates to methods of reducing the progression rate of kidney disease, comprising administering to a patient in need thereof an effective amount of an activin and/or GDF antagonist, or combination of activin and/or GDF antagonists. In certain aspects, the disclosure relates to methods of reducing the severity of kidney disease, comprising administering to a patient in need thereof an effective amount of an activin and/or GDF antagonist, or combination of activin and/or GDF antagonists. In certain aspects, the disclosure relates to methods of reducing the frequency of kidney-related disease events (e.g., kidney tissue damage, fibrosis, and/or inflammation), comprising administering to a patient in need thereof an effective amount of an activin and/or GDF antagonist, or combination of activin and/or GDF antagonists. In certain aspects, the disclosure relates to methods of treating one or more complications (e.g., kidney tissue damage, fibrosis, and/or inflammation) of kidney disease, comprising administering to a patient in need thereof an effective amount of an activin and/or GDF antagonist, or combination of activin and/or GDF antagonists. In certain aspects, the disclosure relates to methods of preventing one or more complication of kidney disease, comprising administering to a patient in need thereof an effective amount an activin and/or GDF antagonist, or combination of activin and/or GDF antagonists. In certain aspects, the disclosure relates to methods of reducing the progression rate of one or more complication of kidney disease, comprising administering to a patient in need thereof an effective amount an activin and/or GDF antagonist, or combination of activin and/or GDF antagonists. In certain aspects, the disclosure relates to methods of reducing the severity of one or more complication of kidney disease, comprising administering to a patient in need thereof an effective amount of an activin and/or GDF antagonist, or combination of activin and/or GDF antagonists. In some embodiments, the method may reduce the frequency of kidney related disease events. In some embodiments, the method may reduce the severity of kidney related disease events. In some embodiments, the methods described herein relate to delaying clinical progression (worsening) of kidney disease. In some embodiments, the patient is further administered one or more supportive therapies or active agents for treating kidney disease in addition to the one or more activin and/or GDF antagonists. For example, the patient also may be administered one or more supportive therapies or active agents, e.g., angiotensin-converting enzyme (ACE) inhibitors, angiotensin II receptor blockers, a water pill or diuretics, optionally with a low-salt diet), statins, hormone erythropoietin, optionally with iron supplement, intravenous (IV) fluid supplement, calcium and/or vitamin D supplement, a phosphate binder, calcium, glucose or sodium polystyrene sulfonate (Kayexalate, Kionex), hemodialysis, peritoneal dialysis, and/or kidney transplant. Some exemplary medications for kidney diseases are Lasix® (furosemide), Demadex® (torsemide), Edecrin® (ethacrynic acid), and sodium edecrin. In certain preferred embodiments, an activin and/or GDF antagonist to be used in accordance with the methods described herein in is an inhibitor (antagonist), or combination of inhibitors (antagonists), of one or more of: activin (e.g., activin A, activin B, activin AB, activin C, activin AC, activin BC, activin E, activin AE, and/or activin BE), GDF8, GDF11, GDF3, GDF1, Nodal, ActRIIA, ActRIIB, ALK4, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least GDF11 (e.g., a GDF11 antagonist). Effects on GDF11 inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least GDF11. Ligand binding activity may be determined, for example, using a binding affinity assay including those described herein. In some embodiments, an activin and/or GDF antagonist, or combination of antagonists, of the disclosure binds to at least GDF11 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit GDF11 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits GDF11 may further inhibit one or more of: activin (e.g., activin A, activin B, activin AB, activin C, activin AC, activin BC, activin E, activin AE, and/or activin BE), GDF8, GDF3, GDF1, Nodal, ActRIIA, ActRIIB, ALK4, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least GDF8 (e.g., a GDF8 antagonist). Effects on GDF8 inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least GDF8. Ligand binding activity may be determined, for example, using a binding affinity assay including those described herein. In some embodiments, an activin and/or GDF antagonist, or combination of antagonists, of the disclosure binds to at least GDF8 with a $K_D$ of at least $1 \times 10^{-7}$ M (e.g., at least $1 \times 10^{-8}$ M, at least $1 \times 10^{-9}$ M, at least $1 \times 10^{-10}$ M, at least $1 \times 10^{-11}$ M, or at least $1 \times 10^{-12}$ M). As described herein, various activin and/or GDF antagonists that inhibit GDF8 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits GDF8 may further inhibit one or more of: activin (e.g., activin A, activin B, activin AB, activin C, activin AC, activin BC, activin E, activin AE, and/or activin BE), GDF11, GDF3, GDF1, Nodal, ActRIIA, ActRIIB, ALK4, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least GDF3 (e.g., a GDF3 antagonist). Effects on GDF3 inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least GDF3. Ligand binding activity may be determined, for example, using a binding affinity assay including those described herein. In some embodiments, an activin and/or GDF antagonist, or combination of antagonists, of the disclosure binds to at least GDF3 with a $K_D$ of at least $1 \times 10^{-7}$ M (e.g., at least $1 \times 10^{-8}$ M, at least $1 \times 10^{-9}$ M, at least $1 \times 10^{-10}$ M, at least $1 \times 10^{-11}$ M, or at least $1 \times 10^{-12}$ M). As described herein, various activin and/or GDF antagonists that inhibit GDF3 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits GDF3 may further inhibit one or more of: activin (e.g., activin A, activin B, activin AB, activin C, activin AC, activin BC, activin E, activin AE, and/or activin BE), GDF8, GDF11, GDF1, Nodal, ActRIIA, ActRIIB, ALK4, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least GDF 1 (e.g., a GDF 1 antagonist). Effects on GDF 1 inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least GDF 1. Ligand binding activity may be determined, for example, using a binding affinity assay including those described herein. In some embodiments, an activin and/or GDF antagonist, or combination of antagonists, of the disclosure binds to at least GDF 1 with a $K_D$ of at least $1 \times 10^7$ M (e.g., at least $1 \times 10^{-8}$ M, at least $1 \times 10^{-9}$ M, at least $1 \times 10^{-10}$ M, at least $1 \times 10^{-11}$ M, or at least $1 \times 10^{-12}$ M). As described herein, various activin and/or GDF antagonists that inhibit BMP6 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits GDF1 may further inhibit one or more of: activin (e.g., activin A, activin B, activin AB, activin C, activin AC, activin BC, activin E, activin AE, and/or activin BE), GDF8, GDF3, GDF11, Nodal, ActRIIA, ActRIIB, ALK4, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least Nodal (e.g., a Nodal antagonist). Effects on Nodal inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least Nodal. Ligand binding activity may be determined, for example, using a binding affinity assay including those described herein. In some embodiments, an activin and/or GDF antagonist, or combination of antagonists, of the disclosure binds to at least Nodal with a $K_D$ of at least $1 \times 10^{-7}$ M (e.g., at least $1 \times 10^{-8}$ M, at least $1 \times 10^{-9}$ M, at least $1 \times 10^{-10}$ M, at least $1 \times 10^{-11}$ M, or at least $1 \times 10^{-12}$ M). As described herein, various activin and/or GDF antagonists that inhibit Nodal can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits Nodal may further inhibit one or more of: activin (e.g., activin A, activin B, activin AB, activin C, activin AC, activin BC, activin E, activin AE, and/or activin BE), GDF8, GDF3, GDF11, GDF1, ActRIIA, ActRIIB, ALK4, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least Cryptic (e.g., a Cryptic antagonist). Effects on Cryptic inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least Cryptic. Ligand binding activity may be determined, for example, using a binding affinity assay including those described herein. In some embodiments, an activin and/or GDF antagonist, or combination of antagonists, of the disclosure binds to at least Cryptic with a $K_D$ of at least $1 \times 10^{-7}$ M (e.g., at least $1 \times 10^{-8}$ M, at least $1 \times 10^{-9}$ M, at least $1 \times 10^{-10}$ M, at least $1 \times 10^{-11}$ M, or at least $1 \times 10^{-12}$ M). As described herein, various activin and/or GDF antagonists that inhibit Cryptic can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits Cryptic may further inhibit one or more of: activin (e.g., activin A, activin B, activin AB, activin C, activin AC, activin BC, activin E, activin AE, and/or activin BE), GDF8, GDF3, GDF11, GDF1, Nodal, ActRIIA, ActRIIB, ALK4, ALK5, ALK7, Cryptic 1B, Smad2, and Smad3.

In certain aspects, an activin and/or GDF antagonist, or combination of antagonists, to be used in accordance with methods and uses described herein is an agent that inhibits at least Cryptic 1B (e.g., a Cryptic 1B antagonist). Effects on Cryptic 1B inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least Cryptic 1B. Ligand binding activity may be determined, for example, using a binding affinity assay including those described herein. In some embodiments, an activin and/or GDF antagonist, or combination of antagonists, of the disclosure binds to at least Cryptic 1B with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit Cryptic 1B can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits Cryptic 1B may further inhibit one or more of: activin (e.g., activin A, activin B, activin AB, activin C, activin AC, activin BC, activin E, activin AE, and/or activin BE), GDF8, GDF3, GDF11, GDF1, Nodal, ActRIIA, ActRIIB, ALK4, ALK5, ALK7, Cryptic, Smad2, and Smad3.

In certain aspects, an activin and/or GDF antagonist, or combination of antagonists, to be used in accordance with methods and uses described herein is an agent that inhibits at least activin (e.g., activin A, activin B, activin AB, activin C, activin AC, activin BC, activin E, activin AE, and/or activin BE) (e.g., an activin antagonist). Effects on activin inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least activin. Ligand binding activity may be determined, for example, using a binding affinity assay including those described herein. In some embodiments, an activin and/or GDF antagonist, or combination of antagonists, of the disclosure binds to at least activin with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit activin can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits activin may further inhibit one or more of: GDF8, GDF3, GDF11, GDF1, Nodal, ActRIIA, ActRIIB, ALK4, ALK5, ALK7, Cryptic, Cryptic 1B, Smad2, and Smad3. In certain preferred embodiments, an activin and/or GDF antagonist, or combination of antagonists, to be used in accordance with methods and uses described herein is an agent that inhibits at least activin B.

In certain aspects, an activin and/or GDF antagonist, or combination of antagonists, to be used in accordance with methods and uses described herein is an agent that inhibits at least ActRII (e.g., ActRIIA and/or ActRIIB) (e.g., an ActRII antagonist). Effects on ActRII inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least ActRII. Ligand binding activity may be determined, for example, using a binding affinity assay including those described herein. In some embodiments, an activin and/or GDF antagonist, or combination of antagonists, of the disclosure binds to at least ActRII with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit ActRII can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits ActRII may further inhibit one or more of: activin (e.g., activin A, activin B, activin AB, activin C, activin AC, activin BC, activin E, activin AE, and/or activin BE), GDF8, GDF3, GDF11, GDF1, Nodal, ALK4, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least ALK4 (e.g., an ALK4 antagonist). Effects on ALK4 inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least ALK4. Ligand binding activity may be determined, for example, using a binding affinity assay including those described herein. In some embodiments, an activin and/or GDF antagonist, or combination of antagonists, of the disclosure binds to at least ALK4 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit ALK4 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits ALK4 may further inhibit one or more of: activin (e.g., activin A, activin B, activin AB, activin C, activin AC, activin BC, activin E, activin AE, and/or activin BE), GDF8, GDF3, GDF11, GDF1, Nodal, ActRIIA, ActRIIB, ALK5, ALK7, Cryptic, Cryptic 1B, Smad2, and Smad3.

In certain aspects, an activin and/or GDF antagonist, or combination of antagonists, to be used in accordance with methods and uses described herein is an agent that inhibits at least ALK5 (e.g., an ALK5 antagonist). Effects on ALK5 inhibition may be determined, for example, using a cell-based assay including those described herein (e.g., a Smad signaling reporter assay). Therefore, in some embodiments, an activin and/or GDF antagonists, or combination of antagonist, of the disclosure may bind to at least ALK5. Ligand binding activity may be determined, for example, using a binding affinity assay including those described herein. In some embodiments, an activin and/or GDF antagonist, or combination of antagonists, of the disclosure binds to at least ALK5 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit ALK5 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits ALK5 may further inhibit one or more of: activin (e.g., activin A, activin B, activin AB, activin C, activin AC, activin BC, activin E, activin AE, and/or activin BE), GDF8, GDF3, GDF11, GDF1, Nodal, ActRIIA, ActRIIB, ALK4, ALK7, Cryptic, Cryptic 1B, Smad2, and Smad3.

In certain aspects, a activin and/or GDF antagonist, or combination of antagonists, to be used in accordance with methods and uses described herein is an agent that inhibits at least ALK7 (e.g., an ALK7 antagonist). Effects on ALK7 inhibition may be determined, for example, using a cell-based assay including those described herein (e.g., a Smad signaling reporter assay). Therefore, in some embodiments, an activin and/or GDF antagonist, or combination of antagonists, of the disclosure may bind to at least ALK7. Ligand binding activity may be determined, for example, using a binding affinity assay including those described herein. In some embodiments, an activin and/or GDF antagonist, or combination of antagonists, of the disclosure binds to at least ALK7 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit ALK7 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits ALK7 may further inhibit one or more of: activin (e.g., activin A, activin B, activin AB, activin C, activin AC, activin BC, activin E, activin AE, and/or activin BE), GDF8, GDF3, GDF11, GDF1, Nodal, ActRIIA, ActRIIB, ALK5, ALK4, Cryptic, Cryptic 1B, Smad2, and Smad3.

In certain aspects, an activin and/or GDF antagonist, or combination of antagonists, to be used in accordance with methods and uses described herein is an agent that inhibits at least Smad2 (e.g., a Smad2 antagonist). Effects on Smad2 inhibition may be determined, for example, using a cell-based assay including those described herein (e.g., a Smad signaling reporter assay). Therefore, in some embodiments, an activin and/or GDF antagonists, or combination of antagonist, of the disclosure may bind to at least Smad2. Ligand binding activity may be determined, for example, using a binding affinity assay including those described herein. In some embodiments, an activin and/or GDF antagonist, or combination of antagonists, of the disclosure binds to at least Smad2 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit Smad2 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits Smad2 may further inhibit one or more of: activin (e.g., activin A, activin B, activin AB, activin C, activin AC, activin BC, activin E, activin AE, and/or activin BE), GDF8, GDF3, GDF11, GDF1, Nodal, ActRIIA, ActRIIB, ALK4, ALK5, ALK7, Cryptic, Cryptic 1B, and Smad3.

In certain aspects, an activin and/or GDF antagonist, or combination of antagonists, to be used in accordance with methods and uses described herein is an agent that inhibits at least Smad3 (e.g., a Smad3 antagonist). Effects on Smad3 inhibition may be determined, for example, using a cell-based assay including those described herein (e.g., a Smad signaling reporter assay). Therefore, in some embodiments, an activin and/or GDF antagonists, or combination of antagonist, of the disclosure may bind to at least Smad3. Ligand binding activity may be determined, for example, using a binding affinity assay including those described herein. In some embodiments, an activin and/or GDF antagonist, or combination of antagonists, of the disclosure binds to at least Smad3 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various activin and/or GDF antagonists that inhibit Smad3 can be used in accordance with the methods and uses described herein including, for example, ligand traps (e.g., ActRII polypeptides, follistatin polypeptides, and FLRG polypeptides), antibodies, small molecules, nucleotide sequences, and combinations thereof. In certain embodiments, an activin and/or GDF antagonist, or combination of antagonists, that inhibits Smad3 may further inhibit one or more of: activin (e.g., activin A, activin B, activin AB, activin C, activin AC, activin BC, activin E, activin AE, and/or activin BE), GDF8, GDF3, GDF11, GDF1, Nodal, ActRIIA, ActRIIB, ALK4, ALK5, ALK7, Cryptic, Cryptic 1B, and Smad2.

In certain aspects, an activin and/or GDF antagonist to be used in accordance with methods and uses described herein is an ActRII polypeptide. The term "ActRII polypeptide" collectively refers to naturally occurring ActRIIA and ActRIIB polypeptides as well as truncations and variants thereof such as those described herein. Preferably, ActRII polypeptides comprise, consist essentially of, or consist of a ligand-binding domain of an ActRII polypeptide or modified (variant) form thereof. For example, in some embodiments, an ActRIIA polypeptide comprises, consists essentially of, or consists of an ActRIIA ligand-binding domain of an ActRIIA polypeptide, for example, a portion of the ActRIIA extracellular domain. Similarly, an ActRIIB polypeptide may comprise, consist essentially of, or consist of an ActRIIB ligand-binding domain of an ActRIIB polypeptide, for example, a portion of the ActRIIB extracellular domain. Preferably, ActRII polypeptides to be used in accordance with the methods described herein are soluble polypeptides.

In certain aspects, the disclosure relates compositions comprising an ActRIIA polypeptide and uses thereof. For example, in some embodiments, an ActRIIA polypeptide of the disclosure comprises an amino acid sequence that is at least 70%, 75%, 80%, 85%, 90%, 91%, 92%, 93%, 94%, 95%, 96%, 97%, 98%, 99%, or 100% identical to the sequence of amino acids 30-110 of SEQ ID NO: 9 or 10. In some embodiments, an ActRIIA polypeptides of the discloses comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to any one of amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134, or 135) of SEQ ID NO: 9. In other embodiments, an ActRIIA polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 9. In other embodiments, an ActRIIA polypeptide may comprise of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 11. In even other embodiments, an ActRIIA polypeptide may comprise of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 12. In still other embodiments, an ActRIIA polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 177. In still even other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 178. In still even other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 179.

In other aspects, the disclosure relates compositions comprising an ActRIIB polypeptide and uses thereof. For example, in some embodiments, an ActRIIB polypeptide of the disclosure comprises an amino acid sequence that is at least 70%, 75%, 80%, 85%, 90%, 91%, 92%, 93%, 94%, 95%, 96%, 97%, 98%, 99%, or 100% identical to the sequence of amino acids 29-109 of SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the sequence of amino acids 29-109 of SEQ ID NO: 1, wherein the ActRIIB polypeptide comprises an acidic amino acid [naturally occurring (E or D) or artificial acidic amino acid] at position 79 with respect to SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the sequence of amino acids 25-131 of SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the sequence of amino acids 25-131 of SEQ ID NO: 1, wherein the ActRIIB polypeptide comprises an acidic amino acid at position 79 with respect to SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to a sequence starting at a residue corresponding to any one of amino acids 20, 21, 22, 23, 24, 25, 26, 27, 28, or 29 of SEQ ID NO: 1 and ending at a residue corresponding to any one of amino acids 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to a sequence starting at a residue corresponding to any one of amino acids 20, 21, 22, 23, 24, 25, 26, 27, 28, or 29 of SEQ ID NO: 1 and ending at a residue corresponding to any one of amino acids 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1, wherein the ActRIIB polypeptide comprises an acidic amino acid at position 79 with respect to SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 1, wherein the ActRIIB polypeptide comprises an acidic amino acid at position 79 with respect to SEQ ID NO: 1. In even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 2. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 2, wherein the ActRIIB polypeptide comprises an acidic amino acid at position 79 with respect to SEQ ID NO: 1. In still other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 3. In other, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 3, wherein the ActRIIB polypeptide comprises an acidic amino acid at position 79 with respect to SEQ ID NO: 1. In still other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 4. In other, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 4, wherein the ActRIIB polypeptide comprises an acidic amino acid at position 79 with respect to SEQ ID NO: 1. In still other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 5. In other, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 5, wherein the ActRIIB polypeptide comprises an acidic amino acid at position 79 with respect to SEQ ID NO: 1. In still other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 6. In other, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 6, wherein the ActRIIB polypeptide comprises an acidic amino acid at position 79 with respect to SEQ ID NO: 1. In still other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 181. In other, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 181, wherein the ActRIIB polypeptide comprises an acidic amino acid at position 79 with respect to SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 182. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 182, wherein the ActRIIB polypeptide comprises an acidic amino acid at position 79 with respect to SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 184. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 184, wherein the ActRIIB polypeptide comprises an acidic amino acid at position 79 with respect to SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 187. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 187, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 188. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 189. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 190. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 192. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 192, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 193. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 193, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 196. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 196, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 197. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 198. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 199. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 201. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 201, wherein the ActRIIB polypeptide comprises an acidic amino acid at position 79 with respect to SEQ ID NO: 1.

As described herein, ActRII polypeptides and variants thereof may be homomultimers, for example, homodimer, homotrimers, homotetramers, homopentamers, and higher order homomultimer complexes. In certain preferred embodiments, ActRII polypeptides and variants thereof are homodimers. In certain embodiments, ActRII polypeptide dimers described herein comprise an first ActRII polypeptide covalently, or non-covalently, associated with an second ActRII polypeptide wherein the first polypeptide comprises an ActRII domain and an amino acid sequence of a first member (or second member) of an interaction pair (e.g., a constant domain of an immunoglobulin) and the second polypeptide comprises an ActRII polypeptide and an amino acid sequence of a second member (or first member) of the interaction pair.

In certain aspects, ActRII polypeptides, including variants thereof, may be fusion proteins. For example, in some embodiments, an ActRII polypeptide may be a fusion protein comprising an ActRII polypeptide domain and one or more heterologous (non-ActRII) polypeptide domains. In some embodiments, an ActRII polypeptide may be a fusion protein that has, as one domain, an amino acid sequence derived from an ActRII polypeptide (e.g., a ligand-binding domain of an ActRII receptor or a variant thereof) and one or more heterologous domains that provide a desirable property, such as improved pharmacokinetics, easier purification, targeting to particular tissues, etc. For example, a domain of a fusion protein may enhance one or more of in vivo stability, in vivo half-life, uptake/administration, tissue localization or distribution, formation of protein complexes, multimerization of the fusion protein, and/or purification. Optionally, an ActRII polypeptide domain of a fusion protein is connected directly (fused) to one or more heterologous polypeptide domains or an intervening sequence, such as a linker, may be positioned between the amino acid sequence of the ActRII polypeptide and the amino acid sequence of the one or more heterologous domains. In certain embodiments, an ActRII fusion protein comprises a relatively unstructured linker positioned between the heterologous domain and the ActRII domain. This unstructured linker may correspond to the roughly 15 amino acid unstructured region at the C-terminal end of the extracellular domain of ActRII (the "tail"), or it may be an artificial sequence of between 3 and 15, 20, 30, 50 or more amino acids that are relatively free of secondary structure. A linker may be rich in glycine and/or proline residues and may, for example, contain repeating sequences of threonine/serine and glycines. Examples of linkers include, but are not limited to, the sequences TGGG (SEQ ID NO: 217), GGG (SEQ ID NO: 223), GGGG (SEQ ID NO: 222), TGGGG (SEQ ID NO: 219), SGGGG (SEQ ID NO: 220), GGGS (SEQ ID NO: 224), and SGGG (SEQ ID NO: 218). In some embodiments, ActRII fusion proteins may comprise a constant domain of an immunoglobulin, including, for example, the Fc portion of an immunoglobulin. For example, an amino acid sequence that is derived from an Fc domain of an IgG (IgG1, IgG2, IgG3, or IgG4), IgA (IgA1 or IgA2), IgE, or IgM immunoglobulin. For example, an Fc portion of an immunoglobulin domain may comprise, consist essentially of, or consist of an amino acid sequence that is at least 70%, 75%, 80%, 85%, 90%, 91%, 92%, 93%, 94%, 95%, 96%, 97%, 98%, 99% or 100% identical to any one of SEQ ID NOs: 135-149. Such immunoglobulin domains may comprise one or more amino acid modifications (e.g., deletions, additions, and/or substitutions) that confer an altered Fc activity, e.g., decrease of one or more Fc effector functions. In some embodiment, an ActRII fusion protein comprises an amino acid sequence as set forth in the formula A-B-C. For example, the B portion is an N- and C-terminally truncated ActRII polypeptide, e.g., as described herein. The A and C portions may be independently zero, one, or more than one amino acids, and both A and C portions are heterologous to B. The A and/or C portions may be attached to the B portion via a linker sequence. In certain embodiments, an ActRII fusion protein comprises a leader sequence. The leader sequence may be a native ActRII leader sequence or a heterologous leader sequence. In certain embodiments, the leader sequence is a tissue plasminogen activator (TPA) leader sequence (e.g., SEQ ID NO: 215).

An ActRII polypeptide, including variants thereof, may comprise a purification subsequence, such as an epitope tag, a FLAG tag, a polyhistidine sequence, and a GST fusion. Optionally, an ActRII polypeptide comprises one or more modified amino acid residues selected from: a glycosylated amino acid, a PEGylated amino acid, a farnesylated amino acid, an acetylated amino acid, a biotinylated amino acid, and/or an amino acid conjugated to a lipid moiety. ActRII polypeptides may comprise at least one N-linked sugar, and may include two, three or more N-linked sugars. Such polypeptides may also comprise O-linked sugars. In general, it is preferable that ActRII polypeptides be expressed in a mammalian cell line that mediates suitably natural glycosylation of the polypeptide so as to diminish the likelihood of an unfavorable immune response in a patient. ActRII polypeptides may be produced in a variety of cell lines that glycosylate the protein in a manner that is suitable for patient use, including engineered insect or yeast cells, and mammalian cells such as COS cells, CHO cells, HEK cells and NSO cells. In some embodiments, an ActRII polypeptide is glycosylated and has a glycosylation pattern obtainable from a Chinese hamster ovary cell line. In some embodiments, ActRII polypeptides of the disclosure exhibit a serum half-life of at least 4, 6, 12, 24, 36, 48, or 72 hours in a mammal (e.g., a mouse or a human). Optionally, ActRII may exhibit a serum half-life of at least 6, 8, 10, 12, 14, 20, 25, or 30 days in a mammal (e.g., a mouse or a human).

In certain aspects, the disclosure provides pharmaceutical preparations comprising one or more ActRII antagonists of the present disclosure and a pharmaceutically acceptable carrier. A pharmaceutical preparation may also comprise one or more additional active agents such as a compound that is used to treat kidney disease, particularly treating or preventing one or more complications of kidney disease (e.g., kidney tissue damage, fibrosis, and/or inflammation). In general pharmaceutical preparation will preferably be pyrogen-free (meaning pyrogen free to the extent required by regulations governing the quality of products for therapeutic use).

In certain instances, when administering an ActRII antagonist, or combination of antagonists, of the disclosure to disorders or conditions described herein, it may be desirable to monitor the effects on red blood cells during administration of the ActRII antagonist, or to determine or adjust the dosing of the ActRII antagonist, in order to reduce undesired effects on red blood cells. For example, increases in red blood cell levels, hemoglobin levels, or hematocrit levels may cause undesirable increases in blood pressure.

In certain aspects, an activin and/or GDF antagonist to be used in accordance with methods and uses of the disclosure is an antibody, or combination of antibodies. In some embodiments, the antibody binds to at least ActRII (ActRIIA and/or ActRIIB). In certain embodiments, an antibody that binds to ActRII inhibits ActRII signaling, optionally as measured in a cell-based assay such as those described herein. In certain embodiments, an antibody that binds to ActRII inhibits one or more GDF ligands, type I receptors, or co-receptors from binding to ActRII. In certain embodiments an antibody that binds to ActRII inhibits one or more GDF ligands from binding to ActRII selected from: activin (e.g., activin A, activin B, activin C, activin AB, activin AC, activin BC, activin E, activin AE, and activin BE), GDF8, GDF11, GDF1, Nodal, GDF3, Cryptic, Cryptic 1B, ALK4, ALK5, ALK7, Smad2, and Smad3. In some embodiments, the antibody binds to at least ALK4. In certain embodiments, an antibody that binds to ALK4 inhibits ALK4 signaling, optionally as measured in a cell-based assay such as those described herein. In certain embodiments, an antibody that binds to ALK4 inhibits one or more GDF ligands, type II receptors, or co-receptors from binding to ALK4. In certain embodiments an antibody that binds to ALK4 inhibits one or more GDF ligands from binding to ALK4 selected from: activin (e.g., activin A, activin B, activin C, activin AB, activin AC, activin BC, activin E, activin AE, and activin BE), GDF8, GDF11, GDF1, Nodal, GDF3, ALK5, ALK7, Cryptic, Cryptic 1B, Smad2, and Smad3. In some embodiments, the antibody binds to at least ALK5. In certain embodiments, an antibody that binds to ALK5 inhibits ALK5 signaling, optionally as measured in a cell-based assay such as those described herein. In certain embodiments, an antibody that binds to ALK5 inhibits one or more GDF ligands, type II receptors, or co-receptors from binding to ALK5. In certain embodiments an antibody that binds to ALK5 inhibits one or more GDF ligands from binding to ALK5 selected from: activin (e.g., activin A, activin B, activin C, activin AB, activin AC, activin BC, activin E, activin AE and activin BE), GDF8, GDF11, GDF1, Nodal, GDF3, ALK4, ALK7, Cryptic, Cryptic 1B, Smad2, and Smad3. In some embodiments, the antibody binds to at least ALK7. In certain embodiments, an antibody that binds to ALK7 inhibits ALK7 signaling, optionally as measured in a cell-based assay such as those described herein. In certain embodiments, an antibody that binds to ALK7 inhibits one or more GDF ligands, type II receptors, or co-receptors from binding to ALK7. In certain embodiments an antibody that binds to ALK7 inhibits one or more GDF ligands from binding to ALK7 selected from: activin (e.g., activin A, activin B, activin C, activin AB, activin AC, activin BC, activin E, activin AE, and activin BE), GDF8, GDF11, GDF1, Nodal, GDF3, ALK4, ALK5, Cryptic, Cryptic 1B, Smad2, and Smad3. In some embodiments, the antibody binds to at least GDF11. In certain embodiments, an antibody that binds to GDF11 inhibits ActRII signaling, optionally as measured in a cell-based assay such as those described herein. In certain embodiments, an antibody that binds to GDF11 inhibits GDF11-ActRII binding and/or GDF11-ALK binding (e.g., GDF11-ALK4, GDF11-ALK5, and/or GDF11-ALK7 binding). In some embodiments, the antibody binds to at least GDF8. In certain embodiments, an antibody that binds to GDF8 inhibits ActRII signaling, optionally as measured in a cell-based assay such as those described herein. In certain embodiments, an antibody that binds to GDF8 inhibits GDF8-ActRII binding and/or GDF8-ALK binding (e.g., GDF8-ALK4, GDF8-ALK5, and/or GDF8-ALK7 binding). In some embodiments, the antibody binds to at least GDF3. In certain embodiments, an antibody that binds to GDF3 inhibits ActRII signaling, optionally as measured in a cell-based assay such as those described herein. In certain embodiments, an antibody that binds to GDF3 inhibits GDF3-ActRII binding and/or GDF3-ALK binding (e.g., GDF3-ALK4, GDF3-ALK5, and/or GDF3-ALK7 binding). In some embodiments, the antibody binds to activin (e.g., activin A, activin B, activin C, activin AB, activin AC, activin BC, activin E, activin AE, and activin BE). In certain embodiments, an antibody that binds to activin (e.g., activin A, activin B, activin C, activin AB, activin AC, activin BC, activin E, activin AE, and activin BE) inhibits ActRII signaling, optionally as measured in a cell-based assay such as those described herein. In certain embodiments, an antibody that binds to activin (e.g., activin A, activin B, activin C, activin AB, activin AC, activin BC, activin E, activin AE, and activin BE) inhibits activin-ActRII binding and/or activin-ALK binding (e.g., activin-ALK4, activin-ALK5, and/or activin-ALK7 binding). In some embodiments, the antibody binds to activin B. In certain embodiments, an antibody that binds to activin B inhibits ActRII signaling, optionally as measured in a cell-based assay such as those described herein. In certain embodiments, an antibody that binds to activin B inhibits activin B-ActRII binding and/or activin B-ALK binding (e.g., activin B-ALK4, activin B-ALK5, and/or activin B-ALK7 binding). In some embodiments, the antibody is a multispecific antibody, or combination of multispecific antibodies that binds to one or more of ActRIIB, ActRIIA, ALK4, ALK5, ALK7, GDF11, GDF8, activin, GDF1, Nodal, GDF3, Cryptic, Cryptic 1B, Smad2, and Smad3. In certain aspects the multispecific antibody, or a combination of multispecific antibodies, inhibits signaling in a cell-based assay of one or more of: ActRIIB, GDF11, GDF8, activin, GDF3, GDF1, Nodal, Cryptic, Cryptic 113, Smad2, and Smad3. In some embodiments, antibody is a chimeric antibody, a humanized antibody, or a human antibody. In some embodiments, the antibody is a single-chain antibody, an F(ab')$_2$ fragment, a single-chain diabody, a tandem single-chain Fv fragment, a tandem single-chain diabody, a or a fusion protein comprising a single-chain diabody and at least a portion of an immunoglobulin heavy-chain constant region.

In certain aspects, the activin and/or GDF antagonist is a small molecule inhibitor or combination of small molecule inhibitors. In some embodiments, the small molecule inhibitor is an inhibitor of at least ActRII (e.g., ActRIIA and/or ActRIIB). In some embodiments, the small molecule inhibitor is an inhibitor of at least ALK4. In some embodiments, the small molecule inhibitor is an inhibitor of at least ALK5. In some embodiments, the small molecule inhibitor is an inhibitor of at least ALK7. In some embodiments, the small molecule inhibitor is an inhibitor of at least GDF11. In some embodiments, the small molecule inhibitor is an inhibitor of at least GDF8. In some embodiments, the small molecule inhibitor is an inhibitor of at least GDF 1. In some embodiments, the small molecule inhibitor is an inhibitor of at least Nodal. In some embodiments, the small molecule inhibitor is an inhibitor of at least Cryptic. In some embodiments, the small molecule inhibitor is an inhibitor of at least Cryptic 1B. In some embodiments, the small molecule inhibitor is an inhibitor of at least Smad2. In some embodiments, the small molecule inhibitor is an inhibitor of at least Smad3. In some embodiments, the small molecule inhibitor is an inhibitor of at least GDF3. In some embodiments, the small molecule inhibitor is an inhibitor of at least activin (e.g., activin A, activin B, activin C, activin AB, activin AC, activin BC, activin E, activin AE, and activin BE). In some embodiments, the small molecule inhibitor is an inhibitor of at least activin B.

In certain aspects, the activin and/or GDF antagonist is a nucleic acid inhibitor or combination of nucleic acid inhibitors. In some embodiments, the nucleic acid inhibitor is an inhibitor of at least ActRII (e.g., ActRIIA and/or ActRIIB). In some embodiments, the nucleic acid inhibitor is an inhibitor of at least ALK4. In some embodiments, the nucleic acid inhibitor is an inhibitor of at least ALK5. In some embodiments, the nucleic acid inhibitor is an inhibitor of at least ALK7. In some embodiments, the nucleic acid inhibitor is an inhibitor of at least GDF11. In some embodiments, the nucleic acid inhibitor is an inhibitor of at least GDF8. In some embodiments, the nucleic acid inhibitor is an inhibitor of at least GDF. In some embodiments, the small molecule inhibitor is an inhibitor of at least Nodal. In some embodiments, the small molecule inhibitor is an inhibitor of at least Cryptic. In some embodiments, the small molecule inhibitor is an inhibitor of at least Cryptic 1B. In some embodiments, the small molecule inhibitor is an inhibitor of at least Smad2. In some embodiments, the small molecule inhibitor is an inhibitor of at least Smad3. In some embodiments, the nucleic acid inhibitor is an inhibitor of at least GDF3. In some embodiments, the nucleic acid inhibitor is an inhibitor of at least activin (e.g., activin A, activin B, activin C, activin AB, activin AC, activin BC, activin E, activin AE, and activin BE). In some embodiments, the nucleic acid inhibitor is an inhibitor of at least activin B.

In certain aspects, the activin and/or GDF antagonist is a follistatin polypeptide. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 150. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 151. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 152. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 153. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to at least one of amino acid sequences of SEQ ID NOs: 154-160.

In certain aspects, the activin and/or GDF antagonist is a FLRG polypeptide. In some embodiments, the FLRG polypeptide comprises an amino acid sequence that is at least 70%, 75% 80%, 85%, 90%, 91%, 92%, 93%, 94%, 95%, 96%, 97%, 98%, 99%, or 100% identical to at least one of amino acid sequences of SEQ ID NOs: 161-164.

In certain aspects, the activin and/or GDF antagonist is a WFIKKN1 polypeptide. In some embodiments, the WFIKKN1 polypeptide comprises an amino acid sequence that is at least 70%, 75% 80%, 85%, 90%, 91%, 92%, 93%, 94%, 95%, 96%, 97%, 98%, 99%, or 100% identical to at least one of amino acid sequences of SEQ ID NOs: 165-167.

In certain aspects, the activin and/or GDF antagonist is a WFIKKN2 polypeptide. In some embodiments, the WFIKKN1 polypeptide comprises an amino acid sequence that is at least 70%, 75% 80%, 85%, 90%, 91%, 92%, 93%, 94%, 95%, 96%, 97%, 98%, 99%, or 100% identical to at least one of amino acid sequences of SEQ ID NOs: 168-172.

In certain aspects, the activin and/or GDF antagonist is a Lefty polypeptide. In some embodiments, the WFIKKN1 polypeptide comprises an amino acid sequence that is at least 70%, 75% 80%, 85%, 90%, 91%, 92%, 93%, 94%, 95%, 96%, 97%, 98%, 99%, or 100% identical to at least one of amino acid sequences of SEQ ID NOs: 173-174.

In certain aspects, the activin and/or GDF antagonist is a Cerberus polypeptide. In some embodiments, the WFIKKN1 polypeptide comprises an amino acid sequence that is at least 70%, 75% 80%, 85%, 90%, 91%, 92%, 93%, 94%, 95%, 96%, 97%, 98%, 99%, or 100% identical to at least one of amino acid sequences of SEQ ID NO: 175.

In certain aspects, the activin and/or GDF antagonist is a Coco polypeptide. In some embodiments, the WFIKKN1 polypeptide comprises an amino acid sequence that is at least 70%, 75% 80%, 85%, 90%, 91%, 92%, 93%, 94%, 95%, 96%, 97%, 98%, 99%, or 100% identical to at least one of amino acid sequences of SEQ ID NO: 176.

In certain aspects, the disclosure relates to use of one or more activin and/or GDF antagonists, optionally in combination of one or more other supportive therapies or active agents for treating kidney disease, in the manufacture of a medicament for treating, preventing, or reducing the progression rate and/or severity of kidney disease or one or more complications of kidney disease as described herein. In certain aspects, the disclosure relates to one or more activin and/or GDF antagonists, optionally in combination of one or more other supportive therapies or active agents for treating kidney disease, for use in treating, preventing, or reducing the progression rate and/or severity of a kidney disease or one or more complications of kidney disease as described herein.

The instant disclosure provides, at least, a combination of agents, e.g., antagonists of cell signaling, for therapeutic uses. Such antagonists may include at least one of activin and/or growth and differentiation factor (GDF) antagonists, including, for example, activin, GDF8, GDF11, GDF3, GDF1, Nodal, activin receptor type IIA (ActRIIA), ActRIIB, ALK4, ALK5, ALK7, Cripto-1, Cryptic, Cryptic 1B, Smad2, and Smad3. The agents may form multimeric complexes with each other through at least one covalent or noncovalent bond. Some exemplary structures of these multimeric complexes are shown in FIGS. 5A to 5D and FIGS. 6A to 6G.

An exemplary list of possible dimers of such agents is given below:

Possible Heterodimers:
I. Type I-Type II heterodimers: ALK4:ActRIIB; ALK4: ActRIIA; ALK4:BMPRII; ALK4:MISRII; ALK5:ActRIIB; ALK5:ActRIIA; ALK5:BMPRII; ALK5:MISRII; ALK7:ActRIIB; ALK7:ActRIIA; ALK7:BMPRII; ALK7:MISRII; ALK1:ActRIIB; ALK1:ActRIIA
II. Type 1-Type 1 heterodimers: ALK1:ALK4; ALK1: ALK5; ALK1:ALK7; ALK4:ALK5; ALK4:ALK7; ALK5:ALK7
III. Type II-Type II heterodimers: ActRIIA:ActRIIB; ActRIIA:BMPRII; ActRIIA:MISRII; ActRIIB:BMPRII; ActRIIB:MISRII
IV. Co-receptor hetero-dimers: Cryptic:Cripto; Cryptic: Cryptic 1B; Cripto:Cryptic 1B; ALK1:Cryptic; ALK1: Cryptic 1B; ALK1:Cripto; ALK4:Cryptic; ALK4: Cryptic 1B; ALK4:Cripto; ALK5:Cryptic; ALK5: Cryptic 1B; ALK5:Cripto; ALK7:Cryptic; ALK7: Cryptic 1B; ALK7:Cripto; ActRIIA:Cryptic; ActRIIA: Cryptic 1B; ActRIIA:Cripto; ActRIIB:Cryptic; ActRIIB:Cryptic 1B; ActRIIB:Cripto; BMPRII:Cryptic; BMPRII:Cryptic 1B; BMPRII:Cripto; MISRII: Cryptic; MISRII:Cryptic 1B; MISRII:Cripto Possible Homodimers:
ALK4:ALK4; ALK5:ALK5; ALK7:ALK7; ActRIIA:ActRIIA; ActRIIB:ActRIIB; Cripto:Cripto; Cryptic 1B:Cryptic 1B; Cryptic-Cryptic Other Antagonists as Monomers for Dimerization:
Inhibitors (e.g., antibodies, small molecule, RNA interference, etc.) of ligands (e.g., activin A, B, C, and E; GDF8; GDF11; GDF3; GDF 1; and Nodal)
Inhibitors (e.g., antibodies, small molecule, RNA interference, etc.) of type I receptors (e.g., ALK4, ALK5, and ALK7)

Inhibitors (e.g., antibodies, small molecule, RNA interference, etc.) of type II receptors (e.g., ActRIIA and ActRIIB)

Inhibitors (e.g., antibodies, small molecule, RNA interference, etc.) of co-receptors (e.g., Cripto, Cryptic, and Cryptic-1B)

Inhibitors (e.g., antibodies, small molecule, RNA interference, etc.) of Smad proteins (e.g., Smad2 and Smad3)

Natural ligand traps (naturally occurring proteins that bind to one or more activin/GDF proteins) (e.g., WFIKKN1, WFIKKN2, FST, FLRG, the Dan-related proteins Cerberus and Coco, Lefty A, Lefty B, WFIKKN1 and WFIKKN2).

Oligomers and polymers may be formed using the same strategy as shown herein and at least in FIGS. 5A to 5D and FIGS. 6A to 6G. For example, tetramers may be formed with two identical or different heterodimers or homodimers. Monomers may be the listed antagonists themselves, or may comprise fusion proteins comprising the listed antagonists. For example, a monomer may comprise a fusion protein of ALK4 and an Fc domain, resulting in a homodimer of ALK4-Fc:ALK4-Fc or a heterodimer of ALK4-Fc and another agent (e.g., ActBRIIA-Fc). In addition, ALK4 may be fused to itself or another agent (e.g., ALK5) as a monodimer, resulting in a homodimer of ALK4-ALK4: ALK4-ALK4 or ALK4-ALK5:ALK4-ALK5, or a heterodimer comprising ALK4-ALK4 or ALK4-ALK5. Thus, the possible dimers also include those comprising the same agents fused in different orientations. For example, ALK4-ALK5:ActRIIA-ActRIIB and ALK5-ALK4:ActRIIA:ActRIIB may form different heterodimer structures.

BRIEF DESCRIPTION OF THE DRAWINGS

FIG. 1 shows an alignment of extracellular domains of human ActRIIA (SEQ ID NO: 11) and human ActRIIB (SEQ ID NO: 3) with the residues that are deduced herein, based on composite analysis of multiple ActRIIB and ActRIIA crystal structures, to directly contact ligand indicated with boxes.

FIG. 2 also discloses SEQ ID NOS 25-27 and 28-29, respectively, in order of appearance.

FIG. 3 shows a multiple sequence alignment of extracellular domains of various vertebrate ActRIIA proteins (SEQ ID NOS 18-24, respectively, in order of appearance) and human ActRIIA (SEQ ID NO: 11).

FIG. 4 shows multiple sequence alignment of Fc domains from human IgG isotypes using Clustal 2.1. Hinge regions are indicated by dotted underline. Double underline indicates examples of positions engineered in IgG1 Fc (SEQ ID NO: 135) to promote asymmetric chain pairing and the corresponding positions with respect to other isotypes IgG2 (SEQ ID NO: 136), IgG3 (SEQ ID NO: 137) and IgG4 (SEQ ID NO: 139).

Figure 5B:
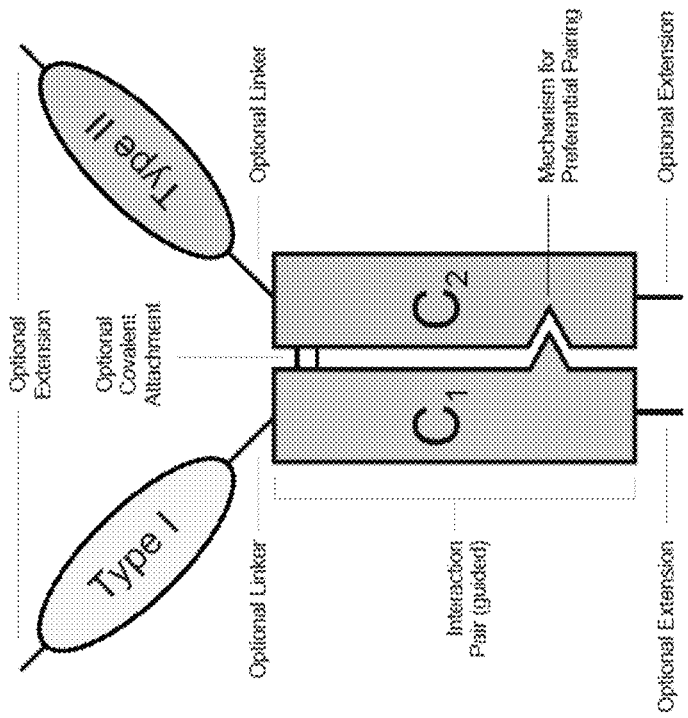
FIGS. 5A-5D show schematic examples of heteromeric protein complexes comprising a type I receptor polypeptide (indicated as "I") (e.g., a polypeptide that is at least 80%, 85%, 90%, 95%, 97%, 98%, 99% or 100% identical to an extracellular domain of an ALK1, ALK4, ALK5, or ALK7 protein from humans or other species such as those described herein) and a type II receptor polypeptide (indicated as "II") (e.g., a polypeptide that is at least 80%, 85%, 90%, 95%, 97%, 98%, 99% or 100% identical to an extracellular domain of an ActRIIA, ActRIIB, MISRII, or BMPRII protein from humans or other species such as those described herein.
Figure 5A:
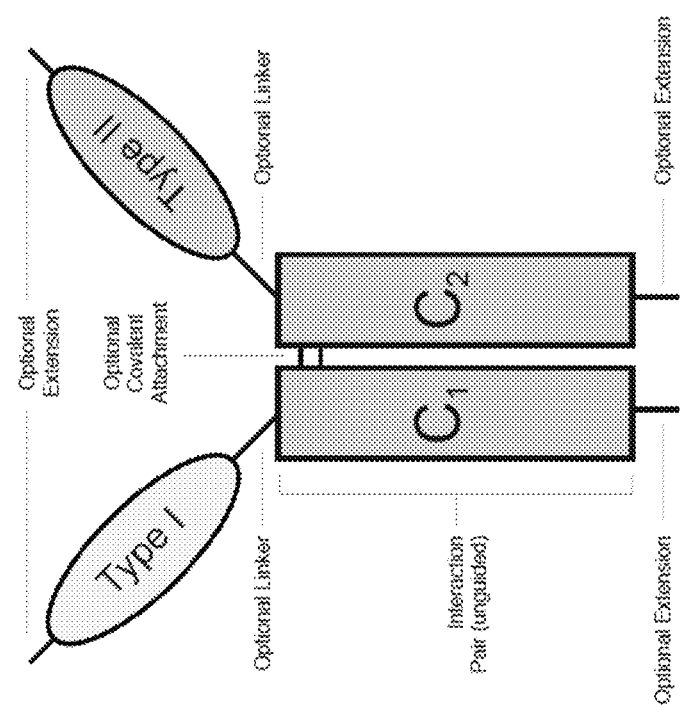
Figure 5C:
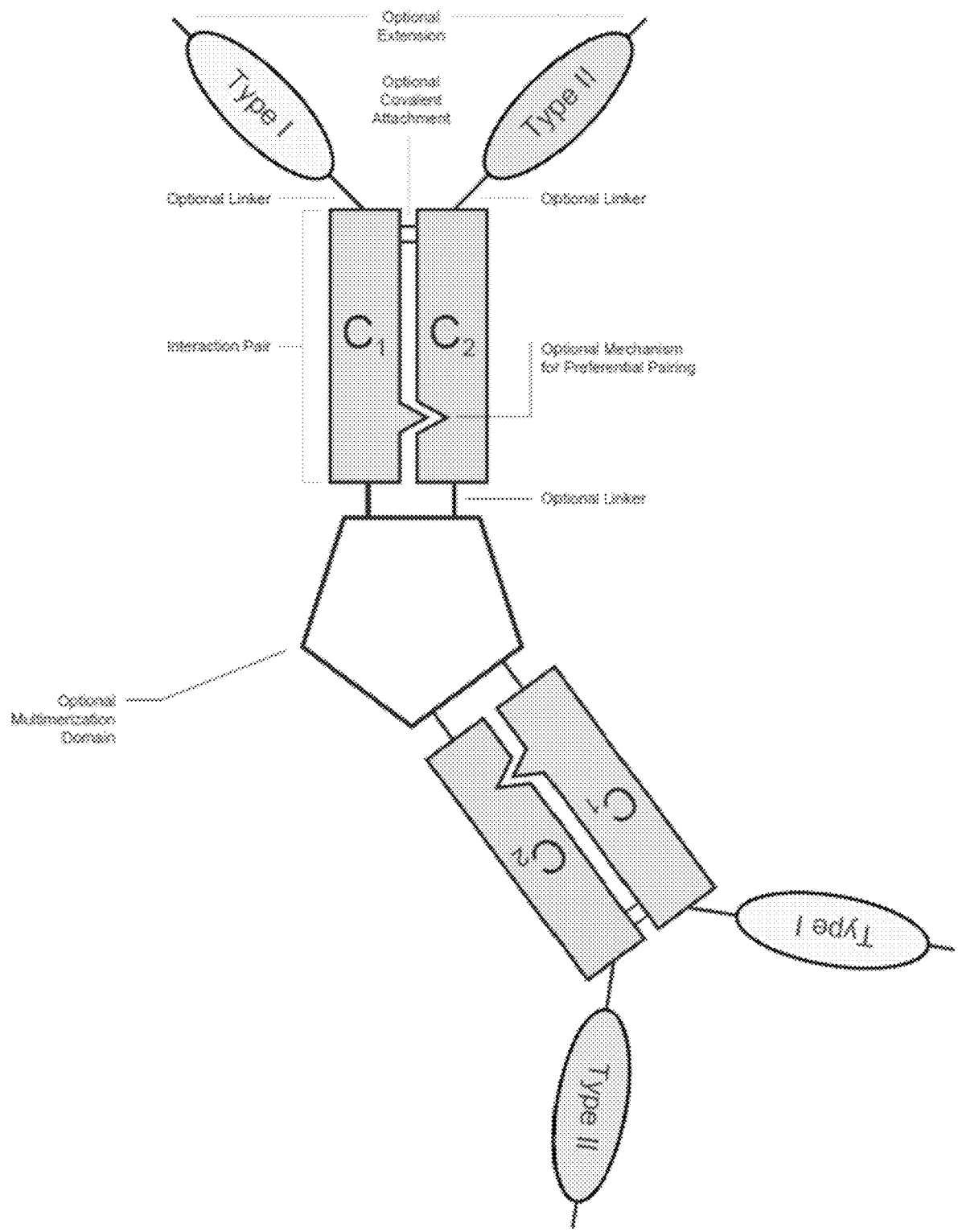
Figure 5D:
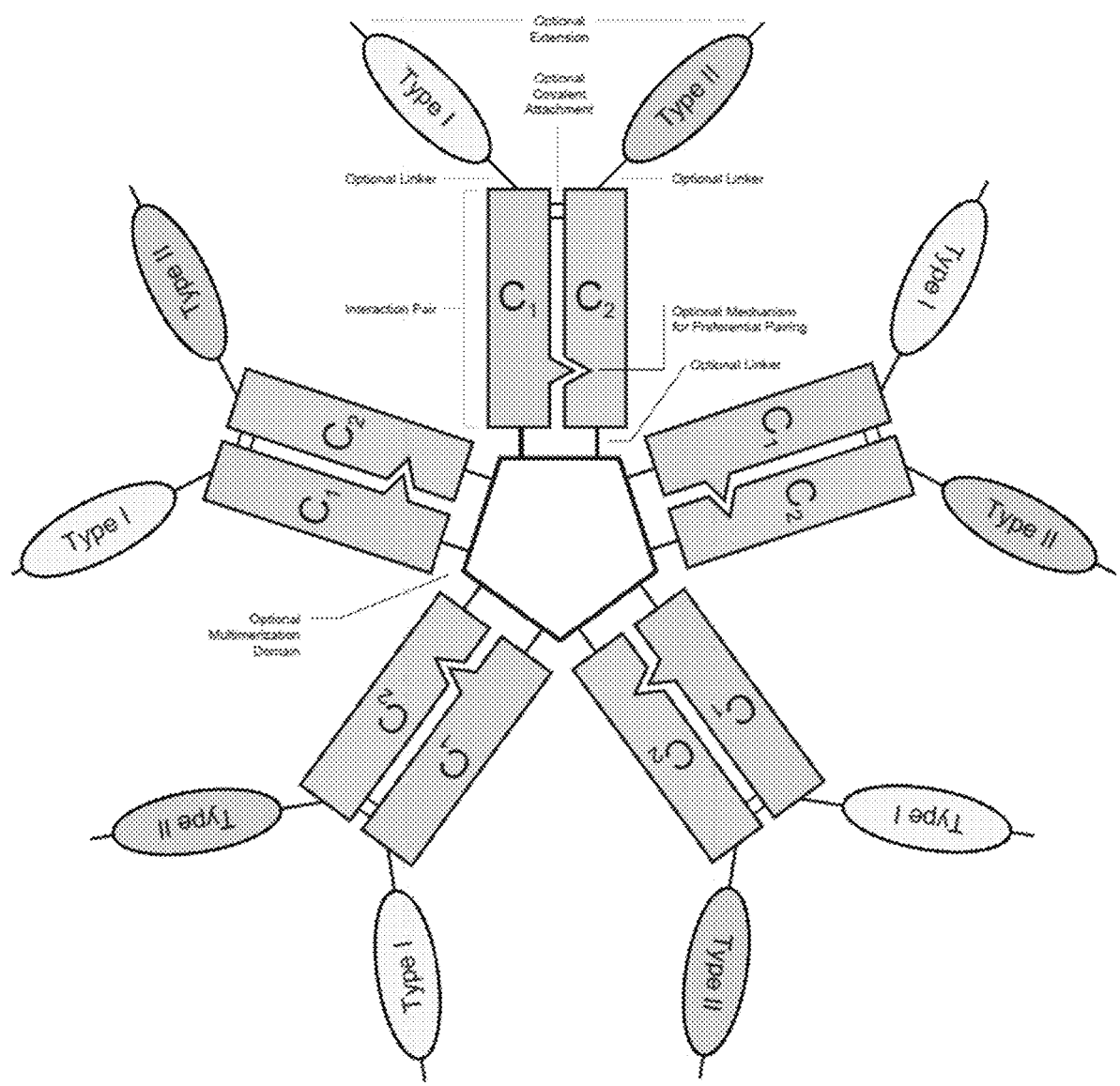
Figure 6C:
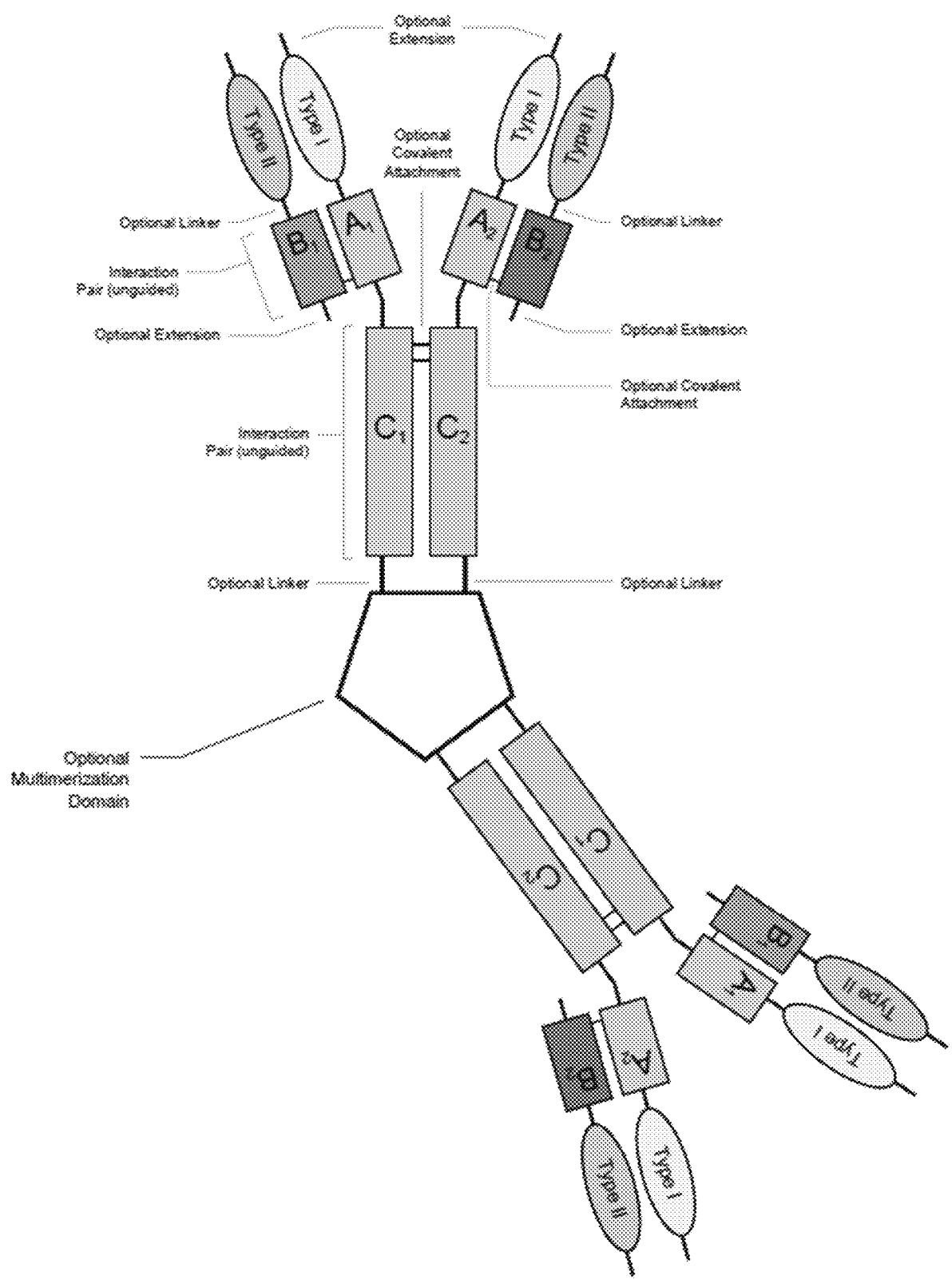
Figure 6D:
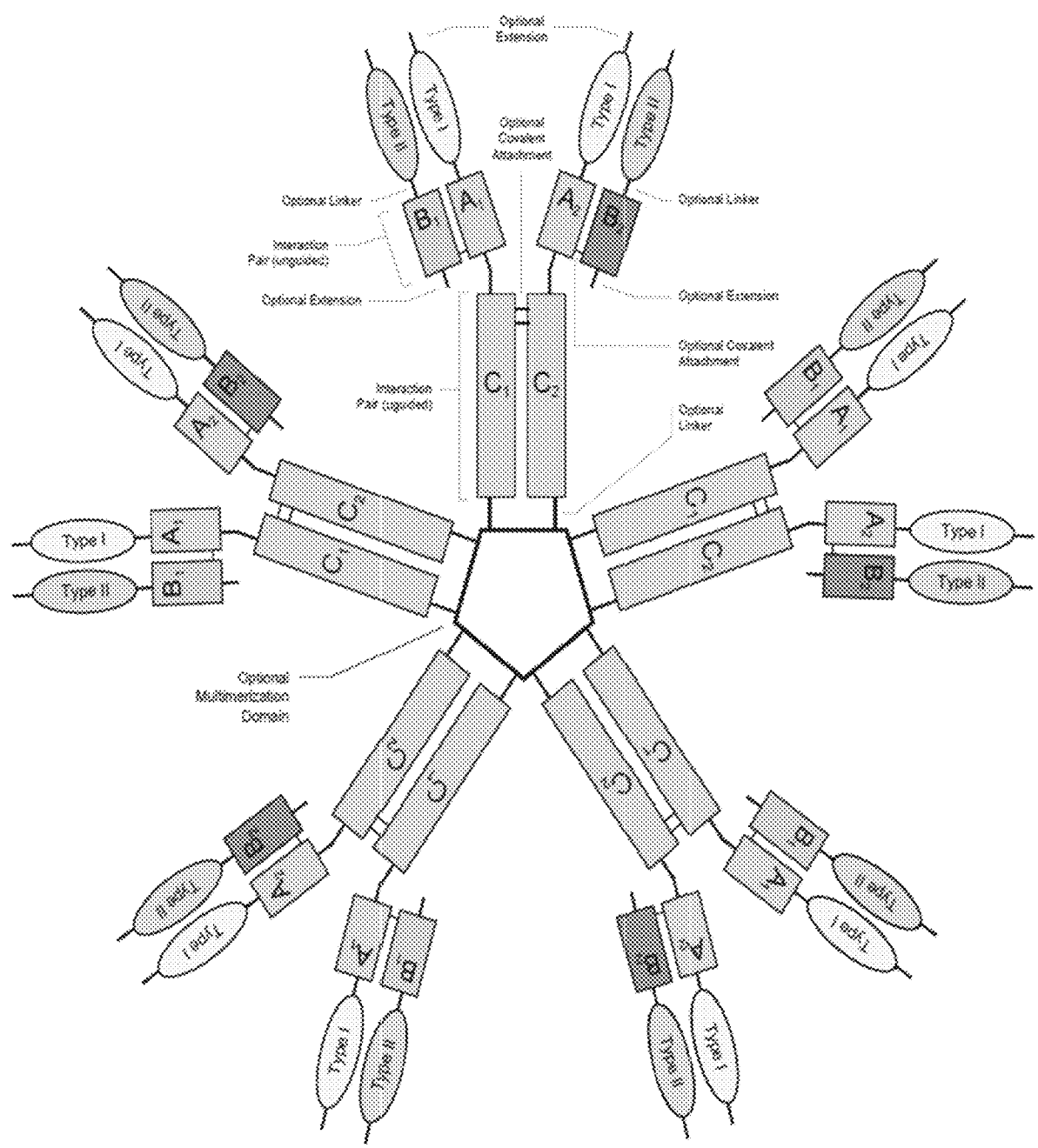
Figure 6E:
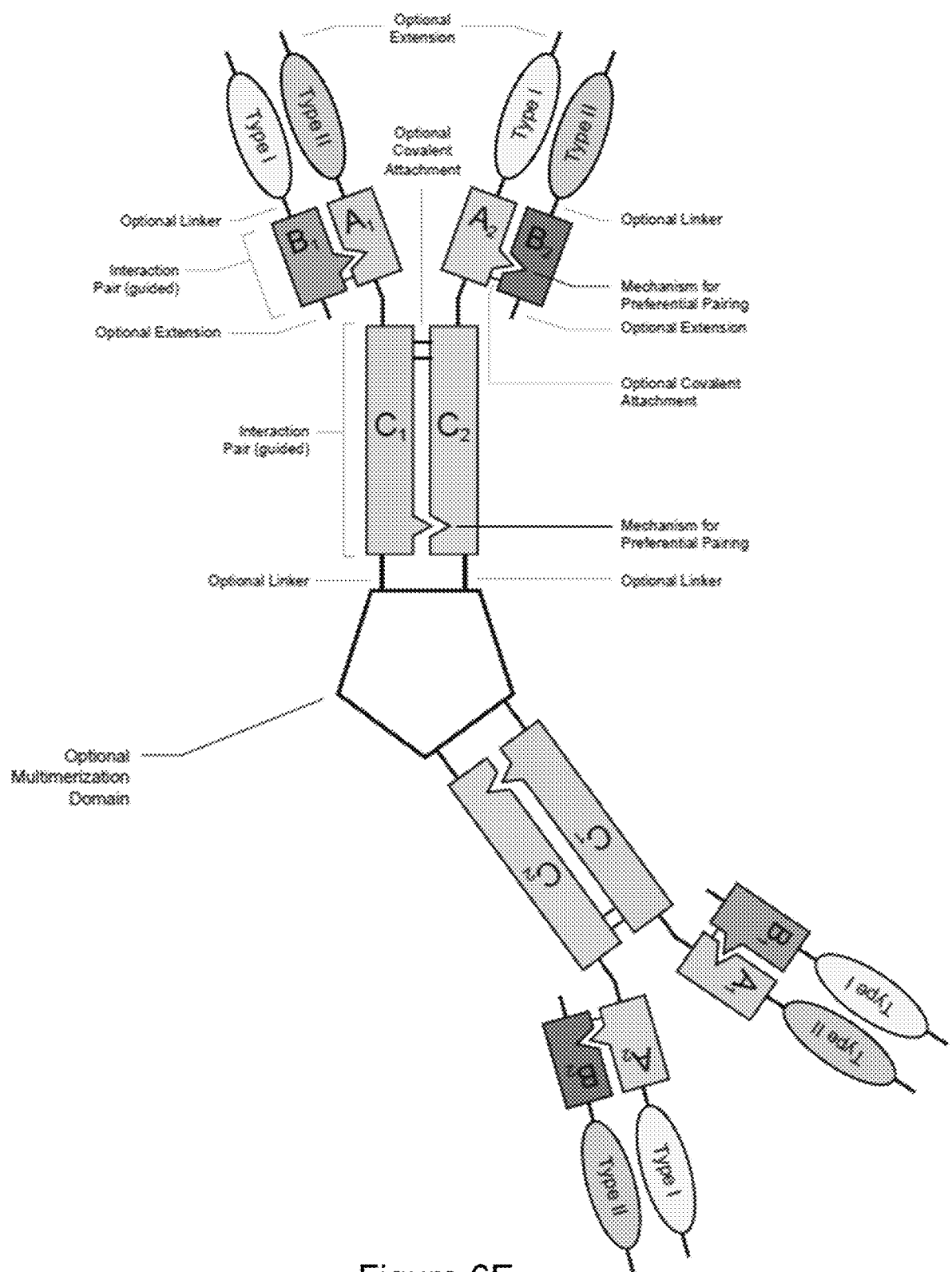
Figure 6F:
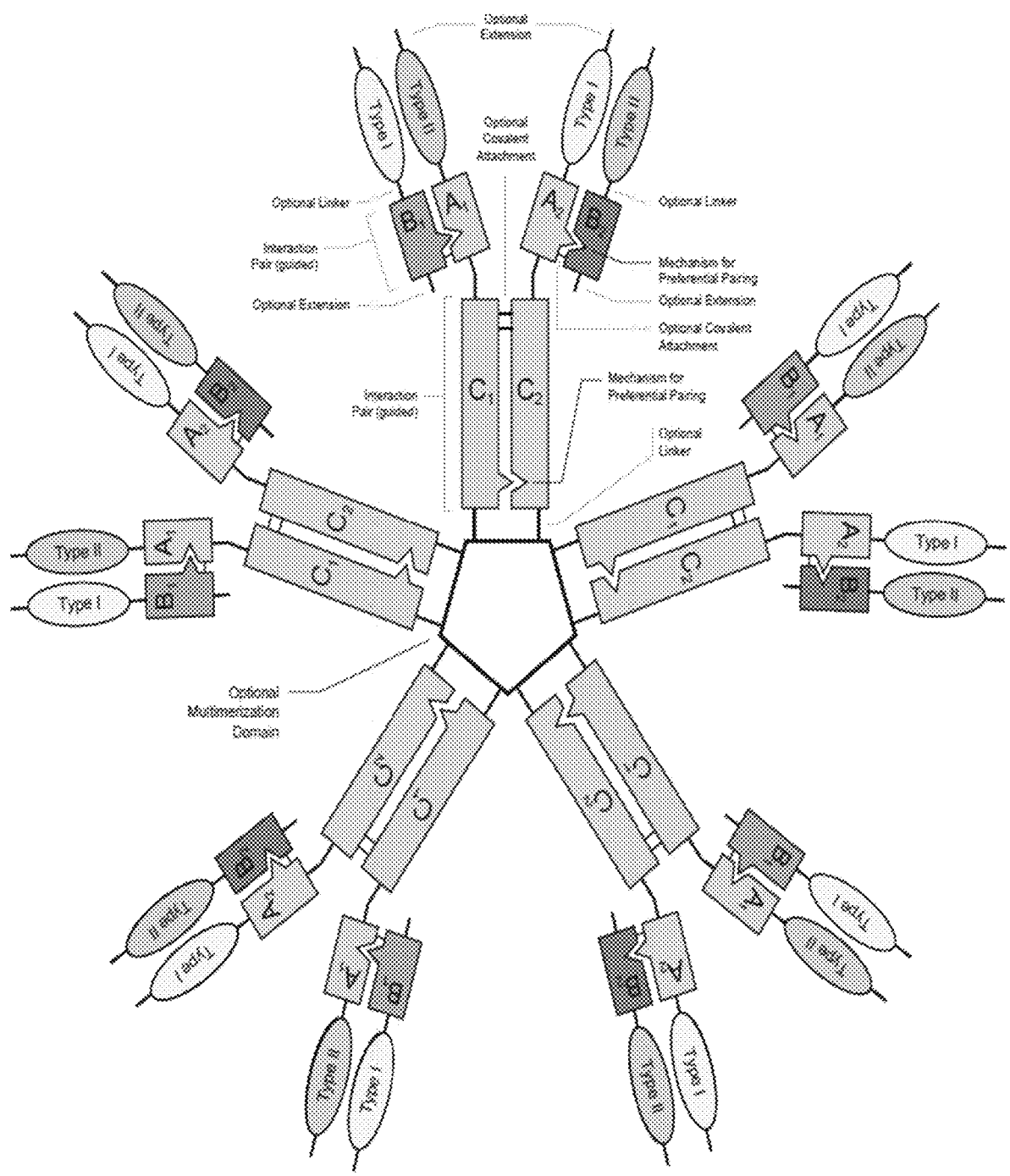
Figure 6G:
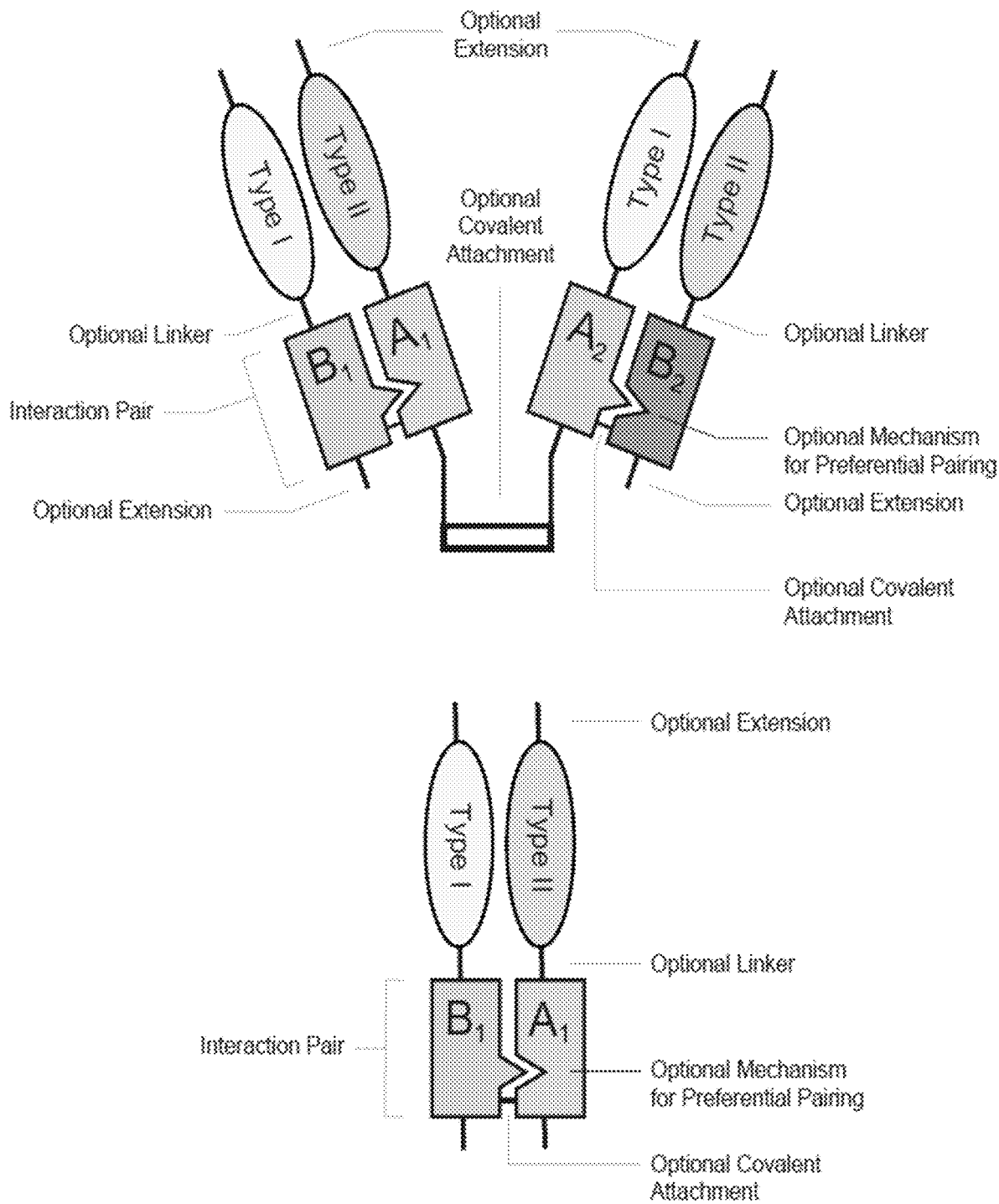

In the illustrated embodiments, the a type I receptor polypeptide is part of a fusion polypeptide that comprises a first member of an interaction pair ("C1"), and a type II receptor polypeptide is part of a fusion polypeptide that comprises a second member of an interaction pair ("C2"). Suitable interaction pairs included, for example, heavy chain and/or light chain immunoglobulin interaction pairs, truncations, and variants thereof such as those described herein (e.g., Spiess et al (2015) *Molecular Immunology* 67(2A): 95-106). In each fusion polypeptide, a linker may be positioned between a type I receptor polypeptide or a type II receptor polypeptide and the corresponding member of the interaction pair. The first and second members of the interaction pair may be unguided, meaning that the members of the pair may associate with each other or self-associate without substantial preference, and they may have the same or different amino acid sequences. See FIG. 5A. Alternatively, the interaction pair may be a guided (asymmetric) pair, meaning that the members of the pair associate preferentially with each other rather than self-associate. See FIG. 5B. Complexes of higher order can be envisioned. See FIGS. 5C and 5D.

FIGS. 6A-6G show schematic examples of heteromeric protein complexes comprising two type I receptor polypeptide (indicated as "I") (e.g., a polypeptide that is at least 80%, 85%, 90%, 95%, 97%, 98%, 99% or 100% identical to an extracellular domain of an ALK1, ALK4, ALK5, or ALK7 protein from humans or other species such as those described herein) and two type II receptor polypeptide (indicated as "II") (e.g., a polypeptide that is at least 80%, 85%, 90%, 95%, 97%, 98%, 99% or 100% identical to an extracellular domain of an ActRIIA, ActRIIB, MISRII, or BMPRII protein from humans or other species such as those described herein).

In the illustrated embodiment in FIG. 6A, the first type I receptor polypeptide (from left to right) is part of a fusion polypeptide that comprises a first member of an interaction pair ("C1") and further comprises an additional first member of an interaction pair ("A1"); and the second type I receptor polypeptide is part of a fusion polypeptide that comprises a second member of an interaction pair ("C2") and further comprises an first member of an interaction pair ("A2"). The first type II receptor polypeptide (from left to right) is part of a fusion polypeptide that comprises a second member of an interaction pair ("B1"); and the second type II receptor polypeptide is part of a fusion polypeptide that comprises a second member of an interaction pair ("B2"). A1 and A2 may be the same or different; B1 and B2 may be the same or different, and C1 and C2 may be the same or different. In each fusion polypeptide, a linker may be positioned between the type I receptor polypeptide or type II receptor polypeptide and the corresponding member of the interaction pair as well as between interaction pairs. FIG. 6A is an example of an association of unguided interaction pairs, meaning that the members of the pair may associate with each other or self-associate without substantial preference and may have the same or different amino acid sequences.

In the illustrated embodiment in FIG. 6B, the first type II receptor polypeptide (from left to right) is part of a fusion polypeptide that comprises a first member of an interaction pair ("C1") and further comprises an additional first member of an interaction pair ("A1"); and the second type II receptor ActRIIB polypeptide is part of a fusion polypeptide that comprises a second member of an interaction pair ("B2"). The first type I receptor polypeptide (from left to right) is part of a fusion polypeptide that comprises a second member of an interaction pair ("B1"); and the second type I receptor polypeptide is part of a fusion polypeptide that comprises a second member of an interaction pair ("C2") and further comprises a first member of an interaction pair ("A2"). In each fusion polypeptide, a linker may be positioned between the type I receptor or type II receptor polypeptide and the corresponding member of the interaction pair as well as between interaction pairs. FIG. 6B is an example of an association of guided (asymmetric) interaction pairs, meaning that the members of the pair associate preferentially with each other rather than self-associate.

Suitable interaction pairs included, for example, heavy chain and/or light chain immunoglobulin interaction pairs, truncations, and variants thereof as described herein (e.g., Spiess et al (2015) *Molecular Immunology* 67(2A): 95-106). Complexes of higher order can be envisioned. See FIG. 6C-6F. Using similar methods, particularly those that employ light and/or heavy chain immunoglobulins, truncations, or variants thereof, interaction pairs may be used to produce heterodimers that resemble antibody Fab and F(ab')$_2$ complexes (e.g., Spiess et al (2015) *Molecular Immunology* 67(2A): 95-106). See FIG. 6G.

Figure 7:
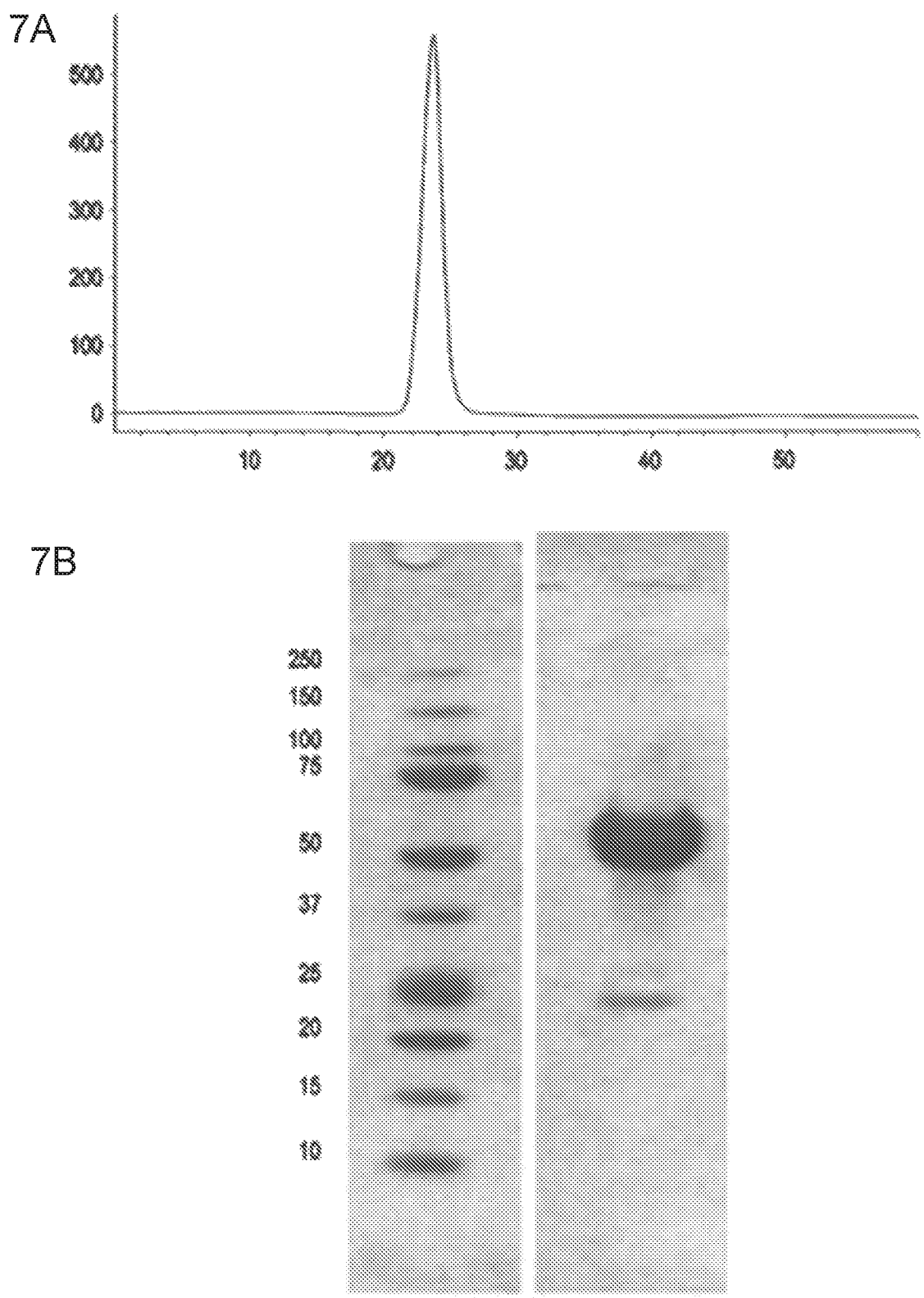

FIG. 7 shows the purification of ActRIIA-hFc expressed in CHO cells, visualized by sizing column (FIG. 7A) and Coomassie stained SDS-PAGE (FIG. 7B, left lane: molecular weight standards; right lane: ActRIIA-hFc).

Figure 8:
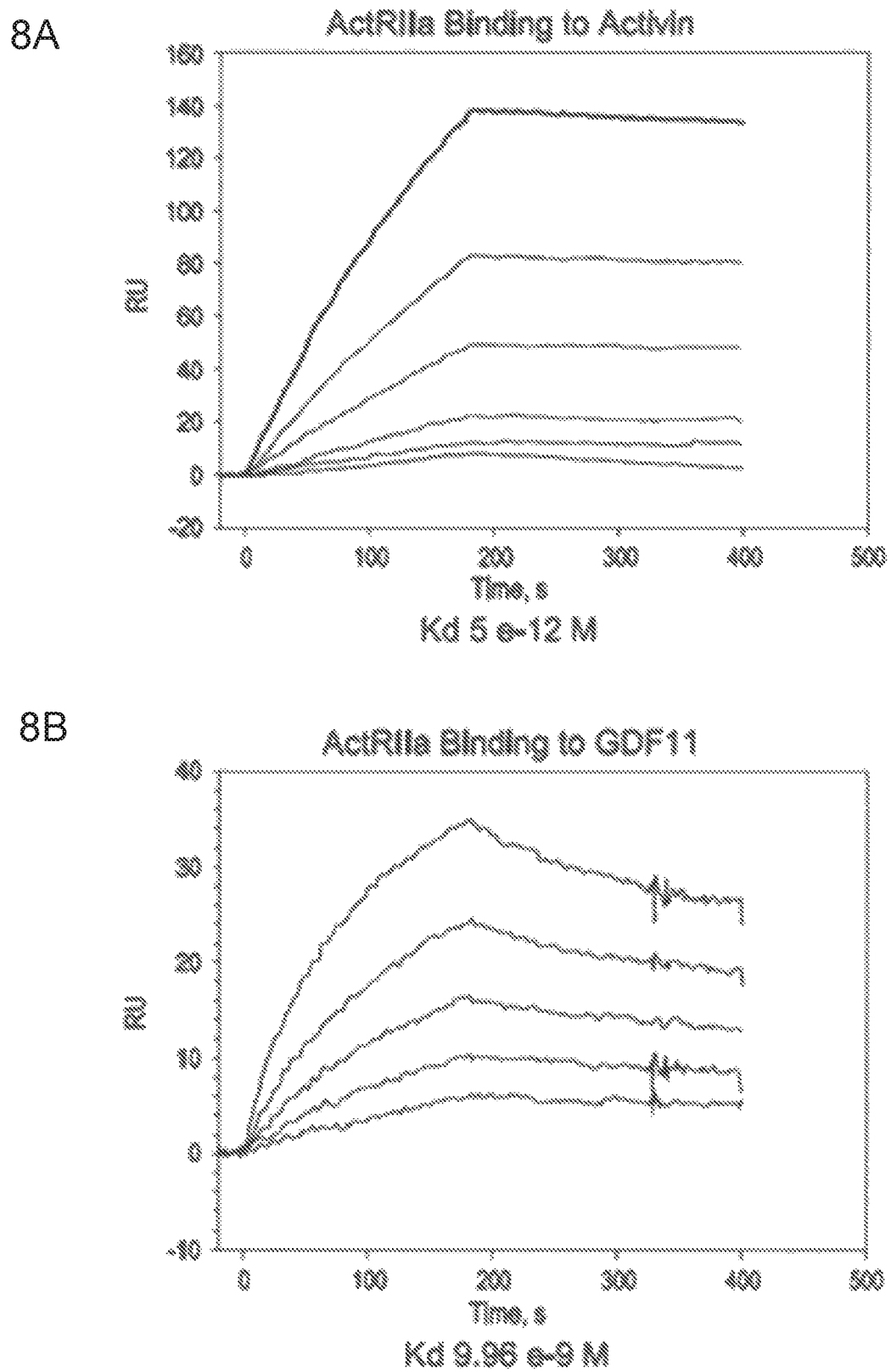

FIG. 8 shows the binding of ActRIIA-hFc to activin (FIG. 8A) and GDF-11 (FIG. 8B), as measured by Biacore™ assay.

FIGS. 9A and 9B show schematic examples of a heteromeric protein complex comprising an ALK4 polypeptide (e.g., a polypeptide that is at least 70%, 75%, 80%, 85%, 90%, 91%, 92%, 93%, 94%, 95%, 97%, 98%, 99% or 100% identical to an extracellular domain of an ALK4 protein from humans or other species as described herein), an ActRIIB polypeptide (e.g., a polypeptide that is at least 70%, 75%, 80%, 85%, 90%, 91%, 92%, 93%, 94%, 95%, 97%, 98%, 99% or 100% identical to an extracellular domain of an ActRIIB protein from humans or other species as such as those described herein), and a ligand-binding domain of an antibody (e.g., a ligand-binding domain derived from an antibody that binds to one or more ALK4:ActRIIB-binding ligands). In the illustrated embodiments, the ALK4 polypeptide is part of a fusion polypeptide that comprises a first member of an interaction pair ("C$_1$"), and further comprises an additional first member of an interaction pair ("A$_1$"). The ActRIIB polypeptide is part of a fusion polypeptide that comprises a second member of an interaction pair ("B$_1$"). The variable heavy chain (V$_H$) polypeptide is part of a fusion polypeptide that comprises a second member of an interaction pair ("C$_2$"), and further comprises a first member of an interaction pair ("A$_2$"). The variable heavy chain (V$_L$) polypeptide is part of a fusion polypeptide that comprises a second member of an interaction pair ("B$_2$"). In each fusion polypeptide, a linker may be positioned between the ALK4 or ActRIIB polypeptide and the corresponding member of the interaction pair, between interaction pairs, and between the V$_H$ and V$_L$ polypeptides and a member of the interaction pair. A$_1$ and A$_2$ may be the same or different; B$_1$ and B$_2$ may be the same or different, and C$_1$ and C$_2$ may be the same or different. Suitable interaction pairs included, for example, constant heavy chain and/or light chain immunoglobulin interaction pairs, truncations, and variants thereof as described herein (e.g., Spiess et al (2015) *Molecular Immunology* 67(2A): 95-106). FIG. 9A is an example of an association of guided (asymmetric) interaction pairs, meaning that the members of the pair associate preferentially with each other rather than self-associate. FIG. 9B is an example of an association of unguided interaction pairs, meaning that the members of the pair may associate with each other or self-associate without substantial preference and may have the same or different amino acid sequences.

Such antibody-ALK4:ActRIIB complexes may be useful in situations where it is desirable to further bind/antagonize an agent that is not an ALK4:ActRIIB ligand. Alternatively, such antibody-ALK4:ActRIIB complexes may be useful in situations where it is desirable to further enhance ALK4:ActRIIB ligand binding/antagonism. For example, as demonstrated by the examples herein, activin B, activin A, GDF11, and GDF8 all bind with strong affinity to an ALK4:ActRIIB heterodimer. In addition, BMP6 binds to ALK4:ActRIIB heterodimers but with weaker affinity. In certain situations where it is desirable to antagonize BMP6 activity, in addition to one or more of the high affinity-binding ligands (e.g., activin B, activin A, GDF11, and GDF8), BMP6 may be outcompeted for binding to the ALK4:ActRIIB heterodimer. In such situations, addition of BMP6-binding domain of an antibody to the ALK4:ActRIIB heteromultimer complex would improve the capacity of such protein complexes to antagonize BMP6 in addition to one or more of activin B, activin A, GDF11, and GDF8.

Figure 10:
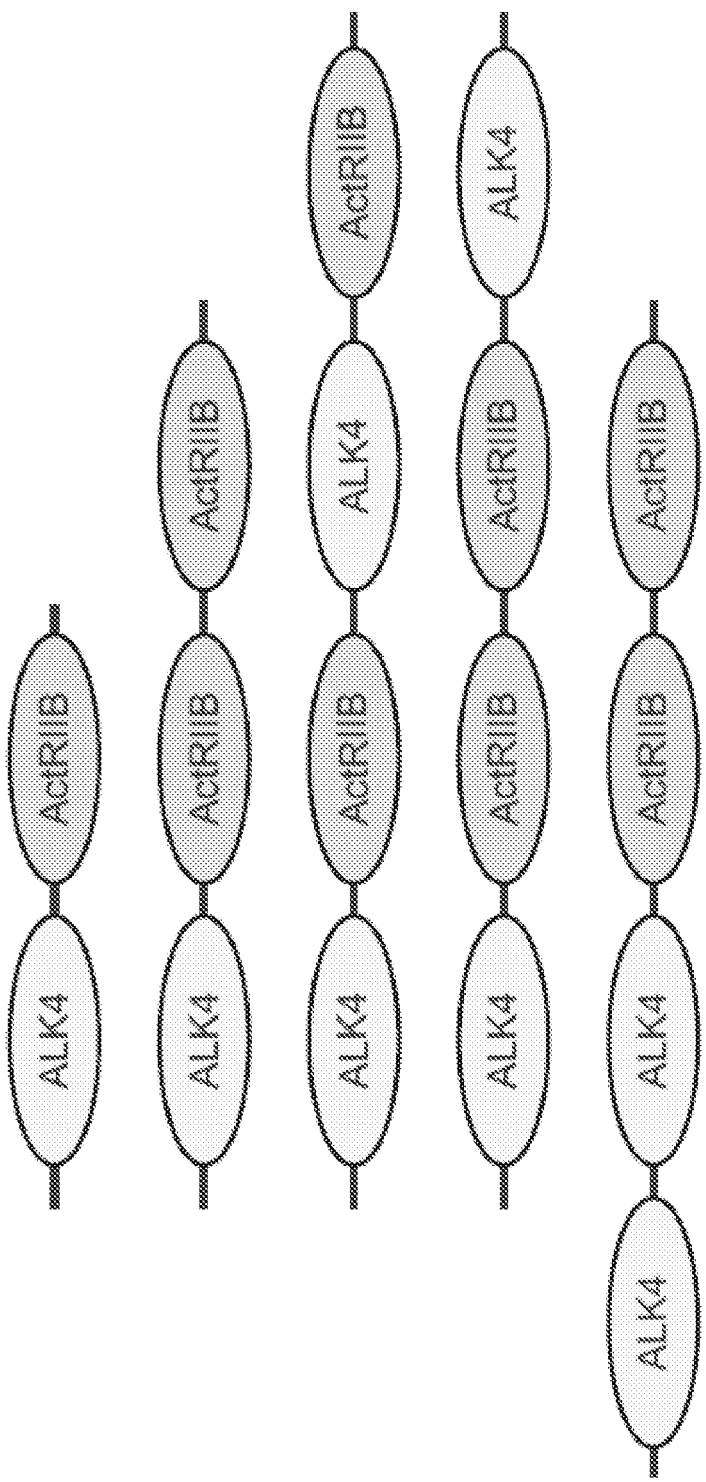

FIG. 10 shows schematic examples of ALK4:ActRIIB single-trap polypeptides. ALK4:ActRIIB single-trap polypeptides may contain multiple ALK4 domains (e.g., 1, 2, 3, 4, 5, 6, 7, 9, 10 or more domains), having the same or different sequences, and multiple ActRIIB domains (e.g., 1, 2, 3, 4, 5, 6, 7, 9, 10 or more domains), having the same or different sequences. These ALK4 and ActRIIB domains may be arranged in any order and may comprise one or more linker domains positions between one or more of the ALK4 and ActRIIB domains. Such ligand traps may be used as therapeutic agents to treat or prevent diseases or conditions described herein.

Figure 11A:
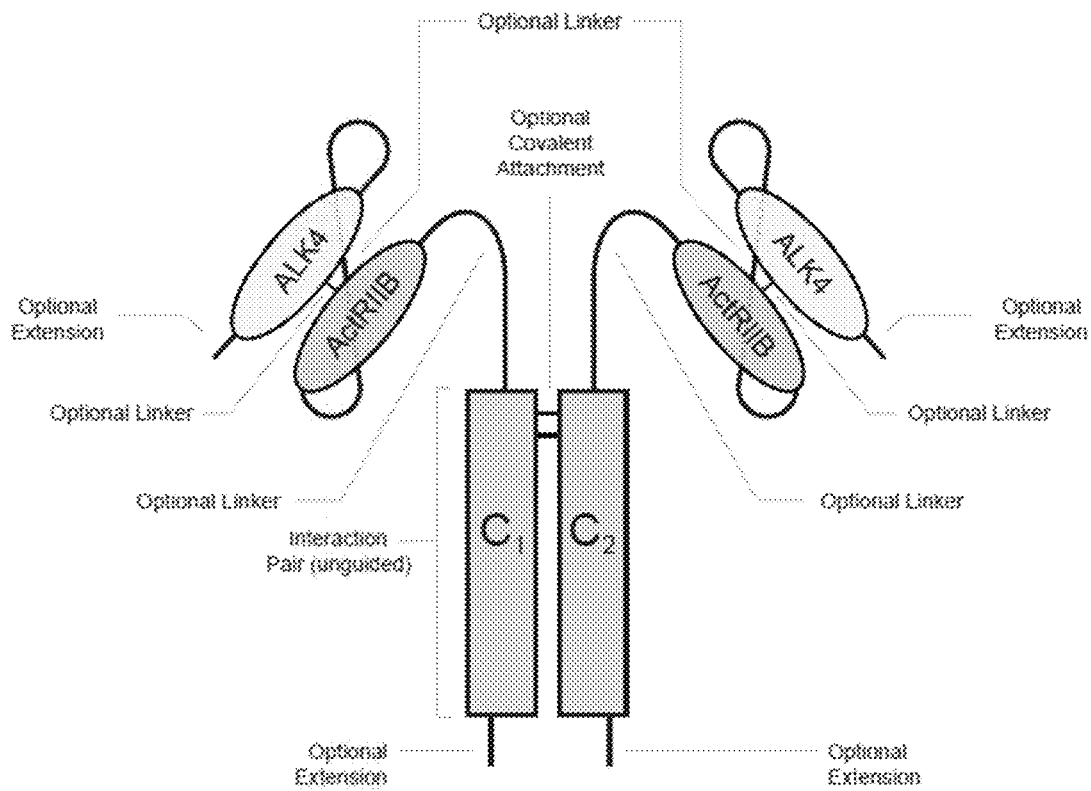
Figure 11B:
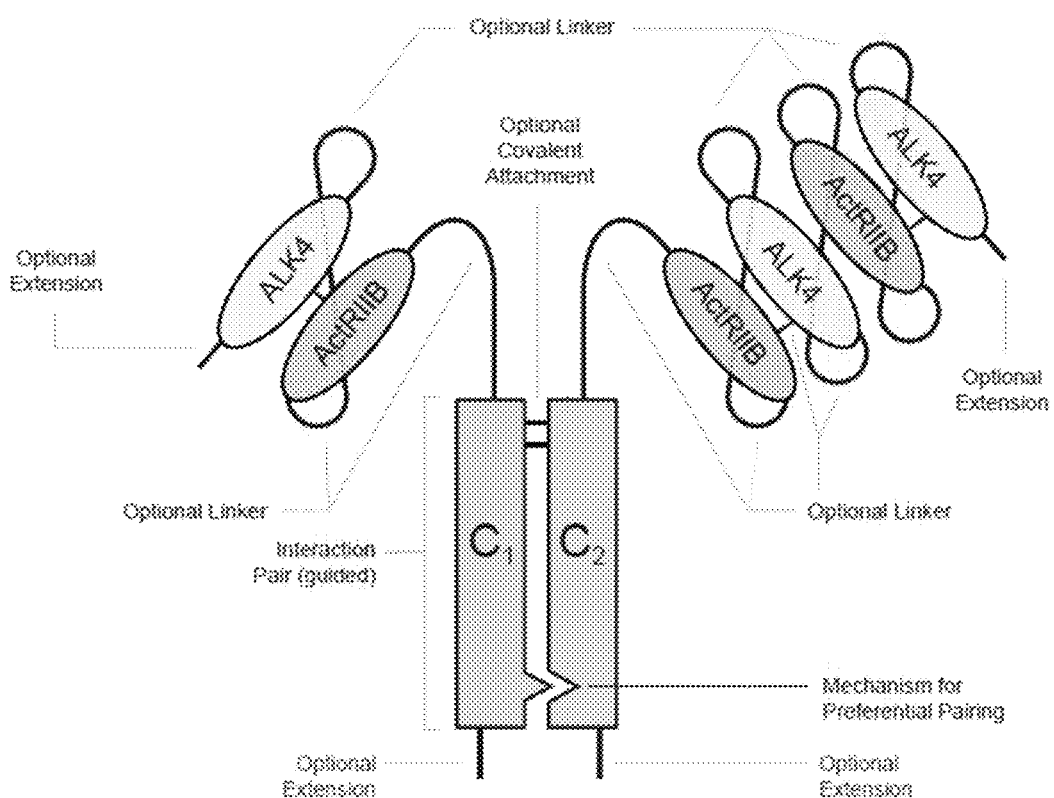
Figure 11C:
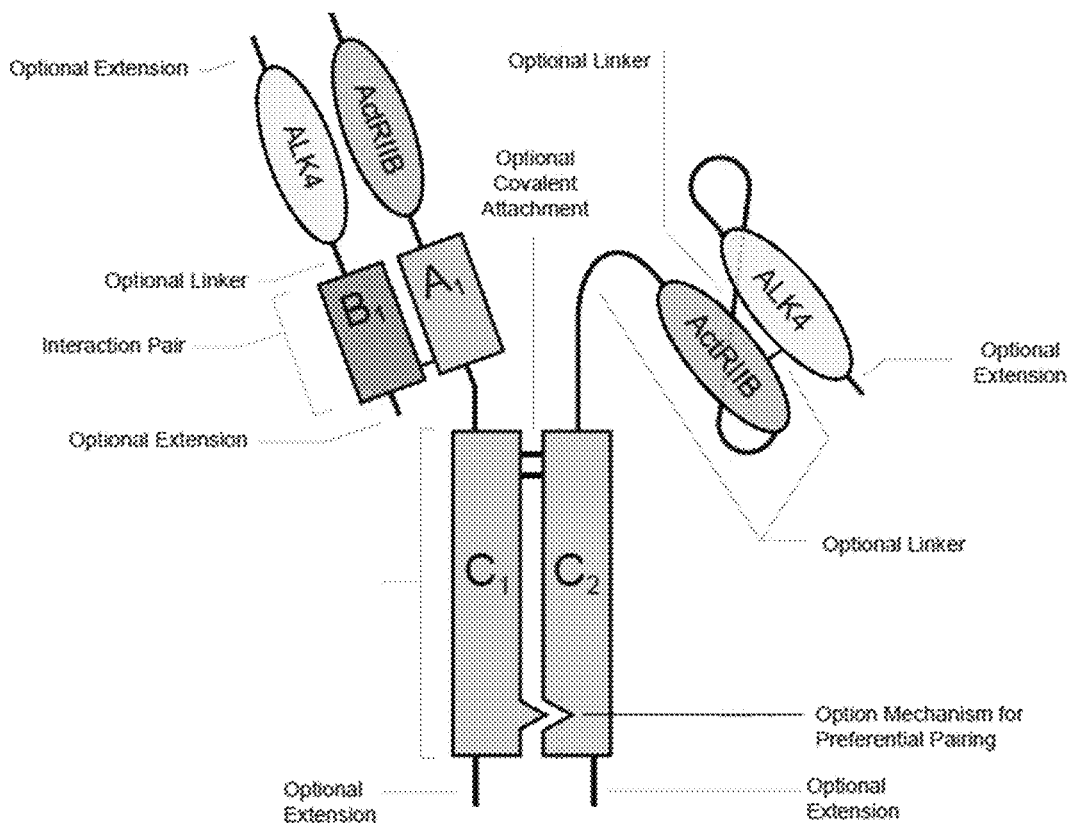
Figure 11D:
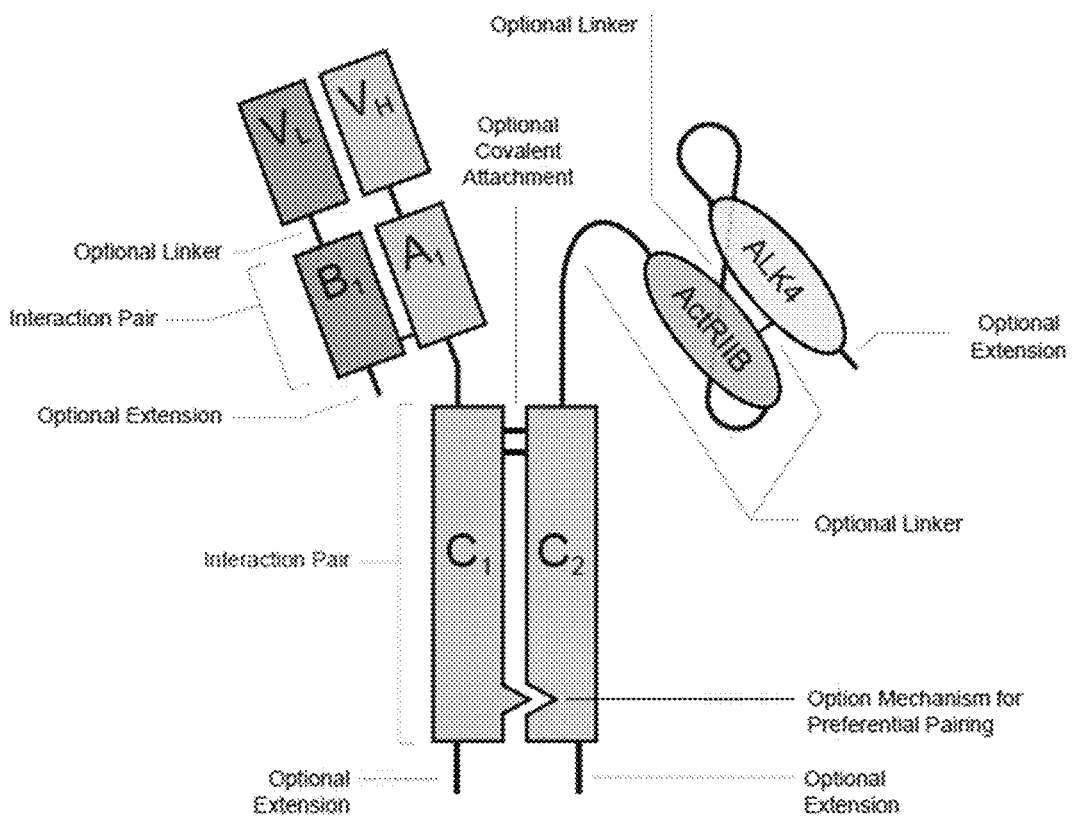

FIGS. 11A-11D show schematic examples of multimeric protein complex comprising at least one ALK4:ActRIIB single-chain trap polypeptides. In the illustrated embodiments 11A and 111B, a first ALK4:ActRIIB single-chain trap polypeptide (from left to right) is part of a fusion polypeptide that comprises a first member of an interaction pair ("C$_1$"); and a second ALK4:ActRIIB single-chain trap polypeptide is part of a fusion polypeptide that comprises a second member of an interaction pair ("C$_2$"). C$_1$ and C$_2$ may be the same or different. The first and second ALK4:ActRIIB single-chain trap polypeptides may be the same or different. In each fusion polypeptide, a linker may be positioned between the ALK4:ActRIIB single-chain trap polypeptide and the corresponding member of the interaction pair. Suitable interaction pairs included, for example, heavy chain and/or light chain immunoglobulin interaction pairs, truncations, and variants thereof as described herein [e.g., Spiess et al (2015) Molecular Immunology 67(2A): 95-106]. FIG. 11A is an example of an association of unguided interaction pairs, meaning that the members of the pair may associate with each other or self-associate without substantial preference and may have the same or different amino acid sequences. FIG. 11B is an example of an association of guided (asymmetric) interaction pairs, meaning that the members of the pair associate preferentially with each other rather than self-associate. Complexes of higher order can be envisioned. In addition, such ALK4:ActRIIB single-chain trap polypeptides may be similarly be associated, covalently or non-covalently, with one or more ALK4 polypeptides and/or one or more ActRIIB polypeptides. See FIG. 11C. Also, such ALK4:ActRIIB single-chain trap polypeptides may be similarly be associated, covalently or non-covalently, with one or more ligand-binding domain of an antibody (e.g., a ligand-biding domain of an antibody that binds to one or more ALK4:ActRIIB binding ligands). See FIG. 11D.

Figure 12:
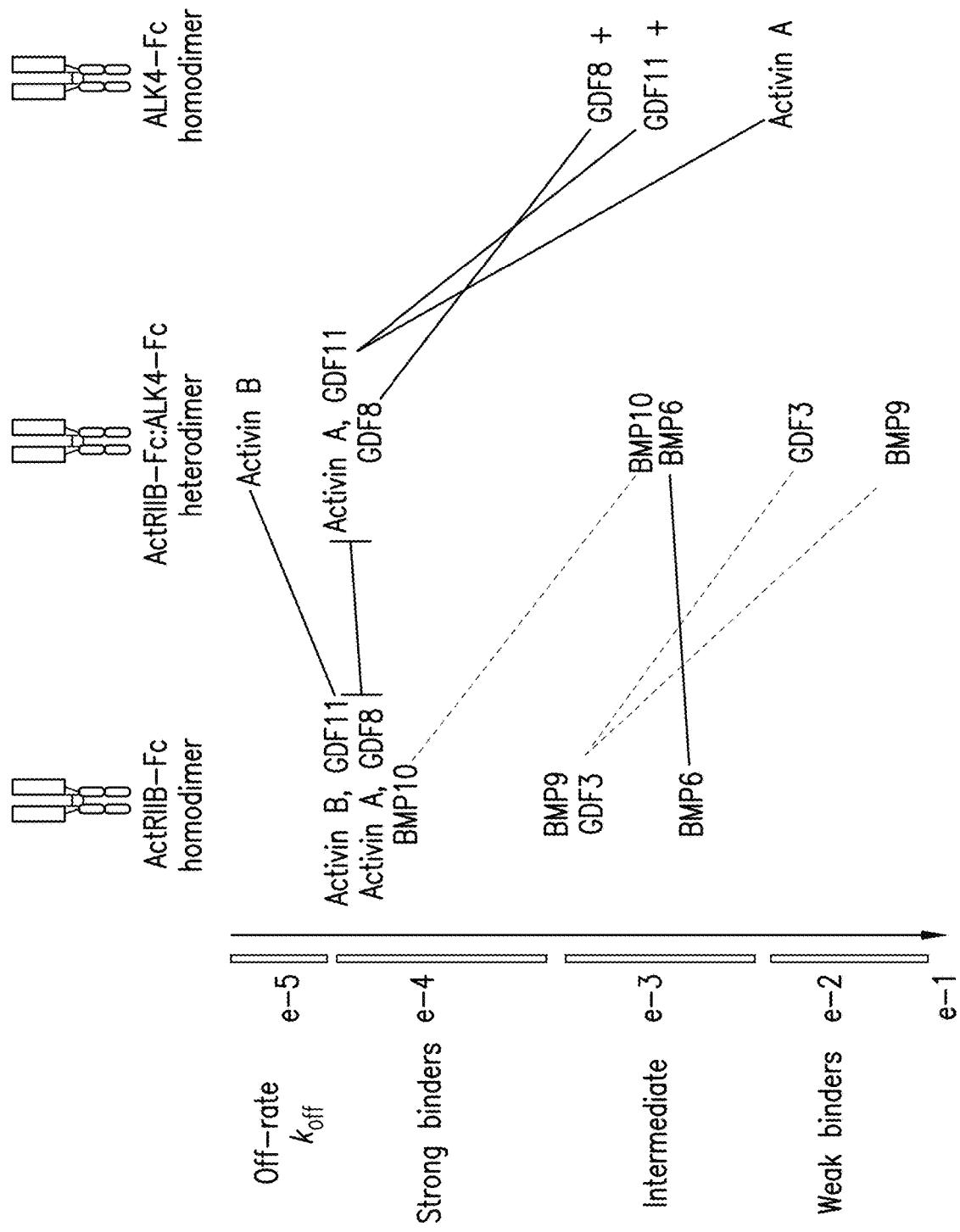

FIG. 12 shows comparative ligand binding data for an ALK4-Fc:ActRIIB-Fc heterodimeric protein complex compared to ActRIIB-Fc homodimer and ALK4-Fc homodimer. For each protein complex, ligands are ranked by $k_{off}$, a kinetic constant that correlates well with ligand signaling inhibition, and listed in descending order of binding affinity (ligands bound most tightly are listed at the top). At left, yellow, red, green, and blue lines indicate magnitude of the off-rate constant. Solid black lines indicate ligands whose binding to heterodimer is enhanced or unchanged compared with homodimer, whereas dashed red lines indicate substantially reduced binding compared with homodimer. As shown, the ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. Like ActRIIB-Fc homodimer, the heterodimer retains intermediate-level binding to BMP6.

Figure 13:
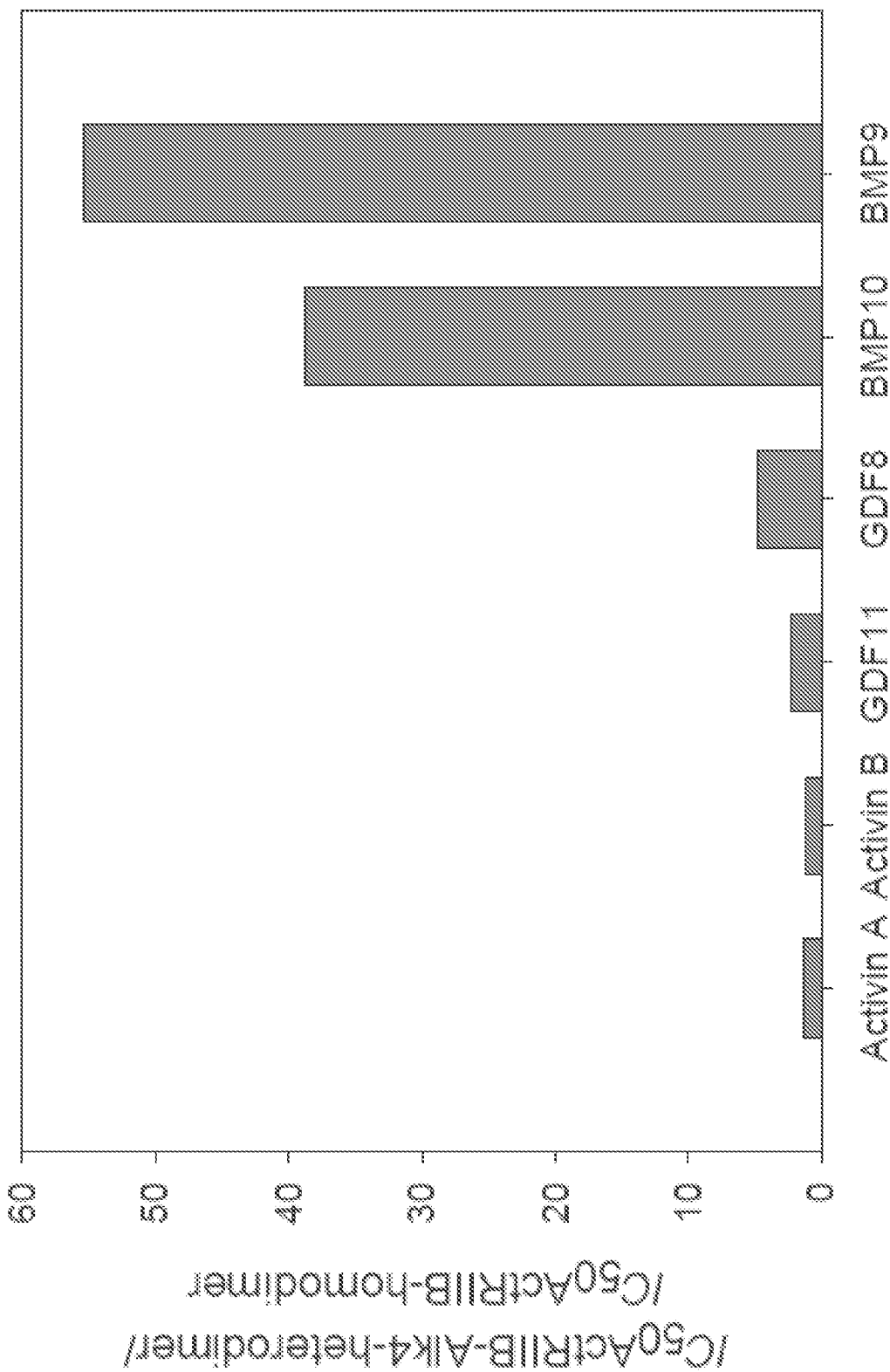

FIG. 13 shows comparative ALK4-Fc:ActRIIB-Fc heterodimer/ActRIIB-Fc:ActRIIB-Fc homodimer IC$_{50}$ data as determined by an A-204 Reporter Gene Assay as described herein. ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. These data demonstrate that ALK4:ActRIIB heterodimers are more selective antagonists of activin A, activin B, GDF8, and GDF11 compared to corresponding ActRIIB:ActRIIB homodimers.

Figure 14A:
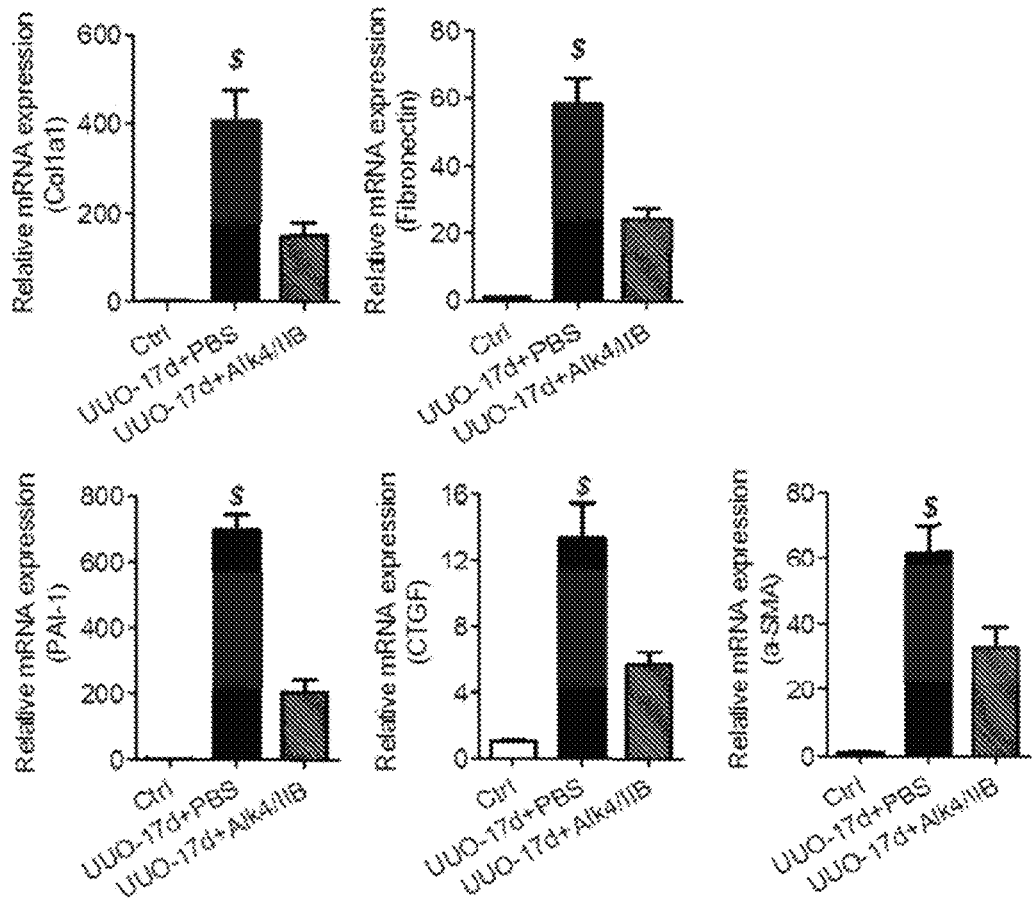
Figure 14B:
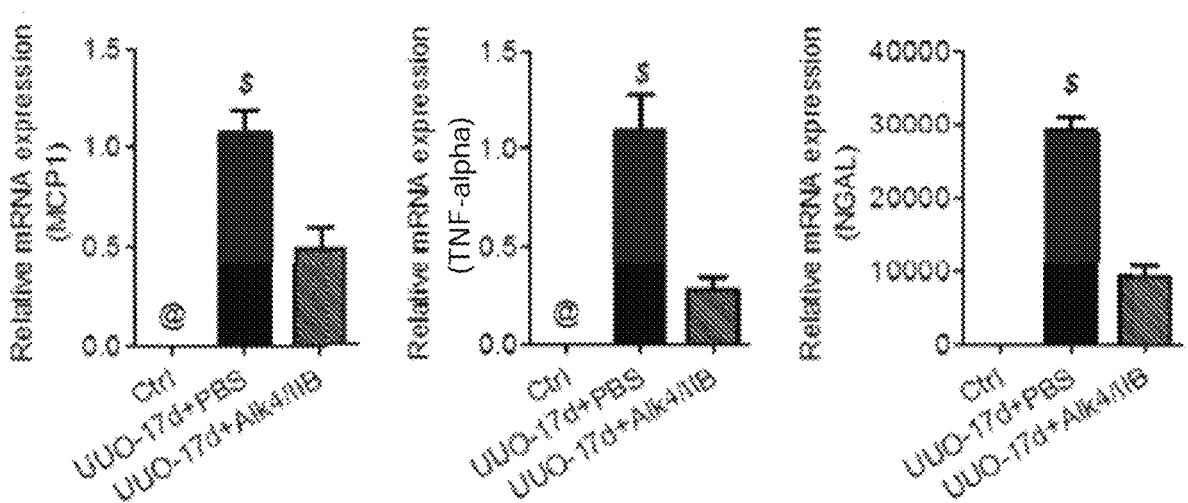
Figure 14C:
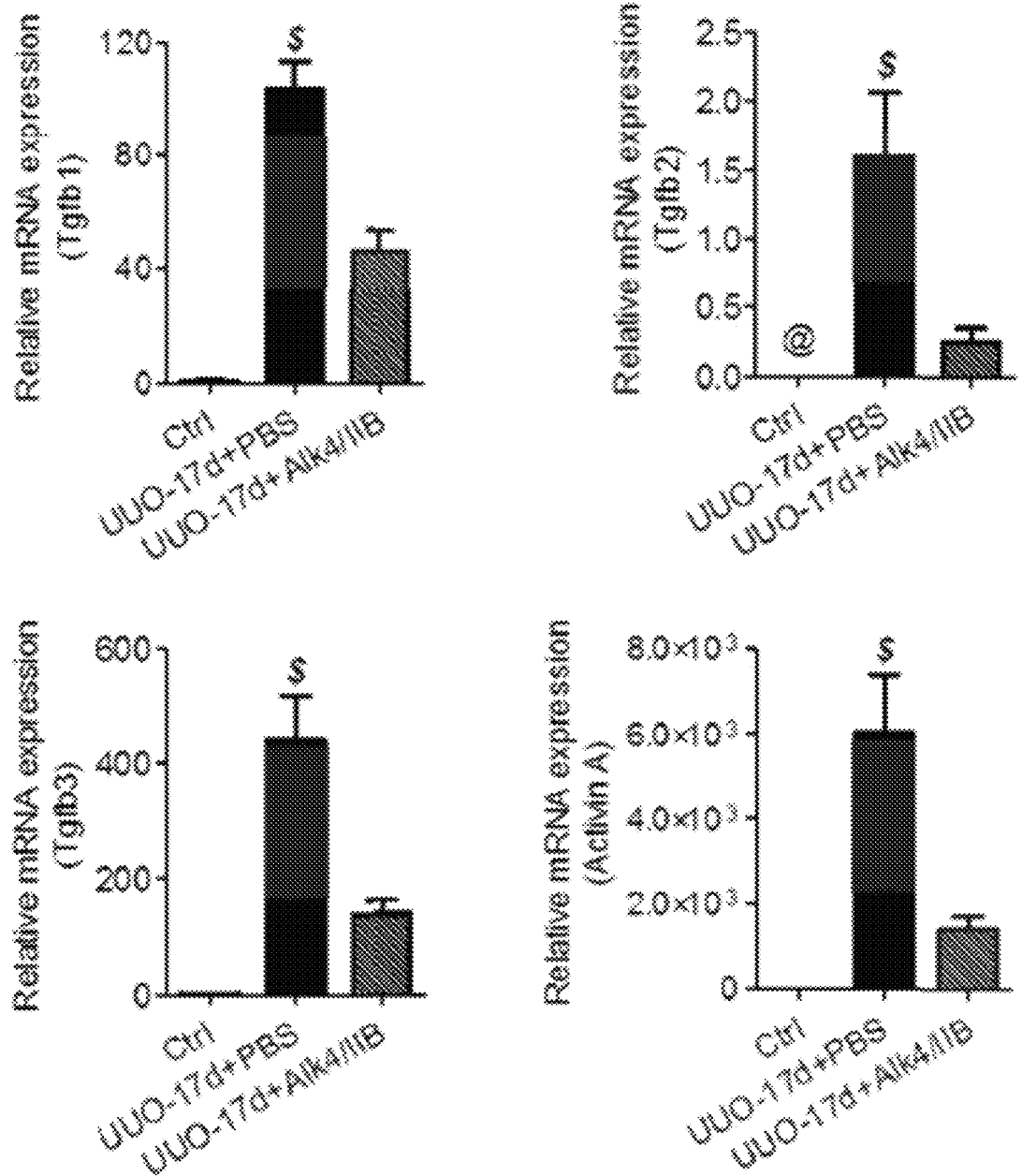

FIGS. 14A-14C show gene expression profiles of fibrotic genes (Col1a1, Fibronectin, PAI-1, CTGF, and a-SMA), inflammatory genes (TNF-alpha, and MCP1), cytokine genes (TGF-beta 1, TGF-beta 2, TGF-beta 3, and activin A), kidney injury gene (NGAL), Hypoxia-inducible factor 1-alpha (HIF 1a), and activin A receptor (Acvr2A) from mouse kidneys subjected to unilateral ureteral obstruction (UUO). Samples from the contralateral, non-surgery kidney were used as a control (Ctrl). Gene expression profiles were obtained at 17 days post-surgery. Mice were administered either PBS or an ALK4-Fc:ActRIIB-Fc homodimer at days 3, 7, 10, and 14 post-surgery. ($) denotes a statistical difference between UUO kidneys at 17 days in mice administered only PBS compared UUO kidneys at 17 days in mice administered the ALK7-Fc:ActRIIB-Fc homodimer. (@) denotes that no transcript was detected.

Figure 15:
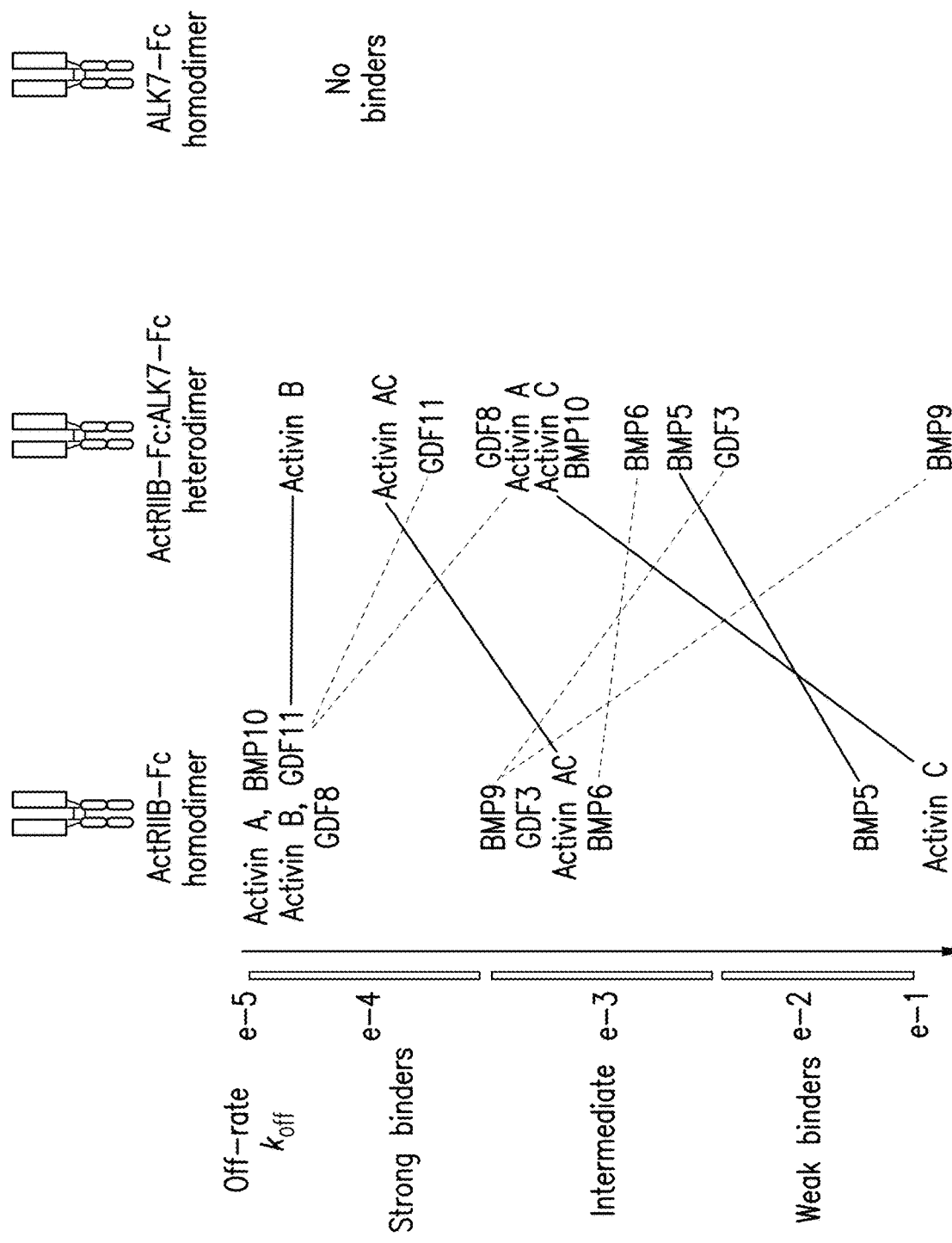

FIG. 15 shows comparative ligand binding data for an ALK7-Fc:ActRIIB-Fc heterodimeric protein complex compared to ActRIIB-Fc homodimer and ALK7-Fc homodimer. For each protein complex, ligands are ranked by $k_{off}$, a kinetic constant that correlates well with ligand signaling inhibition, and listed in descending order of binding affinity (ligands bound most tightly are listed at the top). At left, yellow, red, green, and blue lines indicate magnitude of the off-rate constant. Solid black lines indicate ligands whose binding to heterodimer is enhanced or unchanged compared with homodimer, whereas dashed red lines indicate substantially reduced binding compared with homodimer. As shown, four of the five ligands with strong binding to ActRIIB-Fc homodimer (activin A, BMP10, GDF8, and GDF11) exhibit reduced binding to the ActRIIB-Fc:ALK7-Fc heterodimer, the exception being activin B which retains tight binding to the heterodimer. Similarly, three of four ligands with intermediate binding to ActRIIB-Fc homodimer (GDF3, BMP6, and particularly BMP9) exhibit reduced binding to the ActRIIB-Fc:ALK7-Fc heterodimer, whereas binding to activin AC is increased to become the second strongest ligand interaction with the heterodimer overall. Finally, activin C and BMP5 unexpectedly bind the ActRIIB-Fc:ALK7 heterodimer with intermediate strength despite no binding (activin C) or weak binding (BMP5) to ActRIIB-Fc homodimer. No ligands tested bind to ALK7-Fc homodimer.

Figure 16A:
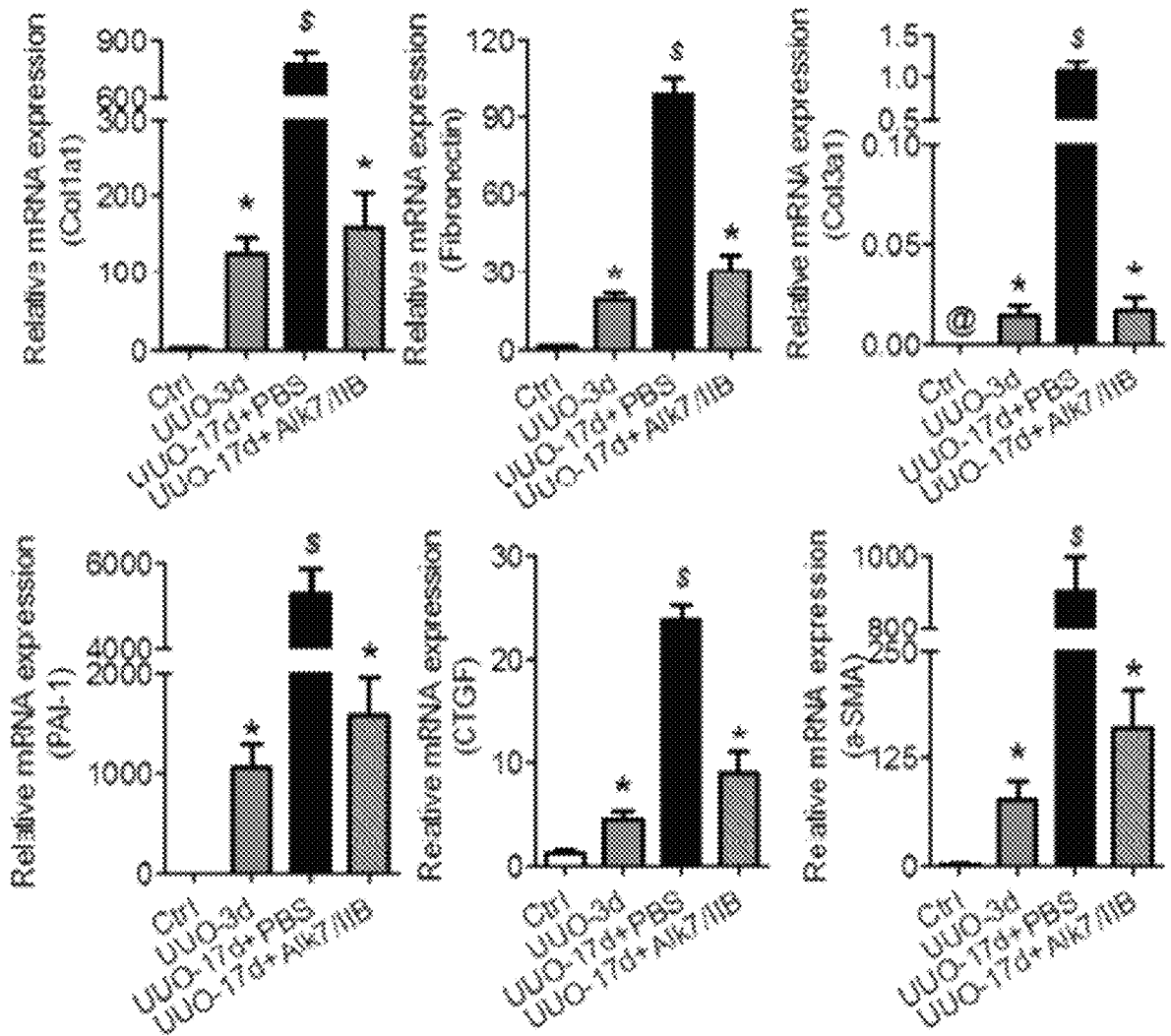
Figure 16B:
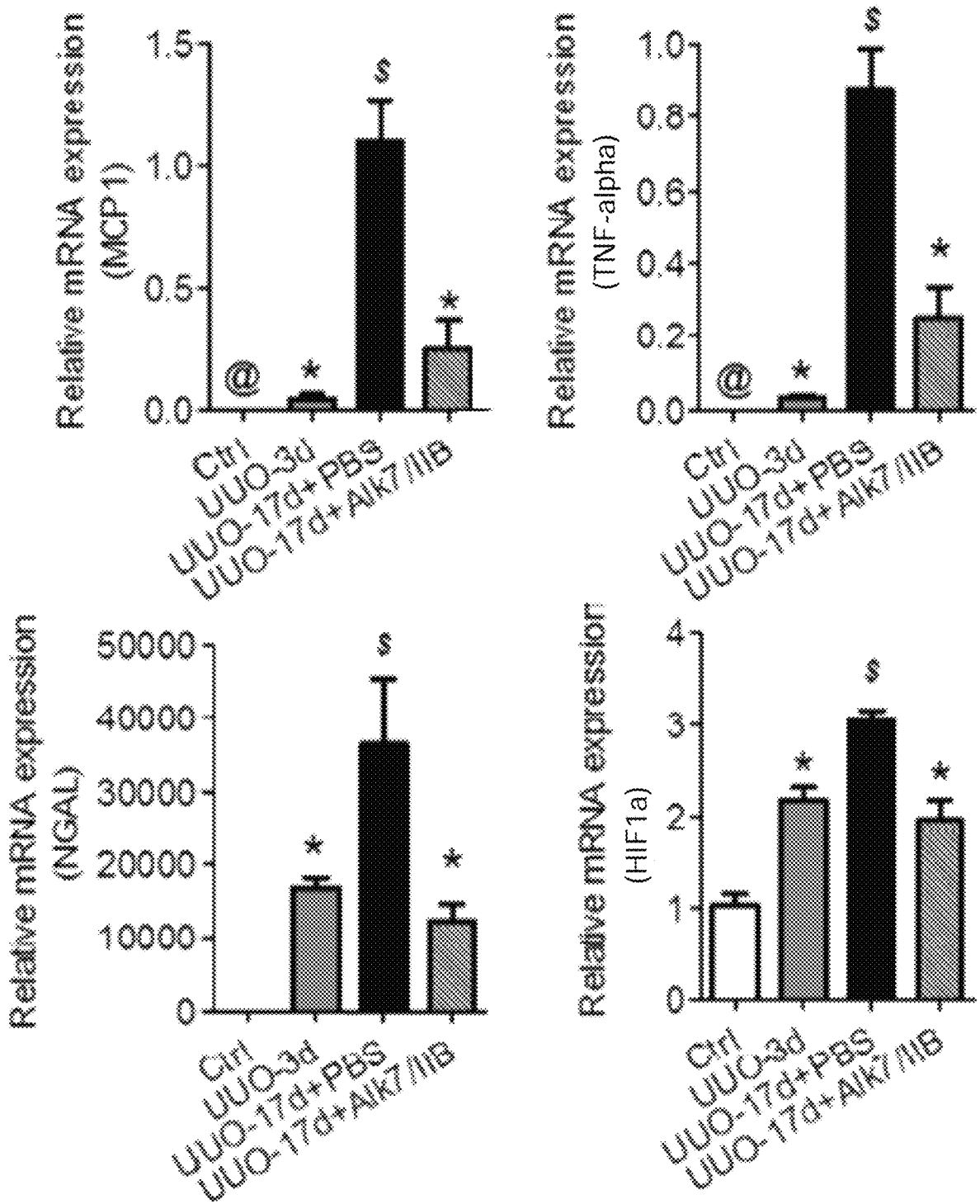
Figure 16C:
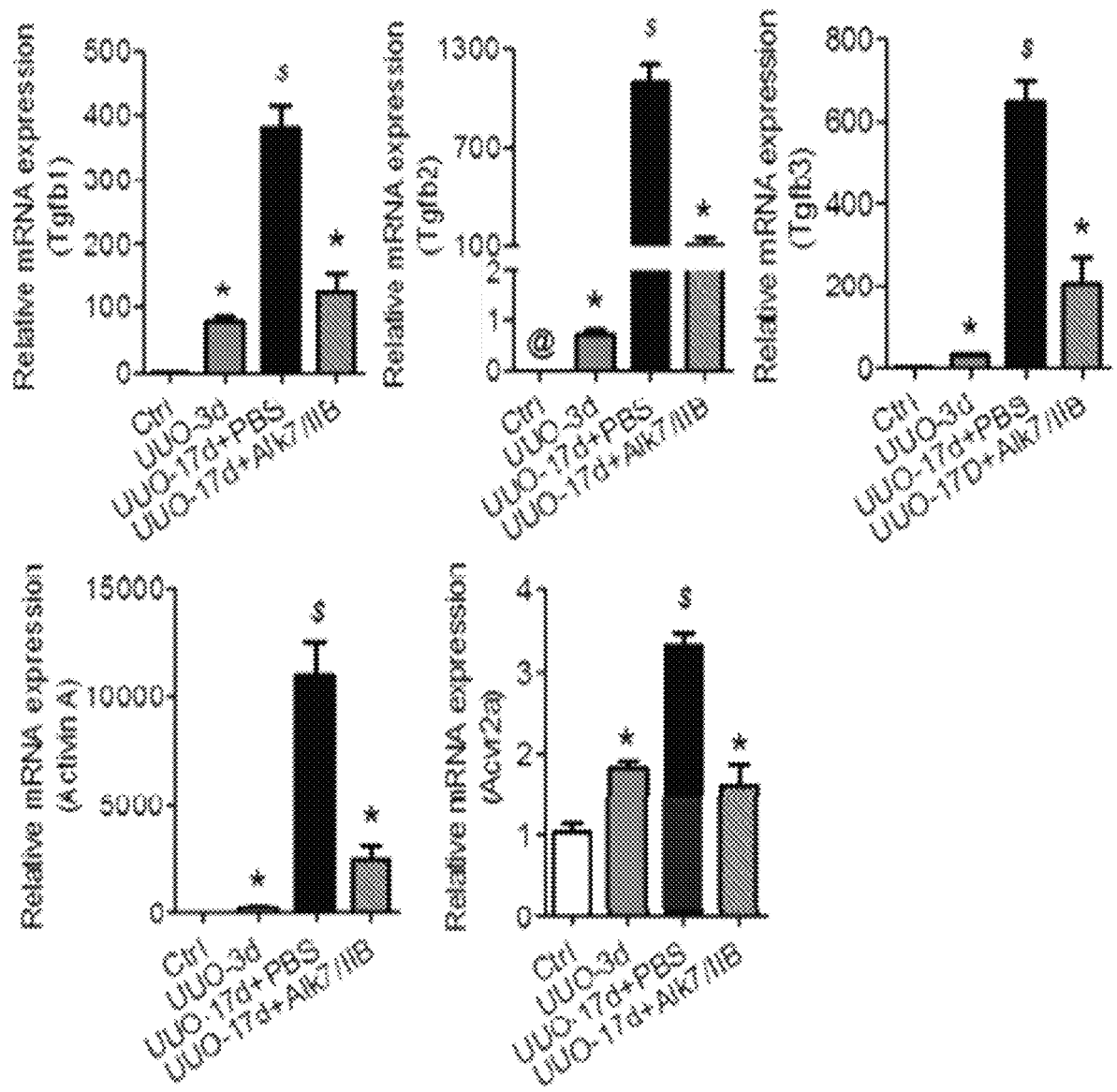

FIGS. 16A-16C show gene expression profiles of fibrotic genes (Col1a1, Col3a1, Fibronectin, PAI-1, CTGF, and a-SMA), inflammatory genes (TNF-alpha, and MCP1), cytokine genes (Tgfb1, Tgfb2, Tgfb3, and activin A), kidney injury gene (NGAL), Hypoxia-inducible factor 1-alpha (HIF 1a), and activin A receptor (Acvr2A) from mouse kidneys subjected to unilateral ureteral obstruction (UUO). Samples from the contralateral, non-surgery kidney were used as a control (Ctrl). Gene expression profiles were obtained at 3 days and 17 days post-surgery. Mice were administered either PBS or an ALK7-Fc:ActRIIB-Fc homodimer at days 3, 7, 10, and 14 post-surgery. Statistical analysis was performed using a one-way ANOVA followed by Tukey analysis. (*) denotes a statistical difference between i) control samples compared to UUO kidneys at 3 days or ii) control samples compared to UUO kidneys at 17 days in mice administered the ALK7-Fc:ActRIIB-Fc homodimer. ($) denotes a statistical difference between UUO kidneys at 17 days in mice administered only PBS compared with UUO kidneys at 17 days in mice administered the ALK7-Fc:ActRIIB-Fc homodimer. (@) denotes that no transcript was detected.

Figure 17:
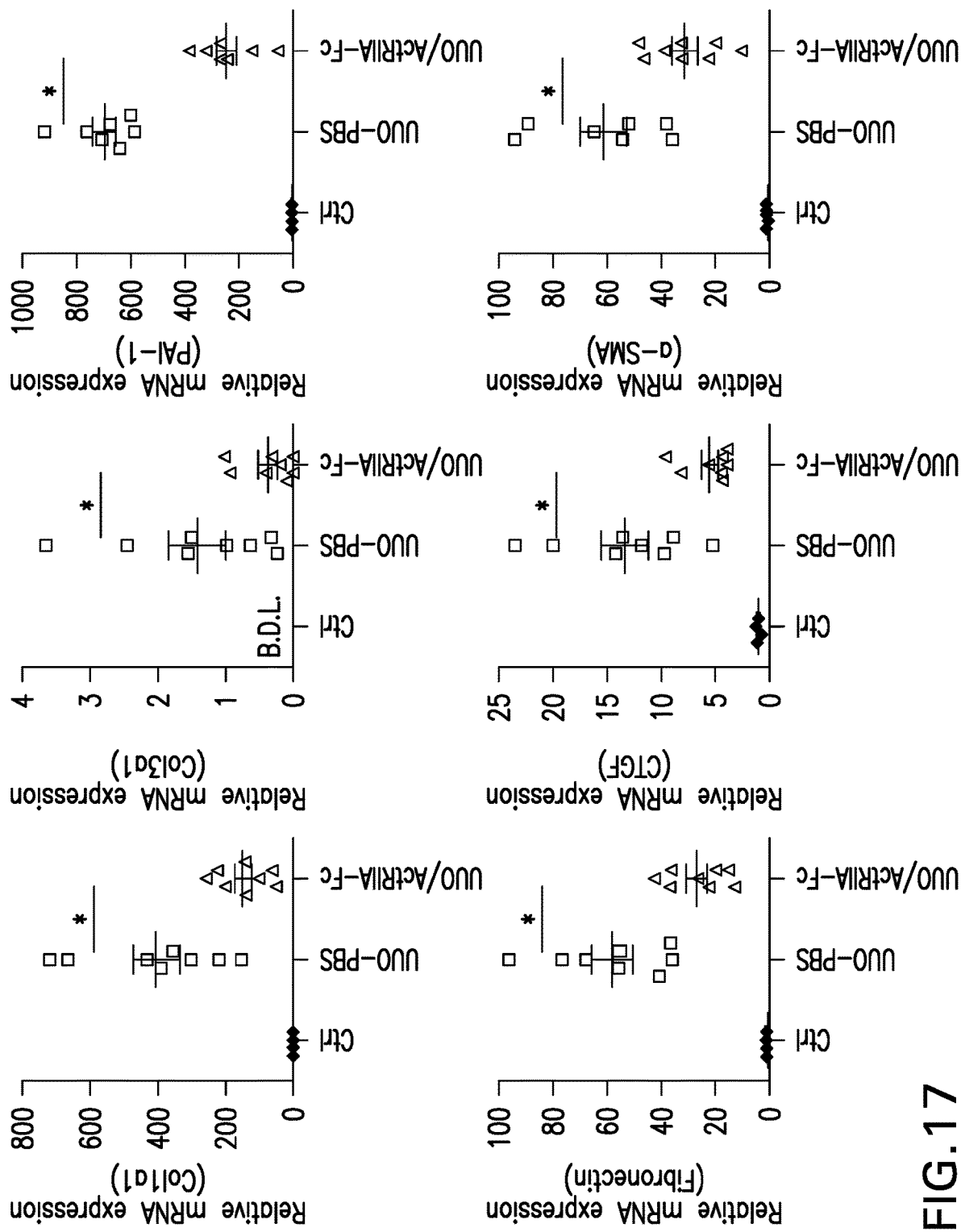

FIG. 17 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of ActRIIa-Fc homodimer.

Figure 18:
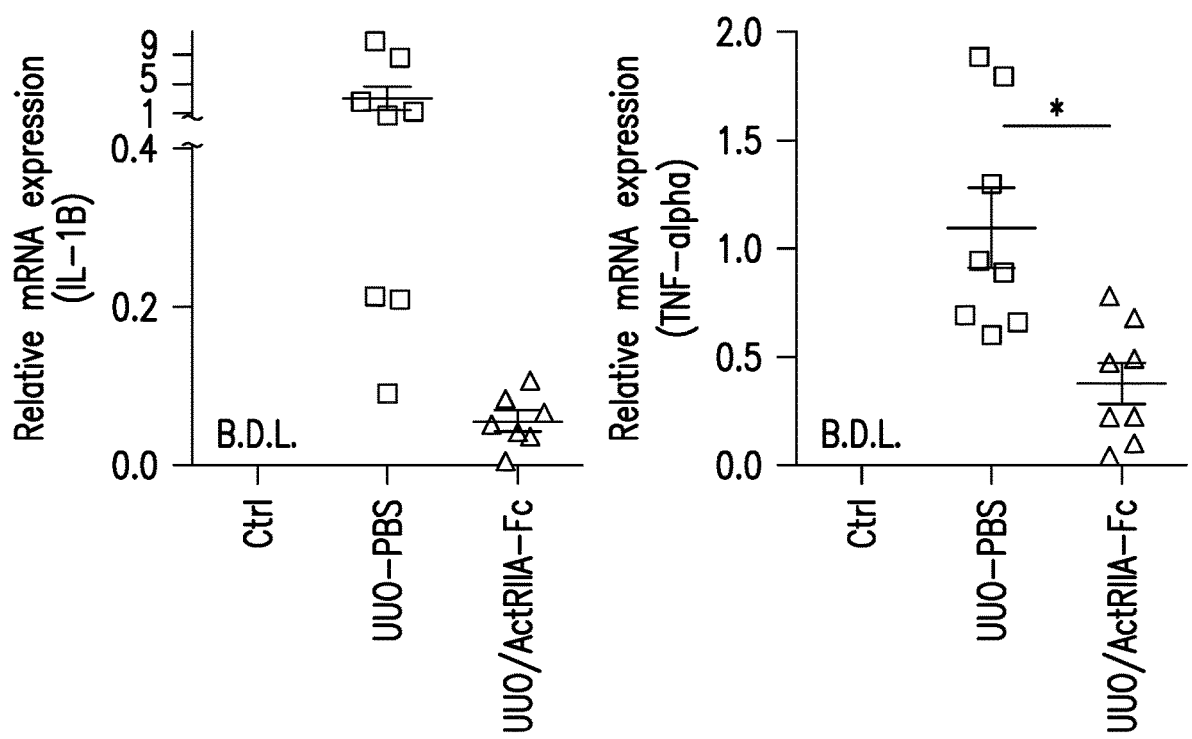

FIG. 18 shows gene expression profiles of inflammatory genes (IL-1B and TNF-alpha) from mouse kidneys subjected to unilateral ureteral obstruction (UUO) after treatment of ActRIIa-Fc homodimer.

Figure 19:
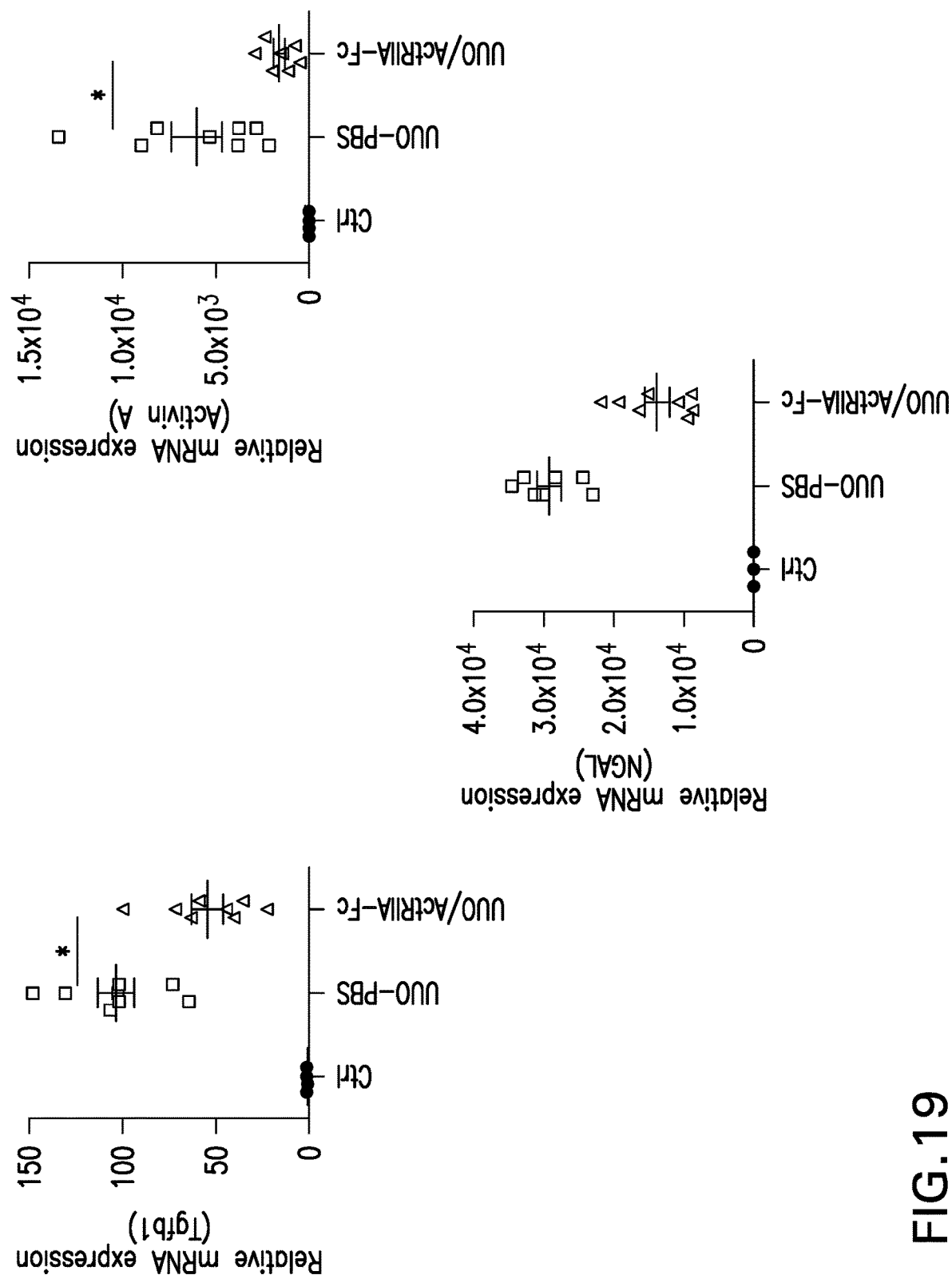

FIG. 19 shows gene expression profiles of cytokine genes (Tgfb1 and activin A) and kidney injury gene (NGAL) from mouse kidneys subjected to unilateral ureteral obstruction (UUO) after treatment of ActRIIa-Fc homodimer.

Figure 20:
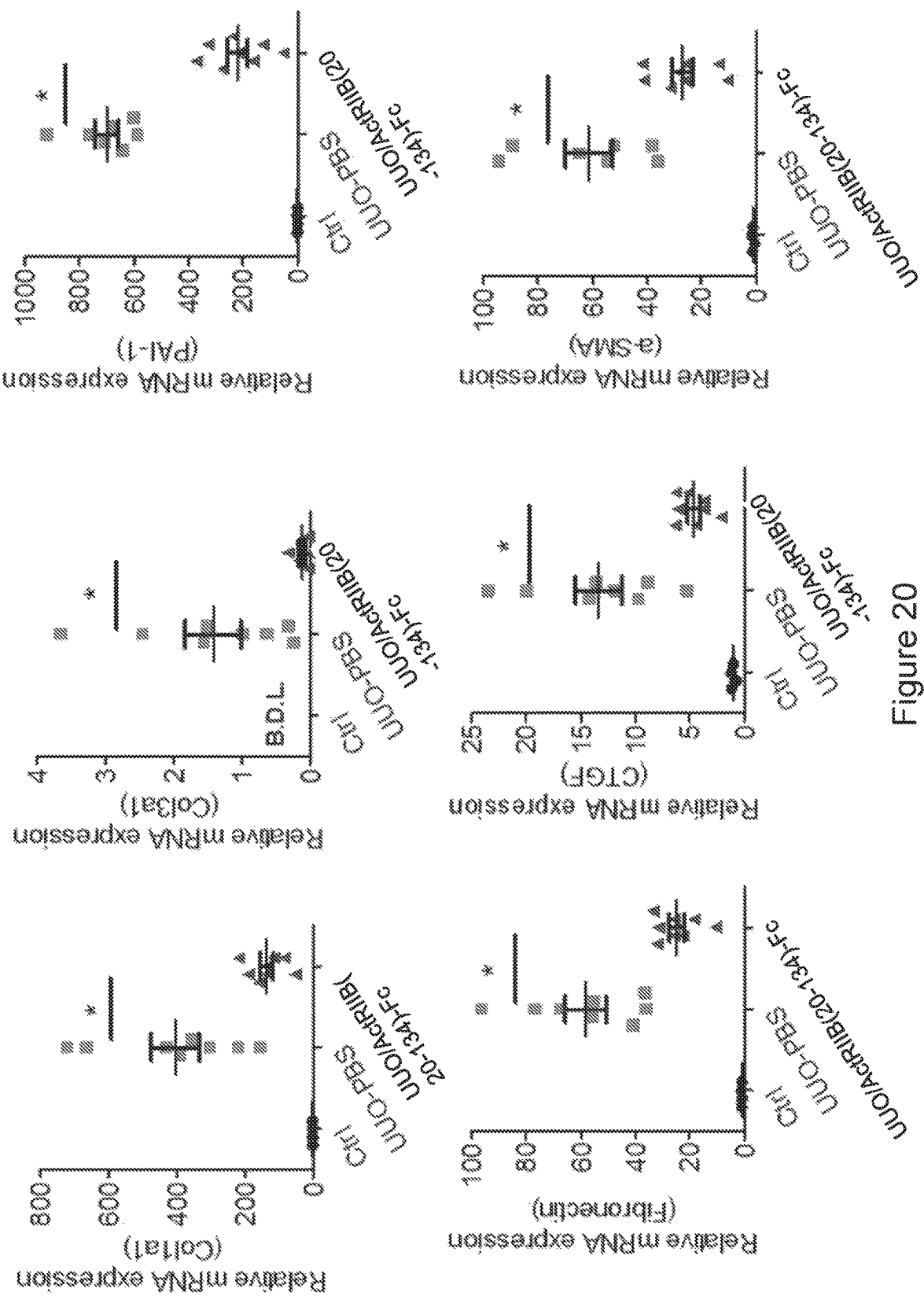

FIG. 20 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of ActRIIB(20-134)-Fc homodimer.

Figure 21:
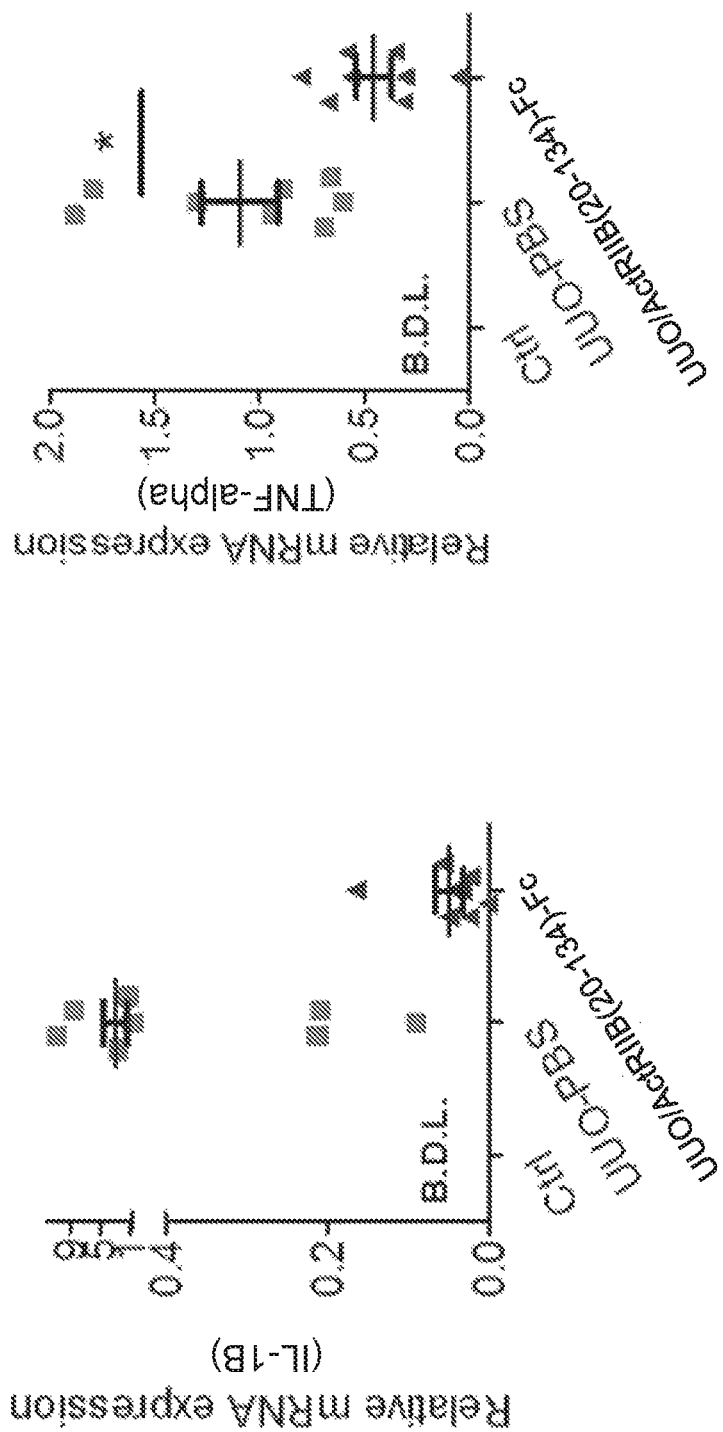

FIG. 21 shows gene expression profiles of inflammatory genes (IL-1B and TNF-alpha) from mouse kidneys subjected to unilateral ureteral obstruction (UUO) after treatment of ActRIIB(20-134)-Fc homodimer.

Figure 22:
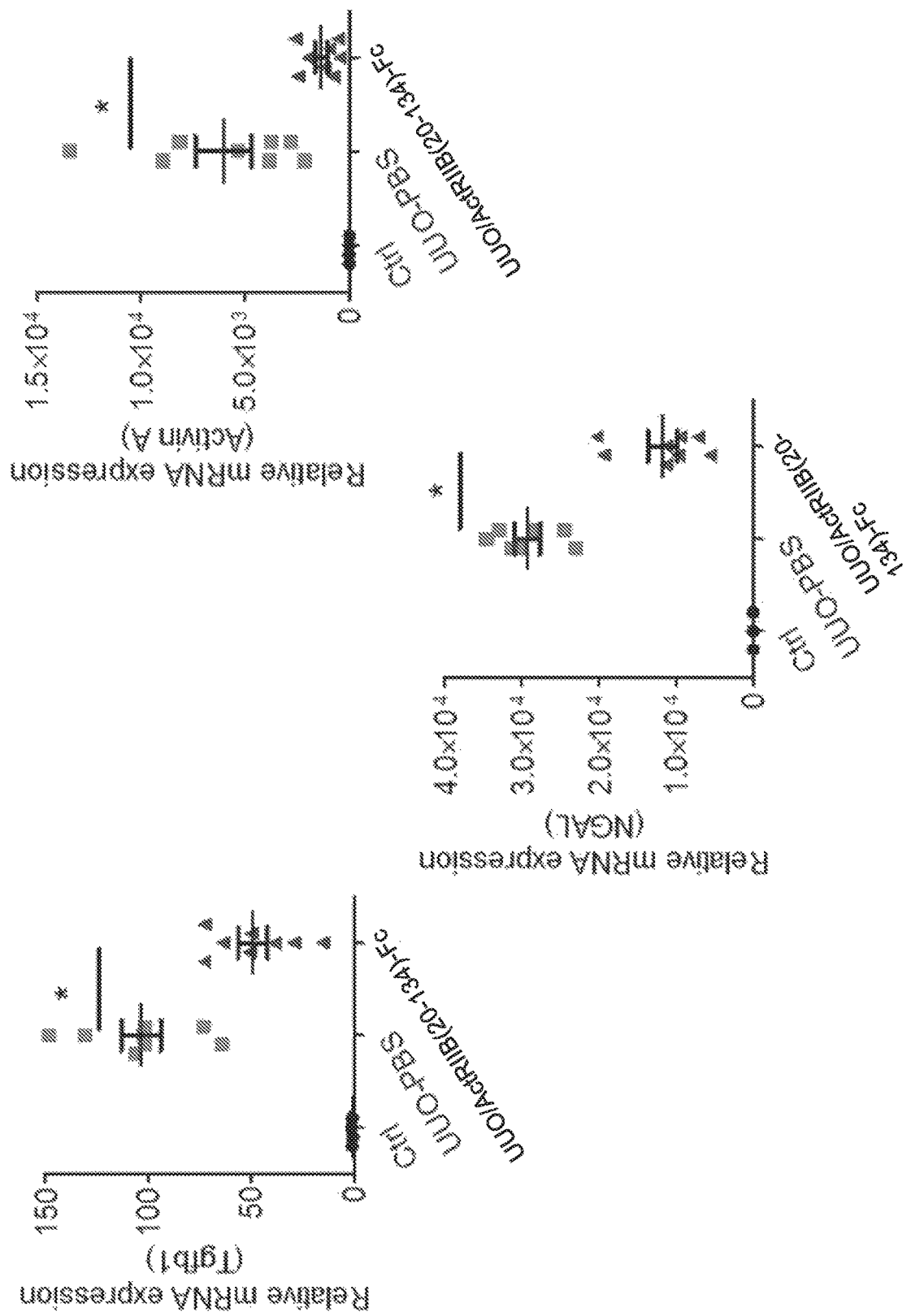

FIG. 22 shows gene expression profiles of cytokine genes (Tgfb1 and activin A) and kidney injury gene (NGAL) from mouse kidneys subjected to unilateral ureteral obstruction (UUO) after treatment of ActRIIB(20-134)-Fc homodimer.

Figure 23:
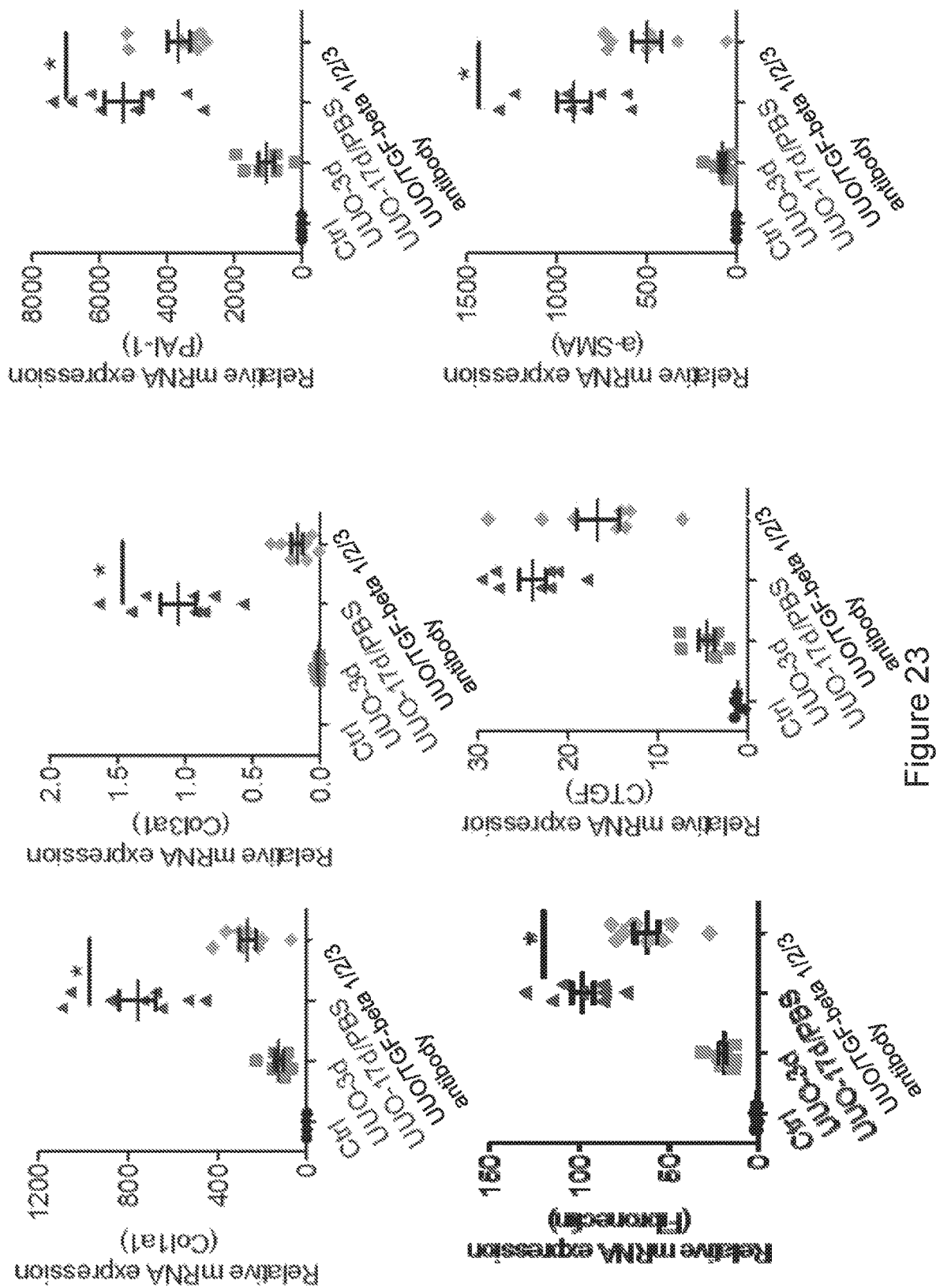

FIG. 23 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an anti-TGF-beta 1/2/3 pan antibody (i.e., binds to isoforms 1, 2, and 3 of TGF-beta).

Figure 24:
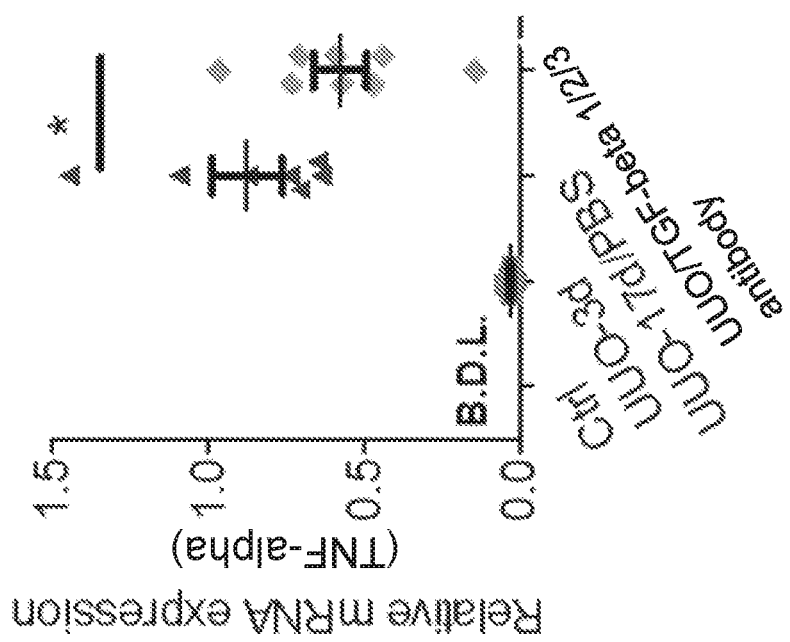

FIG. 24 shows gene expression profiles of inflammatory gene (TNF-alpha) from mouse kidneys subjected to unilateral ureteral obstruction (UUO) after treatment of the anti-TGF-beta 1/2/3 pan antibody (i.e., binds to isoforms 1, 2, and 3 of TGF-beta).

Figure 25:
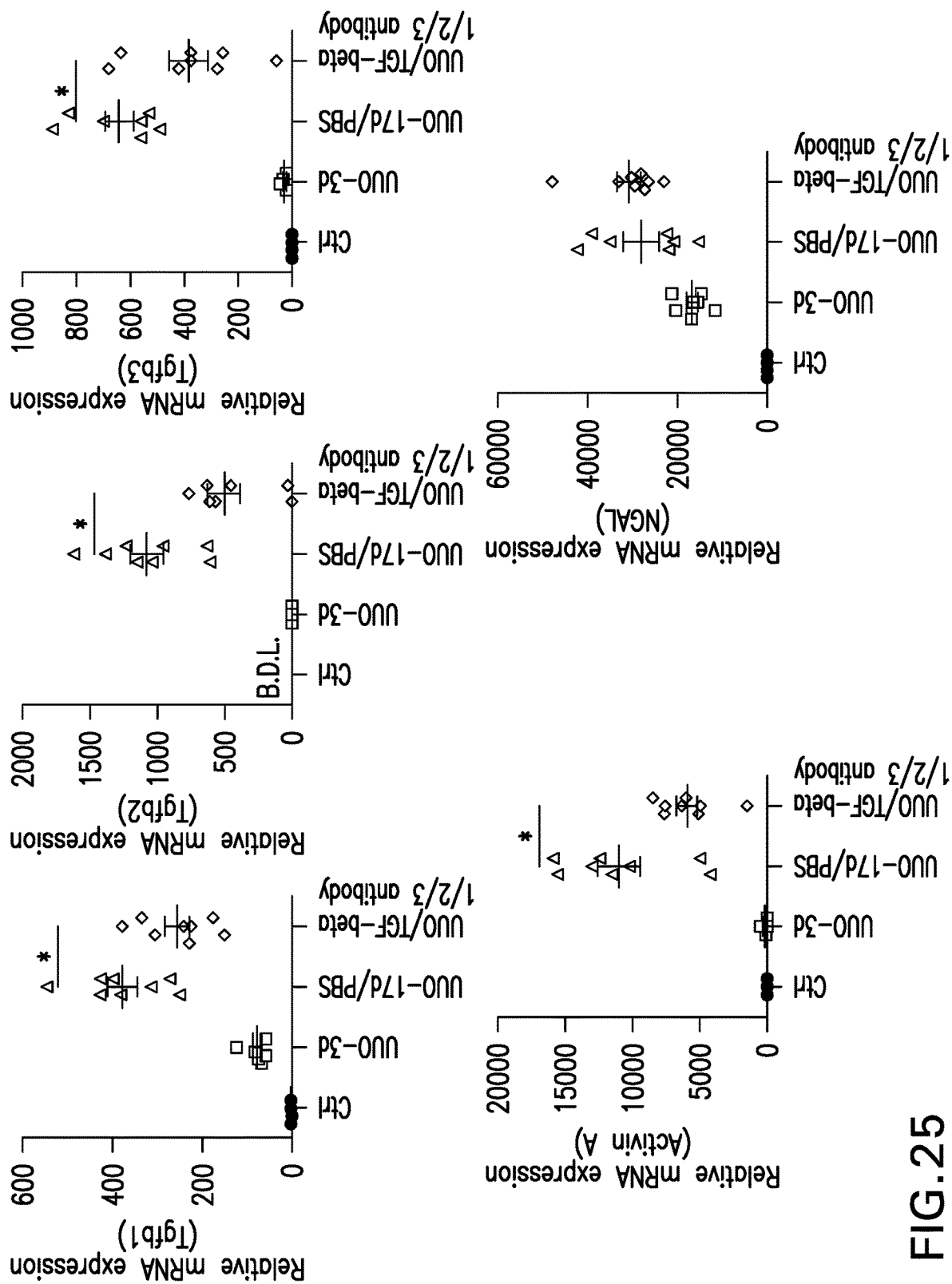

FIG. 25 shows gene expression profiles of cytokine genes (Tgfb1/2/3 and activin A) and kidney injury gene (NGAL) from mouse kidneys subjected to unilateral ureteral obstruction (UUO) after treatment of the anti-TGF-beta 1/2/3 pan antibody (i.e., binds to isoforms 1, 2, and 3 of TGF-beta).

Figure 26:
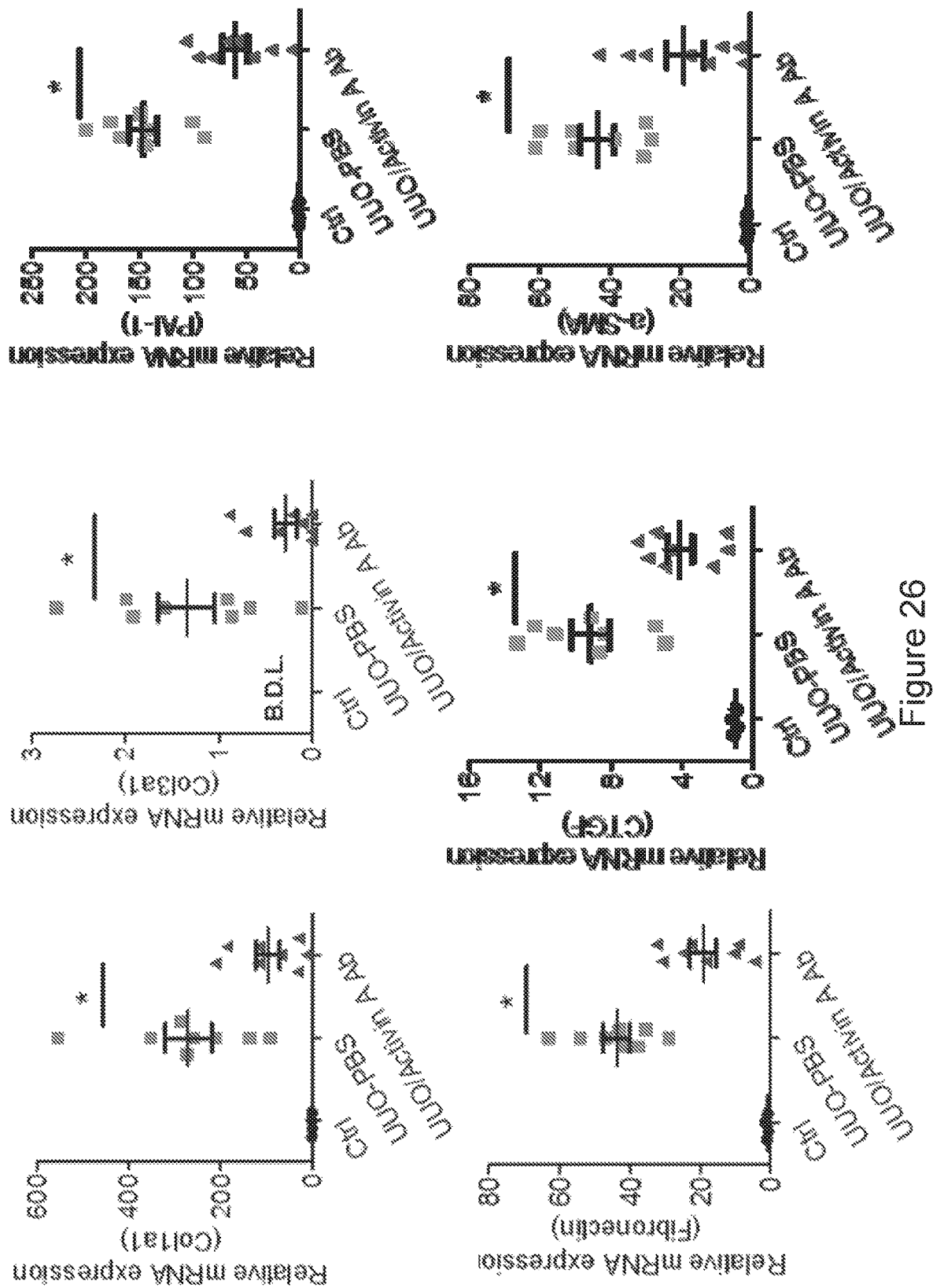

FIG. 26 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an anti-activin A antibody.

Figure 27:
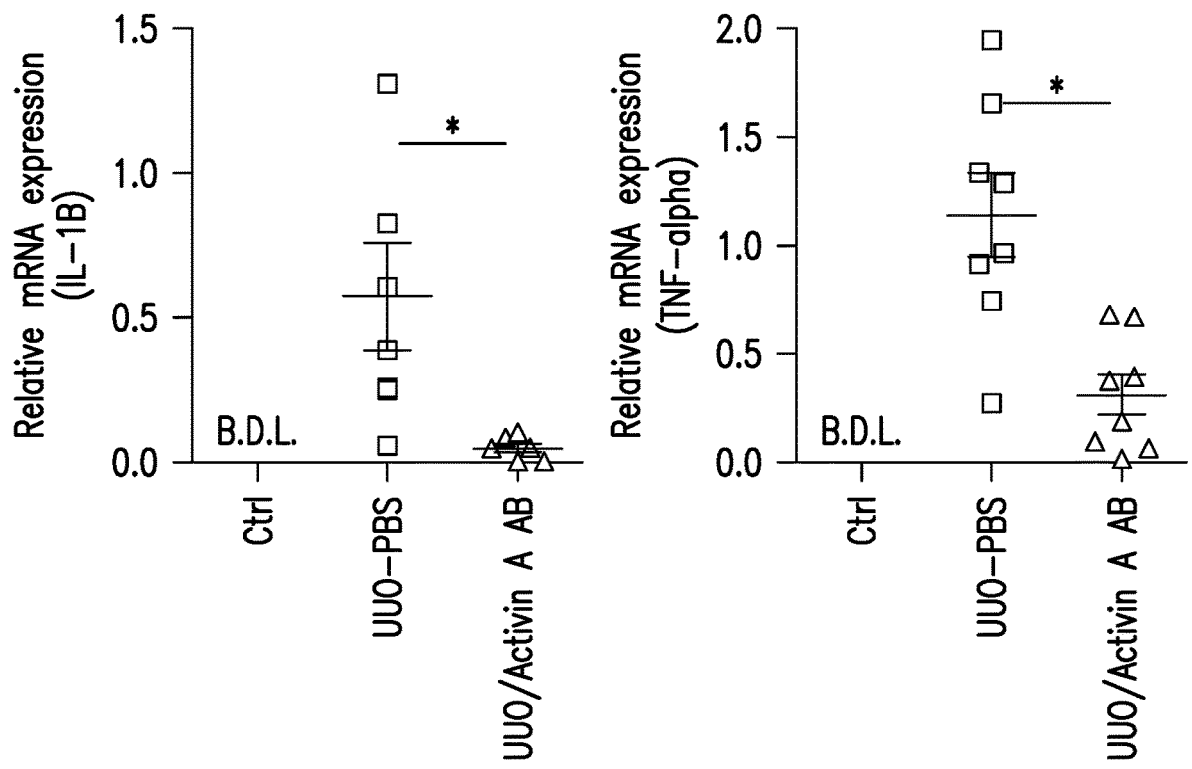

FIG. 27 shows gene expression profiles of inflammatory genes (IL-1B and TNF-alpha) from mouse kidneys subjected to unilateral ureteral obstruction (UUO) after treatment of the anti-activin A antibody.

Figure 28:
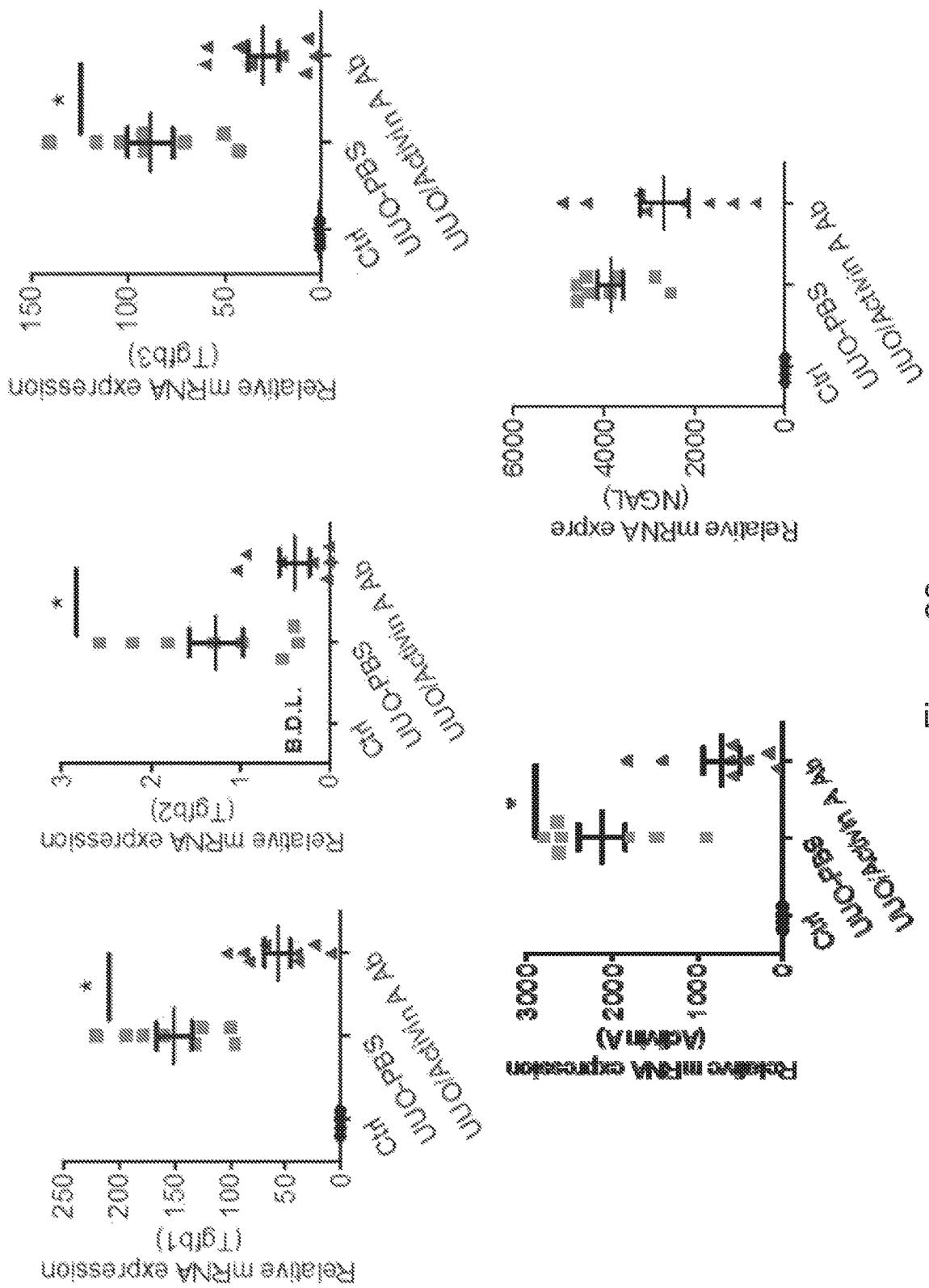

FIG. 28 shows gene expression profiles of cytokine genes (Tgfb1/2/3 and activin A) and kidney injury gene (NGAL) from mouse kidneys subjected to unilateral ureteral obstruction (UUO) after treatment of the anti-activin A antibody.

Figure 29:
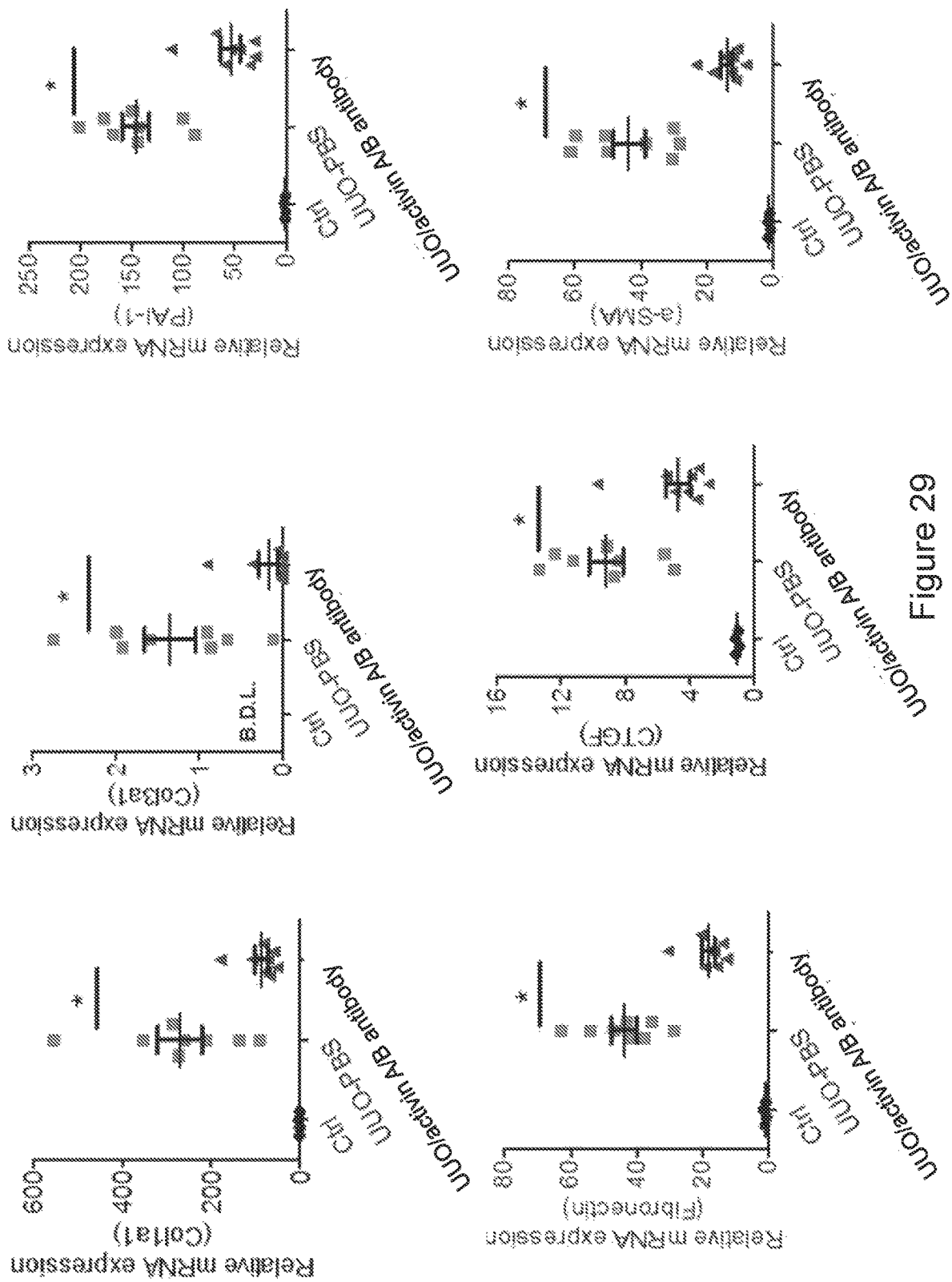

FIG. 29 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an anti-activin A/B antibody.

Figure 30:
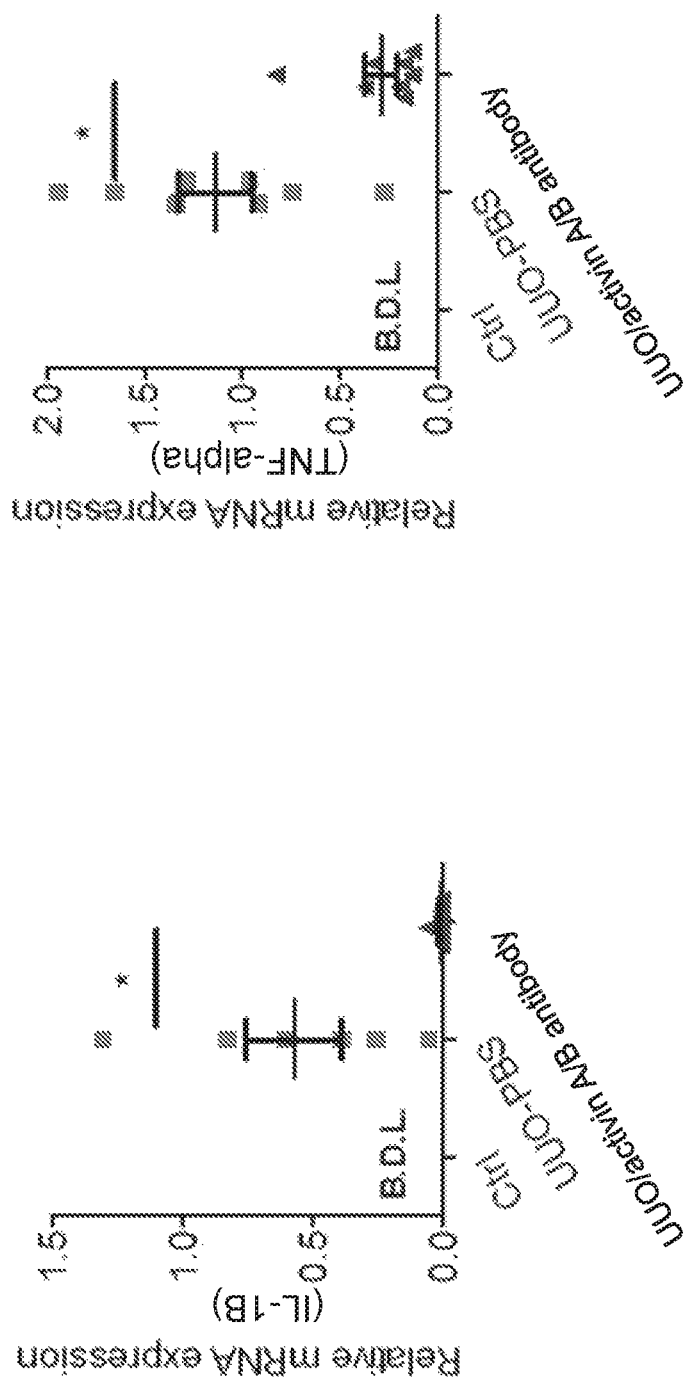

FIG. 30 shows gene expression profiles of inflammatory genes (IL-1B and TNF-alpha) from mouse kidneys subjected to unilateral ureteral obstruction (UUO) after treatment of the anti-activin A/B antibody.

Figure 31:
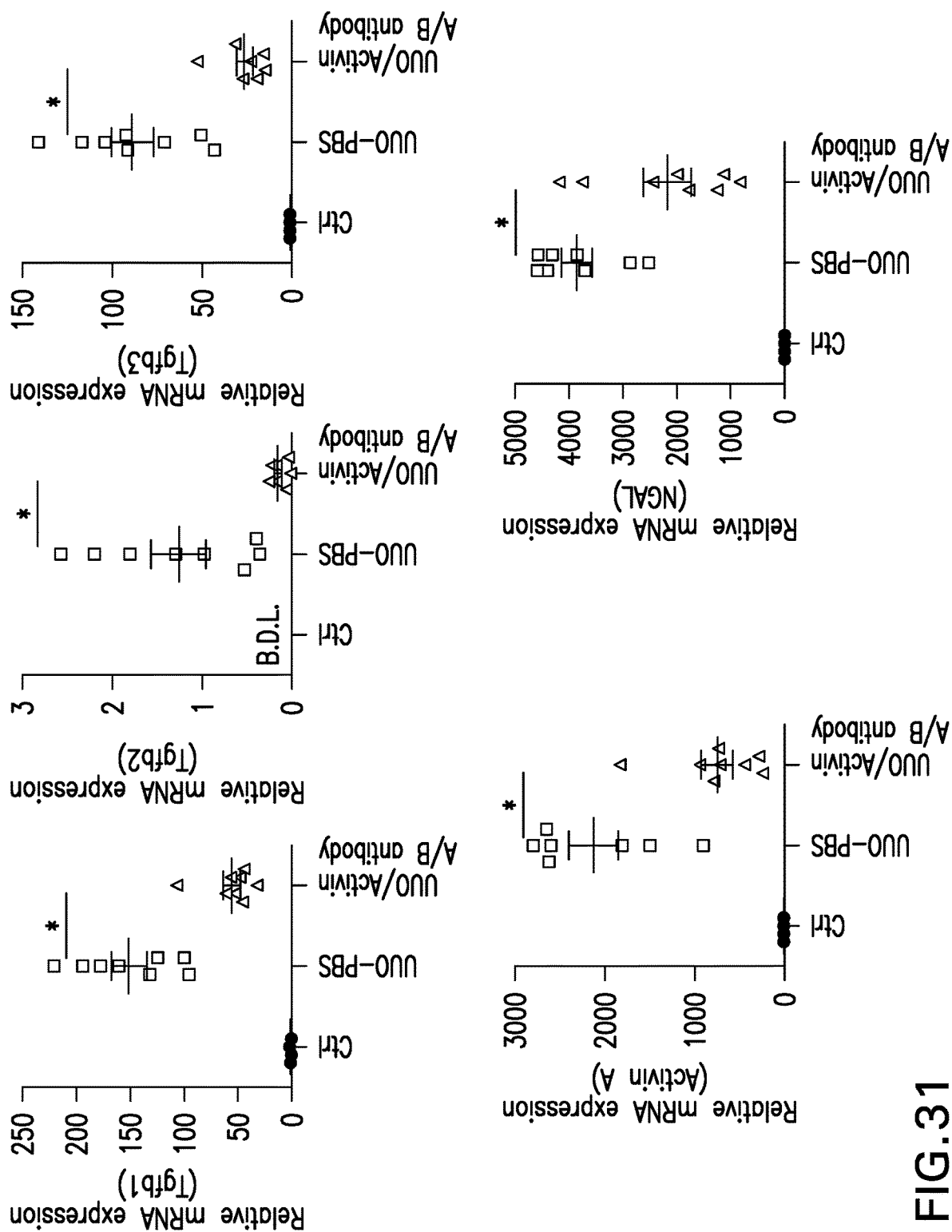

FIG. 31 shows gene expression profiles of cytokine genes (Tgfb1/2/3 and activin A) and kidney injury gene (NGAL) from mouse kidneys subjected to unilateral ureteral obstruction (UUO) after treatment of the anti-activin A/B antibody.

Figure 32:
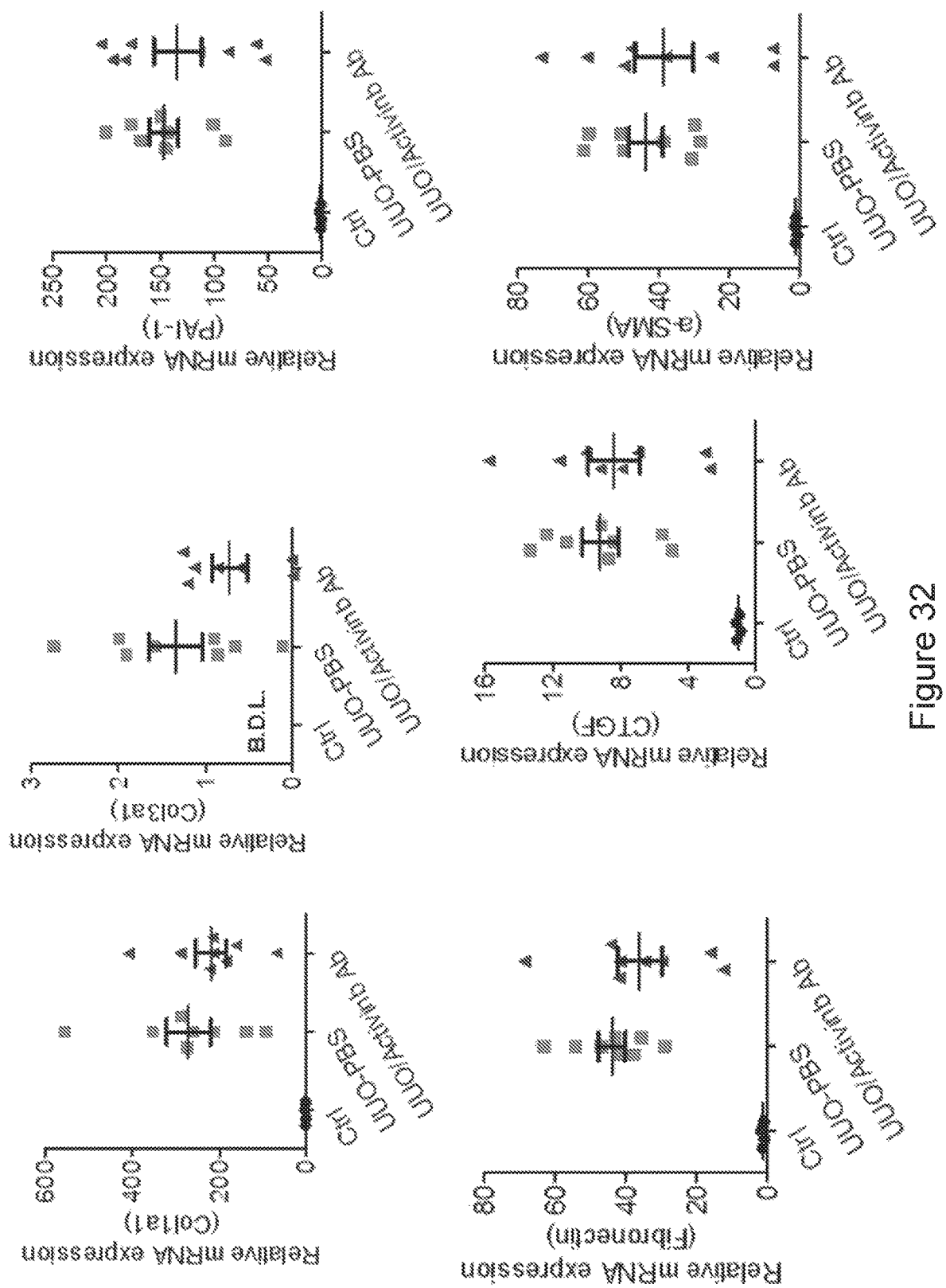

FIG. 32 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an anti-activin B antibody.

FIG. 33 shows gene expression profiles of inflammatory genes (IL-1B and TNF-alpha) from mouse kidneys subjected to unilateral ureteral obstruction (UUO) after treatment of the anti-activin B antibody.

Figure 34:
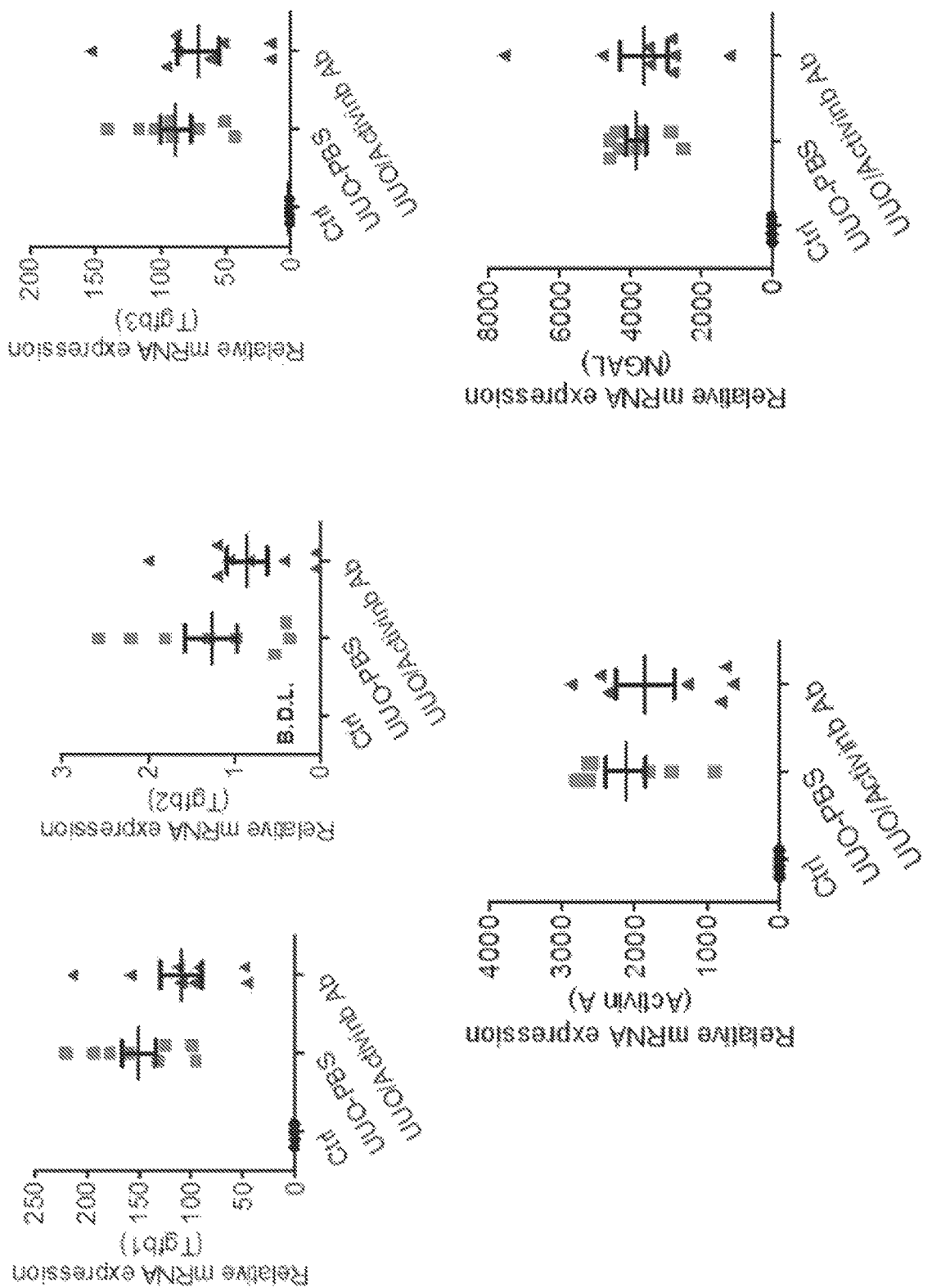

FIG. 34 shows gene expression profiles of cytokine genes (Tgfb1/2/3 and activin A) and kidney injury gene (NGAL) from mouse kidneys subjected to unilateral ureteral obstruction (UUO) after treatment of the anti-activin B antibody.

Figure 35:
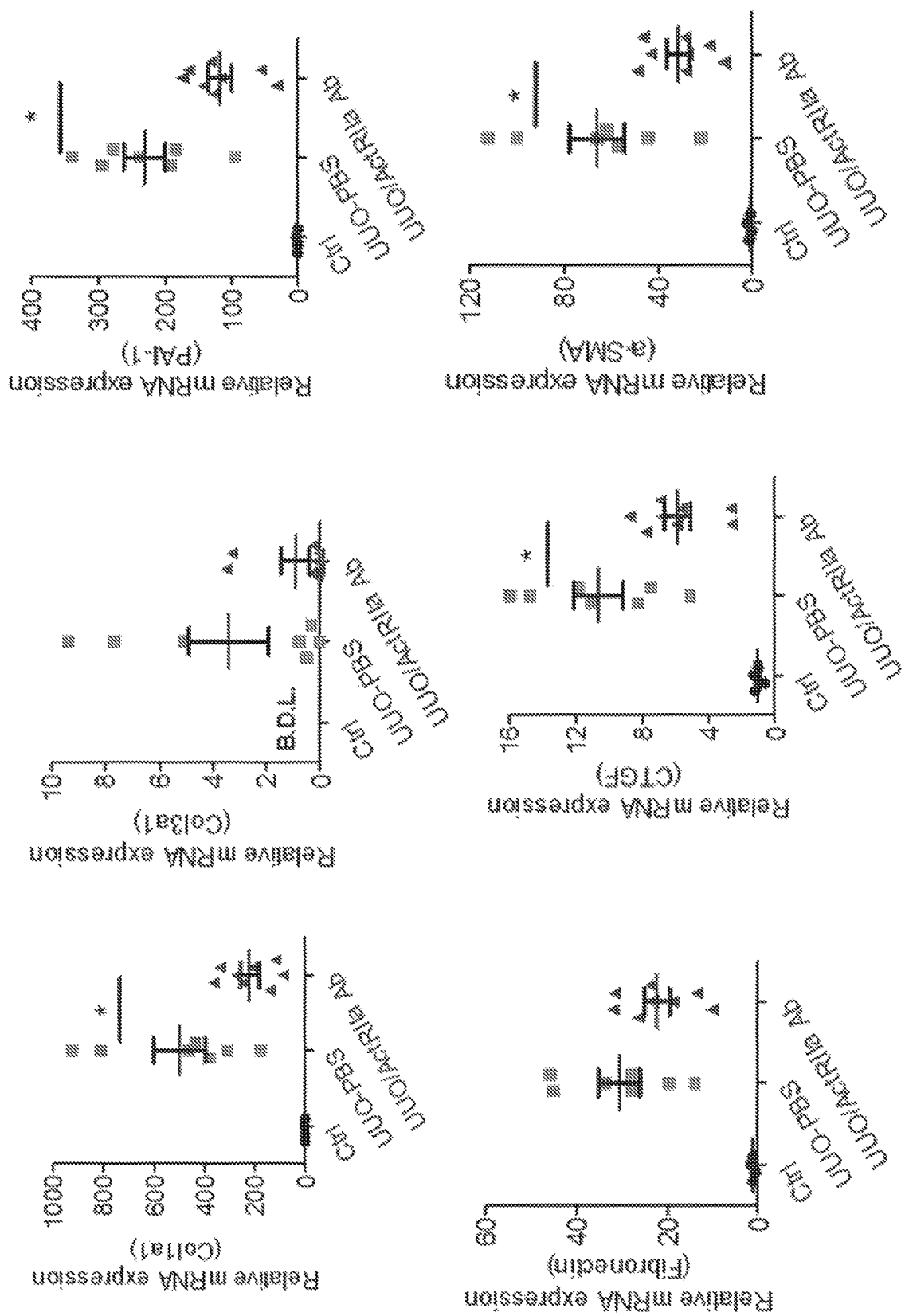

FIG. 35 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an anti-ActRIIA antibody.

Figure 36:
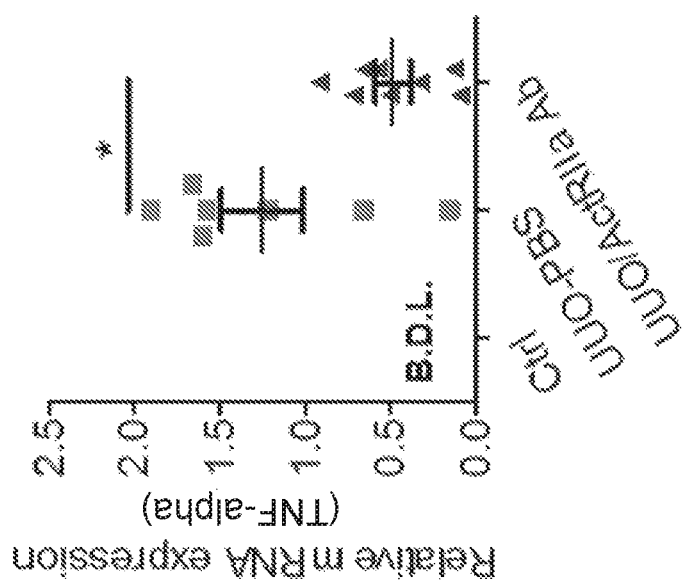

FIG. 36 shows gene expression profiles of inflammatory gene (TNF-alpha) from mouse kidneys subjected to unilateral ureteral obstruction (UUO) after treatment of the anti-ActRIIA antibody.

Figure 37:
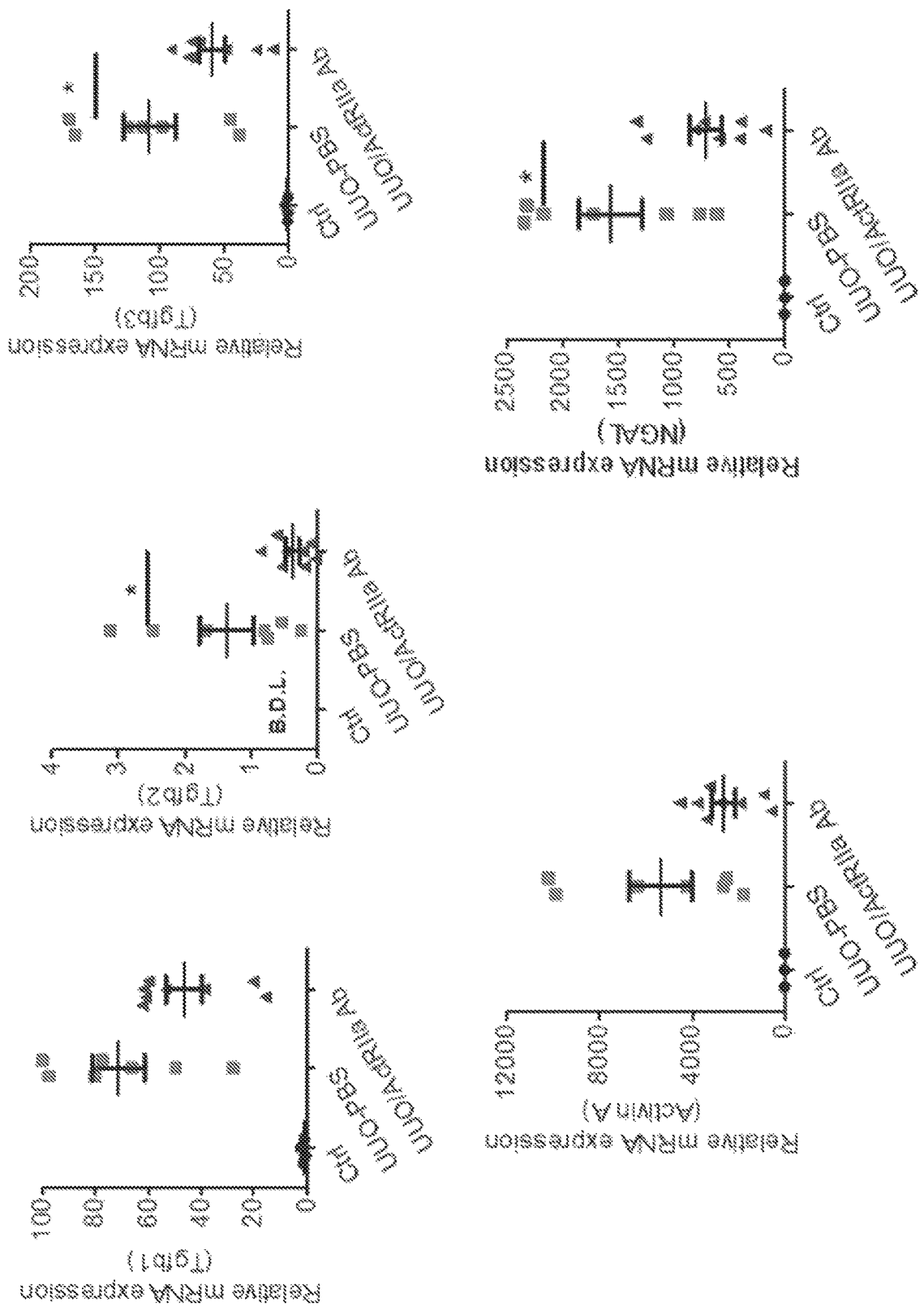

FIG. 37 shows gene expression profiles of cytokine genes (Tgfb1/2/3 and activin A) and kidney injury gene (NGAL) from mouse kidneys subjected to unilateral ureteral obstruction (UUO) after treatment of the anti-ActRIIA antibody.

Figure 38:
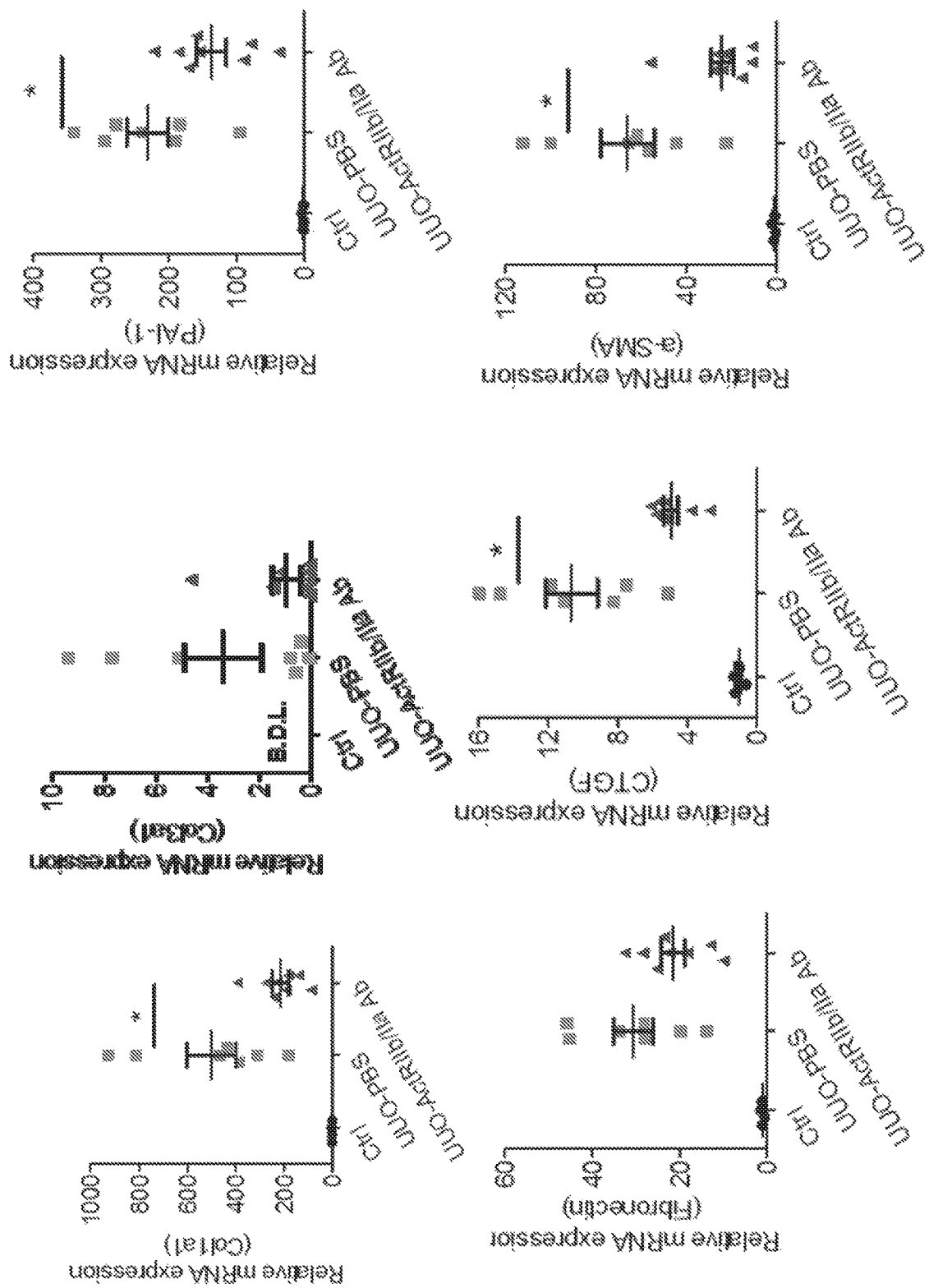

FIG. 38 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an anti-ActRIIA/IIB antibody.

Figure 39:
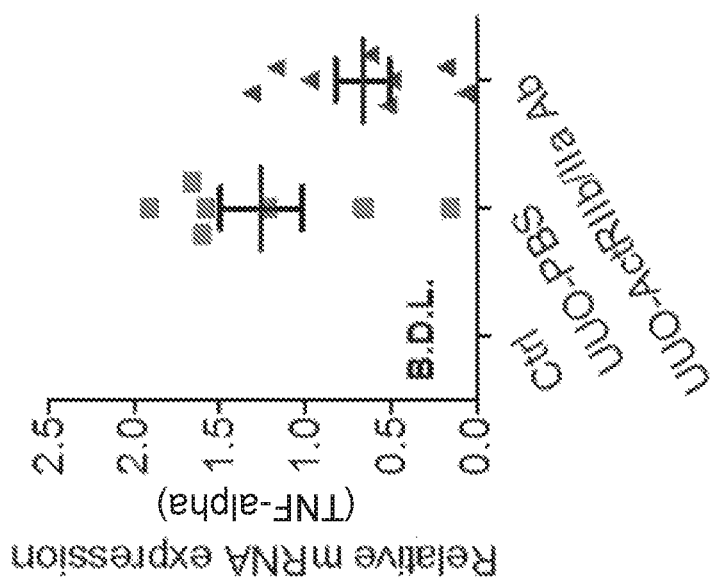

FIG. 39 shows gene expression profiles of inflammatory gene (TNF-alpha) from mouse kidneys subjected to unilateral ureteral obstruction (UUO) after treatment of the anti-ActRIIA/IIB antibody.

Figure 40:
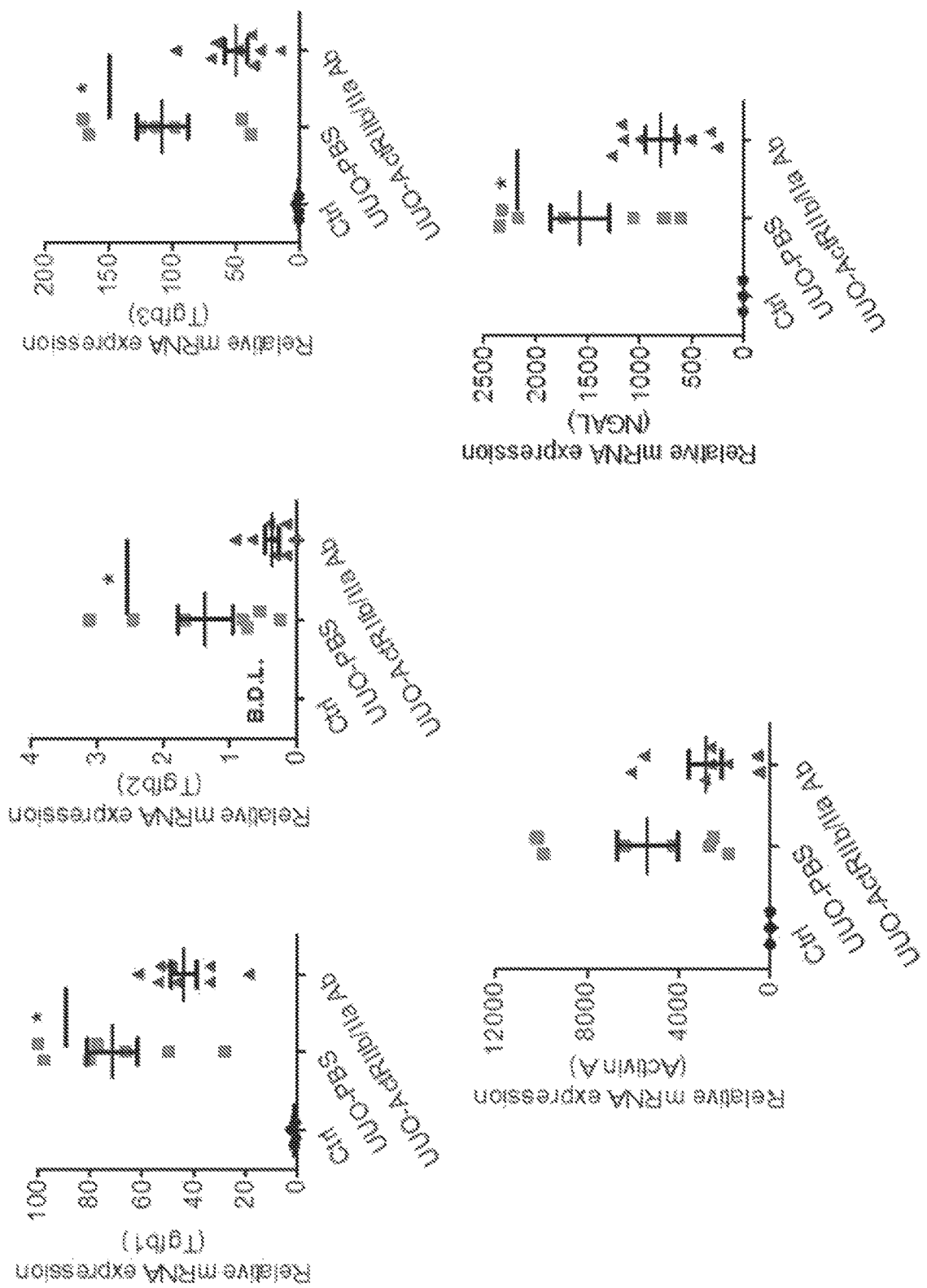

FIG. 40 shows gene expression profiles of cytokine genes (Tgfb1/2/3 and activin A) and kidney injury gene (NGAL) from mouse kidneys subjected to unilateral ureteral obstruction (UUO) after treatment of the anti-ActRIIA/IIB antibody.

Figure 41:
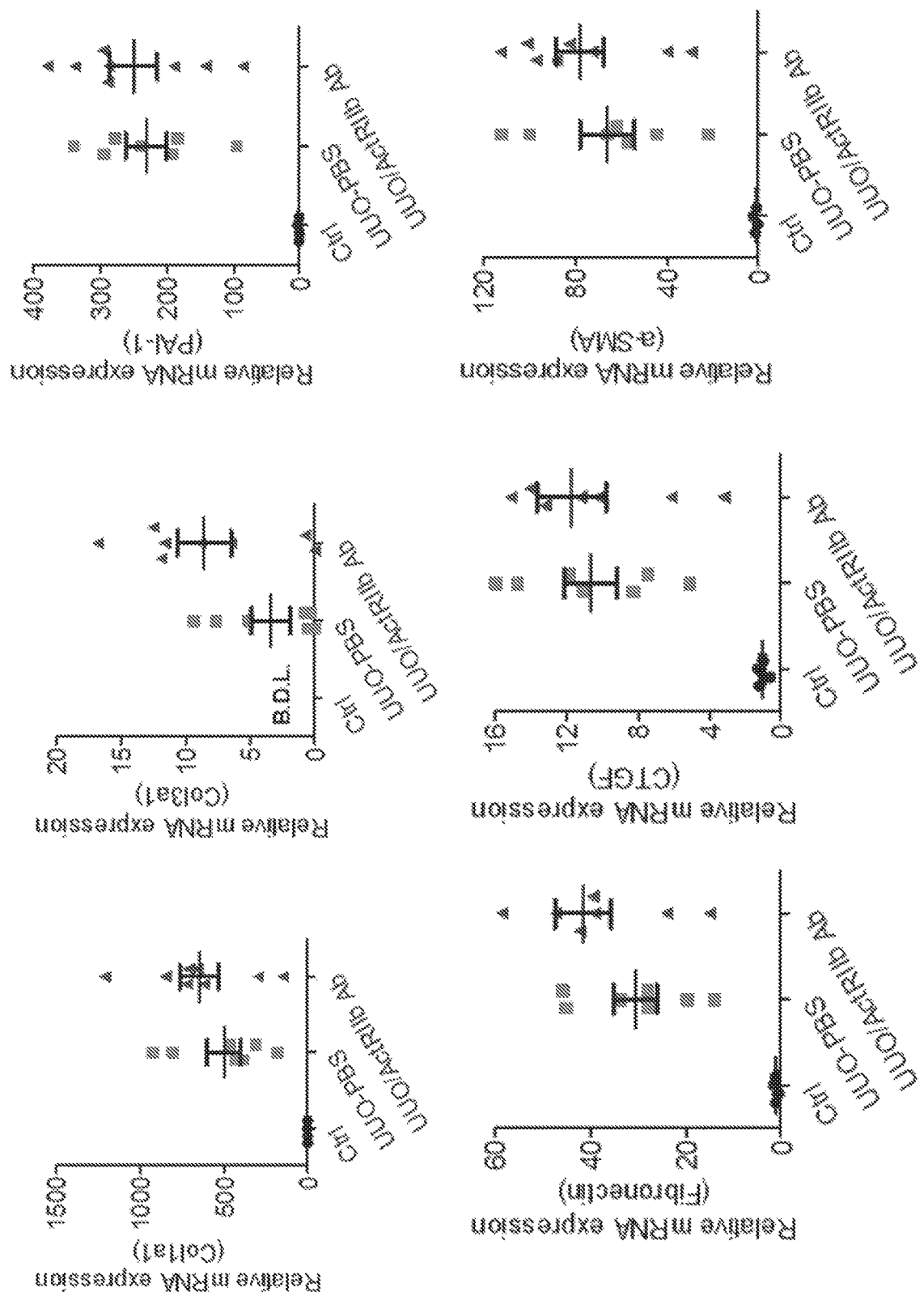

FIG. 41 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an anti-ActRIIB antibody.

Figure 42:
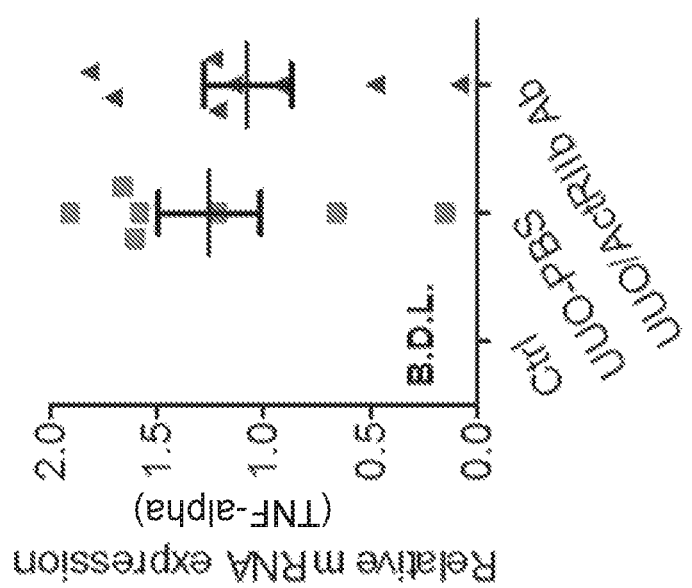

FIG. 42 shows gene expression profiles of inflammatory gene (TNF-alpha) from mouse kidneys subjected to unilateral ureteral obstruction (UUO) after treatment of the anti-ActRIIB antibody.

Figure 43:
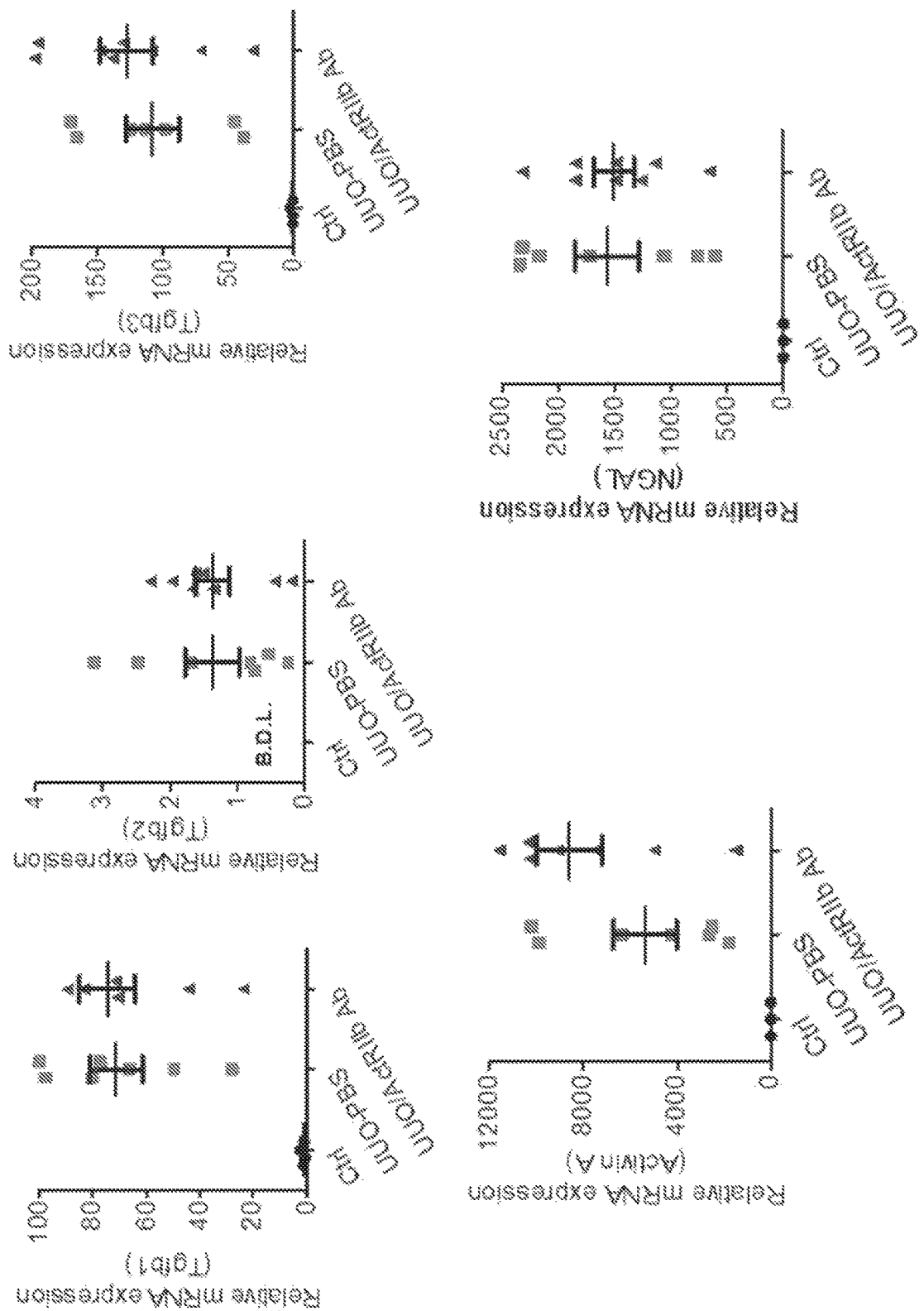

FIG. 43 shows gene expression profiles of cytokine genes (Tgfb1/2/3 and activin A) and kidney injury gene (NGAL) from mouse kidneys subjected to unilateral ureteral obstruction (UUO) after treatment of the anti-ActRIIB antibody.

Figure 44:
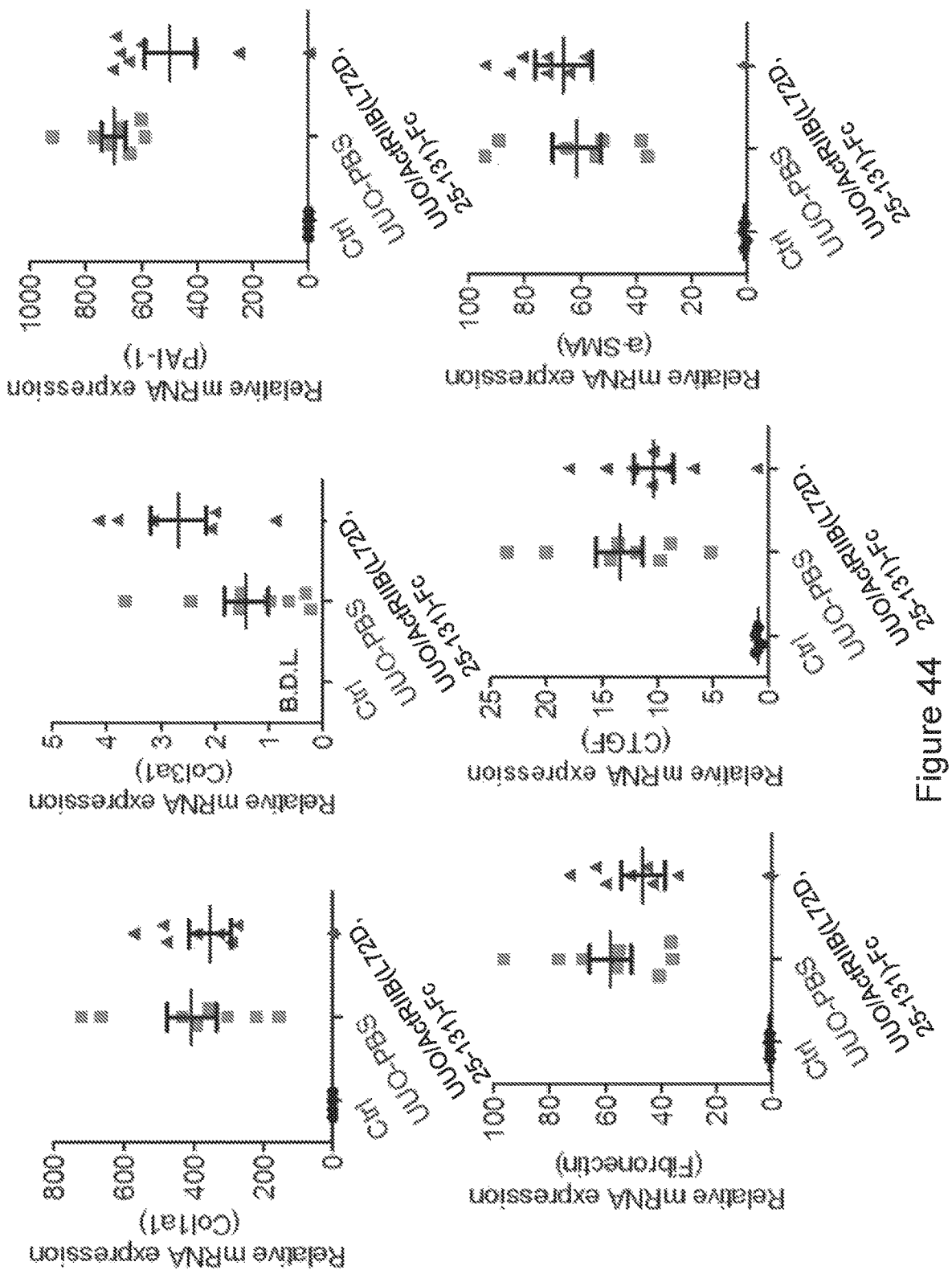

FIG. 44 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an ActRIIB(L79D, 25-131)-hFc homodimer.

Figure 45:
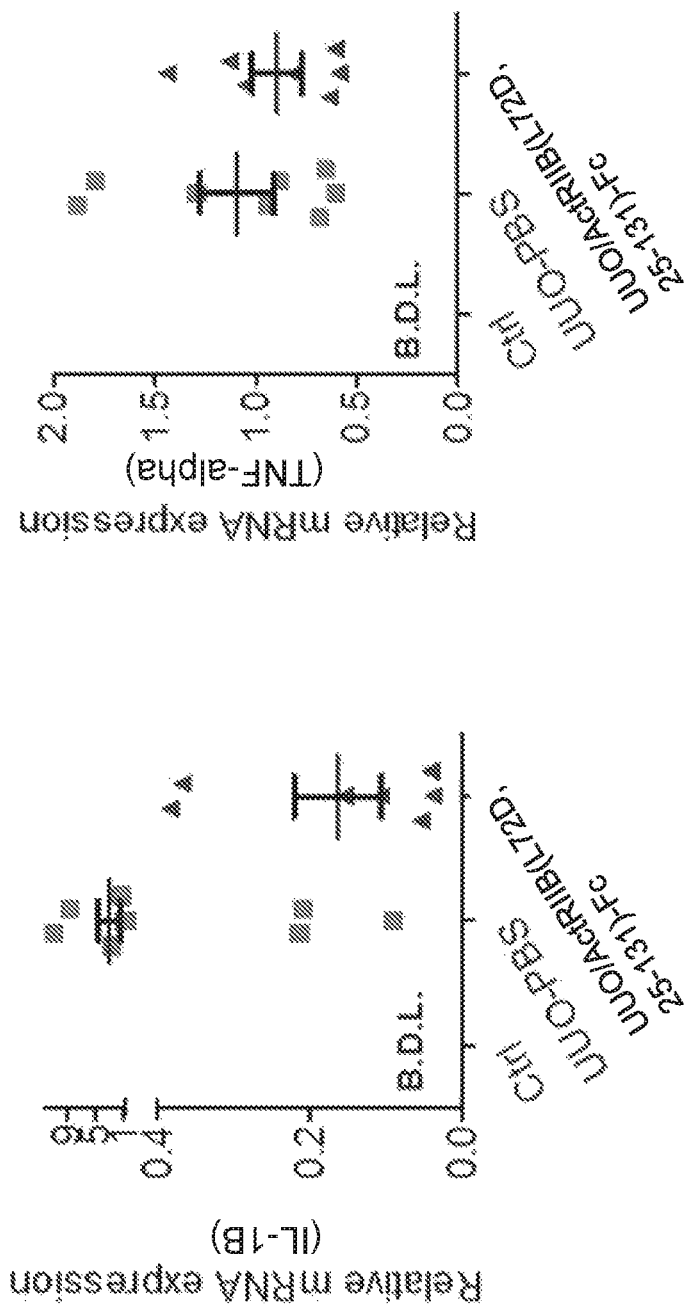

FIG. 45 shows gene expression profiles of inflammatory genes (IL-1B and TNF-alpha) from mouse kidneys subjected to unilateral ureteral obstruction (UUO) after treatment of the ActRIIB(L79D, 25-131)-hFc homodimer.

Figures 46, 47, 48:
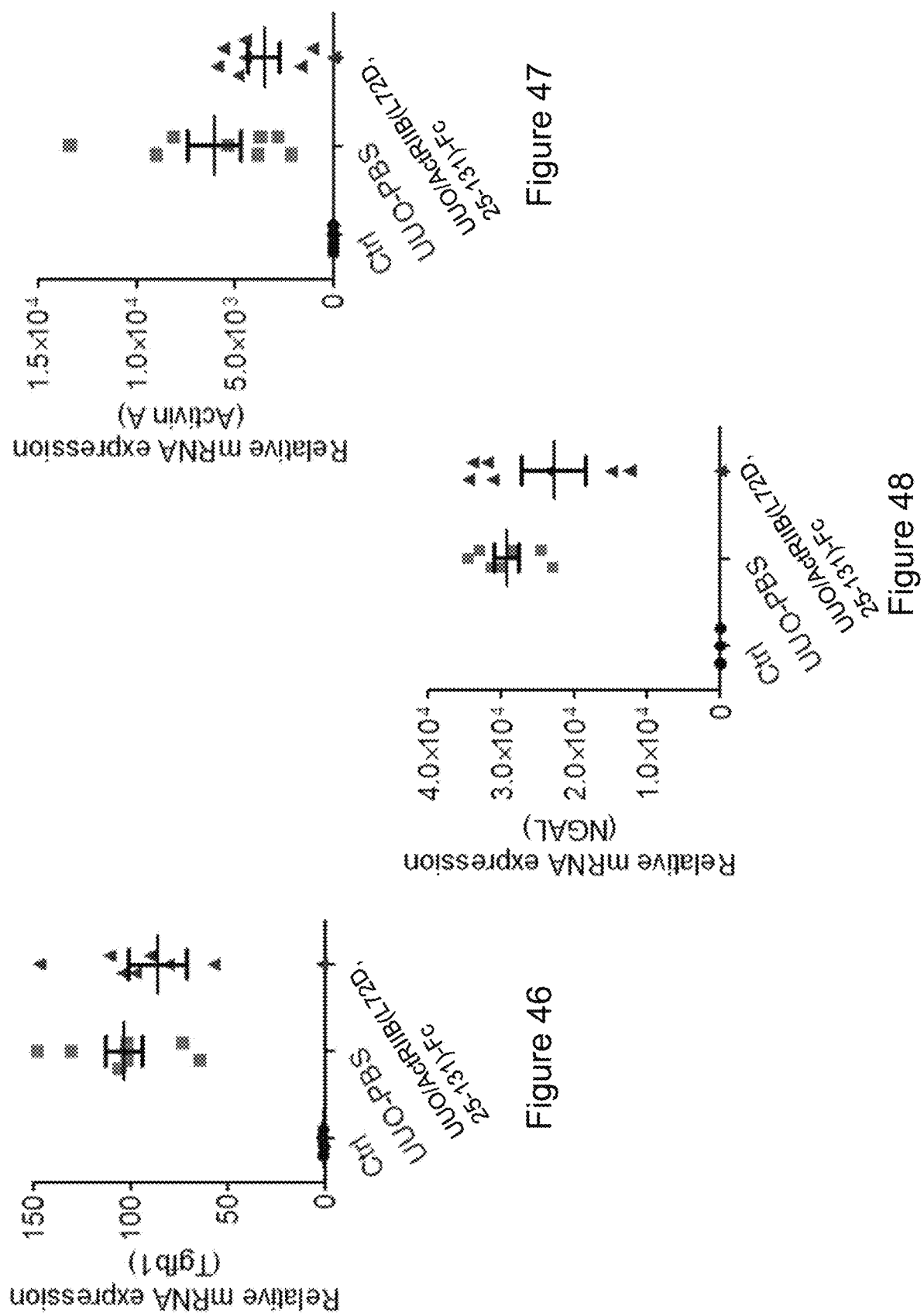

FIG. 46 shows gene expression profile of cytokine gene Tgfb1 from mouse kidneys subjected to unilateral ureteral obstruction (UUO) after treatment of the ActRIIB(L79D, 25-131)-hFc homodimer.

FIG. 47 shows gene expression profile of cytokine gene activin A from mouse kidneys subjected to unilateral ureteral obstruction (UUO) after treatment of the ActRIIB(L79D, 25-131)-hFc homodimer.

FIG. 48 shows gene expression profile of kidney injury gene (NGAL) from mouse kidneys subjected to unilateral ureteral obstruction (UUO) after treatment of the ActRIIB (L79D, 25-131)-hFc homodimer.

Figure 49:
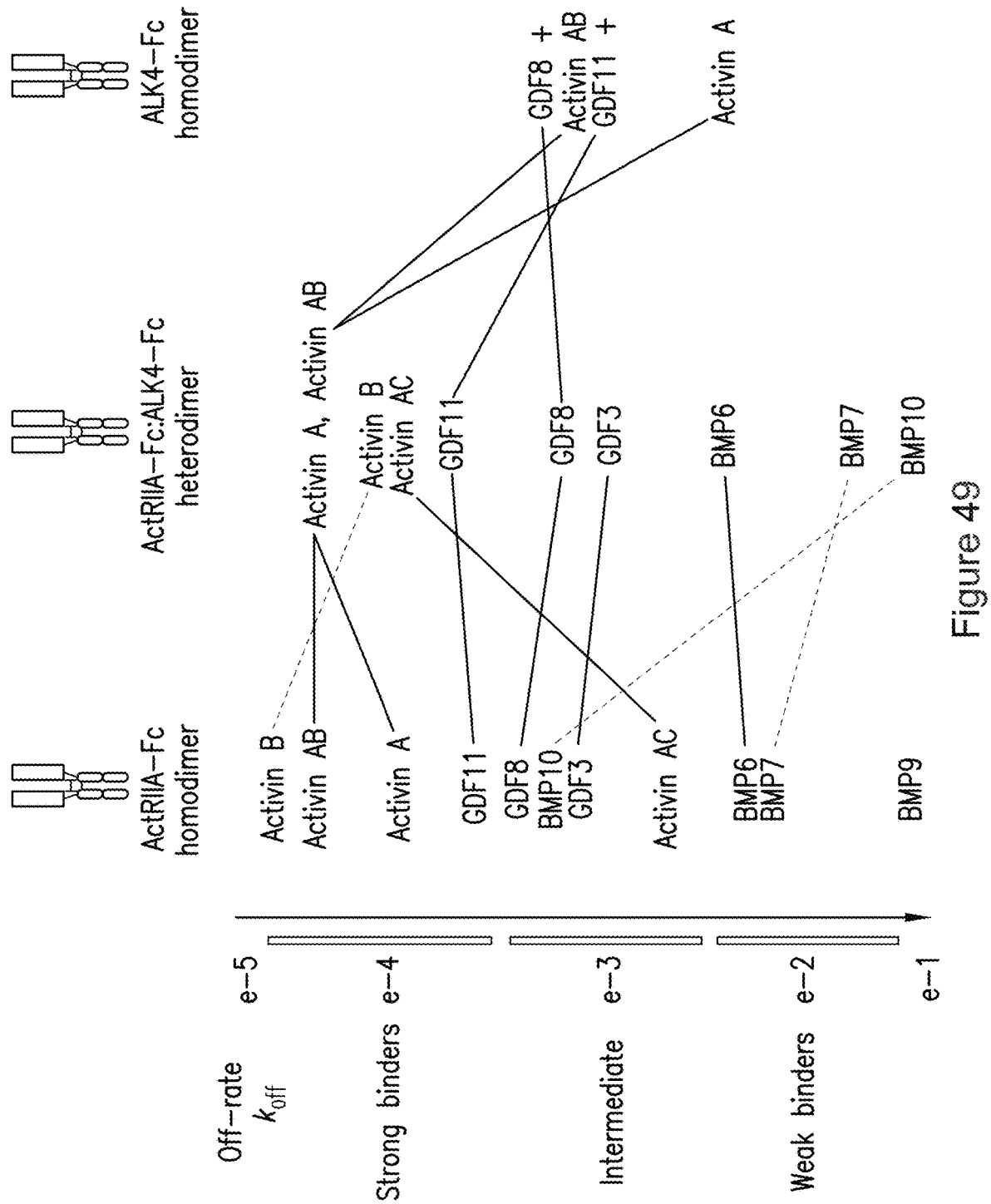

FIG. 49 shows ligand binding data for an ActRIIA-Fc:ALK4-Fc heterodimeric protein complex as compared to ActRIIA-Fc homodimer and ALK4-Fc homodimer. As shown, the ActRIIA-Fc:ALK4-Fc heterodimer exhibits enhanced binding to activin A, and particularly enhanced binding to activin AC, compared to ActRIIA-Fc homodimer, while retaining strong binding to activin AB and GDF11. In addition, the ligand with highest affinity for ActRIIA-Fc homodimer, activin B, displays reduced affinity (albeit still within the high-affinity range) for the ActRIIA-Fc:ALK4-Fc heterodimer. The ActRIIA-Fc:ALK4-Fc heterodimer also exhibits markedly reduced binding to BMP10 compared to ActRIIA-Fc homodimer.

Figure 50:
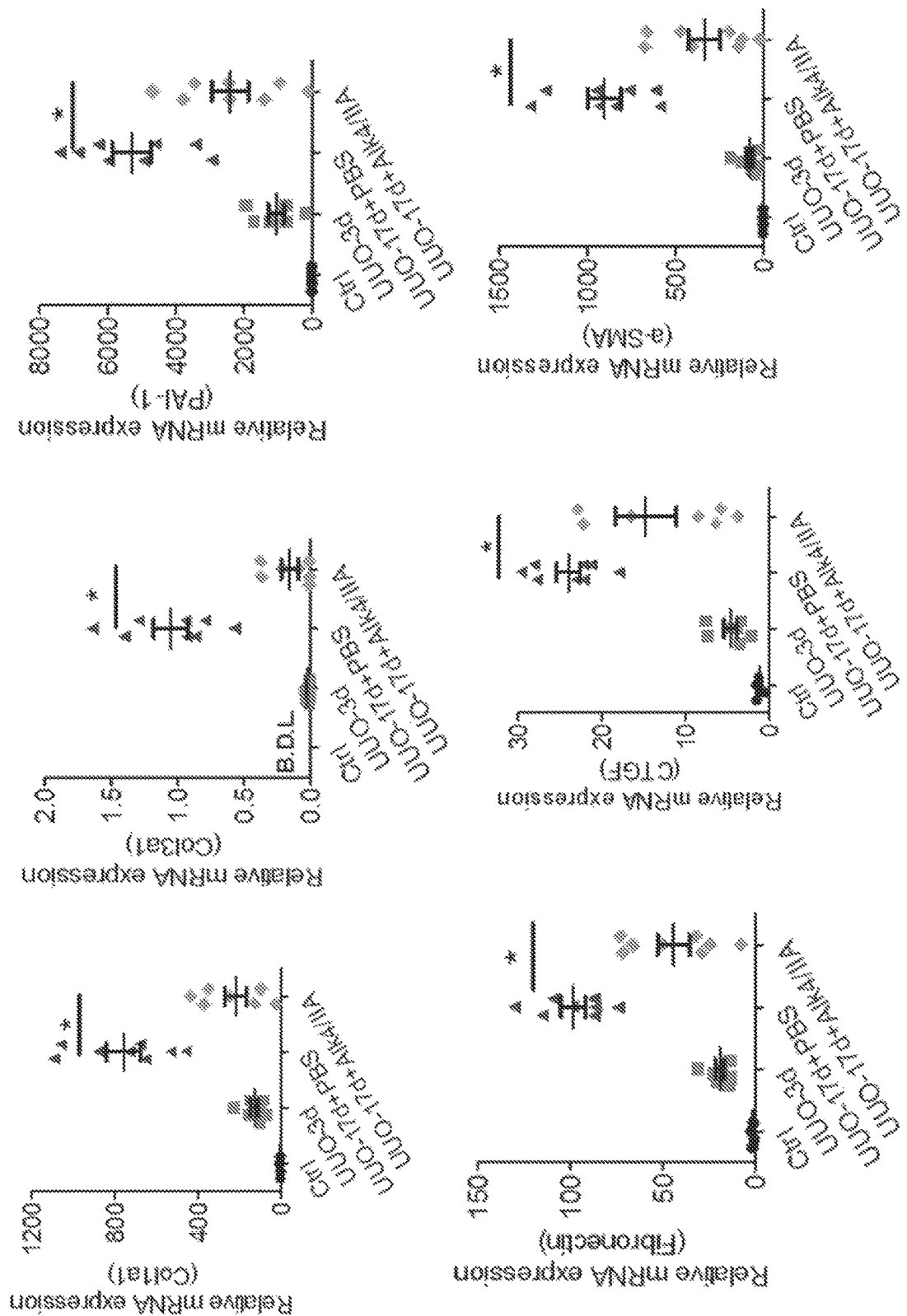

FIG. 50 shows gene expression profiles of fibrotic genes (Col1a1, Col3a1, PAI-1, Fibronectin, CTGF, and a-SMA) from mouse kidneys subjected to unilateral ureteral obstruction (UUO) after treatment of an ALK4-Fc:ActRIIA-Fc heterodimer.

Figure 51:
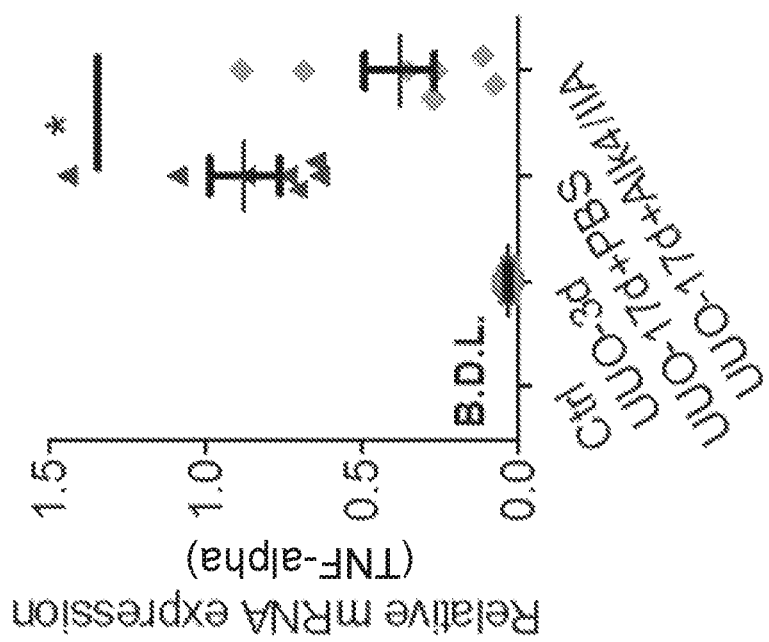

FIG. 51 shows gene expression profiles of inflammatory gene (TNF-alpha) from mouse kidneys subjected to unilateral ureteral obstruction (UUO) after treatment of an ALK4-Fc:ActRIIA-Fc heterodimer.

Figure 52:
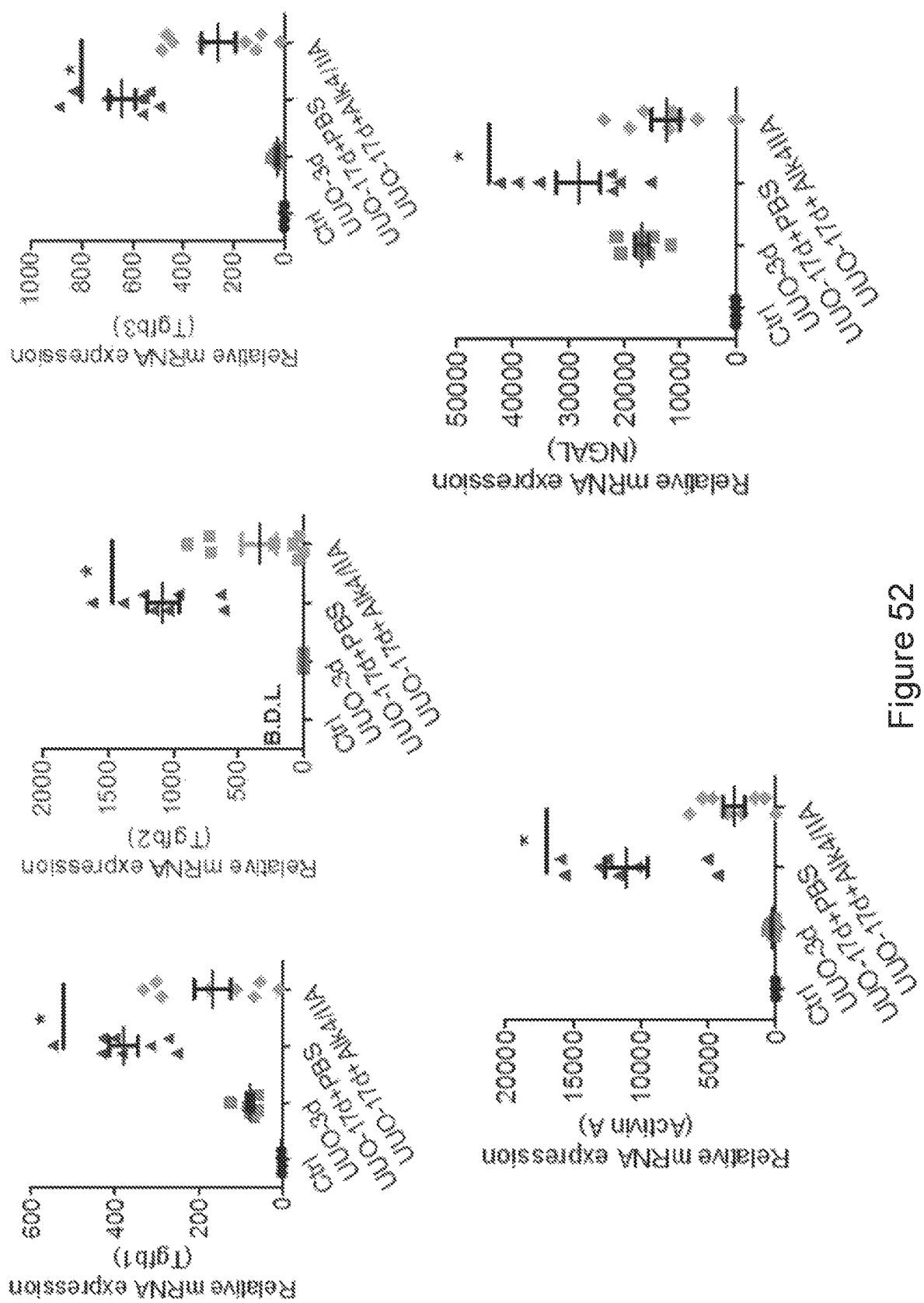

FIG. 52 shows gene expression profiles of cytokine genes (Tgfb1/2/3 and activin A) and kidney injury gene (NGAL)

from mouse kidneys subjected to unilateral ureteral obstruction (UUO) after treatment of an ALK4-Fc:ActRIIA-Fc heterodimer.

Figure 53:
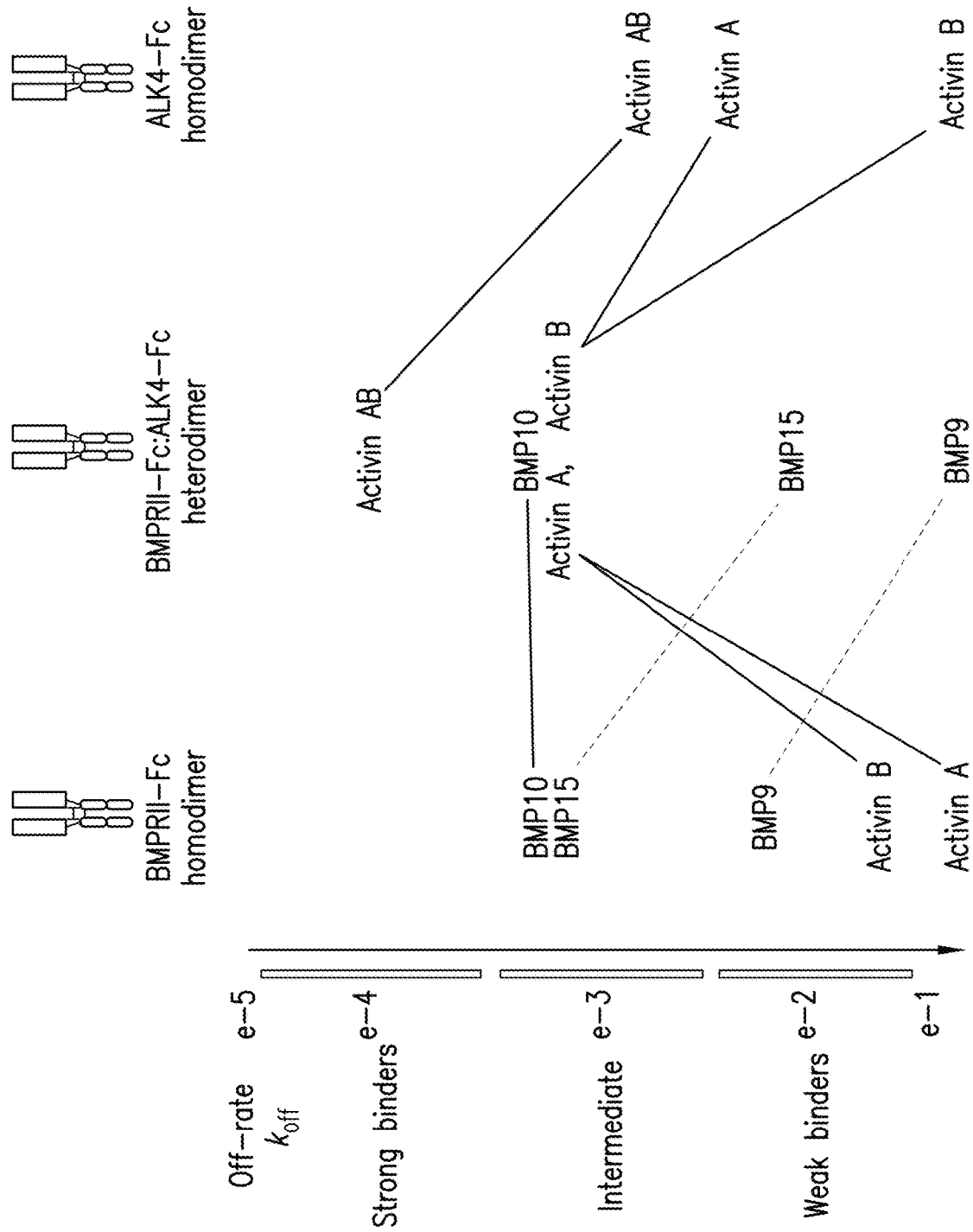

FIG. 53 shows ligand binding data for a BMPRII-Fc:ALK4-Fc heterodimeric protein complex as compared to BMPRII-Fc homodimer and ALK4-Fc homodimer. BMPRII-Fc:ALK4-Fc heterodimer differs from both homodimers by binding several activin ligands with high or intermediate strength and differs from BMPRII-Fc homodimer by binding BMP15 only weakly. Most notably, BMPRII-Fc:ALK4-Fc heterodimer binds strongly and with high selectivity to the heterodimeric ligand activin AB.

DETAILED DESCRIPTION OF THE INVENTION

1. Overview

The TGF-β superfamily includes over 30 secreted factors including TGF-betas, activins, nodals, bone morphogenetic proteins (BMPs), growth and differentiation factors (GDFs), and anti-Mullerian hormone (AMH) (Weiss et al. (2013) *Developmental Biology*, 2(1): 47-63). Members of the superfamily, which are found in both vertebrates and invertebrates, are ubiquitously expressed in diverse tissues and function during the earliest stages of development throughout the lifetime of an animal. Indeed, TGF-β superfamily proteins are key mediators of stem cell self-renewal, gastrulation, differentiation, organ morphogenesis, and adult tissue homeostasis. Consistent with this ubiquitous activity, aberrant TGF-beta superfamily signaling is associated with a wide range of human pathologies.

Ligands of the TGF-beta superfamily share the same dimeric structure in which the central 3½ turn helix of one monomer packs against the concave surface formed by the beta-strands of the other monomer. The majority of TGF-beta family members are further stabilized by an intermolecular disulfide bond. This disulfide bonds traverses through a ring formed by two other disulfide bonds generating what has been termed a 'cysteine knot' motif (Lin et al. (2006) Reproduction 132: 179-190; and Hinck et al. (2012) *FEBS Letters* 586: 1860-1870).

TGF-beta superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation [Massagué (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGF-beta superfamily ligands. Type I and II receptors form a stable complex after ligand binding, resulting in phosphorylation of type I receptors by type II receptors.

The TGF-beta family can be divided into two phylogenetic branches based on the type I receptors they bind and the Smad proteins they activate. One is the more recently evolved branch, which includes, e.g., the TGF-betas, activins, GDF8, GDF9, GDF11, BMP3 and nodal, which signal through type I receptors that activate Smads 2 and 3 (Hinck (2012) *FEBS Letters* 586:1860-1870). The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8.

Activins are members of the TGF-beta superfamily and were initially discovered as regulators of secretion of follicle-stimulating hormone, but subsequently various reproductive and non-reproductive roles have been characterized. There are three principal activin forms (A, B, and AB) that are homo/heterodimers of two closely related p subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al. (1991) *Proc Soc Ep Biol Med.* 198:500-512; Dyson et al. (1997) *Curr Biol.* 7:81-84; and Woodruff (1998) *Biochem Pharmacol.* 55:953-963). In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and a2-macroglobulin.

As described herein, agents that bind to "activin A" are agents that specifically bind to the $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the RA subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the JA subunit and one or more activities as mediated by the $\beta_B$ subunit.

The BMPs and GDFs together form a family of cysteine-knot cytokines sharing the characteristic fold of the TGF-beta superfamily (Rider et al. (2010) *Biochem J.,* 429(1):1-12). This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several specific BMP antagonist proteins that bind with high affinity to the cytokines. Curiously, a number of these antagonists resemble TGF-beta superfamily ligands.

Growth and differentiation factor-8 (GDF8) is also known as myostatin. GDF8 is a negative regulator of skeletal muscle mass and is highly expressed in developing and adult skeletal muscle. The GDF8 null mutation in transgenic mice is characterized by a marked hypertrophy and hyperplasia of skeletal muscle [McPherron et al. Nature (1997) 387:83-90]. Similar increases in skeletal muscle mass are evident in naturally occurring mutations of GDF8 in cattle and, strikingly, in humans (Ashmore et al. (1974) *Growth*, 38:501-507; Swatland and Kieffer, *J. Anim. Sci.* (1994) 38:752-757; McPherron and Lee, *Proc. Natl. Acad. Sci.* USA (1997) 94:12457-12461; Kambadur et al. *Genome Res.* (1997) 7:910-915; and Schuelke et al. (2004) *N Engl J Med*, 350:2682-8). Studies have also shown that muscle wasting associated with HIV-infection in humans is accompanied by increases in GDF8 protein expression (Gonzalez-Cadavid et al., *PNAS* (1998) 95:14938-43). In addition, GDF8 can modulate the production of muscle-specific enzymes (e.g., creatine kinase) and modulate myoblast cell proliferation [International Patent Application Publication No. WO 00/43781]. The GDF8 propeptide can noncovalently bind to the processed GDF8 domain dimer, inactivating its biological activity [Miyazono et al. (1988) J. Biol. Chem., 263: 6407-6415; Wakefield et al. (1988) J. Biol. Chem., 263; 7646-7654; and Brown et al. (1990) Growth Factors, 3: 35-43]. Other proteins which bind to GDF8 or structurally related proteins and inhibit their biological activity include follistatin, and potentially, follistatin-related proteins [Gamer et al. (1999) Dev. Biol., 208: 222-232].

GDF11, also known as BMP11, is a secreted protein that is expressed in the tail bud, limb bud, maxillary and mandibular arches, and dorsal root ganglia during mouse development [McPherron et al. (1999) Nat. Genet., 22: 260-264; and Nakashima et al. (1999) Mech. Dev., 80: 185-189]. GDF11 plays a unique role in patterning both mesodermal and neural tissues [Gamer et al. (1999) Dev Biol., 208:222-32]. GDF11 was shown to be a negative regulator of chondrogenesis and myogenesis in developing chick limb [Gamer et al. (2001) Dev Biol., 229:407-20]. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium [Wu et al. (2003) Neuron., 37:197-207]. Hence, GDF11 may have in vitro and in vivo applications in the treatment of diseases such as muscle diseases and neurodegenerative diseases (e.g., amyotrophic lateral sclerosis).

In part, the disclosure relates to the discovery that activin and/or GDF antagonists (inhibitors) treat or reduce the progression rate and/or severity of kidney disease, particularly treating, preventing or reducing the progression rate and/or severity of one or more kidney disease-associated complications (e.g., kidney tissue damage, fibrosis, and/or inflammation). In some embodiments, the disclosure relates to the use of activin and/or GDF antagonists that inhibit one or more of activin (e.g., activin A, activin B, activin AB, activin C, activin AC, activin BC, activin E, activin AE, and/or activin BE), GDF11, GDF8, GDF3, GDF1, Nodal, ALK4, ALK5, ALK7, ActRIIA, ActRIIB, ALK4, ALK5, ALK7, Cryptic, Cryptic 1B, Smad 2, and Smad 3, etc.) for use in treating, preventing, or reducing the progression rate and/or severity of kidney disease or treating, preventing, or reducing the progression rate, frequency, and/or severity of one or more kidney disease-associated complications (e.g., kidney tissue damage, fibrosis, and/or inflammation).

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is +10%. Alternatively, and particularly in biological systems, the terms "about" and "approximately" may mean values that are within an order of magnitude, preferably <5-fold and more preferably <2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. TGF-beta Superfamily Type I Receptor, Type II Receptor, and Co-Receptor Polypeptides, Variants Thereof, and Protein Complexes In certain aspects, an activin and/or GDF antagonist to be used in accordance with the methods and uses disclosed herein is an ActRII polypeptide (e.g., an ActRIIA or ActRIIB polypeptide), variant thereof, or a protein complex comprising at least one ActRII polypeptide (e.g., a homodimer comprising two ActRII polypeptides or a heterodimer comprising one ActRII polypeptide and a heterologous polypeptide (e.g., ALK4)). As used herein, the term "ActRII" refers to the family of type II activin receptors. This family includes activin receptor type IIA (ActRIIA) and activin receptor type IIB (ActRIIB). An ActRII polypeptide, or protein complex comprising an ActRII polypeptide, may inhibit, for example, one or more ActRII-binding ligands (e.g., activin, GDF8, GDF11, GDF3, GDF1 and Nodal), ActRII receptor (e.g., ActRIIA and ActRIIB), ActRII-associated type I receptor (e.g., ALK4, ALK5, ALK7, etc.), and/or ActRII-associated co-receptor (e.g, Cripto, Cryptic, Cryptic 1, etc.). In some embodiments, the ability for an ActRII polypeptide, or protein complex comprising an ActRII polypeptide, to inhibit signaling (e.g., Smad signaling) is determined in a cell-based assay including, for example, those described herein. An ActRII polypeptide, or protein complex comprising an ActRII polypeptide, may be used alone or in combination with one or more additional supportive therapies or active agents to treat, prevent, or reduce the progression rate and/or severity of kidney disease or one or more complications of kidney disease.

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication Nos. WO 2006/012627, WO 2008/097541, WO 2010/151426, and WO 2011/020045, which are incorporated herein by reference in their entirety. Numbering of amino acids for all ActRIIB-related polypeptides described herein is based on the numbering of the human ActRIIB precursor protein sequence (SEQ ID NO: 1; NCBI database accession No. NP_001097.2), unless specifically designated otherwise. Another ActRIIB mutant containing an arginine-to-alanine substitution at position 64 is showing in SEQ ID NO: 2.

A processed extracellular ActRIIB polypeptide sequence is set forth in SEQ ID NO: 3. A processed extracellular ActRIIB polypeptide sequence of the alternative A64 form is set forth in SEQ ID NO: 4. The C-terminal "tail" of the extracellular domain in SEQ ID NO: 3 is indicated by single underline in FIG. 1.

In some embodiments, the protein may be produced with an "SGR . . . " sequence at the N-terminus. The sequence with the "tail" deleted (a Δ15 sequence) is set forth in SEQ ID NOs: 5 and 6, representing the wild type and a R64A mutant, respectively.

A nucleic acid sequence encoding the human ActRIIB precursor protein is shown as SEQ ID NO: 7, representing nucleotides 25-1560 of Genbank Reference Sequence NM_001106.3, which encode amino acids 1-513 of the ActRIIB precursor. The sequence as shown provides an arginine at position 64 and may be modified to provide an alanine instead.

A nucleic acid sequence encoding processed extracellular human ActRIIB polypeptide (SEQ ID NO: 3) is set forth in SEQ ID NO: 8. The codon for arginine at position 64 of this sequence may be replaced by a codon for an alanine instead.

An alignment of the amino acid sequences of human ActRIIB extracellular domain and human ActRIIA extracellular domain are illustrated in FIG. 1. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

Figure 2:
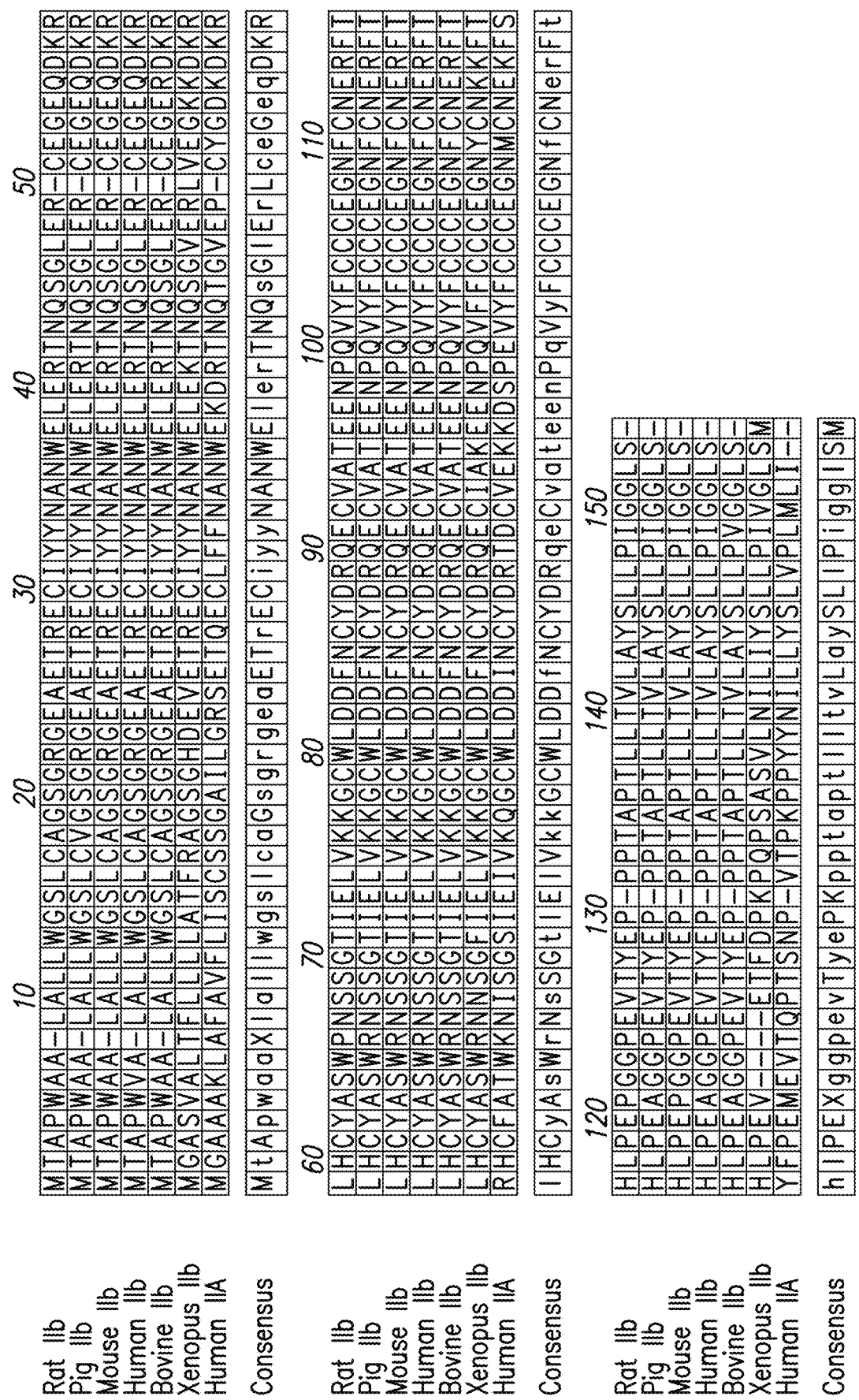
FIG. 2 shows a multiple sequence alignment of various vertebrate ActRIIB precursor proteins without their intracellular domains (including human ActRIIB precursor protein without its intracellular domain (SEQ ID NO: 16)) and human ActRIIA precursor protein without its intracellular domain (SEQ ID NO: 15), and a consensus ActRII precursor protein without intracellular domain (SEQ ID NO: 17).

In addition, ActRIIB is well-conserved among vertebrates, with large stretches of the extracellular domain completely conserved. For example, FIG. 2 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant to substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences. Without meaning to be limiting, the following examples illustrate this approach to defining an active ActRIIB variant. L46 in the human extracellular domain is a valine in *Xenopus* ActRIIB, and so this position may be altered, and optionally may be altered to another hydrophobic residue, such as V, I or F, or a non-polar residue such as A. E52 in the human extracellular domain is a K in *Xenopus*, indicating that this site may be tolerant of a wide variety of changes, including polar residues, such as E, D, K, R, H, S, T, P, G, Y and probably A. T93 in the human extracellular domain is a K in *Xenopus*, indicating that a wide structural variation is tolerated at this position, with polar residues favored, such as S, K, R, E, D, H, G, P, G and Y. F108 in the human extracellular domain is a Y in *Xenopus*, and therefore Y or other hydrophobic group, such as I, V or L should be tolerated. E111 in the human extracellular domain is K in *Xenopus*, indicating that charged residues will be tolerated at this position, including D, R, K and H, as well as Q and N. R112 in the human extracellular domain is K in *Xenopus*, indicating that basic residues are tolerated at this position, including R and H. A at position 119 in the human extracellular domain is relatively poorly conserved, and appears as P in rodents and V in *Xenopus*, thus essentially any amino acid should be tolerated at this position.

Moreover, ActRII proteins have been characterized in the art in terms of structural and functional characteristics, particularly with respect to ligand binding [Attisano et al. (1992) *Cell* 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide ample guidance for how to generate ActRIIB variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor (Greenwald et al. (1999) *Nat Struct Biol* 6:18-22; and Hinck (2012) *FEBS Lett* 586:1860-1870). Accordingly, the core ligand-binding domains of human ActRIIB, as demarcated by the outermost of these conserved cysteines, corresponds to positions 29-109 of SEQ ID NO: 1 (ActRIIB precursor). The structurally less-ordered amino acids flanking these cysteine-demarcated core sequences can be truncated by 1, 2, 3, 4, 5, 6, 7, 8, 9, 10, 11, 12, 13, 14, 15, 16, 17, 18, 19, 20, 21, 22, 23, 24, 25, 26, 27, or 28 residues at the N-terminus and/or 1, 2, 3, 4, 5, 6, 7, 8, 9, 10, 11, 12, 13, 14, 15, 16, 17, 18, 19, 20, 21, or 22 residues at the C-terminus without necessarily altering ligand binding. Exemplary ActRIIB extracellular domains for N-terminal and/or C-terminal truncation include SEQ ID NOs: 3, 4, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted.

Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO:1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding (U.S. Pat. No. 7,842,663). This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S. Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) of SEQ ID NO: 1 and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) of SEQ ID NO: 1 and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, 133, or 134) or 129-134 (e.g., any one of positions 129, 130, 131, 132, 133, or 134) of SEQ ID NO: 1. Variants within these ranges are also contemplated, particularly those comprising, consisting essentially of, or consisting of an amino acid sequence that has at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, optionally zero, one or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) does not appear to decrease ligand binding in the R64 background (U.S. Pat. No. 7,842,663). This change probably eliminates glycosylation at N65 in the A64 background, thus demonstrating that a significant change in this region is likely to be tolerated. While an R64A change is poorly tolerated, R64K is well-tolerated, and thus another basic residue, such as H, may be tolerated at position 64 (U.S. Pat. No. 7,842,663). Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

It has been previously demonstrated that the addition of a further N-linked glycosylation site (N-X-S/T) into the ActRIIB extracellular domain is well-tolerated (see, e.g., U.S. Pat. No. 7,842,663). Therefore, N-X-S/T sequences may be generally introduced at positions outside the ligand binding pocket defined in FIG. 1 in ActRIIB polypeptide of the present disclosure. Particularly suitable sites for the introduction of non-endogenous N-X-S/T sequences include amino acids 20-29, 20-24, 22-25, 109-134, 120-134 or 129-134 (with respect to SEQ ID NO: 1). N-X-S/T sequences may also be introduced into the linker between the ActRIIB sequence and an Fc domain or other fusion component as well as optionally into the fusion component itself. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E105N, R112N, G120N, E123N, P129N, A132N, R112S and R112T (with respect to SEQ ID NO: 1). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T (with respect to SEQ ID NO: 1) are contemplated. Likewise, in an A24N variant, an S26T alteration may be used. Accordingly, an ActRIIB polypeptide of the present disclosure may be a variant having one or more additional, non-endogenous N-linked glycosylation consensus sequences as described above.

In certain aspects, an activin and/or GDF antagonist to be used in accordance with the methods and uses disclosed herein is an ActRIIB polypeptide (which includes fragments and functional variants variant thereof) as well as protein complexes comprising at least one ActRIIB polypeptide (e.g., an homodimer comprising two ActRIIB polypeptides or a heterodimer comprising one ActRIIB polypeptide and a heterologous polypeptide (e.g., ALK4)). Preferably, ActRIIB polypeptides are soluble (e.g., comprise an extracellular domain of ActRIIB). In some embodiments, ActRIIB polypeptides antagonize activity (e.g., Smad signaling) of one or more activin and/or GDF ligands (e.g., GDF11, GDF8, activin (activin A, activin B, activin AB, activin C, activin E), GDF3, GDF1, Nodal, ActRIIA, ActRIIB, ALK4, ALK5, ALK7, Cryptic, Cryptic 1B, Smad 2, and Smad 3). Therefore, in some embodiments, ActRIIB polypeptides bind to one or more activin and/or GDF ligands (e.g., GDF11, GDF8, activin (activin A, activin B, activin AB, activin C, activin AC, activin BC, activin E, activin AE, and/or activin BE), GDF3, GDF1, Nodal, ActRIIA, ALK4, ALK5, ALK7, Cryptic, Cryptic 1, Smad 2, and Smad 3, etc.)). In some embodiments, ActRIIB polypeptides of the disclosure comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 of SEQ ID NO: 1 and ending at a position corresponding to amino acids 109-134 of SEQ ID NO: 1. In some embodiments, ActRIIB polypeptides comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1. In certain embodiments, ActRIIB polypeptides of the disclosure comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1. In some embodiments, ActRIIB polypeptide of disclosure comprise an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 181, 182, 184, 187, 188, 189, 190, 192, 193, 196, 197, 198, 199, 201, 205, and 206. In some embodiments, ActRIIB polypeptides of the disclosure comprise an ActRIIB polypeptide wherein the position corresponding to L79 of SEQ ID NO: 1 is not an acidic amino acid (i.e., is not naturally occurring acid amino acids D or E or an artificial acidic amino acid residue).

In certain embodiments, the present disclosure relates to ActRIIA polypeptides. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication Nos. WO 2006/012627 and WO 2007/062188, which are incorporated herein by reference in their entirety.

The human ActRIIA precursor protein sequence is set forth in SEQ ID NO: 9 or 10.

A processed extracellular human ActRIIA polypeptide sequence is set in SEQ ID NO: 11. A nucleic acid sequence encoding the processed extracellular ActRIIA polypeptide has a sequence of SEQ ID NO: 14.

A sequence having the C-terminal "tail" of the extracellular domain deleted (a Δ15 sequence) is set forth in SEQ ID NO: 12.

A nucleic acid sequence encoding the human ActRIIA precursor protein (SEQ ID NO: 9) is shown below (SEQ ID NO: 13), corresponding to nucleotides 159-1700 of Genbank Reference Sequence NM_001616.4.

ActRIIA is well-conserved among vertebrates, with large stretches of the extracellular domain completely conserved. For example, FIG. 3 depicts a multi-sequence alignment of a human ActRIIA extracellular domain compared to various ActRIIA orthologs. Many of the ligands that bind to ActRIIA are also highly conserved. Accordingly, from these alignments, it is possible to predict key amino acid positions within the ligand-binding domain that are important for normal ActRIIA-ligand binding activities as well as to predict amino acid positions that are likely to be tolerant to substitution without significantly altering normal ActRIIA-ligand binding activities. Therefore, an active, human ActRIIA variant polypeptide useful in accordance with the presently disclosed methods may include one or more amino acids at corresponding positions from the sequence of another vertebrate ActRIIA, or may include a residue that is similar to that in the human or other vertebrate sequences.

Without meaning to be limiting, the following examples illustrate this approach to defining an active ActRIIA variant. As illustrated in FIG. 3, F13 in the human extracellular domain is Y in *Ovis aries* (SEQ ID NO: 18), *Gallus gallus* (SEQ ID NO: 21), *Bos Taurus* (SEQ ID NO: 22), *Tyto alba* (SEQ ID NO: 23), and *Myotis davidii* (SEQ ID NO: 24) ActRIIA, indicating that aromatic residues are tolerated at this position, including F, W, and Y. Q24 in the human extracellular domain is R in *Bos Taurus* ActRIIA, indicating that charged residues will be tolerated at this position, including D, R, K, H, and E. S95 in the human extracellular domain is F in *Gallus gallus* and *Tyto alba* ActRIIA, indicating that this site may be tolerant of a wide variety of changes, including polar residues, such as E, D, K, R, H, S, T, P, G, Y, and probably hydrophobic residue such as L, I, or F. E52 in the human extracellular domain is D in *Ovis aries* ActRIIA, indicating that acidic residues are tolerated at this position, including D and E. P29 in the human extracellular domain is relatively poorly conserved, appearing as S in *Ovis aries* ActRIIA and L in *Myotis davidii* ActRIIA, thus essentially any amino acid should be tolerated at this position.

Moreover, as discussed above, ActRII proteins have been characterized in the art in terms of structural/functional characteristics, particularly with respect to ligand binding [Attisano et al. (1992) *Cell* 68(1):97-108; Greenwald et al. (1999) *Nature Structural Biology* 6(1): 18-22; Allendorph et al. (2006) *PNAS* 103(20: 7643-7648; Thompson et al. (2003) *The EMBO Journal* 22(7): 1555-1566; as well as U.S. Pat. Nos. 7,709,605, 7,612,041, and 7,842,663]. In addition to the teachings herein, these references provide amply guidance for how to generate ActRII variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) *Nat Struct Biol* 6:18-22; and Hinck (2012) *FEBS Lett* 586:1860-1870].

Accordingly, the core ligand-binding domains of human ActRIIA, as demarcated by the outermost of these conserved cysteines, corresponds to positions 30-110 of SEQ ID NO: 9 (ActRIIA precursor). Therefore, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, 28, or 29 residues at the N-terminus and by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRIIA extracellular domains truncations include SEQ ID NO: 12.

Accordingly, a general formula for an active portion (e.g., ligand binding) of ActRIIA is a polypeptide that comprises, consists essentially of, or consists of amino acids 30-110 of SEQ ID NO: 9. Therefore ActRIIA polypeptides may, for example, comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to any one of amino acids 21-30 of SEQ ID NO: 9 and ending at a position corresponding to any one amino acids 110-135 of SEQ ID NO: 9. Other examples include constructs that begin at a position selected from 21-30, 22-30, 23-30, 24-30 of SEQ ID NO: 9, and end at a position selected from 111-135, 112-135, 113-135, 120-135, 130-135, 111-134, 111-133, 111-132, or 111-131 of SEQ ID NO: 9. Variants within these ranges are also contemplated, particularly those comprising an amino acid sequence that has at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 9. Thus, in some embodiments, an ActRIIA polypeptide may comprise a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9. Optionally, ActRIIA polypeptides comprise a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9, and comprising no more than 1, 2, 5, 10 or 15 conservative amino acid changes in the ligand-binding pocket.

In certain aspects, an activin and/or GDF antagonist to be used in accordance with the methods and uses disclosed herein is an ActRIIA polypeptide (which includes fragments and functional variants variant thereof) or a protein complex comprising at least one ActRIIA polypeptide (e.g., an homodimer comprising two ActRIIA polypeptides or a heterodimer comprising one ActRIIA polypeptide and a heterologous polypeptide (e.g., ALK4)). Preferably, ActRIIA polypeptides are soluble (e.g., an extracellular domain of ActRIIA). In some embodiments, ActRIIA polypeptides inhibit (e.g., Smad signaling) of one or more activin and/or GDF ligands (e.g., GDF11, GDF8, activin (activin A, activin B, activin AB, activin C, activin AC, activin BC, activin E, activin AE, and/or activin BE), GDF3, GDF1, Nodal, ActRIIB, ALK4, ALK5, ALK7, Cryptic, Cryptic 1B, Smad 2, and Smad 3, etc.). In some embodiments, ActRIIA polypeptides bind to one or more activin and/or GDF ligands (e.g., GDF11, GDF8, activin (activin A, activin B, activin AB, activin C, activin AC, activin BC, activin E, activin AE, and/or activin BE), GDF3, GDF1, Nodal, ActRIIB, ALK4, ALK5, ALK7, Cryptic, Cryptic 1, Smad 2, and Smad 3, etc.)). In some embodiments, ActRIIA polypeptide of the disclosure comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to amino acids 21-30 of SEQ ID NO: 9 and ending at a position corresponding to any one amino acids 110-135 of SEQ ID NO: 9. In some embodiments, ActRIIA polypeptides comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 30-110 of SEQ ID NO: 9. In certain embodiments, ActRIIA polypeptides comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 21-135 of SEQ ID NO: 9. In some embodiments, ActRIIA polypeptides comprise an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 9, 10, 11, 12, 15, 18-24, 177, 178, and 180.

In certain aspects, the present disclosure relates to heteromultimers that comprise a BMPRII polypeptide. As used herein, the term "BMPRII" refers to a family of bone morphogenetic protein receptor type II (BMPRII) proteins from any species and variants derived from such BMPRII proteins by mutagenesis or other modification. Reference to BMPRII herein is understood to be a reference to any one of the currently identified forms. Members of the BMPRII family are generally transmembrane proteins, having a ligand-binding extracellular domain with a cysteine-rich region, a transmembrane domain, and a cytoplasmic domain with predicted serine/threonine kinase activity.

The term "BMPRII polypeptide" includes polypeptides comprising any naturally occurring polypeptide of a BMPRII family member as well as any variants thereof (including mutants, fragments, fusions, and peptidomimetic forms) that retain a useful activity. Numbering of amino acids for all BMPRII-related polypeptides described herein is based on the numbering of the human BMPRII precursor protein sequence (SEQ ID NO: 34, NCBI Ref Seq NP_001195.2), unless specifically designated otherwise. In SEQ ID NO: 34, the signal peptide is indicated and the extracellular domain is indicated. A nucleic acid sequence encoding BMPRII precursor protein is shown in SEQ ID NO: 35, as nucleotides 1149-4262 of Genbank Reference Sequence NM_001204.6. A processed extracellular BMPRII polypeptide sequence is set forth in SEQ ID NO: 36, which is encodable by a nucleic acid sequence of SEQ ID NO: 37. An alternative isoform of BMPRII, isoform 2 (GenBank: AAA86519.1) is set forth in SEQ ID NO: 38 (the signal peptide is indicated and the extracellular domain is indicated), which is encodable by a nucleic acid sequence of SEQ ID NO: 39 (corresponding to nucleotides 163-1752 of Genbank Reference Sequence U25110.1). A processed extracellular BMPRII polypeptide sequence (isoform 2) is set forth in SEQ ID NO: 40, which is encodable by a nucleic acid sequence of SEQ ID NO: 41.

In certain embodiments, the disclosure relates to heteromultimers that comprise at least one BMPRII polypeptide, which includes fragments, functional variants, and modified forms thereof. Preferably, BMPRII polypeptides for use in accordance with inventions of the disclosure (e.g., heteromultimers comprising a BMPRII polypeptide and uses thereof) are soluble (e.g., an extracellular domain of BMPRII). In other preferred embodiments, BMPRII polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to the amino acid sequence of SEQ ID NO: 34, 36, 38, or 40. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 27-34 (e.g., amino acid residues 27, 28, 29, 30, 31, 32, 33, or 34) of SEQ ID NO: 34, and ends at any one of amino acids 123-150 (e.g., amino acid residues 123, 124, 125, 126, 127, 128, 129, 130, 131, 132, 133, 134, 135, 136, 137, 138, 139, 140, 141, 142, 143, 144, 145, 146, 147, 148, 149, or 150) of SEQ ID NO: 34. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 27-123 of SEQ ID NO: 34. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 27-150 of SEQ ID NO: 34. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 34-123 of SEQ ID NO: 34. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 34-150 of SEQ ID NO: 34. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 27-34 (e.g., amino acid residues 27, 28, 29, 30, 31, 32, 33, or 34) of SEQ ID NO: 38, and ends at any one of amino acids 123-150 (e.g., amino acid residues 123, 124, 125, 126, 127, 128, 129, 130, 131, 132, 133, 134, 135, 136, 137, 138, 139, 140, 141, 142, 143, 144, 145, 146, 147, 148, 149, or 150) of SEQ ID NO: 38. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 27-123 of SEQ ID NO: 38. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 27-150 of SEQ ID NO: 38. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 34-123 of SEQ ID NO: 38. In some embodiments, heteromultimers of the disclosure comprise at least one BMPRII polypeptide that is at least 70%, 75%, 80%, 85%, 90%, 91%. 92%, 93%, 94%, 95%, 96%, 97%, 98%, 99%, or 100% identical to amino acids of 34-150 of SEQ ID NO: 38.

In certain aspects, the present disclosure relates to heteromultimers that comprise an MISRII polypeptide. As used herein, the term "MISRII" refers to a family of Müllerian inhibiting substance receptor type II (MISRII) proteins from any species and variants derived from such MISRII proteins by mutagenesis or other modification. Reference to MISRII herein is understood to be a reference to any one of the currently identified forms. Members of the MISRII family are generally transmembrane proteins, composed of a ligand-binding extracellular domain with a cysteine-rich region, a transmembrane domain, and a cytoplasmic domain with predicted serine/threonine kinase activity.

The term "MISRII polypeptide" includes polypeptides comprising any naturally occurring polypeptide of an MISRII family member as well as any variants thereof (including mutants, fragments, fusions, and peptidomimetic forms) that retain a useful activity. Numbering of amino acids for all MISRII-related polypeptides described herein is based on the numbering of the human MISRII precursor protein sequence (SEQ ID NO: 42, NCBI Ref Seq NP_065434.1), unless specifically designated otherwise. In SEQ ID NO: 42, the signal peptide is indicated and the extracellular domain is indicated. A nucleic acid sequence encoding the MISRII precursor protein is shown in SEQ ID NO: 43, corresponding to nucleotides 81-1799 of Genbank Reference Sequence NM_020547.2. A processed extracellular MISRII polypeptide sequence (isoform 1) is set forth in SEQ ID NO: 44, which is encodable by a nucleic acid sequence of SEQ ID NO: 45. An alternative isoform of the human MISRII precursor protein sequence, isoform 2 (NCBI Ref Seq NP_001158162.1), is set forth in SEQ ID NO: 46 (the signal peptide is indicated and the extracellular domain is indicated), which is encodable by a nucleic acid sequence of SEQ ID NO: 47, corresponding to nucleotides 81-1514 of Genbank Reference Sequence NM_001164690.1. A processed extracellular MISRII polypeptide sequence (isoform 2) is 100% identical to the corresponding processed extracellular MISRII polypeptide sequence (isoform 1) (i.e., having an amino acid sequence of SEQ ID NO: 44, which is encodable by a nucleic acid sequence of SEQ ID NO: 45). An alternative isoform of the human MISRII precursor protein sequence, isoform 3 (NCBI Ref Seq NP_001158163.1), is set forth in SEQ ID NO: 48 (the signal peptide is indicated and the extracellular domain is indicated), which is encodable by a nucleic acid sequence of SEQ ID NO: 49, corresponding to nucleotides 81-1514 of Genbank Reference Sequence NM_001164691.1. A processed extracellular MISRII polypeptide sequence (isoform 3) is 100% identical to the corresponding processed extracellular MISRII polypeptide sequence (isoform 1) (i.e., having an amino acid sequence of SEQ ID NO: 44, which is encodable by a nucleic acid sequence of SEQ ID NO: 45).

In certain embodiments, the disclosure relates to heteromultimers that comprise at least one MISRII polypeptide, which includes fragments, functional variants, and modified forms thereof. Preferably, MISRII polypeptides for use in accordance with inventions of the disclosure (e.g., heteromultimers comprising a MISRII polypeptide and uses thereof) are soluble (e.g., an extracellular domain of MISRII). In other preferred embodiments, MISRII polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to the amino acid sequence of SEQ ID NOs: 42, 44, 46, or 48. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 17-24 (e.g., amino acid residues 17, 18, 19, 20, 21, 22, 23, or 24) of SEQ ID NO: 42, and ends at any one of amino acids 116-149 (e.g., amino acid residues 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149) of SEQ ID NO: 42. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 17-116 of SEQ ID NO: 42. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 17-149 of SEQ ID NO: 42. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 24-116 of SEQ ID NO: 42. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 24-149 of SEQ ID NO: 42. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 17-24 (e.g., amino acid residues 17, 18, 19, 20, 21, 22, 23, or 24) of SEQ ID NO: 46, and ends at any one of amino acids 116-149 (e.g., amino acid residues 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149) of SEQ ID NO: 46. In some embodiments, heteromultimers of the disclosure comprise at least one MISRII polypeptide that is at least 70%, 75%, 80%, 85%, 90%, 91%.

92%, 93%, 94%, 95%, 96%, 97%, 98%, 99%, or 100% identical to amino acids of 17-116 of SEQ ID NO: 46. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 17-149 of SEQ ID NO: 46. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 24-116 of SEQ ID NO: 46. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 24-149 of SEQ ID NO: 46. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 17-24 (e.g., amino acid residues 17, 18, 19, 20, 21, 22, 23, or 24) of SEQ ID NO: 42, and ends at any one of amino acids 116-149 (e.g., amino acid residues 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149) of SEQ ID NO: 48. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 17-116 of SEQ ID NO: 48. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 17-149 of SEQ ID NO: 48. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 24-116 of SEQ ID NO: 48. In some embodiments, heteromultimers of the disclosure comprise at least one MISRII polypeptide that is at least 70%, 75%, 80%, 85%, 90%, 91%. 92%, 93%, 94%, 95%, 96%, 97%, 98%, 99%, or 100% identical to amino acids of 24-149 of SEQ ID NO: 48.

In certain aspects, the present disclosure relates to heteromultimers that comprise an ALK1 polypeptide. As used herein, the term "ALK1" refers to a family of activin receptor-like kinase-1 proteins from any species and variants derived from such ALK1 proteins by mutagenesis or other modification. Reference to ALK1 herein is understood to be a reference to any one of the currently identified forms. Members of the ALK1 family are generally transmembrane proteins, composed of a ligand-binding extracellular domain with a cysteine-rich region, a transmembrane domain, and a cytoplasmic domain with predicted serine/threonine kinase activity.

The term "ALK1 polypeptide" includes polypeptides comprising any naturally occurring polypeptide of an ALK1 family member as well as any variants thereof (including mutants, fragments, fusions, and peptidomimetic forms) that retain a useful activity. Numbering of amino acids for all ALK1-related polypeptides described herein is based on the numbering of the human ALK1 precursor protein sequence (SEQ ID NO: 52, NCBI Ref Seq NP_000011.2), unless specifically designated otherwise. In SEQ ID NO: 52, the signal peptide is indicated and the extracellular domain is indicated. A nucleic acid sequence encoding human ALK1 precursor protein is set forth in SEQ ID NO: 53, corresponding to nucleotides 284-1792 of Genbank Reference Sequence NM_000020.2. A processed extracellular ALK1 polypeptide sequence is set forth in SEQ ID NO: 54, which is encodable by a nucleic acid sequence of SEQ ID NO: 55.

In certain embodiments, the disclosure relates to heteromultimers that comprise at least one ALK1 polypeptide, which includes fragments, functional variants, and modified forms thereof. Preferably, ALK1 polypeptides for use in accordance with inventions of the disclosure (e.g., heteromultimers comprising an ALK1 polypeptide and uses thereof) are soluble (e.g., an extracellular domain of ALK1). In other preferred embodiments, ALK1 polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one ALK1 polypeptide that is at least 70%, 75%, 80%, 85%, 90%, 91%, 92%, 93%, 94%, 95%, 96%, 97%, 98%, 99%, or 100% identical to the amino acid sequence of SEQ ID NOs: 52 or 54. In some embodiments, heteromultimers of the disclosure comprise at least one ALK1 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 22-34 (e.g., amino acid residues 22, 23, 24, 25, 26, 27, 28, 29, 30, 31, 32, 33, or 34) of SEQ ID NO: 52, and ends at any one of amino acids 95-118 (e.g., amino acid residues 95, 96, 97, 98, 99, 100, 101, 102, 103, 104, 105, 106, 107, 108, 109, 110, 111, 112,113, 114, 115, 116, 117, 118, or 119) of SEQ ID NO: 52. In some embodiments, heteromultimers of the disclosure comprise at least one ALK1 polypeptide that is at least 70%, 75%, 80%, 85%, 90%, 91%. 92%, 93%, 94%, 95%, 96%, 97%, 98%, 99%, or 100% identical to amino acids of 22-95 of SEQ ID NO: 52. In some embodiments, heteromultimers of the disclosure comprise at least one ALK1 polypeptide that is at least 70%, 75%, 80%, 85%, 90%, 91%. 92%, 93%, 94%, 95%, 96%, 97%, 98%, 99%, or 100% identical to amino acids of 22-118 of SEQ ID NO: 52. In some embodiments, heteromultimers of the disclosure comprise at least one ALK1 polypeptide that is at least 70%, 75%, 80%, 85%, 90%, 91%. 92%, 93%, 94%, 95%, 96%, 97%, 98%, 99%, or 100% identical to amino acids of 34-95 of SEQ ID NO: 52. In some embodiments, heteromultimers of the disclosure comprise at least one ALK1 polypeptide that is at least 70%, 75%, 80%, 85%, 90%, 91%. 92%, 93%, 94%, 95%, 96%, 97%, 98%, 99%, or 100% identical to amino acids of 34-118 of SEQ ID NO: 52.

In certain aspects, the present disclosure relates to heteromultimers that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity. Numbering of amino acids for all ALK4-related polypeptides described herein is based on the numbering of the human ALK4 precursor protein sequence (SEQ ID NO: 56, NCBI Ref Seq NP_004293), unless specifically designated otherwise. In SEQ ID NO: 56, the signal peptide is indicated and the extracellular domain is indicated. A nucleic acid sequence encoding the ALK4 precursor protein is set forth in SEQ ID NO: 57, corresponding to nucleotides 78-1592 of Genbank Reference Sequence NM_004302.4. The signal sequence and the extracellular domain is indicated. A processed extracellular human ALK4 polypeptide sequence is set forth in SEQ ID NO: 58, which is encodable by a nucleic acid sequence of SEQ ID NO: 59. An alternative isoform of human ALK4 precursor protein sequence, isoform C (NCBI Ref Seq NP_064733.3) is set forth in SEQ ID NO: 60, where the signal peptide is indicated and the extracellular domain is indicated. A nucleic acid sequence encoding the ALK4 precursor protein (isoform C) is set forth in SEQ ID NO: 61, corresponding to nucleotides 78-1715 of Genbank Reference Sequence NM_020328.3. A processed extracellular ALK4 polypeptide sequence (isoform C) is 100% identical to the corresponding processed extracellular ALK4 polypeptide sequence (i.e., having an amino acid sequence of SEQ ID NO: 58, which is encodable by a nucleic acid sequence of SEQ ID NO: 59).

In certain embodiments, the disclosure relates to heteromultimers that comprise at least one ALK4 polypeptide, which includes fragments, functional variants, and modified forms thereof. Preferably, ALK4 polypeptides for use in accordance with inventions of the disclosure (e.g., heteromultimers comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one ALK4 polypeptide that is at least 70%, 75%, 80%, 85%, 90%, 91%, 92%, 93%, 94%, 95%, 96%, 97%, 98%, 99%, or 100% identical to the amino acid sequence of SEQ ID NOs: 56, 58 or 60. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 24-34 (e.g., amino acid residues 24, 25, 26, 27, 28, 29, 30, 31, 32, 33, or 34) of SEQ ID NO: 56, and ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, or 126) of SEQ ID NO: 56. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 24-101 of SEQ ID NO: 56. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 24-126 of SEQ ID NO: 56. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 34-101 of SEQ ID NO: 56. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 34-126 of SEQ ID NO: 56. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 24-34 (e.g., amino acid residues 24, 25, 26, 27, 28, 29, 30, 31, 32, 33, or 34) of SEQ ID NO: 83, and ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, or 126) of SEQ ID NO: 60. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 24-101 of SEQ ID NO: 60. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 24-126 of SEQ ID NO: 60. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 34-101 of SEQ ID NO: 60. In some embodiments, heteromultimers of the disclosure comprise at least one ALK4 polypeptide that is at least 70%, 75%, 80%, 85%, 90%, 91%. 92%, 93%, 94%, 95%, 96%, 97%, 98%, 99%, or 100% identical to amino acids of 34-126 of SEQ ID NO: 60.

In certain aspects, the present disclosure relates to heteromultimers that comprise an ALK5 polypeptide. As used herein, the term "ALK5" refers to a family of activin receptor-like kinase-5 proteins from any species and variants derived from such ALK5 proteins by mutagenesis or other modification. Reference to ALK5 herein is understood to be a reference to any one of the currently identified forms. Members of the ALK5 family are generally transmembrane proteins, having a ligand-binding extracellular domain with a cysteine-rich region, a transmembrane domain, and a cytoplasmic domain with predicted serine/threonine kinase activity.

The term "ALK5 polypeptide" includes polypeptides comprising any naturally occurring polypeptide of an ALK5 family member as well as any variants thereof (including mutants, fragments, fusions, and peptidomimetic forms) that retain a useful activity. Numbering of amino acids for all ALK5-related polypeptides described herein is based on the numbering of the human ALK5 precursor protein sequence (SEQ ID NO: 62, NCBI Ref Seq NP_004603.1), unless specifically designated otherwise. In SEQ ID NO: 62, the signal peptide is indicated and the extracellular domain is indicated. A nucleic acid sequence encoding the ALK5 precursor protein is set forth in SEQ ID NO: 63, corresponding to nucleotides 77-1585 of Genbank Reference Sequence NM_004612.2. A processed extracellular ALK5 polypeptide sequence is set forth in SEQ ID NO: 64, which is encodable by a nucleic acid sequence of SEQ ID NO: 65. An alternative isoform of the human ALK5 precursor protein sequence, isoform 2 (NCBI Ref Seq XP_005252207.1), is set forth in SEQ ID NO: 66 (the signal peptide is indicated and the extracellular domain is indicated). A nucleic acid sequence encoding human ALK5 precursor protein (isoform 2) is set forth in SEQ ID NO: 67 (the signal sequence and the extracellular domain is indicated), corresponding to nucleotides 77-1597 of Genbank Reference Sequence XM_005252150.1.

A processed extracellular ALK5 polypeptide sequence (isoform 2) is set forth in SEQ ID NO: 68, which is encodable by a nucleic acid sequence of SEQ ID NO: 69.

In certain embodiments, the disclosure relates to heteromultimers that comprise at least one ALK5 polypeptide, which includes fragments, functional variants, and modified forms thereof. Preferably, ALK5 polypeptides for use in accordance with inventions of the disclosure (e.g., heteromultimers comprising an ALK5 polypeptide and uses thereof) are soluble (e.g., an extracellular domain of ALK5). In other preferred embodiments, ALK5 polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to the amino acid sequence of SEQ ID NOs: 62, 64, 66, or 68. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 25-36 (e.g., amino acid residues 25, 26, 27, 28, 29, 30, 31, 32, 33, 34, 35, or 36) of SEQ ID NO: 62, and ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, or 126) of SEQ ID NO: 62. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 25-101 of SEQ ID NO: 62. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 25-126 of SEQ ID NO: 62. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 36-101 of SEQ ID NO: 62. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 36-126 of SEQ ID NO: 62. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 25-36 (e.g., amino acid residues 25, 26, 27, 28, 29, 30, 31, 32, 33, 34, 35, or 36) of SEQ ID NO: 66, and ends at any one of amino acids 101-130 (e.g., amino acid residues 101, 102, 103, 104, 105, 106, 107, 108, 109, 110, 111, 112,113, 114, 115, 116, 117, 118, 119, 120, 121, 122, 123, 124, 125, 126, 127, 128, 129 or 130) of SEQ ID NO: 66. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 25-101 of SEQ ID NO: 66. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 25-130 of SEQ ID NO: 66. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 36-101 of SEQ ID NO: 66. In some embodiments, heteromultimers of the disclosure comprise at least one ALK5 polypeptide that is at least 70%, 75%, 80%, 85%, 90%, 91%. 92%, 93%, 94%, 95%, 96%, 97%, 98%, 99%, or 100% identical to amino acids of 36-130 of SEQ ID NO: 66.

In certain aspects, the present disclosure relates to heteromultimers that comprise an ALK7 polypeptide. As used herein, the term "ALK7" refers to a family of activin receptor-like kinase-7 proteins from any species and variants derived from such ALK7 proteins by mutagenesis or other modification. Reference to ALK7 herein is understood to be a reference to any one of the currently identified forms. Members of the ALK7 family are generally transmembrane proteins, composed of a ligand-binding extracellular domain with a cysteine-rich region, a transmembrane domain, and a cytoplasmic domain with predicted serine/threonine kinase activity.

The term "ALK7 polypeptide" includes polypeptides comprising any naturally occurring polypeptide of an ALK7 family member as well as any variants thereof (including mutants, fragments, fusions, and peptidomimetic forms) that retain a useful activity. Numbering of amino acids for all ALK7-related polypeptides described herein is based on the numbering of the human ALK7 precursor protein sequence (SEQ ID NO: 70, NCBI Ref Seq NP_660302.2), unless specifically designated otherwise. In SEQ ID NO: 70, the signal peptide is indicated and the extracellular domain is indicated. A nucleic acid sequence encoding human ALK7 isoform 1 precursor protein is set forth in SEQ ID NO: 71, corresponding to nucleotides 244-1722 of Genbank Reference Sequence NM_145259.2. A processed extracellular ALK7 isoform 1 polypeptide sequence is set forth in SEQ ID NO: 72, which is encodable by a nucleic acid sequence of SEQ ID NO: 73. The amino acid sequence of an alternative isoform of human ALK7, isoform 2 (NCBI Ref Seq NP_001104501.1), is shown in SEQ ID NO: 74, where the extracellular domain is indicated. A nucleic acid sequence encoding the processed ALK7 polypeptide (isoform 2) is set forth in SEQ ID NO: 75, corresponding to nucleotides 279-1607 of *NCBI Reference Sequence* NM_001111031.1. An amino acid sequence of the extracellular ALK7 polypeptide (isoform 2) is set forth in SEQ ID NO: 76, which is encodable by a nucleic acid sequence of SEQ ID NO: 77. An amino acid sequence of an alternative human ALK7 precursor protein, isoform 3 (NCBI Ref Seq NP_001104502.1), is set forth in SEQ ID NO: 78, where the signal peptide is indicated. A nucleic acid sequence encoding the unprocessed ALK7 polypeptide precursor protein (isoform 3) is set forth in SEQ ID NO: 79, corresponding to nucleotides 244-1482 of *NCBI Reference Sequence* NM_001111032.1. An amino acid sequence of the processed ALK7 polypeptide (isoform 3) is set forth in SEQ ID NO: 80. This isoform lacks a transmembrane domain and is therefore proposed to be soluble in its entirety (Roberts et al., 2003, *Biol Reprod* 68:1719-1726). N-terminal variants of SEQ ID NO: 80 are predicted as described below. A nucleic acid sequence encoding the processed ALK7 polypeptide (isoform 3) is set forth in SEQ ID NO: 81. An amino acid sequence of an alternative human ALK7 precursor protein, isoform 4 (NCBI Ref Seq NP_001104503.1), is set forth in SEQ ID NO: 82, where the signal peptide is indicated. A nucleic acid sequence encoding the unprocessed ALK7 polypeptide precursor protein (isoform 4) is set forth in SEQ ID NO: 83, corresponding to nucleotides 244-1244 of *NCBI Reference Sequence* NM_001111033.1. An amino acid sequence of the processed ALK7 polypeptide (isoform 4) is set forth in SEQ ID NO: 84. Like ALK7 isoform 3, isoform 4 lacks a transmembrane domain and is therefore proposed to be soluble in its entirety (Roberts et al., 2003, *Biol Reprod*

68:1719-1726). A nucleic acid sequence encoding the processed ALK7 polypeptide (isoform 4) is set forth in SEQ ID NO: 85.

Based on the signal sequence of full-length ALK7 (isoform 1) in the rat (see NCBI Reference Sequence NP_620790.1) and on the high degree of sequence identity between human and rat ALK7, it is predicted that a processed form of human ALK7 isoform 1 is set forth in SEQ ID NO: 86.

Active variants of processed ALK7 isoform 1 are predicted in which SEQ ID NO: 72 is truncated by 1, 2, 3, 4, 5, 6, or 7 amino acids at the N-terminus and SEQ ID NO: 86 is truncated by 1 or 2 amino acids at the N-terminus. Consistent with SEQ ID NO: 86, it is further expected that leucine is the N-terminal amino acid in the processed forms of human ALK7 isoform 3 (SEQ ID NO: 80) and human ALK7 isoform 4 (SEQ ID NO: 84). In certain embodiments, the disclosure relates to heteromultimers that comprise at least one ALK7 polypeptide, which includes fragments, functional variants, and modified forms thereof. Preferably, ALK7 polypeptides for use in accordance with inventions of the disclosure (e.g., heteromultimers comprising an ALK7 polypeptide and uses thereof) are soluble (e.g., an extracellular domain of ALK7). In other preferred embodiments, ALK7 polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one ALK7 polypeptide that is at least 70%, 70%, 75%, 80%, 85%, 90%, 91%, 92%, 93%, 94%, 95%, 96%, 97%, 98%, 99%, or 100% identical to the amino acid sequence of SEQ ID NO: 70, 72, 74, 76, 78, 80, 82, 84, or 86. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 21-28 (e.g., amino acid residues 21, 22, 23, 24, 25, 26, 27, or 28) of SEQ ID NO: 70, and ends at any one of amino acids 92-113 (e.g., amino acid residues 92, 93, 94, 95, 96, 97, 98, 99, 100, 101, 102, 103, 104, 105, 106, 107, 108, 109, 110, 111, 112, or 113) of SEQ ID NO: 70. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 21-92 of SEQ ID NO: 70. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 21-113 of SEQ ID NO: 70. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 28-92 of SEQ ID NO: 70. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 28-113 of SEQ ID NO: 70. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 1-13 (e.g., amino acid residues 1, 2, 3, 4, 5, 6, 7, 8, 9, 10, 11, 12, or 13) of SEQ ID NO: 74, and ends at any one of amino acids 42-63 (e.g., amino acid residues 42, 43, 44, 45, 46, 47, 48, 49, 50, 51, 52, 53, 54, 55, 56, 57, 58, 59, 60, 61, 62, or 63) of SEQ ID NO: 74. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 1-42 of SEQ ID NO: 74. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 1-63 of SEQ ID NO: 74. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 13-42 of SEQ ID NO: 74. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 13-63 of SEQ ID NO: 74. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 21-28 (e.g., amino acid residues 21, 22, 23, 24, 25, 26, 27, or 28) of SEQ ID NO: 78, and ends at any one of amino acids 411-413 (e.g., amino acid residues 411, 412, or 413) of SEQ ID NO: 78. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 21-411 of SEQ ID NO: 78. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 21-413 of SEQ ID NO: 78. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 28-411 of SEQ ID NO: 78. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 28-413 of SEQ ID NO: 78. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 21-28 (e.g., amino acid residues 21, 22, 23, 24, 25, 26, 27, or 28) of SEQ ID NO: 82, and ends at any one of amino acids 334-336 (e.g., amino acid residues 334, 335, or 336) of SEQ ID NO: 82. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 21-334 of SEQ ID NO: 82. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 21-336 of SEQ ID NO: 82. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 28-334 of SEQ ID NO: 82. In some embodiments, heteromultimers of the disclosure comprise at least one ALK7 polypeptide that is at least 70%, 75%, 80%, 85%, 90%, 91%. 92%, 93%, 94%, 95%, 96%, 97%, 98%, 99%, or 100% identical to amino acids of 28-336 of SEQ ID NO: 82.

The term "Cripto-1 polypeptide" includes polypeptides comprising any naturally occurring Cripto-1 protein (encoded by TDGF1 or one of its nonhuman orthologs) as well as any variants thereof (including mutants, fragments, fusions, and peptidomimetic forms) that retain a useful activity. Numbering of amino acids for all Cripto-1 polypeptides described herein is based on the numbering of the human Cripto-1 precursor protein sequence (SEQ ID NO: 87, NCBI Ref Seq NP_003203.1), unless specifically designated otherwise. A nucleic acid sequence encoding unprocessed human Cripto-1 isoform 1 precursor protein is set forth in SEQ ID NO: 88, corresponding to nucleotides 385-948 of NCBI Reference Sequence NM_003212.3. A processed Cripto-1 isoform 1 polypeptide sequence is set forth in SEQ ID NO: 89, which is encodable by a nucleic acid sequence of SEQ ID NO: 90. The human Cripto-1 isoform 2 protein sequence (NCBI Ref Seq NP_001167607.1) is set forth in SEQ ID NO: 91, which is encodable by a nucleic acid sequence of SEQ ID NO: 92, corresponding to nucleotides 43-558 of NCBI Reference Sequence NM_001174136.1. A processed Cripto-1 polypeptide sequence (isoform 2) is set forth in SEQ ID NO: 93, which is encodable by a nucleic acid sequence of SEQ ID NO: 94.

In certain embodiments, the disclosure relates to heteromultimers that comprise at least one Cripto-1 polypeptide, which includes fragments, functional variants, and modified forms thereof. Preferably, Cripto-1 polypeptides for use in accordance with inventions of the disclosure (e.g., heteromultimers comprising a Cripto-1 polypeptide and uses thereof) are soluble (e.g., an extracellular domain of Cripto-1). In other preferred embodiments, Cripto-1 polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to the amino acid sequence of SEQ ID NOs: 87, 89, 91, or 93. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 31-82 (e.g., amino acid residues 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, or 82) of SEQ ID NO: 87, and ends at any one of amino acids 172-188 (e.g., amino acid residues 172, 173, 174, 175, 176, 177, 178, 179, 180, 181, 182, 183, 184, 185, 186, 187, or 188) of SEQ ID NO: 87. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 31-188 of SEQ ID NO: 87. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 63-172 of SEQ ID NO: 87. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 82-172 of SEQ ID NO: 87. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 82-188 of SEQ ID NO: 87. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 31-172 of SEQ ID NO: 87. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 63-188 of SEQ ID NO: 87. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 15-66 (e.g., amino acid residues 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66) of SEQ ID NO: 91, and ends at any one of amino acids 156-172 (e.g., amino acid residues 156, 157, 158, 159, 160, 161, 162, 163, 164, 165, 166, 167, 168, 169, 170, 171, or 172) of SEQ ID NO: 91. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 15-172 of SEQ ID NO: 91. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 47-172 of SEQ ID NO: 91. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 47-156 of SEQ ID NO: 91. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 66-165 of SEQ ID NO: 91. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 15-156 of SEQ ID NO: 91. In some embodiments, heteromultimers of the disclosure comprise at least one Cripto-1 polypeptide that is at least 70%, 75%, 80%, 85%, 90%, 91%. 92%, 93%, 94%, 95%, 96%, 97%, 98%, 99%, or 100% identical to amino acids of 66-172 of SEQ ID NO: 91.

The term "Cryptic polypeptide" includes polypeptides comprising any naturally occurring Cryptic protein (encoded by CFC1 or one of its nonhuman orthologs) as well as any variants thereof (including mutants, fragments, fusions, and peptidomimetic forms) that retain a useful activity. Numbering of amino acids for all Cryptic polypeptides described herein is based on the numbering of the human Cryptic isoform 1 precursor protein sequence (SEQ ID NO: 95, NCBI Ref Seq NP_115934.1), unless specifically designated otherwise. A nucleic acid sequence encoding unprocessed human Cryptic isoform 1 precursor protein is set forth in SEQ ID NO: 96, corresponding to nucleotides 289-957 of NCBI Reference Sequence NM_032545.3. A processed Cryptic isoform 1 polypeptide sequence is set forth in SEQ ID NO: 97, which is encodable by a nucleic acid sequence of SEQ ID NO: 98. The human Cryptic isoform 2 precursor protein sequence (NCBI Ref Seq NP_001257349.1) is set forth in SEQ ID NO: 99. A nucleic acid sequence encoding unprocessed human Cryptic isoform 2 precursor protein is set forth in SEQ ID NO: 100, corresponding to nucleotides 289-861 of NCBI Reference Sequence NM_001270420.1. A processed Cryptic isoform 2 polypeptide sequence is set forth in SEQ ID NO: 101, which is encodable by a nucleic acid sequence of SEQ ID NO: 102. The human Cryptic isoform 3 precursor protein sequence (NCBI Ref Seq NP_001257350.1) is set forth in SEQ ID NO: 103. A nucleic acid sequence encoding unprocessed human Cryptic isoform 3 precursor protein is set forth in SEQ ID NO: 104, corresponding to nucleotides 289-732 of NCBI Reference Sequence NM_001270421.1. A processed Cryptic isoform 3 polypeptide sequence is set forth in SEQ ID NO: 105, which is encodable by a nucleic acid sequence of SEQ ID NO: 106.

In certain embodiments, the disclosure relates to heteromultimers that comprise at least one Cryptic polypeptide, which includes fragments, functional variants, and modified forms thereof. Preferably, Cryptic polypeptides for use in accordance with inventions of the disclosure (e.g., heteromultimers comprising a Cryptic polypeptide and uses thereof) are soluble (e.g., an extracellular domain of Cryptic). In other preferred embodiments, Cryptic polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to the amino acid sequence of SEQ ID NOs: 95, 97, 99, 101, 103, or 105. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 26-90 (e.g., amino acid residues 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90) of SEQ ID NO: 95, and ends at any one of amino acids 157-233 (e.g., amino acid residues 157, 158, 159, 160, 161, 162, 163, 164, 165, 166, 167, 168, 169, 170, 171, 172, 173, 174, 175, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 126, 217, 218, 219, 220, 221, 222, 223, 224, 225, 226, 227, 228, 229, 230, 231, 232, or 233) of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-233 of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-157 of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 90-157 of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-169 of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 90-169 of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 90-233 of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-82 of SEQ ID NO: 95. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 26-30 (e.g., amino acid residues 26, 27, 28, 29, or 30) of SEQ ID NO: 99, and ends at any one of amino acids 82-191 (e.g., amino acid residues 82, 83, 84, 85, 86, 57, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 178, 179, 180, 181, 182, 183, 184, 185, 186, 187, 188, 189, 190, or 191) of SEQ ID NO: 99. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-82 of SEQ ID NO: 99. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-191 of SEQ ID NO: 99. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 30-82 of SEQ ID NO: 99. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 30-191 of SEQ ID NO: 99. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 26-30 (e.g., amino acid residues 26, 27, 28, 29, or 30) of SEQ ID NO: 103, and ends at any one of amino acids 82-148 (e.g., amino acid residues 82, 83, 84, 85, 86, 57, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, or 148) of SEQ ID NO: 103. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-148 of SEQ ID NO: 103. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 26-82 of SEQ ID NO: 103. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 30-148 of SEQ ID NO: 103. In some embodiments, heteromultimers of the disclosure comprise at least one Cryptic polypeptide that is at least 70%, 75%, 80%, 85%, 90%, 91%. 92%, 93%, 94%, 95%, 96%, 97%, 98%, 99%, or 100% identical to amino acids of 30-82 of SEQ ID NO: 103.

The term "Cryptic family protein 1B polypeptide" (Cryptic 1B) includes polypeptides comprising any naturally occurring Cryptic family protein 1B protein (encoded by CFC1B or one of its nonhuman orthologs) as well as any variants thereof (including mutants, fragments, fusions, and peptidomimetic forms) that retain a useful activity. Numbering of amino acids for all Cryptic family protein 1B polypeptides described herein is based on the numbering of the human Cryptic family protein 1B precursor protein sequence (SEQ ID NO: 107, NCBI Ref Seq NP_001072998.1), unless specifically designated otherwise. A nucleic acid sequence encoding unprocessed human Cryptic family protein 1B precursor protein is set forth in SEQ ID NO: 108, corresponding to nucleotides 392-1060 of NCBI Reference Sequence NM_001079530.1. A processed Cryptic family protein 1B polypeptide sequence is set forth in SEQ ID NO: 109, which is encodable by a nucleic acid sequence of SEQ ID NO: 110.

In certain embodiments, the disclosure relates to heteromultimers that comprise at least one Cryptic family protein 1B polypeptide, which includes fragments, functional variants, and modified forms thereof. Preferably, Cryptic family protein 1B polypeptides for use in accordance with inventions of the disclosure (e.g., heteromultimers comprising a Cryptic family protein 1B polypeptide and uses thereof) are soluble (e.g., an extracellular domain of Cryptic family protein 1B). In other preferred embodiments, Cryptic family protein 1B polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to the amino acid sequence of SEQ ID NOs: 107 or 109. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to a polypeptide that begins at any one of amino acids of 26-30 (e.g., amino acid residues 26, 27, 28, 29, or 30) of SEQ ID NO: 107, and ends at any one of amino acids 82-223 (e.g., amino acid residues 82, 83, 84, 85, 86, 57, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 126, 217, 218, 219, 220, 221, 222, or 223) of SEQ ID NO: 107. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to amino acids of 26-223 of SEQ ID NO: 107. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to amino acids of 26-82 of SEQ ID NO: 107. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to amino acids of 30-82 of SEQ ID NO: 107. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to amino acids of 30-223 of SEQ ID NO: 107. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to amino acids of 26-169 of SEQ ID NO: 107. In some embodiments, heteromultimers of the disclosure comprise at least one Cryptic family protein 1B polypeptide that is at least 70%, 75%, 80%, 85%, 90%, 91%. 92%, 93%, 94%, 95%, 96%, 97%, 98%, 99%, or 100% identical to amino acids of 30-169 of SEQ ID NO: 107.

In certain aspects, the disclosure relates to homomultimers that comprise at least two ALK4 polypeptides, which includes fragments, functional variants, and modified forms thereof (e.g., any of the ALK4 polypeptides described herein). In certain preferred embodiments, ALK4 homomultimers of the disclosure are homodimers.

In certain aspects, the disclosure relates to homomultimers that comprise at least two ALK5 polypeptides, which includes fragments, functional variants, and modified forms thereof (e.g., any of the ALK5 polypeptides described herein). In certain preferred embodiments, ALK5 homomultimers of the disclosure are homodimers.

In certain aspects, the disclosure relates to homomultimers that comprise at least two ALK7 polypeptides, which includes fragments, functional variants, and modified forms thereof (e.g., any of the ALK7 polypeptides described herein). In certain preferred embodiments, ALK7 homomultimers of the disclosure are homodimers.

In certain aspects, the disclosure relates to homomultimers that comprise at least two ActRIIA polypeptides, which includes fragments, functional variants, and modified forms thereof (e.g., any of the ActRIIA polypeptides described herein). In certain preferred embodiments, ActRIIA homomultimers of the disclosure are homodimers.

In certain aspects, the disclosure relates to homomultimers that comprise at least two ActRIIB polypeptides, which includes fragments, functional variants, and modified forms thereof (e.g., any of the ActRIIB polypeptides described herein). In certain preferred embodiments, ActRIIB homomultimers of the disclosure are homodimers.

In certain aspects, the disclosure relates to homomultimers that comprise at least two Cripto-1 polypeptides, which includes fragments, functional variants, and modified forms thereof (e.g., any of the Cripto-1 polypeptides described herein). In certain preferred embodiments, Cripto-1 homomultimers of the disclosure are homodimers.

In certain aspects, the disclosure relates to homomultimers that comprise at least two Cryptic polypeptides, which includes fragments, functional variants, and modified forms thereof (e.g., any of the Cryptic polypeptides described herein). In certain preferred embodiments, Cryptic homomultimers of the disclosure are homodimers.

In certain aspects, the disclosure relates to homomultimers that comprise at least two Cryptic 1B polypeptides, which includes fragments, functional variants, and modified forms thereof (e.g., any of the Cryptic 1B polypeptides described herein). In certain preferred embodiments, Cryptic 1B homomultimers of the disclosure are homodimers.

In certain aspects, the disclosure relates to heteromultimers that comprise at least one ALK1 polypeptide, which includes fragments, functional variants, and modified forms thereof (e.g., any of those described herein), and at least one ActRIIB polypeptide, which includes fragments, functional variants, and modified forms thereof (e.g., any of those described herein). In certain preferred embodiments, ALK1: ActRIIB heteromultimer complexes of the disclosure are heterodimers.

In certain aspects, the disclosure relates to heteromultimers that comprise at least one ALK4 polypeptide, which includes fragments, functional variants, and modified forms thereof (e.g., any of those described herein), and at least one ActRIIB polypeptide, which includes fragments, functional variants, and modified forms thereof (e.g., any of those described herein). In certain preferred embodiments, ALK4: ActRIIB heteromultimer complexes of the disclosure are heterodimers.

In certain aspects, the disclosure relates to heteromultimers that comprise at least one ALK5 polypeptide, which includes fragments, functional variants, and modified forms thereof (e.g., any of those described herein), and at least one ActRIIB polypeptide, which includes fragments, functional variants, and modified forms thereof (e.g., any of those described herein). In certain preferred embodiments, ALK5: ActRIIB heteromultimer complexes of the disclosure are heterodimers.

In certain aspects, the disclosure relates to heteromultimers that comprise at least one ALK7 polypeptide, which includes fragments, functional variants, and modified forms thereof (e.g., any of those described herein), and at least one ActRIIB polypeptide, which includes fragments, functional variants, and modified forms thereof (e.g., any of those described herein). In certain preferred embodiments, ALK7: ActRIIB heteromultimer complexes of the disclosure are heterodimers.

In certain aspects, the disclosure relates to heteromultimers that comprise at least one ALK1 polypeptide, which includes fragments, functional variants, and modified forms thereof (e.g., any of those described herein), and at least one ActRIIA polypeptide, which includes fragments, functional variants, and modified forms thereof (e.g., any of those described herein). In certain preferred embodiments, ALK1: ActRIIA heteromultimer complexes of the disclosure are heterodimers.

In certain aspects, the disclosure relates to heteromultimers that comprise at least one ALK4 polypeptide, which includes fragments, functional variants, and modified forms thereof (e.g., any of those described herein), and at least one ActRIIA polypeptide, which includes fragments, functional variants, and modified forms thereof (e.g., any of those described herein). In certain preferred embodiments, ALK4: ActRIIA heteromultimer complexes of the disclosure are heterodimers.

In certain aspects, the disclosure relates to heteromultimers that comprise at least one ALK5 polypeptide, which includes fragments, functional variants, and modified forms thereof (e.g., any of those described herein), and at least one ActRIIA polypeptide, which includes fragments, functional variants, and modified forms thereof (e.g., any of those described herein). In certain preferred embodiments, ALK5: ActRIIA heteromultimer complexes of the disclosure are heterodimers.

In certain aspects, the disclosure relates to heteromultimers that comprise at least one ALK7 polypeptide, which includes fragments, functional variants, and modified forms thereof (e.g., any of those described herein), and at least one ActRIIA polypeptide, which includes fragments, functional variants, and modified forms thereof (e.g., any of those described herein). In certain preferred embodiments, ALK7: ActRIIA heteromultimer complexes of the disclosure are heterodimers.

In certain aspects, the disclosure relates to heteromultimers that comprise at least one ALK4 polypeptide, which includes fragments, functional variants, and modified forms thereof (e.g., any of those described herein), and at least one BMPRII polypeptide, which includes fragments, functional variants, and modified forms thereof (e.g., any of those described herein). In certain preferred embodiments, ALK4: BMPRII heteromultimer complexes of the disclosure are heterodimers.

In certain aspects, the disclosure relates to heteromultimers that comprise at least one ALK5 polypeptide, which includes fragments, functional variants, and modified forms thereof (e.g., any of those described herein), and at least one BMPRII polypeptide, which includes fragments, functional variants, and modified forms thereof (e.g., any of those described herein). In certain preferred embodiments, ALK5: BMPRII heteromultimer complexes of the disclosure are heterodimers.

In certain aspects, the disclosure relates to heteromultimers that comprise at least one ALK7 polypeptide, which includes fragments, functional variants, and modified forms thereof (e.g., any of those described herein), and at least one BMPRII polypeptide, which includes fragments, functional variants, and modified forms thereof (e.g., any of those described herein). In certain preferred embodiments, ALK7: BMPRII heteromultimer complexes of the disclosure are heterodimers.

In certain aspects, the disclosure relates to heteromultimers that comprise at least one ALK4 polypeptide, which includes fragments, functional variants, and modified forms thereof (e.g., any of those described herein), and at least one MISRII polypeptide, which includes fragments, functional variants, and modified forms thereof (e.g., any of those described herein). In certain preferred embodiments, ALK4: MISRII heteromultimer complexes of the disclosure are heterodimers.

In certain aspects, the disclosure relates to heteromultimers that comprise at least one ALK5 polypeptide, which includes fragments, functional variants, and modified forms thereof (e.g., any of those described herein), and at least one MISRII polypeptide, which includes fragments, functional variants, and modified forms thereof (e.g., any of those described herein). In certain preferred embodiments, ALK5: MISRII heteromultimer complexes of the disclosure are heterodimers.

In certain aspects, the disclosure relates to heteromultimers that comprise at least one ALK7 polypeptide, which includes fragments, functional variants, and modified forms thereof (e.g., any of those described herein), and at least one MISRII polypeptide, which includes fragments, functional variants, and modified forms thereof (e.g., any of those described herein). In certain preferred embodiments, ALK7:MISRII heteromultimer complexes of the disclosure are heterodimers.

In certain aspects, the disclosure relates to heteromultimers that comprise at least one ALK1 polypeptide, which includes fragments, functional variants, and modified forms thereof (e.g., any of those described herein), and at least one ALK4 polypeptide, which includes fragments, functional variants, and modified forms thereof (e.g., any of those described herein). In certain preferred embodiments, ALK1:ALK4 heteromultimers of the disclosure are heterodimers.

In certain aspects, the disclosure relates to heteromultimers that comprise at least one ALK1 polypeptide, which includes fragments, functional variants, and modified forms thereof (e.g., any of those described herein), and at least one ALK5 polypeptide, which includes fragments, functional variants, and modified forms thereof (e.g., any of those described herein). In certain preferred embodiments, ALK1:ALK5 heteromultimers of the disclosure are heterodimers.

In certain aspects, the disclosure relates to heteromultimers that comprise at least one ALK1 polypeptide, which includes fragments, functional variants, and modified forms thereof (e.g., any of those described herein), and at least one ALK7 polypeptide, which includes fragments, functional variants, and modified forms thereof (e.g., any of those described herein). In certain preferred embodiments, ALK1:ALK7 heteromultimers of the disclosure are heterodimers.

In certain aspects, the disclosure relates to heteromultimers that comprise at least one ALK4 polypeptide, which includes fragments, functional variants, and modified forms thereof (e.g., any of those described herein), and at least one ALK5 polypeptide, which includes fragments, functional variants, and modified forms thereof (e.g., any of those described herein). In certain preferred embodiments, ALK4:ALK5 heteromultimers of the disclosure are heterodimers.

In certain aspects, the disclosure relates to heteromultimers that comprise at least one ALK4 polypeptide, which includes fragments, functional variants, and modified forms thereof (e.g., any of those described herein), and at least one ALK7 polypeptide, which includes fragments, functional variants, and modified forms thereof (e.g., any of those described herein). In certain preferred embodiments, ALK4:ALK7 heteromultimers of the disclosure are heterodimers.

In certain aspects, the disclosure relates to heteromultimers that comprise at least one ALK5 polypeptide, which includes fragments, functional variants, and modified forms thereof (e.g., any of those described herein), and at least one ALK7 polypeptide, which includes fragments, functional variants, and modified forms thereof (e.g., any of those described herein). In certain preferred embodiments, ALK5:ALK7 heteromultimers of the disclosure are heterodimers.

In certain aspects, the disclosure relates to heteromultimers that comprise at least one ActRIIA polypeptide, which includes fragments, functional variants, and modified forms thereof (e.g., any of those described herein), and at least one ActRIIB polypeptide, which includes fragments, functional variants, and modified forms thereof (e.g., any of those described herein). In certain preferred embodiments, ActRIIA:ActRIIB heteromultimers of the disclosure are heterodimers.

In certain aspects, the disclosure relates to heteromultimers that comprise at least one ActRIIA polypeptide, which includes fragments, functional variants, and modified forms thereof (e.g., any of those described herein), and at least one BMPRII polypeptide, which includes fragments, functional variants, and modified forms thereof (e.g., any of those described herein). In certain preferred embodiments, ActRIIA:BMPRII heteromultimers of the disclosure are heterodimers.

In certain aspects, the disclosure relates to heteromultimers that comprise at least one ActRIIA polypeptide, which includes fragments, functional variants, and modified forms thereof (e.g., any of those described herein), and at least one MISRII polypeptide, which includes fragments, functional variants, and modified forms thereof (e.g., any of those described herein). In certain preferred embodiments, ActRIIA:MISRII heteromultimers of the disclosure are heterodimers.

In certain aspects, the disclosure relates to heteromultimers that comprise at least one ActRIIB polypeptide, which includes fragments, functional variants, and modified forms thereof (e.g., any of those described herein), and at least one BMPRII polypeptide, which includes fragments, functional variants, and modified forms thereof (e.g., any of those described herein). In certain preferred embodiments, ActRIIB:BMPRII heteromultimers of the disclosure are heterodimers.

In certain aspects, the disclosure relates to heteromultimers that comprise at least one ActRIIB polypeptide, which includes fragments, functional variants, and modified forms thereof (e.g., any of those described herein), and at least one MISRII polypeptide, which includes fragments, functional variants, and modified forms thereof (e.g., any of those described herein). In certain preferred embodiments, ActRIIB:MISRII heteromultimers of the disclosure are heterodimers.

In certain aspects, the disclosure relates to heteromultimers that comprise at least one Cripto-1 polypeptide, which includes fragments, functional variants, and modified forms thereof (e.g., any of those described herein), and at least one ALK1 polypeptide, which includes fragments, functional variants, and modified forms thereof (e.g., any of those described herein). In some embodiments, a Cripto-1:ALK1 heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one ALK4 polypeptide, which includes fragments, functional variants, and modified forms thereof (e.g., any of those described herein). In some embodiments, a Cripto-1:ALK4 heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one ALK5 polypeptide, which includes fragments, functional variants, and modified forms thereof (e.g., any of those described herein). In some embodiments, a Cripto-1:ALK5 heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one ALK7 polypeptide, which includes fragments, functional variants, and modified forms thereof (e.g., any of those described herein). In some embodiments, a Cripto-1:ALK7 heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one ALK1 polypeptide, which includes fragments, functional variants, and modified forms thereof (e.g., any of those described herein). In some embodiments, a Cryptic polypeptide:ALK1 heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one ALK4 polypeptide, which includes fragments, functional variants, and modified forms thereof (e.g., any of those described herein). In some embodiments, a Cryptic polypeptide:ALK4 heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one ALK5 polypeptide, which includes fragments, functional variants, and modified forms thereof (e.g., any of those described herein). In some embodiments, a Cryptic polypeptide:ALK5 heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one ALK7 polypeptide, which includes fragments, functional variants, and modified forms thereof (e.g., any of those described herein). In some embodiments, a Cryptic polypeptide:ALK7 heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one ALK1 polypeptide, which includes fragments, functional variants, and modified forms thereof (e.g., any of those described herein). In some embodiments, a Cryptic 1B:ALK1 heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one ALK4 polypeptide, which includes fragments, functional variants, and modified forms thereof (e.g., any of those described herein). In some embodiments, a Cryptic 1B:ALK4 heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one ALK5 polypeptide, which includes fragments, functional variants, and modified forms thereof (e.g., any of those described herein). In some embodiments, a Cryptic 1B:ALK5 heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one ALK7 polypeptide, which includes fragments, functional variants, and modified forms thereof (e.g., any of those described herein). In some embodiments, a Cryptic 1B:ALK7 heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one ActRIIA polypeptide, which includes fragments, functional variants, and modified forms thereof (e.g., any of those described herein). In some embodiments, a Cripto-1:ActRIIA heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one ActRIIB polypeptide, which includes fragments, functional variants, and modified forms thereof (e.g., any of those described herein). In some embodiments, a Cripto-1:ActRIIB heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one BMPRII polypeptide, which includes fragments, functional variants, and modified forms thereof (e.g., any of those described herein). In some embodiments, a Cripto-1:BMPRII heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one MISRII polypeptide, which includes fragments, functional variants, and modified forms thereof (e.g., any of those described herein). In some embodiments, a Cripto-1:MISRII heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one ActRIIA polypeptide, which includes fragments, functional variants, and modified forms thereof (e.g., any of those described herein). In some embodiments, a Cryptic polypeptide:ActRIIA heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one ActRIIB polypeptide, which includes fragments, functional variants, and modified forms thereof (e.g., any of those described herein). In some embodiments, a Cryptic polypeptide:ActRIIB heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one BMPRII polypeptide, which includes fragments, functional variants, and modified forms thereof (e.g., any of those described herein). In some embodiments, a Cryptic polypeptide:BMPRII heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one MISRII polypeptide, which includes fragments, functional variants, and modified forms thereof (e.g., any of those described herein). In some embodiments, a Cryptic polypeptide:MISRII heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one ActRIIA polypeptide, which includes fragments, functional variants, and modified forms thereof (e.g., any of those described herein). In some embodiments, a Cryptic 1B:ActRIIA heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one ActRIIB polypeptide, which includes fragments, functional variants, and modified forms thereof (e.g., any of those described herein). In some embodiments, a Cryptic 1B:ActRIIB heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one BMPRII polypeptide, which includes fragments, functional variants, and modified forms thereof (e.g., any of those described herein). In some embodiments, a Cryptic 1B:BMPRII heteromultimer of the disclosure is a heterodimer.

In certain aspects, the disclosure relates to heteromultimers that comprise at least one Cryptic 1B polypeptide, which includes fragments, functional variants, and modified forms thereof (e.g., any of those described herein), and at least one MISRII polypeptide, which includes fragments, functional variants, and modified forms thereof (e.g., any of those described herein). In some embodiments, a Cryptic 1B:MISRII heteromultimer of the disclosure is a heterodimer.

In certain aspects, the disclosure relates to heteromultimers that comprise at least one Cripto-1 polypeptide, which includes fragments, functional variants, and modified forms thereof (e.g., any of those described herein), and at least one Cryptic polypeptide, which includes fragments, functional variants, and modified forms thereof (e.g., any of those described herein). In some embodiments, a Cripto-1:Cryptic polypeptide heteromultimer of the disclosure is a heterodimer.

In certain aspects, the disclosure relates to heteromultimers that comprise at least one Cripto-1 polypeptide, which includes fragments, functional variants, and modified forms thereof, and at least one Cryptic 1B polypeptide, which includes fragments, functional variants, and modified forms thereof. In some embodiments, a Cripto-1:Cryptic 1B heteromultimer of the disclosure is a heterodimer.

In certain aspects, the disclosure relates to heteromultimers that comprise at least one Cryptic polypeptide, which includes fragments, functional variants, and modified forms thereof (e.g., any of those described herein), and at least one Cryptic 1B polypeptide, which includes fragments, functional variants, and modified forms thereof (e.g., any of those described herein). In certain preferred embodiments, Cryptic polypeptide:Cryptic 1B heteromultimers are soluble. In some embodiments, a Cryptic polypeptide:Cryptic 1B heteromultimer of the disclosure is a heterodimer.

In some embodiments, the present disclosure contemplates making functional variants by modifying the structure of a TGF-beta superfamily type I receptor polypeptide (e.g., ALK1, ALK4, ALK5, and ALK7), a TGF-beta superfamily type II receptor polypeptide (e.g., ActRIIA, ActRIIB, BMPRII, and MISRII), and/or a TGF-beta superfamily co-receptor (e.g., Cripto-1, Cryptic, and Cryptic 1B) for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta superfamily ligands including, for example, GDF3, GDF5, GDF1, GDF8, GDF11, activin A, activin B, activin C, activin E, activin AB, activin AC, activin AE, activin BC, activin BE, Nodal.

In certain embodiments, the present disclosure contemplates specific mutations of a TGF-beta superfamily type I receptor polypeptide (e.g., ALK1, ALK2, ALK3, ALK4, ALK5, ALK6, and ALK7), a TGF-beta superfamily type II receptor polypeptide (e.g., ActRIIA, ActRIIB, BMPRII, and MISRII), and/or a TGF-beta superfamily co-receptor polypeptide (e.g., endoglin, betaglycan, Cripto-1, Cryptic, Cryptic 1B, CRIM1, CRIM2, BAMBI, BMPER, RGM-A, RGM-B, and hemojuvelin) of the disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, heteromultimers of the disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of a TGF-beta superfamily type I receptor polypeptide (e.g., ALK1, ALK2, ALK3, ALK4, ALK5, ALK6, and ALK7), a TGF-beta superfamily type II receptor polypeptide (e.g., ActRIIA, ActRIIB, BMPRII, and MISRII), and/or TGF-beta superfamily co-receptor polypeptide (e.g., endoglin, betaglycan, Cripto-1, Cryptic, Cryptic 1, CRIM1, CRIM2, BAMBI, BMPER, RGM-A, RGM-B, and hemojuvelin) of the present disclosure, as well as truncation mutants. Pools of combinatorial mutants are especially useful for identifying functionally active (e.g., ligand binding) TGF-beta superfamily type I receptor, TGF-beta superfamily type II receptor, and/or TGF-beta superfamily co-receptor sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, TGF-beta co-receptor variants may be screened for ability to bind to a TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), to prevent binding of a TGF-beta superfamily ligand to a TGF-beta superfamily co-receptor, and/or to interfere with signaling caused by an TGF-beta superfamily ligand.

The activity of a TGF-beta superfamily receptor polypeptide, including heteromultimers and homomultimers thereof, of the disclosure also may be tested, for example in a cell-based or in vivo assay. For example, the effect of a TGF-beta superfamily receptor polypeptide on the expression of genes or the activity of proteins involved in muscle production in a muscle cell may be assessed. This may, as needed, be performed in the presence of one or more recombinant TGF-beta superfamily ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), and cells may be transfected so as to produce a TGF-beta superfamily receptor polypeptide, and optionally, a TGF-beta superfamily ligand. Likewise, a TGF-beta superfamily receptor polypeptide of the disclosure may be administered to a mouse or other animal, and one or more measurements, such as muscle formation and strength may be assessed using art-recognized methods. Similarly, the activity of a heteromultimer, or variants thereof, may be tested in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference TGF-beta superfamily receptor polypeptide. Such variants, when expressed from recombinant DNA constructs, can be used in gene therapy protocols. Likewise, mutagenesis can give rise to variants which have intracellular half-lives dramatically different than the corresponding unmodified TGF-beta superfamily receptor polypeptide. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter one or more activities of the TGF-beta superfamily receptor polypeptide including, for example, immunogenicity, half-life, and solubility.

A combinatorial library may be produced by way of a degenerate library of genes encoding a library of polypeptides which each include at least a portion of potential TGF-beta superfamily type I receptor polypeptide, type II receptor polypeptide, and/or co-receptor polypeptide sequences. For instance, a mixture of synthetic oligonucleotides can be enzymatically ligated into gene sequences such that the degenerate set of potential TGF-beta superfamily type I receptor polypeptide, type II receptor polypeptide, and/or co-receptor encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art. See, e.g., Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins. See, e.g., Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815.

Alternatively, other forms of mutagenesis can be utilized to generate a combinatorial library. For example, heteromultimers of the disclosure can be generated and isolated from a library by screening using, for example, alanine scanning mutagenesis [see, e.g., Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [see, e.g., Gustin et al. (1993) Virology 193:653-660; and Brown et al. (1992) Mol. Cell Biol. 12:2644-2652; McKnight et al. (1982) Science 232:316], by saturation mutagenesis [see, e.g., Meyers et al., (1986) Science 232: 613]; by PCR mutagenesis [see, e.g., Leung et al. (1989) Method Cell Mol Biol 1:11-19]; or by random mutagenesis, including chemical mutagenesis [see, e.g., Miller et al. (1992) A Short Course in Bacterial Genetics, CSHL Press, Cold Spring Harbor, NY; and Greener et al. (1994) Strategies in Mol Biol 7:32-34]. Linker scanning mutagenesis, particularly in a combinatorial setting, is an attractive method for identifying truncated (bioactive) forms of TGF-beta superfamily type I receptor, type II receptor, and/or co-receptor polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of heteromultimers of the disclosure. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, activin A, activin B, activin C, activin E, activin AB, activin AC, activin AE, activin BC, activin BE, nodal, glial cell-derived neurotrophic factor (GDNF), neurturin, artemin, persephin, MIS, and Lefty) binding assays and/or TGF-beta superfamily ligand-mediated cell signaling assays.

In certain embodiments, heteromultimers TGF-beta superfamily receptor polypeptide, including heteromultimers and homomultimers thereof) of the disclosure may further comprise post-translational modifications in addition to any that are naturally present in the TGF-beta superfamily type I receptor, type II receptor, or co-receptor polypeptide. Such modifications include, but are not limited to, acetylation, carboxylation, glycosylation, phosphorylation, lipidation, and acylation. As a result, the TGF-beta superfamily receptor polypeptide may comprise non-amino acid elements, such as polyethylene glycols, lipids, polysaccharide or monosaccharide, and phosphates. Effects of such non-amino acid elements on the functionality of a TGF-beta superfamily receptor polypeptide may be tested as described herein for other TGF-beta superfamily receptor polypeptide variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, W138, NIH-3T3 or HEK293) have specific cellular machinery and characteristic mechanisms for such post-translational activities and may be chosen to ensure the correct modification and processing of the TGF-beta superfamily type I receptor, type II receptor, and/or co-receptor polypeptides as well as heteromultimers comprising the same.

In some embodiments, TGF-beta superfamily type I receptor polypeptides, type II receptor polypeptides, and/or co-receptor polypeptides further comprise one or more heterologous portions (e.g., a polypeptide comprising a TGF-beta superfamily type I receptor polypeptide domain and second polypeptide domain that is heterologous to the TGF-beta superfamily type I receptor polypeptide domain) so as to confer a desired property. For example, some fusion domains are particularly useful for isolation of the fusion proteins by affinity chromatography. Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) (SEQ ID NO: 225) fusion partners. As another example, a fusion domain may be selected so as to facilitate detection of the polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation.

In some embodiments, TGF-beta superfamily type I receptor polypeptides, type II receptor polypeptides, and/or co-receptor polypeptides of the present disclosure comprise one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising a type I receptor polypeptide, type II receptor polypeptide, or co-receptor polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol.

It is understood that different elements of a fusion protein (e.g., immunoglobulin Fc fusion protein) may be arranged in any manner that is consistent with desired functionality. For example, a TGF-beta superfamily type I receptor polypeptide, type II receptor polypeptide, or co-receptor polypeptide domain may be placed C-terminal to a heterologous domain, or alternatively, a heterologous domain may be placed C-terminal to a TGF-beta superfamily type I receptor polypeptide, type II receptor polypeptide, and/or co-receptor polypeptide domain. The TGF-beta superfamily type I receptor polypeptide, type II receptor polypeptide, or co-receptor domain and the heterologous domain need not be adjacent in a fusion protein, and additional domains or amino acid sequences may be included C- or N-terminal to either domain or between the domains.

For example, a TGF-beta superfamily type I receptor, type II receptor, or co-receptor fusion protein may comprise an amino acid sequence as set forth in the formula A-B-C. The B portion corresponds to a TGF-beta superfamily type I receptor polypeptide, type II receptor polypeptide, or co-receptor polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines (e.g., GGG (SEQ ID NO: 223), GGGG (SEQ ID NO: 222), TGGGG (SEQ ID NO: 219), SGGGG (SEQ ID NO: 220), TGGG (SEQ ID NO: 217), GGGS (SEQ ID NO: 224), or SGGG (SEQ ID NO: 218)), singlets, or repeats. In certain embodiments, a TGF-beta superfamily type I receptor, type II receptor, or co-receptor fusion protein comprises an amino acid sequence as set forth in the formula A-B-C, wherein A is a leader (signal) sequence, B consists of a TGF-beta superfamily type I receptor polypeptide, type II receptor polypeptide, or co-receptor polypeptide domain, and C is a polypeptide portion that enhances one or more of in vivo stability, in vivo half-life, uptake/administration, tissue localization or distribution, formation of protein complexes, and/or purification. In certain embodiments, a TGF-beta superfamily type I receptor, type II receptor, or co-receptor fusion protein comprises an amino acid sequence as set forth in the formula A-B-C, wherein A is a TPA leader sequence, B consists of a TGF-beta superfamily type I receptor polypeptide, type II receptor polypeptide, or co-receptor polypeptide domain, and C is an immunoglobulin Fc domain.

As specific examples, the present disclosure provides fusion proteins comprising TGF-beta superfamily type I receptor, type II receptor, or co-receptor polypeptides fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimers of the disclosure. Optionally, the IgG1 Fc domain of SEQ ID NO: 135 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

An example of a native amino acid sequence that may be used for the Fc portion of human IgG1 (G1Fc) is shown below (SEQ ID NO: 135). In FIG. 4, Dotted underline indicates the hinge region, and solid underline indicates positions with naturally occurring variants. In part, the disclosure provides polypeptides comprising an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 135. Naturally occurring variants in G1Fc would include E134D and M136L according to the numbering system used in SEQ ID NO: 135 (see Uniprot P01857).

An example of a native amino acid sequence that may be used for the Fc portion of human IgG2 (G2Fc) is shown below (SEQ ID NO: 136). In FIG. 4, Dotted underline indicates the hinge region and double underline indicates positions where there are data base conflicts in the sequence (according to UniProt P01859). In part, the disclosure provides polypeptides comprising an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 136.

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 137) contains a short hinge region consisting of a single 15-residue segment, whereas the second G3Fc sequence (SEQ ID NO: 138) contains a full-length hinge region. In each case, dotted underline indicates the hinge region, and solid underline indicates positions with naturally occurring variants according to UniProt P01859. In part, the disclosure provides polypeptides comprising an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 137 or 138.

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 137, and the present disclosure provides fusion proteins comprising G3Fc domains containing one or more of these variations. In addition, the human immunoglobulin IgG3 gene (IGHG3) shows a structural polymorphism characterized by different hinge lengths (see Uniprot P01859). Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 139). Dotted underline indicates the hinge region. In part, the disclosure provides polypeptides comprising an amino acid sequence with 70%, 80%, 85%, 86%, 87%, 88%, 89%, 90%, 91%, 92%, 93%, 94%, 95%, 96%, 97%, 98%, 99%, or 10000 identity to SEQ ID NO: 139.

A variety of engineered mutations in the Fc domain are presented herein with respect to the G1Fc sequence (SEQ ID NO: 135), and analogous mutations in G2Fc, G3Fc, and G4Fc can be derived from their alignment with G1Fc in FIG. 4. Due to unequal hinge lengths, analogous Fc positions based on isotype alignment (FIG. 4) possess different amino acid numbers in SEQ ID NOs: 135, 136, 137, and 139. It can also be appreciated that a given amino acid position in an immunoglobulin sequence consisting of hinge, $C_H2$, and $C_H3$ regions (e.g., SEQ ID NOs: 135, 136, 137, 138, or 139) will be identified by a different number than the same position when numbering encompasses the entire IgG1 heavy-chain constant domain (consisting of the CH1, hinge, $C_H2$, and $C_H3$ regions) as in the Uniprot database. For example, correspondence between selected $C_H3$ positions in a human G1Fc sequence (SEQ ID NO: 135), the human IgG1 heavy chain constant domain (Uniprot P01857), and the human IgG1 heavy chain is as follows.

TABLE 1

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
|---|---|---|
| Y127 | Y232 | Y349 |
| S132 | S237 | S354 |
| E134 | E239 | E356 |
| T144 | T249 | T366 |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in *Sequences of Proteins of Immunological Interest*, 5th ed., Vol. 1, NIH, Bethesda, MD.

In certain aspects, a TGF-beta superfamily type I receptor polypeptide, type II receptor polypeptide, or co-receptor polypeptide (e.g., those described herein) may form heteromultimers, covalently or non-covalently, with at least one additional TGF-beta superfamily type I receptor polypeptide, type II receptor polypeptide, and/or co-receptor polypeptide. Many methods known in the art can be used to generate heteromultimers. For example, non-naturally occurring disulfide bonds may be constructed by replacing on a first polypeptide (e.g., TGF-beta superfamily type I polypeptide) a naturally occurring amino acid with a free thiol-containing residue, such as cysteine, such that the free thiol interacts with another free thiol-containing residue on a second polypeptide (e.g., TGF-beta superfamily type II polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S.20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology. Preferably, polypeptides disclosed herein form heterodimers, although higher order heteromultimers are also included such as, but not limited to, heterotrimers, heterotetramers, and further oligomeric structures (see, e.g., FIGS. 5A to 5D and FIGS. 6A to 6G).

In some embodiments, TGF-beta superfamily type I receptor, type II receptor, and/or co-receptor polypeptides of the present disclosure comprise at least one multimerization domain. As disclosed herein, the term "multimerization domain" refers to an amino acid or sequence of amino acids that promote covalent or non-covalent interaction between at least a first polypeptide and at least a second polypeptide. Polypeptides disclosed herein may be joined covalently or non-covalently to a multimerization domain. In some embodiments, a multimerization domain promotes interaction between a first polypeptide and a second polypeptide to promote heteromultimer formation (e.g., heterodimer formation), and optionally hinders or otherwise disfavors homomultimer formation (e.g., homodimer formation), thereby increasing the yield of desired heteromultimer (see, e.g., FIGS. 5A to 5D and FIGS. 6A to 6G).

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of a first TGF-beta superfamily receptor polypeptide and the amino acid sequence of a first member of an interaction pair; and the second polypeptide comprises the amino acid sequence of a second TGF-beta superfamily receptor polypeptide and the amino acid sequence of a second member of an interaction pair. The interaction pair may be any two polypeptide sequences that interact to form a complex, particularly a heterodimeric complex although operative embodiments may also employ an interaction pair that can form a homodimeric complex. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form, or example, a heterodimeric complex (see, e.g., FIGS. 5A and 5B). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

A problem that arises in large-scale production of asymmetric immunoglobulin-based proteins from a single cell line is known as the "chain association issue". As confronted prominently in the production of bispecific antibodies, the chain-association issue concerns the challenge of efficiently producing a desired multichain protein from among the multiple combinations that inherently result when different heavy chains and/or light chains are produced in a single cell line (see, for example, Klein et al (2012) mAbs 4:653-663). This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields (see, for example, Klein et al (2012) mAbs 4:653-663; and Spiess et al (2015) *Molecular Immunology* 67(2A): 95-106). Methods to obtain desired pairing of Fc-containing chains include, but are not limited to, charge-based pairing (electrostatic steering), "knobs-into-holes" steric pairing, SEEDbody pairing, and leucine zipper-based pairing. See, for example, Ridgway et al (1996) *Protein Eng* 9:617-621; Merchant et al (1998) *Nat Biotech* 16:677-681; Davis et al (2010) *Protein Eng Des Sel* 23:195-202; Gunasekaran et al (2010); 285:19637-19646; Wranik et al (2012) *J Biol Chem* 287:43331-43339; U.S. Pat. No. 5,932,448; WO 1993/011162; WO 2009/089004, and WO 2011/034605. As described herein, these methods may be used to generate heterodimers comprising two or more TGF-beta superfamily receptor polypeptides. See FIGS. 5A to 5D and FIGS. 6A to 6G.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' (residue numbering in the second chain is indicated by (')). It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The Table 2 below lists possible charge change mutations that can be used, alone or in combination, to enhance heteromultimer formation of the heteromultimers disclosed herein.

TABLE 2

Examples of Pair-Wise Charged Residue Mutations to Enhance Heterodimer Formation

| Position in first chain | Mutation in first chain | Interacting position in second chain | Corresponding mutation in second chain |
| --- | --- | --- | --- |
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positively-charged amino acid in the interface (e.g., a lysine, arginine, or histidine) is replaced with a negatively charged amino acid (e.g., aspartic acid or glutamic acid). Alternatively, or in combination with the forgoing substitution, a negatively-charged amino acid in the interface is replaced with a positively-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to the TGF-beta superfamily type I receptor polypeptide, type II receptor polypeptide, or co-receptor polypeptide of the construct, with or without an optional linker, to generate a TGF-beta superfamily type I, type II, or co-receptor receptor fusion polypeptide. This single chain can be coexpressed in a cell of choice along with the Fc sequence complementary to the first Fc to favor generation of the desired multichain construct (e.g., a TGF-beta superfamily heteromultimer). In this example based on electrostatic steering, SEQ ID NO: 140 (human G1Fc(E134K/D177K)) and SEQ ID NO: 141 (human G1Fc(K170D/K187D)) are examples of complementary Fc sequences in which the engineered amino acid substitutions are double underlined (see FIG. 4), and the TGF-beta superfamily type I, type II receptor, or co-receptor polypeptide of the construct can be fused to either SEQ ID NO: 140 or SEQ ID NO: 141, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 140 and 141).

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the TGF-beta superfamily type I receptor polypeptide, type II receptor polypeptide, or co-receptor polypeptide of the construct, with or without an optional linker, to generate a TGF-beta superfamily type I, type II, or co-receptor fusion polypeptide. This single chain can be coexpressed in a cell of choice along with the Fc sequence complementary to the first Fc to favor generation of the desired multichain construct. In this example based on knobs-into-holes pairing, SEQ ID NO: 142 (human G1Fc(T144Y)) and SEQ ID NO: 143 (human G1Fc(Y185T)) are examples of complementary Fc sequences in which the engineered amino acid substitutions are double underlined (see FIG. 4), and the TGF-beta superfamily type I receptor polypeptide, type II receptor polypeptide, or co-receptor polypeptide of the construct can be fused to either SEQ ID NO: 142 or SEQ ID NO: 143, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 142 and 143).

An example of Fc complementarity based on knobs-into-holes pairing combined with an engineered disulfide bond is disclosed in SEQ ID NO: 144 (hG1Fc(S132C/T144W)) and SEQ ID NO: 145 (hG1Fc(Y127C/T144S/L146A/Y185V)). The engineered amino acid substitutions in these sequences are double underlined (see FIG. 4), and the TGF-beta superfamily type I, type II or co-receptor of the construct can be fused to either SEQ ID NO: 144 or SEQ ID NO: 145, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 144 and 145).

In part, the disclosure provides desired pairing of asymmetric Fc-containing polypeptide chains using Fc sequences engineered to generate interdigitating β-strand segments of human IgG and IgA $C_H3$ domains. Such methods include the use of strand-exchange engineered domain (SEED) $C_H3$ heterodimers allowing the formation of SEEDbody fusion proteins (see, for example, Davis et al (2010) *Protein Eng Design Sel* 23:195-202). One of a pair of Fc sequences with SEEDbody complementarity can be arbitrarily fused to the TGF-beta superfamily type I receptor polypeptide, type II receptor polypeptide or co-receptor polypeptide of the construct, with or without an optional linker, to generate a TGF-beta superfamily fusion polypeptide. This single chain can be coexpressed in a cell of choice along with the Fc sequence complementary to the first Fc to favor generation of the desired multichain construct. In this example based on SEEDbody (Sb) pairing, SEQ ID NO: 146 (hG1Fc($Sb_{AG}$)) and SEQ ID NO: 147 (hG1Fc($Sb_{GA}$)) are examples of complementary IgG Fc sequences in which the engineered amino acid substitutions from IgA Fc are double underlined (see FIG. 4), and the TGF-beta superfamily type I, type II, or co-receptor polypeptide of the construct can be fused to either SEQ ID NO: 146 or SEQ ID NO: 147, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 4) will generate an Fc monomer which may be used in the complementary IgG-IgA pair below (SEQ ID NOs: 146 and 147).

In part, the disclosure provides desired pairing of asymmetric Fc-containing polypeptide chains with a cleavable leucine zipper domain attached at the C-terminus of the Fc $C_H3$ domains. Attachment of a leucine zipper is sufficient to cause preferential assembly of heterodimeric antibody heavy chains. See, e.g., Wranik et al (2012) *J Biol Chem* 287:43331-43339. As disclosed herein, one of a pair of Fc sequences attached to a leucine zipper-forming strand can be arbitrarily fused to the TGF-beta superfamily type I receptor polypeptide, type II receptor polypeptide, or co-receptor polypeptide of the construct, with or without an optional linker, to generate a TGF-beta superfamily fusion polypeptide. This single chain can be coexpressed in a cell of choice along with the Fc sequence attached to a complementary leucine zipper-forming strand to favor generation of the desired multichain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 148 (hG1Fc-Ap1 (acidic)) and SEQ ID NO: 149 (hG1Fc-Bp1 (basic)) are examples of complementary IgG Fc sequences in which the engineered complimentary leucine zipper sequences are underlined, and the TGF-beta superfamily type I, type II, or co-receptor polypeptide or co-receptor polypeptide of the construct can be fused to either SEQ ID NO: 148 or SEQ ID NO: 149, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 4) will generate an Fc monomer which may be used in the complementary leucine zipper-forming pair below (SEQ ID NOs: 148 and 149).

In preferred embodiments, TGF-beta superfamily receptor polypeptides, including heteromultimers and homomultimers thereof, to be used in accordance with the methods described herein are isolated polypeptide complexes. As used herein, an isolated protein (or protein complex) or polypeptide (or polypeptide complex) is one which has been separated from a component of its natural environment. In some embodiments, a heteromultimer complex of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art (See, e.g., Flatman et al., (2007) *J. Chromatogr. B* 848:79-87). In some embodiments, heteromultimer preparations of the disclosure are substantially free of TGF-beta superfamily type I receptor polypeptide homomultimers, TGF-beta superfamily type II receptor polypeptide homomultimers, and/or TGF-beta superfamily co-receptor polypeptide homomultimers. For example, in some embodiments, heteromultimer preparations comprise less than about 10%, 9%, 8%, 7%, 5%, 4%, 3%, 2%, or less than 1% of TGF-beta superfamily type I receptor polypeptide homomultimers. In some embodiments, heteromultimer preparations comprise less than about 10%, 9%, 8%, 7%, 5%, 4%, 3%, 2%, or less than 1% of TGF-beta superfamily type II receptor polypeptide homomultimers. In some embodiments, heteromultimer preparations comprise less than about 10%, 9%, 8%, 7%, 5%, 4%, 3%, 2%, or less than 1% of TGF-beta superfamily co-receptor polypeptide homomultimers. In some embodiments, heteromultimer preparations comprise less than about 10%, 9%, 8%, 7%, 5%, 4%, 3%, 2%, or less than 1% of TGF-beta superfamily type I receptor polypeptide homomultimers and less than about 10%, 9%, 8%, 7%, 5%, 4%, 3%, 2%, or less than 1% of TGF-beta superfamily co-receptor polypeptide homomultimers. In some embodiments, heteromultimer preparations comprise less than about 10%, 9%, 8%, 7%, 5%, 4%, 3%, 2%, or less than 1% of TGF-beta superfamily type II receptor polypeptide homomultimers and less than about 10%, 9%, 8%, 7%, 5%, 4%, 3%, 2%, or less than 1% of TGF-beta superfamily co-receptor polypeptide homomultimers.

In certain embodiments, TGFβ superfamily type I receptor polypeptides, type II receptor polypeptides, and co-receptor polypeptides as well as heteromultimer complexes thereof, of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (see, e.g., Advanced ChemTech Model 396; Milligen/Biosearch 9600). Alternatively, the polypeptides and complexes of the disclosure, including fragments or variants thereof, may be recombinantly produced using various expression systems (e.g., *E. coli*, Chinese Hamster Ovary (CHO) cells, COS cells, baculovirus) as is well known in the art. In a further embodiment, the modified or unmodified polypeptides of the disclosure may be produced by digestion of recombinantly produced full-length TGFβ superfamily type I receptor, type II receptor and/or co-receptor polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites.

3. Nucleic Acids Encoding TGFβ Superfamily Type I Receptor Polypeptides, Type II Receptor Polypeptides, and Co-Receptor Polypeptides In certain embodiments, the present disclosure provides isolated and/or recombinant nucleic acids encoding TGFβ superfamily type I receptors, type II receptors, and co-receptors (including fragments, functional variants, and fusion proteins thereof) disclosed herein. For example, SEQ ID NO: 13 encodes a naturally occurring human ActRIIA precursor polypeptide, while SEQ ID NO: 14 encodes a processed extracellular domain of ActRIIA. The subject nucleic acids may be single-stranded or double stranded. Such nucleic acids may be DNA or RNA molecules. These nucleic acids may be used, for example, in methods for making TGF-beta superfamily heteromultimers of the present disclosure.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding TGFβ superfamily type I receptor polypeptides, type II receptor polypeptides, and/or co-receptor polypeptides of the present disclosure are understood to include nucleic acids of any one of SEQ ID NOs: 7, 8, 13, 14, 35, 37, 39, 41, 43, 45, 47, 49, 53, 55, 57, 59, 61, 63, 65, 67, 69, 71, 73, 75, 77, 79, 81, 83, 85, 88, 90, 92, 94, 96, 98, 100, 102, 104, 106, 108, 110, 112, 114, 116, 118, 120, 122, 124, 126, 128, 130, 132, 134, 179, 183, 185, 186, 191, 194, 195, 200, 203, and 210, as well as variants thereof. Variant nucleotide sequences include sequences that differ by one or more nucleotide substitutions, additions, or deletions including allelic variants, and therefore, will include coding sequences that differ from the nucleotide sequence designated in any one of SEQ ID NOs: 7, 8, 13, 14, 35, 37, 39, 41, 43, 45, 47, 49, 53, 55, 57, 59, 61, 63, 65, 67, 69, 71, 73, 75, 77, 79, 81, 83, 85, 88, 90, 92, 94, 96, 98, 100, 102, 104, 106, 108, 110, 112, 114, 116, 118, 120, 122, 124, 126, 128, 130, 132, 134, 179, 183, 185, 186, 191, 194, 195, 200, 203, and 210.

In certain embodiments, TGFβ superfamily type I receptor polypeptides, type II receptor polypeptides, and/or co-receptor polypeptides of the present disclosure are encoded by isolated or recombinant nucleic acid sequences that are at least 70%, 75%, 80%, 85%, 90%, 91%, 92%, 93%, 94%, 95%, 96%, 97%, 98%, 99%, or 100% identical to SEQ ID NOs: 7, 8, 13, 14, 35, 37, 39, 41, 43, 45, 47, 49, 53, 55, 57, 59, 61, 63, 65, 67, 69, 71, 73, 75, 77, 79, 81, 83, 85, 88, 90, 92, 94, 96, 98, 100, 102, 104, 106, 108, 110, 112, 114, 116, 118, 120, 122, 124, 126, 128, 130, 132, 134, 179, 183, 185, 186, 191, 194, 195, 200, 203, and 210. One of ordinary skill in the art will appreciate that nucleic acid sequences that are at least 70%, 75%, 80%, 85%, 90%, 91%, 92%, 93%, 94%, 95%, 96%, 97%, 98%, 99%, or 100% identical to the sequences complementary to SEQ ID NOs: 7, 8, 13, 14, 35, 37, 39, 41, 43, 45, 47, 49, 53, 55, 57, 59, 61, 63, 65, 67, 69, 71, 73, 75, 77, 79, 81, 83, 85, 88, 90, 92, 94, 96, 98, 100, 102, 104, 106, 108, 110, 112, 114, 116, 118, 120, 122, 124, 126, 128, 130, 132, 134, 179, 183, 185, 186, 191, 194, 195, 200, 203, and 210 are also within the scope of the present disclosure. In further embodiments, the nucleic acid sequences of the disclosure can be isolated, recombinant, and/or fused with a heterologous nucleotide sequence or in a DNA library.

In other embodiments, nucleic acids of the present disclosure also include nucleotide sequences that hybridize under highly stringent conditions to the nucleotide sequence designated in SEQ ID NOs: 7, 8, 13, 14, 35, 37, 39, 41, 43, 45, 47, 49, 53, 55, 57, 59, 61, 63, 65, 67, 69, 71, 73, 75, 77, 79, 81, 83, 85, 88, 90, 92, 94, 96, 98, 100, 102, 104, 106, 108, 110, 112, 114, 116, 118, 120, 122, 124, 126, 128, 130, 132, 134, 179, 183, 185, 186, 191, 194, 195, 200, 203, and 210, the complement sequence of SEQ ID NOs: 7, 8, 13, 14, 35, 37, 39, 41, 43, 45, 47, 49, 53, 55, 57, 59, 61, 63, 65, 67, 69, 71, 73, 75, 77, 79, 81, 83, 85, 88, 90, 92, 94, 96, 98, 100, 102, 104, 106, 108, 110, 112, 114, 116, 118, 120, 122, 124, 126, 128, 130, 132, 134, 179, 183, 185, 186, 191, 194, 195, 200, 203, and 210, or fragments thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 13, 14, 35, 37, 39, 41, 43, 45, 47, 49, 53, 55, 57, 59, 61, 63, 65, 67, 69, 71, 73, 75, 77, 79, 81, 83, 85, 88, 90, 92, 94, 96, 98, 100, 102, 104, 106, 108, 110, 112, 114, 116, 118, 120, 122, 124, 126, 128, 130, 132, 134, 179, 183, 185, 186, 191, 194, 195, 200, 203, and 210 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects of the present disclosure, the subject nucleic acid is provided in an expression vector comprising a nucleotide sequence encoding a TGFβ superfamily type I receptor polypeptide, type II receptor polypeptide, and/or co-receptor polypeptide and operably linked to at least one regulatory sequence. Regulatory sequences are art-recognized and are selected to direct expression of the TGFβ superfamily type I receptor polypeptide, type II receptor polypeptide, and/or co-receptor polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, CA (1990). For instance, any of a wide variety of expression control sequences that control the expression of a DNA sequence when operatively linked to it may be used in these vectors to express DNA sequences encoding a TGFβ superfamily type I receptor polypeptide, type II receptor polypeptide, and/or co-receptor polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant TGFβ superfamily type I receptor polypeptide, type II receptor polypeptide, and/or co-receptor polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III). In a preferred embodiment, a vector will be designed for production of the subject TGFβ superfamily type I receptor polypeptides, type II receptor polypeptides, and/or co-receptor polypeptides in CHO cells, such as a Pcmv-Script vector (Stratagene, La Jolla, Calif.), pcDNA4 vectors (Invitrogen, Carlsbad, Calif) and pCI-neo vectors (Promega, Madison, Wisc.). As will be apparent, the subject gene constructs can be used to cause expression of the subject TGFβ superfamily type I receptor polypeptides, type II receptor polypeptides, and/or co-receptor polypeptides in cells propagated in culture, e.g., to produce proteins, including fusion proteins or variant proteins, for purification.

This disclosure also pertains to a host cell transfected with a recombinant gene including a coding sequence for one or more of the subject TGFβ superfamily type I receptor polypeptides, type II receptor polypeptides, and/or co-receptor polypeptides. The host cell may be any prokaryotic or eukaryotic cell. For example, a TGFβ superfamily type I receptor polypeptide, type II receptor polypeptide, and/or co-receptor polypeptide of the disclosure may be expressed in bacterial cells such as E. coli, insect cells (e.g., using a baculovirus expression system), yeast, or mammalian cells [e.g., a Chinese hamster ovary (CHO) cell line]. Other suitable host cells are known to those skilled in the art.

Accordingly, the present disclosure further pertains to methods of producing the subject TGFβ superfamily type I receptor polypeptides, type II receptor polypeptides, and/or co-receptor polypeptides. For example, a host cell transfected with an expression vector encoding a TGFβ superfamily type I receptor polypeptide, type II receptor polypeptide, and/or co-receptor polypeptide can be cultured under appropriate conditions to allow expression of the TGFβ superfamily type I receptor polypeptide, type II receptor polypeptide, and/or co-receptor polypeptide to occur. The polypeptide may be secreted and isolated from a mixture of cells and medium containing the polypeptide. Alternatively, the TGFβ superfamily type I receptor polypeptide, type II receptor polypeptide, and/or co-receptor polypeptide may be isolated from a cytoplasmic or membrane fraction obtained from harvested and lysed cells. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration, ultrafiltration, electrophoresis, immunoaffinity purification with antibodies specific for particular epitopes of the TGFβ superfamily type I receptor polypeptides, type II receptor polypeptides, and/or co-receptor polypeptides and affinity purification with an agent that binds to a domain fused to TGFβ superfamily type I receptor polypeptides, type II receptor polypeptides, and/or co-receptor polypeptides (e.g., a protein A column may be used to purify a TGFβ superfamily type I receptor-Fc fusion protein, type II receptor-Fc fusion protein, and/or co-receptor-Fc fusion protein). In some embodiments, the TGFβ superfamily type I receptor polypeptide, type II receptor polypeptide, and/or co-receptor polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. A TGFβ superfamily type I receptor-Fc fusion protein, type II receptor-Fc fusion protein, and/or co-receptor-Fc fusion protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant TGFβ superfamily type I receptor polypeptide, type II receptor polypeptide, and/or co-receptor polypeptide, can allow purification of the expressed fusion protein by affinity chromatography using a $Ni^{2+}$ metal resin. The purification leader sequence can then be subsequently removed by treatment with enterokinase to provide the purified TGFβ superfamily type I receptor polypeptide, type II receptor polypeptide, and/or co-receptor polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. Antibody Antagonists

In certain aspects, an activin and/or GDF antagonist to be used in accordance with the methods and uses disclosed herein is an antibody (activin and/or GDF antagonist antibody), or combination of antibodies. An activin and/or GDF antagonist antibody, or combination of antibodies, may bind to, for example, one or more ActRII ligands (e.g., activin (such as activin A, activin B, activin C, activin E, activin AB, activin AC, activin AE, activin BC, and/or activin BE), GDF8, GDF3, GDF1, GDF11, Nodal, and/or GDF3), ActRII receptors (ActRIIA and/or ActRIIB), type I receptors (ALK4, ALK5, and/or ALK7), and/or their co-receptors (e.g., Cripto, Cryptic, and/or Cryptic 1B). As described herein, activin and/or GDF antagonist antibodies may be used, alone or in combination with one or more supportive therapies or active agents, to treat or reduce the progression rate, frequency, and/or severity of kidney diseases, particularly treating, preventing or reducing the progression rate, frequency, and/or severity of one or more kidney disease-associated complications (e.g., kidney tissue damage, fibrosis, and/or inflammation).

In certain aspects, an activin and/or GDF antagonist antibody, or combination of antibodies, is an antibody that inhibits at least activin (e.g., activin A, activin B, activin C, activin E, activin AB, activin AC, activin BC, activin AE, and/or activin BE). Therefore, in some embodiments, an activin and/or GDF antagonist antibody, or combination of antibodies, binds to at least activin. As used herein, an activin antibody (or anti-activin antibody) generally refers to an antibody that binds to activin with sufficient affinity such that the antibody is useful as a diagnostic and/or therapeutic agent in targeting activin. In certain embodiments, the extent of binding of an activin antibody to an unrelated, non-activin protein is less than about 10%, 9%, 8%, 7%, 6%, 5%, 4%, 3%, 2%, or less than about 1% of the binding of the antibody to activin as measured, for example, by a radioimmunoassay (RIA), Biacore, or other protein interaction or binding affinity assay. In certain embodiments, an activin antibody binds to an epitope of activin that is conserved among activin from different species. In certain preferred embodiments, an anti-activin antibody binds to human activin. In some embodiments, an activin antibody may inhibit activin from binding to a type I and/or type II receptor (e.g., ActRIIA, ActRIIB, ALK4, ALK5, and/or ALK7) and thus inhibit activin-mediated signaling (e.g., Smad signaling). In some embodiments, an activin antibody may inhibit activin from binding to an ActRII co-receptor (e.g., Cripto, Cryptic, and/or Cryptic 1B) and thus inhibit activin-mediated signaling (e.g., Smad signaling). It should be noted that activin A has similar sequence homology to activin B and therefore antibodies that bind to activin A, in some instances, may also bind to and/or inhibit activin B, which also applies to anti-activin B antibodies. In some embodiments, the disclosure relates to a multispecific antibody (e.g., bi-specific antibody), and uses thereof, that binds to activin and further binds to, for example, one or more additional GDF ligands (e.g., GDF11, GDF8, GDF3, GDF 1 and/or Nodal), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a multispecific antibody that binds to activin does not bind or does not substantially bind to activin B (e.g., binds to activin B with a $K_D$ of greater than $1 \times 10^7$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises an activin antibody and one or more additional antibodies that bind to, for example, one or more additional GDF superfamily ligands (e.g., GDF8, GDF11, GDF3, GDF 1 and/or Nodal), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a combination of antibodies that comprises an activin A antibody does not comprise an activin B antibody.

In certain aspects, an activin and/or GDF antagonist antibody, or combination of antibodies, is an antibody that inhibits at least GDF8. Therefore, in some embodiments, an activin and/or GDF antagonist antibody, or combination of antibodies, binds to at least GDF8. As used herein, a GDF8 antibody (or anti-GDF8 antibody) generally refers to an antibody that binds to GDF8 with sufficient affinity such that the antibody is useful as a diagnostic and/or therapeutic agent in targeting GDF8. In certain embodiments, the extent of binding of a GDF8 antibody to an unrelated, non-GDF8 protein is less than about 10%, 9%, 8%, 7%, 6%, 5%, 4%, 3%, 2%, or less than about 1% of the binding of the antibody to GDF8 as measured, for example, by a radioimmunoassay (RIA), Biacore, or other protein interaction or binding affinity assay. In certain embodiments, a GDF8 antibody binds to an epitope of GDF8 that is conserved among GDF8 from different species. In certain preferred embodiments, an anti-GDF8 antibody binds to human GDF8. In some embodiments, a GDF8 antibody may inhibit GDF8 from binding to a type I and/or type II receptor (e.g., ActRIIA, ActRIIB, ALK4, ALK5, and/or ALK7) and thus inhibit GDF8-mediated signaling (e.g., Smad signaling). In some embodiments, a GDF8 antibody may inhibit GDF8 from binding to a co-receptor and thus inhibit GDF8-mediated signaling (e.g., Smad signaling). It should be noted that GDF8 has high sequence homology to GDF11 and therefore antibodies that bind to GDF8, in some instances, may also bind to and/or inhibit GDF11. In some embodiments, the disclosure relates to a multispecific antibody (e.g., bi-specific antibody), and uses thereof, that binds to GDF8 and further binds to, for example, one or more additional GDF ligands (e.g., activin (e.g., activin A, activin B, activin C, activin E, activin AB, activin AC, activin BC, activin AE, activin BE), GDF11, GDF3, GDF 1 and/or Nodal), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a multispecific antibody that binds to GDF8 does not bind or does not substantially bind to activin B (e.g., binds to activin B with a $K_D$ of greater than $1 \times 10^{-7}$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a GDF8 antibody and one or more additional antibodies that bind to, for example, one or more additional GDF ligands (e.g., activin (e.g., activin A, activin B, activin C, activin E, activin AB, activin AC, activin BC, activin AE, activin BE), GDF11, GDF3, GDF1, and/or Nodal), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a combination of antibodies that comprises a GDF8 antibody does not comprise an activin B antibody.

In certain aspects, an activin and/or GDF antagonist antibody, or combination of antibodies, is an antibody that inhibits at least GDF11. Therefore, in some embodiments, an activin and/or GDF antagonist antibody, or combination of antibodies, binds to at least GDF11. As used herein, a GDF11 antibody (or anti-GDF11 antibody) generally refers to an antibody that binds to GDF11 with sufficient affinity such that the antibody is useful as a diagnostic and/or therapeutic agent in targeting GDF11. In certain embodiments, the extent of binding of a GDF11 antibody to an unrelated, non-GDF11 protein is less than about 10%, 9%, 8%, 7%, 6%, 5%, 4%, 3%, 2%, or less than about 1% of the binding of the antibody to GDF11 as measured, for example, by a radioimmunoassay (RIA), Biacore, or other protein interaction or binding affinity assay. In certain embodiments, a GDF11 antibody binds to an epitope of GDF11 that is conserved among GDF11 from different species. In certain preferred embodiments, an anti-GDF11 antibody binds to human GDF11. In some embodiments, a GDF11 antibody may inhibit GDF11 from binding to a type I and/or type II receptor (e.g., ActRIIA, ActRIIB, ALK4, ALK5, and/or ALK7) and thus inhibit GDF11-mediated signaling (e.g., Smad signaling). In some embodiments, a GDF11 antibody may inhibit GDF11 from binding to a co-receptor and thus inhibit GDF11-mediated signaling (e.g., Smad signaling). It should be noted that GDF11 has high sequence homology to GDF8 and therefore antibodies that bind to GDF11, in some instances, may also bind to and/or inhibit GDF8. In some embodiments, the disclosure relates to a multispecific antibody (e.g., bi-specific antibody), and uses thereof, that binds to GDF11 and further binds to, for example, one or more additional GDF ligands [e.g., activin (e.g., activin A, activin B, activin C, activin E, activin AB, activin AC, activin BC, activin AE, activin BE), GDF8, GDF3, GDF 1 and/or Nodal), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a multispecific antibody that binds to GDF11 does not bind or does not substantially bind to activin B (e.g., binds to activin B with a $K_D$ of greater than $1 \times 10^7$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a GDF11 antibody and one or more additional antibodies that bind to, for example, one or more additional GDF ligands [e.g., activin (e.g., activin A, activin B, activin C, activin E, activin AB, activin AC, activin BC, activin AE, activin BE), GDF8, GDF3, GDF 1 and/or Nodal], one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a combination of antibodies that comprises a GDF11 antibody does not comprise an activin B antibody.

In certain aspects, an activin and/or GDF antagonist antibody, or combination of antibodies, is an antibody that inhibits at least GDF 1. Therefore, in some embodiments, an activin and/or GDF antagonist antibody, or combination of antibodies, binds to at least GDF 1. As used herein, a GDF 1 antibody (or anti-GDF 1 antibody) generally refers to an antibody that can bind to GDF 1 with sufficient affinity such that the antibody is useful as a diagnostic and/or therapeutic agent in targeting GDF 1. In certain embodiments, the extent of binding of a GDF 1 antibody to an unrelated, non-GDF1 protein is less than about 10%, 9%, 8%, 7%, 6%, 5%, 4%, 3%, 2%, or less than about 1% of the binding of the antibody to GDF 1 as measured, for example, by a radioimmunoassay (RIA), Biacore, or other protein interaction or binding affinity assay. In certain embodiments, a GDF 1 antibody binds to an epitope of GDF 1 that is conserved among GDF1 from different species. In certain preferred embodiments, an anti-GDF1 antibody binds to human GDF 1. In some embodiments, a GDF 1 antibody may inhibit GDF 1 from binding to a type I and/or type II receptor (e.g., ActRIIA, ActRIIB, ALK4, ALK5, and/or ALK7) and thus inhibit GDF 1-mediated signaling (e.g., Smad signaling). In some embodiments, a GDF 1 antibody may inhibit GDF 1 from binding to a co-receptor and thus inhibit GDF 1-mediated signaling (e.g., Smad signaling). In some embodiments, the disclosure relates to a multispecific antibody (e.g., bi-specific antibody), and uses thereof, that binds to GDF 1 and further binds to, for example, one or more additional GDF ligands (e.g., activin (e.g., activin A, activin B, activin C, activin E, activin AB, activin AC, activin BC, activin AE, activin BE), GDF8, GDF3, Nodal, and/or GDF11), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B. In some embodiments, a multispecific antibody that binds to GDF 1 does not bind or does not substantially bind to activin B (e.g., binds to activin B with a $K_D$ of greater than $1 \times 10^7$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a GDF 1 antibody and one or more additional antibodies that bind to, for example, one or more additional GDF ligands (e.g., activin (e.g., activin A, activin B, activin C, activin E, activin AB, activin AC, activin BC, activin AE, activin BE), GDF8, GDF11, GDF3, and/or Nodal), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a combination of antibodies that comprises a GDF1 antibody does not comprise an activin B antibody.

In certain aspects, an activin and/or GDF antagonist antibody, or combination of antibodies, is an antibody that inhibits at least GDF3. Therefore, in some embodiments, an activin and/or GDF antagonist antibody, or combination of antibodies, binds to at least GDF3. As used herein, a GDF3 antibody (or anti-GDF3 antibody) generally refers to an antibody that can bind to GDF3 with sufficient affinity such that the antibody is useful as a diagnostic and/or therapeutic agent in targeting GDF3. In certain embodiments, the extent of binding of a GDF3 antibody to an unrelated, non-GDF3 protein is less than about 10%, 9%, 8%, 7%, 6%, 5%, 4%, 3%, 2%, or less than about 1% of the binding of the antibody to GDF3 as measured, for example, by a radioimmunoassay (RIA), Biacore, or other protein interaction or binding affinity assay. In certain embodiments, a GDF3 antibody binds to an epitope of GDF3 that is conserved among GDF3 from different species. In certain preferred embodiments, an anti-GDF3 antibody binds to human GDF3. In some embodiments, a GDF3 antibody may inhibit GDF3 from binding to a type I and/or type II receptor (e.g., ActRIIA, ActRIIB, ALK4, ALK5, and/or ALK7) and thus inhibit GDF3-mediated signaling (e.g., Smad signaling). In some embodiments, a GDF3 antibody may inhibit GDF3 from binding to a co-receptor and thus inhibit GDF3-mediated signaling (e.g., Smad signaling). In some embodiments, the disclosure relates to a multispecific antibody (e.g., bi-specific antibody), and uses thereof, that binds to GDF3 and further binds to, for example, one or more additional GDF ligands (e.g., activin (e.g., activin A, activin B, activin C, activin E, activin AB, activin AC, activin BC, activin AE, activin BE), GDF8, GDF1, Nodal, and/or GDF11), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a multispecific antibody that binds to GDF3 does not bind or does not substantially bind to activin B (e.g., binds to activin B with a $K_D$ of greater than $1 \times 10^{-7}$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a GDF3 antibody and one or more additional antibodies that bind to, for example, one or more additional GDF ligands [e.g., activin (e.g., activin A, activin B, activin C, activin E, activin AB, activin AC, activin BC, activin AE, activin BE), GDF8, GDF11, GDF 1 and/or Nodal), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a combination of antibodies that comprises a GDF3 antibody does not comprise an activin B antibody In certain aspects, an activin and/or GDF antagonist antibody, or combination of antibodies, is an antibody that inhibits at least Nodal. Therefore, in some embodiments, an activin and/or GDF antagonist antibody, or combination of antibodies, binds to at least Nodal. As used herein, a Nodal antibody (or anti-Nodal antibody) generally refers to an antibody that can bind to Nodal with sufficient affinity such that the antibody is useful as a diagnostic and/or therapeutic agent in targeting Nodal. In certain embodiments, the extent of binding of a Nodal antibody to an unrelated, non-Nodal protein is less than about 10%, 9%, 8%, 7%, 6%, 5%, 4%, 3%, 2%, or less than about 1% of the binding of the antibody to Nodal as measured, for example, by a radioimmunoassay (RIA), Biacore, or other protein interaction or binding affinity assay. In certain embodiments, a Nodal antibody binds to an epitope of Nodal that is conserved among Nodal from different species. In certain preferred embodiments, an anti-Nodal antibody binds to human Nodal. In some embodiments, a Nodal antibody may inhibit Nodal from binding to a type I and/or type II receptor (e.g., ActRIIA, ActRIIB, ALK4, ALK5, and/or ALK7) and thus inhibit Nodal-mediated signaling (e.g., Smad signaling). In some embodiments, a Nodal antibody may inhibit Nodal from binding to a co-receptor and thus inhibit Nodal-mediated signaling (e.g., Smad signaling). In some embodiments, the disclosure relates to a multispecific antibody (e.g., bi-specific antibody), and uses thereof, that binds to Nodal and further binds to, for example, one or more additional GDF ligands (e.g., activin (e.g., activin A, activin B, activin C, activin E, activin AB, activin AC, activin BC, activin AE and activin BE), GDF8, GDF11, GDF3, and/or GDF1), one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B. In some embodiments, a multispecific antibody that binds to Nodal does not bind or does not substantially bind to activin B (e.g., binds to activin B with a $K_D$ of greater than $1 \times 10^{-7}$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a Nodal antibody and one or more additional antibodies that bind to, for example, one or more additional GDF ligands (e.g., activin (e.g., activin A, activin B, activin C, activin E, activin AB, activin AC, activin BC, activin AE and activin BE), GDF8, GDF3, GDF1 and/or GDF11], one or more type I receptor and/or type II receptors (e.g., ActRIIA, ActRIIB, ALK4, ALK5, and/or ALK7), and/or one or more co-receptors (e.g., Cripto, Cryptic, and/or Cryptic 1B). In some embodiments, a combination of antibodies that comprises a Nodal antibody does not comprise activin B antibody.

In certain aspects, an activin and/or GDF antagonist antibody, or combination of antibodies, is an antibody that inhibits at least ActRIIB. Therefore, in some embodiments, an activin and/or GDF antagonist antibody, or combination of antibodies, binds to at least ActRIIB. As used herein, an ActRIIB antibody (anti-ActRIIB antibody) generally refers to an antibody that binds to ActRIIB with sufficient affinity such that the antibody is useful as a diagnostic and/or therapeutic agent in targeting ActRIIB. In certain embodiments, the extent of binding of an anti-ActRIIB antibody to an unrelated, non-ActRIIB protein is less than about 10%, 9%, 8%, 7%, 6%, 5%, 4%, 3%, 2%, or less than about 1% of the binding of the antibody to ActRIIB as measured, for example, by a radioimmunoassay (RIA), Biacore, or other protein-protein interaction or binding affinity assay. In certain embodiments, an anti-ActRIIB antibody binds to an epitope of ActRIIB that is conserved among ActRIIB from different species. In certain preferred embodiments, an anti-ActRIIB antibody binds to human ActRIIB. In some embodiments, an anti-ActRIIB antibody may inhibit one or more GDF ligands (e.g., GDF8, activin (e.g., activin A, activin B, activin C, activin E, activin AB, activin AC, activin BC, activin AE and activin BE), GDF11, GDF8, GDF3, GDF1, and/or Nodal) from binding to ActRIIB. In some embodiments, an anti-ActRIIB antibody is a multi-specific antibody (e.g., bi-specific antibody) that binds to ActRIIB and one or more GDF ligands (e.g., GDF11, GDF8, activin (e.g., activin A, activin B, activin C, activin E, activin AB, activin AC, activin BC, activin AE, and/or activin BE), GDF3, GDF1, and/or Nodal], type I receptor (e.g., ALK4, ALK5, and/or ALK7), one or more co-receptors (e.g., Cripto, Cryptic, and/or Cryptic 1B), and/or an additional type II receptor (e.g., ActRIIA). In some embodiments, the disclosure relates to combinations of antibodies, and uses thereof, wherein the combination of antibodies comprises an anti-ActRIIB antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF1, GDF3, and/or Nodal, co-receptors (e.g., Cripto, Cryptic, and/or Cryptic 1B), type I receptors (e.g., ALK4, ALK5, and/or ALK7), and/or additional type II receptors (e.g., ActRIIA). It should be noted that ActRIIB has sequence similarity to ActRIIA and therefore antibodies that bind to ActRIIB, in some instances, may also bind to and/or inhibit ActRIIA. In some embodiments, a multispecific antibody that binds to ActRIIB does not bind or does not substantially bind to activin B (e.g., binds to activin B with a $K_D$ of greater than $1 \times 10^{-7}$ M or has relatively modest binding, e.g., about $1 \times 10^{-8}$ M or about $1 \times 10^{-9}$ M). In some embodiments, a combination of antibodies that comprises an ActRIIB antibody does not comprise an activin B antibody.

In certain aspects, an activin and/or GDF antagonist antibody, or combination of antibodies, is an antibody that inhibits at least ActRIIA. Therefore, in some embodiments, an activin and/or GDF antagonist antibody, or combination of antibodies, binds to at least ActRIIA. As used herein, an ActRIIA antibody (anti-ActRIIA antibody) generally refers to an antibody that binds to ActRIIA with sufficient affinity such that the antibody is useful as a diagnostic and/or therapeutic agent in targeting ActRIIA. In certain embodiments, the extent of binding of an anti-ActRIIA antibody to an unrelated, non-ActRIIA protein is less than about 10%, 9%, 8%, 7%, 6%, 5%, 4%, 3%, 2%, or less than about 1% of the binding of the antibody to ActRIIA as measured, for example, by a radioimmunoassay (RIA), Biacore, or other protein-protein interaction or binding affinity assay. In certain embodiments, an anti-ActRIIA antibody binds to an epitope of ActRIIA that is conserved among ActRIIA from different species. In certain preferred embodiments, an anti-ActRIIA antibody binds to human ActRIIA. In some embodiments, an anti-ActRIIA antibody may inhibit one or more GDF ligands (e.g., GDF8, activin (e.g., activin A, activin B, activin C, activin E, activin AB, activin AC, activin BC, activin AE and activin BE), GDF11, GDF1, GDF3, and/or Nodal) from binding to ActRIIA. In some embodiments, an anti-ActRIIA antibody is a multispecific antibody (e.g., bi-specific antibody) that binds to ActRIIA and one or more GDF ligands (e.g., GDF11, GDF8, activin (e.g., activin A, activin B, activin C, activin E, activin AB, activin AC), GDF3, GDF1, and/or Nodal), type I receptor (e.g., ALK4, ALK5, and/or ALK7), co-receptor (e.g., Cripto, Cryptic, and/or Cryptic 1B), and/or an additional type II receptor (e.g., ActRIIB). In some embodiments, the disclosure relates to combinations of antibodies, and uses thereof, wherein the combination of antibodies comprises an anti-ActRIIA antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF1, GDF3, and/or Nodal, co-receptors (e.g., Cripto, Cryptic, and/or Cryptic 1B), type I receptors (e.g., ALK4, ALK5, and/or ALK7), and/or additional type II receptors (e.g., ActRIIB). It should be noted that ActRIIA has sequence similarity to ActRIIB and therefore antibodies that bind to ActRIIA, in some instances, may also bind to and/or inhibit ActRIIB. In some embodiments, a multispecific antibody that binds to ActRIIA does not bind or does not substantially bind to activin B (e.g., binds to activin B with a $K_D$ of greater than $1\times10^{-7}$ M or has relatively modest binding, e.g., about $1\times10^{-8}$ M or about $1\times10^{-9}$ M). In some embodiments, a combination of antibodies that comprises an ActRIIA antibody does not comprise an activin B antibody.

In certain aspects, an activin and/or GDF antagonist antibody, or combination of antibodies, is an antibody that inhibits at least ALK4. Therefore, in some embodiments, an activin and/or GDF antagonist antibody, or combination of antibodies, binds to at least ALK4. As used herein, an ALK4 antibody (anti-ALK4 antibody) generally refers to an antibody that binds to ALK4 with sufficient affinity such that the antibody is useful as a diagnostic and/or therapeutic agent in targeting ALK4. In certain embodiments, the extent of binding of an anti-ALK4 antibody to an unrelated, non-ALK4 protein is less than about 10%, 9%, 8%, 7%, 6%, 5%, 4%, 3%, 2%, or less than about 1% of the binding of the antibody to ALK4 as measured, for example, by a radioimmunoassay (RIA), Biacore, or other protein-protein interaction or binding affinity assay. In certain embodiments, an anti-ALK4 antibody binds to an epitope of ALK4 that is conserved among ALK4 from different species. In certain preferred embodiments, an anti-ALK4 antibody binds to human ALK4. In some embodiments, an anti-ALK4 antibody may inhibit one or more GDF ligands (e.g., GDF8, activin (e.g., activin A, activin B, activin C, activin E, activin AB, activin AC, activin BC, activin AE and activin BE), GDF11, GDF1, GDF3, and/or Nodal) from binding to ALK4. In some embodiments, an anti-ALK4 antibody is a multispecific antibody (e.g., bi-specific antibody) that binds to ALK4 and one or more GDF ligands (e.g., GDF11, GDF8, activin (e.g., activin A, activin B, activin C, activin E, activin AB, activin AC), GDF3, GDF1, and/or Nodal), type II receptor (e.g., ActRIIA and/or ActRIIB), co-receptor (e.g., Cripto, Cryptic, and/or Cryptic 1B), and/or an additional type I receptor (e.g., ALK5 and/or ALK7). In some embodiments, the disclosure relates to combinations of antibodies, and uses thereof, wherein the combination of antibodies comprises an anti-ALK4 antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF1, GDF3, and/or Nodal), co-receptors (e.g., Cripto, Cryptic, and/or Cryptic 1), type II receptors (e.g., ActRIIA and/or ActRIIB), and/or additional type I receptors (e.g., ALK5 and/or ALK7). In some embodiments, a multispecific antibody that binds to ALK4 does not bind or does not substantially bind to activin B (e.g., binds to activin B with a $K_D$ of greater than $1\times10^{-7}$ M or has relatively modest binding, e.g., about $1\times10^{-8}$ M or about $1\times10^{-9}$ M). In some embodiments, a combination of antibodies that comprises an ALK4 antibody does not comprise an activin B antibody.

In certain aspects, an activin and/or GDF antagonist antibody, or combination of antibodies, is an antibody that inhibits at least ALK5. Therefore, in some embodiments, an activin and/or GDF antagonist antibody, or combination of antibodies, binds to at least ALK5. As used herein, an ALK5 antibody (anti-ALK5 antibody) generally refers to an antibody that binds to ALK5 with sufficient affinity such that the antibody is useful as a diagnostic and/or therapeutic agent in targeting ALK5. In certain embodiments, the extent of binding of an anti-ALK5 antibody to an unrelated, non-ALK5 protein is less than about 10%, 9%, 8%, 7%, 6%, 5%, 4%, 3%, 2%, or less than about 1% of the binding of the antibody to ALK5 as measured, for example, by a radioimmunoassay (RIA), Biacore, or other protein-protein interaction or binding affinity assay. In certain embodiments, an anti-ALK5 antibody binds to an epitope of ALK5 that is conserved among ALK5 from different species. In certain preferred embodiments, an anti-ALK5 antibody binds to human ALK5. In some embodiments, an anti-ALK5 antibody may inhibit one or more GDF ligands (e.g., GDF8, activin (e.g., activin A, activin B, activin C, activin E, activin AB, activin AC, activin BC, activin AE and activin BE), GDF11, GDF1, GDF3, and/or Nodal) from binding to ALK5. In some embodiments, an anti-ALK5 antibody is a multispecific antibody (e.g., bi-specific antibody) that binds to ALK5 and one or more GDF ligands (e.g., GDF11, GDF8, activin (e.g., activin A, activin B, activin C, activin E, activin AB, activin AC), GDF3, GDF1, and/or Nodal), type II receptor (e.g., ActRIIA and/or ActRIIB), co-receptor (e.g., Cripto, Cryptic, and/or Cryptic 1B), and/or an additional type I receptor (e.g., ALK4 and/or ALK7). In some embodiments, the disclosure relates to combinations of antibodies, and uses thereof, wherein the combination of antibodies comprises an anti-ALK5 antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF3, GDF1, and/or Nodal), co-receptors (e.g., Cripto, Cryptic, and/or Cryptic 1B), type II receptors (e.g., ActRIIA and/or ActRIIB), and/or additional type I receptors (e.g., ALK4 and/or ALK7). In some embodiments, a multispecific antibody that binds to ALK5 does not bind or does not substantially bind to activin B (e.g., binds to activin B with a $K_D$ of greater than $1\times10^{-7}$ M or has relatively modest binding, e.g., about $1\times10^{-8}$ M or about $1\times10^{-9}$ M). In some embodiments, a combination of antibodies that comprises an ALK5 antibody does not comprise an activin B antibody.

In certain aspects, an activin and/or GDF antagonist antibody, or combination of antibodies, is an antibody that inhibits at least ALK7. Therefore, in some embodiments, an activin and/or GDF antagonist antibody, or combination of antibodies, binds to at least ALK7. As used herein, an ALK7 antibody (anti-ALK7 antibody) generally refers to an antibody that binds to ALK7 with sufficient affinity such that the antibody is useful as a diagnostic and/or therapeutic agent in targeting ALK7. In certain embodiments, the extent of binding of an anti-ALK7 antibody to an unrelated, non- ALK7 protein is less than about 10%, 9%, 8%, 7%, 6%, 5%, 4%, 3%, 2%, or less than about 1% of the binding of the antibody to ALK7 as measured, for example, by a radioimmunoassay (RIA), Biacore, or other protein-protein interaction or binding affinity assay. In certain embodiments, an anti-ALK7 antibody binds to an epitope of ALK7 that is conserved among ALK7 from different species. In certain preferred embodiments, an anti-ALK7 antibody binds to human ALK7. In some embodiments, an anti-ALK7 antibody may inhibit one or more GDF ligands (e.g., GDF8, activin (e.g., activin A, activin B, activin C, activin E, activin AB, activin AC, activin BC, activin AE and activin BE), GDF11, GDF1, GDF3, and/or Nodal) from binding to ALK7. In some embodiments, an anti-ALK7 antibody is a multispecific antibody (e.g., bi-specific antibody) that binds to ALK7 and one or more GDF ligands (e.g., GDF11, GDF8, activin (e.g., activin A, activin B, activin C, activin E, activin AB, activin AC), GDF3, GDF1, and/or Nodal), type II receptor (e.g., ActRIIA and/or ActRIIB), co-receptor (e.g., Cripto, Cryptic, and/or Cryptic 1B), and/or an additional type I receptor (e.g., ALK4 and/or ALK5). In some embodiments, the disclosure relates to combinations of antibodies, and uses thereof, wherein the combination of antibodies comprises an anti-ALK7 antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF3, GDF1, and/or Nodal), co-receptors (e.g., Cripto, Cryptic, and/or Cryptic 1B), type II receptors (e.g., ActRIIA and/or ActRIIB), and/or additional type I receptors (e.g., ALK4 and/or ALK5). In some embodiments, a multispecific antibody that binds to ALK7 does not bind or does not substantially bind to activin B (e.g., binds to activin B with a $K_D$ of greater than $1\times10^7$ M or has relatively modest binding, e.g., about $1\times10^{-8}$ M or about $1\times10^{-9}$ M). In some embodiments, a combination of antibodies that comprises an ALK7 antibody does not comprise an activin B antibody.

In certain aspects, an activin and/or GDF antagonist antibody, or combination of antibodies, is an antibody that inhibits at least Cripto. Therefore, in some embodiments, an activin and/or GDF antagonist antibody, or combination of antibodies, binds to at least Cripto. As used herein, a Cripto antibody (anti-Cripto antibody) generally refers to an antibody that binds to Cripto with sufficient affinity such that the antibody is useful as a diagnostic and/or therapeutic agent in targeting Cripto. In certain embodiments, the extent of binding of an anti-Cripto antibody to an unrelated, non-Cripto protein is less than about 10%, 9%, 8%, 7%, 6%, 5%, 4%, 3%, 2%, or less than about 1% of the binding of the antibody to Cripto as measured, for example, by a radioimmunoassay (RIA), Biacore, or other protein-protein interaction or binding affinity assay. In certain embodiments, an anti-Cripto antibody binds to an epitope of Cripto that is conserved among Cripto from different species. In certain preferred embodiments, an anti-Cripto antibody binds to human Cripto. In some embodiments, an anti-Cripto antibody may inhibit one or more GDF ligands (e.g., GDF8, activin (e.g., activin A, activin B, activin C, activin E, activin AB, activin AC, activin BC, activin AE and activin BE), GDF11, GDF1, GDF3, and/or Nodal) from binding to Cripto. In some embodiments, an anti-Cripto antibody is a multispecific antibody (e.g., bi-specific antibody) that binds to Cripto and one or more GDF ligands (e.g., GDF11, GDF8, activin (e.g., activin A, activin B, activin C, activin E, activin AB, activin AC), GDF3, GDF1, and/or Nodal), one or more type II receptors (e.g., ActRIIA and/or ActRIIB), type I receptors (e.g., ALK4, ALK7, and/or ALK5), and/or an additional co-receptor (e.g., Cryptic and/or Cryptic 1B). In some embodiments, the disclosure relates to combinations of antibodies, and uses thereof, wherein the combination of antibodies comprises an anti-Cripto antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF3, GDF1, and/or Nodal), type II receptors (e.g., ActRIIA and/or ActRIIB), type I receptors (e.g., ALK4, ALK7, and/or ALK5), and/or an additional co-receptor (e.g., Cryptic and/or Cryptic 1B). In some embodiments, a multispecific antibody that binds to Cripto does not bind or does not substantially bind to activin B (e.g., binds to activin B with a $K_D$ of greater than $1\times10^{-7}$ M or has relatively modest binding, e.g., about $1\times10^{-8}$ M or about $1\times10^{-9}$ M). In some embodiments, a combination of antibodies that comprises a Cripto antibody does not comprise an activin B antibody.

In certain aspects, an activin and/or GDF antagonist antibody, or combination of antibodies, is an antibody that inhibits at least Cryptic. Therefore, in some embodiments, an activin and/or GDF antagonist antibody, or combination of antibodies, binds to at least Cryptic. As used herein, a Cryptic antibody (anti-Cryptic antibody) generally refers to an antibody that binds to Cryptic with sufficient affinity such that the antibody is useful as a diagnostic and/or therapeutic agent in targeting Cryptic. In certain embodiments, the extent of binding of an anti-Cryptic antibody to an unrelated, non-Cryptic protein is less than about 10%, 9%, 8%, 7%, 6%, 5%, 4%, 3%, 2%, or less than about 1% of the binding of the antibody to Cryptic as measured, for example, by a radioimmunoassay (RIA), Biacore, or other protein-protein interaction or binding affinity assay. In certain embodiments, an anti-Cryptic antibody binds to an epitope of Cryptic that is conserved among Cryptic from different species. In certain preferred embodiments, an anti-Cryptic antibody binds to human Cryptic. In some embodiments, an anti-Cryptic antibody may inhibit one or more GDF ligands (e.g., GDF8, activin (e.g., activin A, activin B, activin C, activin E, activin AB, activin AC, activin BC, activin AE and activin BE), GDF11, GDF1, GDF3, and/or Nodal) from binding to Cryptic. In some embodiments, an anti-Cryptic antibody is a multispecific antibody (e.g., bi-specific antibody) that binds to Cryptic and one or more GDF ligands (e.g., GDF11, GDF8, activin (e.g., activin A, activin B, activin C, activin E, activin AB, activin AC), GDF3, GDF1, and/or Nodal), type II receptors (e.g., ActRIIA and/or ActRIIB), type I receptors (e.g., ALK4, ALK7, and/or ALK5), and/or an additional co-receptor (e.g., Cripto and/or Cryptic 1B). In some embodiments, the disclosure relates to combinations of antibodies, and uses thereof, wherein the combination of antibodies comprises an anti-Cryptic antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF3, GDF1, and/or Nodal), type II receptors (e.g., ActRIIA and/or ActRIIB), type I receptors (e.g., ALK4, ALK7, and/or ALK5), and/or an additional co-receptor (e.g., Cripto and/or Cryptic 1B). In some embodiments, a multispecific antibody that binds to Cryptic does not bind or does not substantially bind to activin B (e.g., binds to activin B with a $K_D$ of greater than $1\times10^{-7}$ M or has relatively modest binding, e.g., about $1\times10^{-8}$ M or about $1\times10^{-9}$ M). In some embodiments, a combination of antibodies that comprises a Cryptic antibody does not comprise an activin B antibody.

In certain aspects, an activin and/or GDF antagonist antibody, or combination of antibodies, is an antibody that inhibits at least Cryptic 1B. Therefore, in some embodiments, an activin and/or GDF antagonist antibody, or combination of antibodies, binds to at least Cryptic 1B. As used herein, a Cryptic 1B antibody (anti-Cryptic 1B antibody) generally refers to an antibody that binds to Cryptic 1B with sufficient affinity such that the antibody is useful as a diagnostic and/or therapeutic agent in targeting Cryptic 1B. In certain embodiments, the extent of binding of an anti-Cryptic 1B antibody to an unrelated, non-Cryptic 1B protein is less than about 10%, 9%, 8%, 7%, 6%, 5%, 4%, 3%, 2%, or less than about 1% of the binding of the antibody to Cryptic 1B as measured, for example, by a radioimmunoassay (RIA), Biacore, or other protein-protein interaction or binding affinity assay. In certain embodiments, an anti-Cryptic 1B antibody binds to an epitope of Cryptic 1B that is conserved among Cryptic 1B from different species. In certain preferred embodiments, an anti-Cryptic 1B antibody binds to human Cryptic 1B. In some embodiments, an anti-Cryptic 1B antibody may inhibit one or more GDF ligands (e.g., GDF8, activin (e.g., activin A, activin B, activin C, activin E, activin AB, activin AC, activin BC, activin AE and activin BE), GDF11, GDF1, GDF3, and/or Nodal) from binding to Cryptic 1B. In some embodiments, an anti-Cryptic 1B antibody is a multispecific antibody (e.g., bi-specific antibody) that binds to Cryptic 1B and one or more GDF ligands (e.g., GDF11, GDF8, activin (e.g., activin A, activin B, activin C, activin E, activin AB, activin AC), GDF3, GDF1, and/or Nodal), type II receptors (e.g., ActRIIA and/or ActRIIB), type I receptors (e.g., ALK4, ALK7, and/or ALK5), and/or an additional co-receptor (e.g., Cripto and/or Cryptic). In some embodiments, the disclosure relates to combinations of antibodies, and uses thereof, wherein the combination of antibodies comprises an anti-Cryptic 1B antibody and one or more additional antibodies that bind to, for example, one or more GDF ligands (e.g., GDF11, GDF8, activin (e.g., activin A, activin B, activin C, activin E, activin AB, activin AC, activin BC, activin AE and activin BE), GDF3, GDF1, and/or Nodal), type II receptors (e.g., ActRIIA and/or ActRIIB), type I receptors (e.g., ALK4, ALK7, and/or ALK5), and/or an additional co-receptor (e.g., Cripto and/or Cryptic). In some embodiments, a multispecific antibody that binds to Cryptic 1B does not bind or does not substantially bind to activin B (e.g., binds to activin B with a $K_D$ of greater than $1\times10^{-7}$ M or has relatively modest binding, e.g., about $1\times10^{-8}$ M or about $1\times10^{-9}$ M). In some embodiments, a combination of antibodies that comprises a Cryptic 1B antibody does not comprise an activin B antibody.

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; diabodies; linear antibodies; single-chain antibody molecules (e.g., scFv); and multispecific antibodies formed from antibody fragments [see, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894; 5,587,458; and 5,869,046]. Diabodies are antibody fragments with two antigen-binding sites that may be bivalent or bispecific [see, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448]. Triabodies and tetrabodies are also described in Hudson et al. (2003) Nat. Med. 9:129-134. Single-domain antibodies are antibody fragments comprising all or a portion of the heavy-chain variable domain or all or a portion of the light-chain variable domain of an antibody. In certain embodiments, a single-domain antibody is a human single-domain antibody (see, e.g., U.S. Pat. No. 6,248,516). Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In certain preferred embodiments, the antibodies of the present disclosure are isolated antibodies. In certain preferred embodiments, the antibodies of the present disclosure are recombinant antibodies.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, IgG$_1$, IgG$_2$, IgG$_3$, IgG$_4$, IgA$_1$, and IgA$_2$. The heavy chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, Biacore, radiolabeled antigen-binding assay (RIA), and ELISA. In some embodiments, antibodies of the present disclosure bind to their target antigens (e.g., ActRIIB, ActRIIA, ALK4, ALK5, ALK7, activin, GDF11, GDF8, GDF3, GDF1, Nodal, Cryptic, Cryptic 1, and/or Cripto) with at least a $K_D$ of $1\times10^{-7}$ or stronger, $1\times10^{-8}$ or stronger, $1\times10^{-9}$ or stronger, $1\times10^{-10}$ or stronger, $1\times10^{-11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radiolabeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (approximately 23° C.). In a non-adsorbent plate, radiolabeled antigen are mixed with serial dilutions of a Fab of interest [e.g., consistent with assessment of the anti-VEGF antibody, Fab-12, in Presta et al. (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE®3000 (BIAcore, Inc., Piscataway, N.J.) with immobilized antigen CM5 chips at about 10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ (see, e.g., Chen et al., (1999) *J. Mol. Biol.* 293:865-881). If the on-rate exceeds, for example, $10^6$ $M^{-1}$ $s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophometer (Aviv Instruments) or a 8000-series SLM-AMINCO® spectrophotometer (ThermoSpectronic) with a stirred cuvette.

Antibody fragments can be made by various techniques, including but not limited to proteolytic digestion of an intact antibody as well as production by recombinant host cells (e.g., *E. coli* or phage), as described herein. The nucleic acid and amino acid sequences of human ActRIIA, ActRIIB, ALK4, ALK5, ALK7, activin (activin A, activin B, activin C, activin E, activin AC, activin AB, activin BC, activin BE, and/or activin AE), GDF11, GDF8, GDF1, GDF3, Nodal, Cryptic, Cryptic 1B, and Cripto are known in the art. In addition, numerous methods for generating antibodies are well known in the art, some of which are described herein. Therefore antibody antagonists for use in accordance with this disclosure may be routinely made by the skilled person in the art based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) *Proc. Natl. Acad. Sci. USA,* 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Humanized antibodies and methods of making them are reviewed, for example, in Almagro and Fransson (2008) *Front. Biosci.* 13:1619-1633 and are further described, for example, in Riechmann et al., (1988) *Nature* 332:323-329; Queen et al. (1989) *Proc. Nat'l Acad. Sci. USA* 86:10029-10033; U.S. Pat. Nos. 5,821,337; 7,527,791; 6,982,321; and U.S. Pat. No. 7,087,409; Kashmiri et al., (2005) *Methods* 36:25-34 [describing SDR (a-CDR) grafting]; Padlan, *Mol. Immunol.* (1991) 28:489-498 (describing "resurfacing"); Dall'Acqua et al. (2005) *Methods* 36:43-60 (describing "FR shuffling"); Osbourn et al. (2005) *Methods* 36:61-68; and Klimka et al. *Br. J. Cancer* (2000) 83:252-260 (describing the "guided selection" approach to FR shuffling). Human framework regions that may be used for humanization include but are not limited to: framework regions selected using the "best-fit" method (see, e.g., Sims et al. (1993) *J. Immunol.* 151:2296); framework regions derived from the consensus sequence of human antibodies of a particular subgroup of light or heavy chain variable regions (see, e.g., Carter et al. (1992) *Proc. Natl. Acad. Sci. USA,* 89:4285; and Presta et al. (1993) *J. Immunol.,* 151:2623); human processed (somatically mutated) framework regions or human germline framework regions (see, e.g., Almagro and Fransson (2008) *Front. Biosci.* 13:1619-1633); and framework regions derived from screening FR libraries (see, e.g., Baca et al., (1997) *J. Biol. Chem.* 272:10678-10684; and Rosok et al., (1996) *J. Biol. Chem.* 271:22611-22618).

In certain embodiments, an antibody provided herein is a human antibody. Human antibodies can be produced using various techniques known in the art. Human antibodies are described generally in van Dijk and van de Winkel (2008) *Curr. Opin. Pharmacol.* 5: 368-74 (2001) and Lonberg, *Curr. Opin. Immunol.* 20:450-459. For example, human antibodies may be prepared by administering an immunogen (e.g., a GDF11 polypeptide, an activin B polypeptide, an ActRIIA polypeptide, or an ActRIIB polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals see, for example, Lonberg (2005) *Nat. Biotech.* 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described (see, e.g., Kozbor *J. Immunol.*, (1984) 133: 3001; Brodeur et al. (1987) Monoclonal Antibody Production Techniques and Applications, pp. 51-63, Marcel Dekker, Inc., New York; and Boerner et al. (1991) *J. Immunol.*, 147: 86). Human antibodies generated via human B-cell hybridoma technology are also described in Li et al., (2006) *Proc. Natl. Acad. Sci. USA*, 103:3557-3562. Additional methods include those described, for example, in U.S. Pat. No. 7,189,826 (describing production of monoclonal human IgM antibodies from hybridoma cell lines) and Ni, *Xiandai Mianyixue* (2006) 26(4):265-268 (2006) (describing human-human hybridomas). Human hybridoma technology (Trioma technology) is also described in Vollmers and Brandlein (2005) *Histol. Histopathol.*, 20(3):927-937 (2005) and Vollmers and Brandlein (2005) *Methods Find Exp. Clin. Pharmacol.*, 27(3):185-91. Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are known in the art and described herein.

For example, antibodies of the present disclosure may be isolated by screening combinatorial libraries for antibodies with the desired activity or activities. A variety of methods are known in the art for generating phage display libraries and screening such libraries for antibodies possessing the desired binding characteristics. Such methods are reviewed, for example, in Hoogenboom et al. (2001) in *Methods in Molecular Biology* 178:1-37, O'Brien et al., ed., Human Press, Totowa, N.J. and further described, for example, in the McCafferty et al. (1991) *Nature* 348:552-554; Clackson et al., (1991) *Nature* 352: 624-628; Marks et al. (1992) *J. Mol. Biol.* 222:581-597; Marks and Bradbury (2003) in *Methods in Molecular Biology* 248:161-175, Lo, ed., Human Press, Totowa, N.J.; Sidhu et al. (2004) *J. Mol. Biol.* 338(2):299-310; Lee et al. (2004) *J. Mol. Biol.* 340(5):1073-1093; Fellouse (2004) *Proc. Natl. Acad. Sci. USA* 101(34): 12467-12472; and Lee et al. (2004) *J. Immunol. Methods* 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., activin A) without the requirement of constructing hybridomas. Alternatively, the naive repertoire can be cloned (e.g., from human) to provide a single source of antibodies to a wide range of non-self and also self-antigens without any immunization as described by Griffiths et al. (1993) *EMBO J*, 12: 725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992) *J. Mol. Biol.*, 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) that have binding specificities for at least two different epitopes (e.g., two, three, four, five, or six or more) on one or more (e.g., two, three, four, five, six or more) antigens.

Techniques for making multispecific antibodies include, but are not limited to, recombinant co-expression of two immunoglobulin heavy-chain/light-chain pairs having different specificities [see, e.g., Milstein and Cuello (1983) *Nature* 305: 537; International patent publication no. WO 93/08829; and Traunecker et al. (1991) *EMBO J.* 10: 3655, and U.S. Pat. No. 5,731,168 ("knob-in-hole" engineering)]. Multispecific antibodies may also be made by engineering electrostatic steering effects for making antibody Fc-heterodimeric molecules (see, e.g., WO 2009/089004A1); cross-linking two or more antibodies or fragments [see, e.g., U.S. Pat. No. 4,676,980; and Brennan et al. (1985) *Science*, 229: 81]; using leucine zippers to produce bispecific antibodies [see, e.g., Kostelny et al. (1992) *J. Immunol.*, 148 (5):1547-1553]; using "diabody" technology for making bispecific antibody fragments [see, e.g., Hollinger et al. (1993) *Proc. Natl. Acad. Sci. USA*, 90:6444-6448]; using single-chain Fv (sFv) dimers (see, e.g., Gruber et al. (1994) *J. Immunol.*, 152:5368); and preparing trispecific antibodies (see, e.g., Tutt et al. (1991) *J. Immunol.* 147: 60. Multispecific antibodies can be prepared as full-length antibodies or antibody fragments. Engineered antibodies with three or more functional antigen-binding sites, including "Octopus antibodies," are also included herein [see, e.g., US 2006/0025576A1].

In certain embodiments, an antibody disclosed herein is a monoclonal antibody. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from activin, anti-protein/anti-peptide antisera or monoclonal antibodies can be made by standard protocols [see, e.g., Antibodies: A Laboratory Manual ed. by Harlow and Lane (1988) Cold Spring Harbor Press: 1988]. A mammal, such as a mouse, hamster, or rabbit, can be immunized with an immunogenic form of the activin polypeptide, an antigenic fragment which is capable of eliciting an antibody response, or a fusion protein. Techniques for conferring immunogenicity on a protein or peptide include conjugation to carriers or other techniques well known in the art. An immunogenic portion of a activin polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of activin, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (see, e.g., Kohler and Milstein (1975) *Nature*, 256: 495-497), the human B cell hybridoma technique (see, e.g., Kozbar et al. (1983) *Immunology Today*, 4:72), and the EBV-hybridoma technique to produce human monoclonal antibodies (Cole et al. (1985) Monoclonal Antibodies and Cancer Therapy, Alan R. Liss, Inc. pp. 77-96). Hybridoma cells can be screened immunochemically for production of antibodies specifically reactive with an activin polypeptide, and monoclonal antibodies isolated from a culture comprising such hybridoma cells.

In certain embodiments, one or more amino acid modifications may be introduced into the Fc region of an antibody provided herein thereby generating an Fc region variant. The Fc region variant may comprise a human Fc region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet certain effector functions (e.g., complement-dependent cytotoxicity (CDC) and antibody-dependent cellular cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in, for example, Ravetch and Kinet (1991) *Annu. Rev. Immunol.* 9:457-492. Non-limiting examples of in vitro assays to assess ADCC activity of a molecule of interest are described in U.S. Pat. No. 5,500,362; Hellstrom, I. et al. (1986) *Proc. Natl. Acad. Sci. USA* 83:7059-7063]; Hellstrom, I et al. (1985) *Proc. Natl. Acad. Sci. USA* 82:1499-1502; U.S. Pat. No. 5,821,337; Bruggemann, M. et al. (1987) *J. Exp. Med.* 166:1351-1361. Alternatively, non-radioactive assays methods may be employed (e.g., ACTI™ non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) *Proc. Natl. Acad. Sci. USA* 95:652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, e.g, Gazzano-Santoro et al. (1996) *J. Immunol. Methods* 202:163; Cragg, M. S. et al. (2003) *Blood* 101:1045-1052; and Cragg, M. S, and M. J. Glennie (2004) *Blood* 103:2738-2743). FcRn binding and in vivo clearance/half-life determinations can also be performed using methods known in the art [see, e.g., Petkova, S. B. et al. (2006) Intl. Immunol. 18(12):1759-1769]. Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interactions between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Maryland), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into and/or substitutions of residues within the amino acid sequences of the antibody and/or binding polypeptide. Any combination of deletion, insertion, and substitution can be made to arrive at the final construct, provided that the final construct possesses the desired characteristics, e.g., target-binding (e.g., and activin such as activin E and/or activin C binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process [see, e.g., Chowdhury (2008) Methods Mol. Biol. 207:179-196 (2008)], and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of the antibody and/or the binding polypeptide that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody-antigen is affected. Further substitutions may be introduced at the amino acid locations demonstrating functional sensitivity to the initial substitutions. Alternatively, or additionally, a crystal structure of an antigen-antibody complex is determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional nonproteinaceous moieties that are known in the art and readily available. The moieties suitable for derivatization of the antibody and/or binding polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

6. Small Molecule Antagonists

In other aspects, an activin and/or GDF antagonist to be used in accordance with the methods and uses described herein is a small molecule (activin and/or GDF small molecule antagonist), or combination of small molecule antagonists. A GDF small molecule antagonist, or combination of small molecule antagonists, may inhibit, for example, one or more GDF ligands (e.g., activin. (e.g., activin A, activin B, activin AB, activin C, activin AC, activin BC, activin E, activin AE, and/or activin BE), GDF11, GDF8, GDF3, GDF1, and/or Nodal), a type I receptor (e.g., ALK4, ALK5, and/or ALK7), a type II receptor (e.g., ActRIIB and/or ActRIIA), a co-receptor (e.g., Cripto, Cryptic, and/or Cryptic 1B), and/or a Smad polypeptide (e.g., Smad2 and/or Smad3). In some embodiments, a GDF small molecule antagonist, or combination of small molecule antagonists, inhibits signaling mediated by one or more GDF ligands, for example, as determined in a cell-based assay such as those described herein. As described herein, GDF small molecule antagonists may be used, alone or in combination with one or more supportive therapies or active agents, to treat or reduce the progression rate, frequency, and/or severity of kidney diseases, particularly treating, preventing or reducing the progression rate, frequency, and/or severity of one or more kidney disease-associated complications (e.g., kidney tissue damage, fibrosis, and/or inflammation).

In some embodiments, a GDF small molecule antagonist, or combination of small molecule antagonists, inhibits at least GDF11, optionally further inhibiting one or more of GDF8, activin (e.g., activin A, activin B, activin C, activin E, activin AB, activin AC, activin BC, activin AE and/or activin BE), GDF3, GDF1, Nodal, ActRIIA, ActRIIB, ALK4, ALK5, ALK7, Cripto, Cryptic, Cryptic 1B, Smad2, and Smad3. In some embodiments, a GDF small molecule antagonist, or combination of small molecule antagonists, inhibits at least GDF8, optionally further inhibiting one or more of GDF11, activin (e.g., activin A, activin B, activin C, activin E, activin AB, activin AC, activin BC, activin AE and/or activin BE), GDF3, GDF1, Nodal, ActRIIA, ActRIIB, ALK4, ALK5, ALK7, Cripto, Cryptic, Cryptic 1B, Smad2, and Smad3. In some embodiments, a GDF small molecule antagonist, or combination of small molecule antagonists, inhibits at least activin (activin A, activin B, activin C, activin E, activin AB, activin AC, activin BC, activin AE and/or activin BE), optionally further inhibiting one or more of GDF8, GDF11, GDF3, GDF1, Nodal, ActRIIA, ActRIIB, ALK4, ALK5, ALK7, Cripto, Cryptic, Cryptic 1B, Smad2, and Smad3. In some embodiments, a GDF small molecule antagonist, or combination of small molecule antagonists, inhibits at least activin B, optionally further inhibiting one or more of activin (e.g., activin A, activin C, activin E, activin AB, activin AC, activin BC, activin AE and/or activin BE), GDF8, GDF11, GDF3, GDF1, Nodal, ActRIIA, ActRIIB, ALK4, ALK5, ALK7, Cripto, Cryptic, Cryptic 1B, Smad2, and Smad3. In some embodiments, a GDF small molecule antagonist, or combination of small molecule antagonists, inhibits at least activin A, optionally further inhibiting one or more of activin (e.g., activin B, activin C, activin E, activin AB, activin AC, activin BC, activin AE and/or activin BE), GDF8, GDF11, GDF3, GDF1, Nodal, ActRIIA, ActRIIB, ALK4, ALK5, ALK7, Cripto, Cryptic, Cryptic 1B, Smad2, and Smad3. In some embodiments, a GDF small molecule antagonist, or combination of small molecule antagonists, inhibits at least GDF1, optionally further inhibiting one or more of GDF8, activin (e.g., activin A, activin B, activin C, activin E, activin AB, activin AC, activin BC, activin AE and/or activin BE), GDF3, GDF11, Nodal, ActRIIA, ActRIIB, ALK4, ALK5, ALK7, Cripto, Cryptic, Cryptic 1B, Smad2, and Smad3. In some embodiments, a GDF small molecule antagonist, or combination of small molecule antagonists, inhibits at least Nodal, optionally further inhibiting one or more of GDF8, activin (e.g., activin A, activin B, activin C, activin E, activin AB, activin AC, activin BC, activin AE and/or activin BE), GDF3, GDF1, GDF11, ActRIIA, ActRIIB, ALK4, ALK5, ALK7, Cripto, Cryptic, Cryptic 1B, Smad2, and Smad3. In some embodiments, a GDF small molecule antagonist, or combination of small molecule antagonists, inhibits at least GDF3, optionally further inhibiting one or more of GDF8, activin (e.g., activin A, activin B, activin C, activin E, activin AB, activin AC, activin BC, activin AE and/or activin BE), GDF11, GDF1, Nodal, ActRIIA, ActRIIB, ALK4, ALK5, ALK7, Cripto, Cryptic, Cryptic, Smad2, and Smad3. In some embodiments, a GDF small molecule antagonist, or combination of small molecule antagonists, inhibits at least Cripto, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK4, ALK5, ALK7, Cryptic, Cryptic, Smad2, and Smad3. In some embodiments, a GDF small molecule antagonist, or combination of small molecule antagonists, inhibits at least Cryptic, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK4, ALK5, ALK7, Cripto, Cryptic 1B, Smad2, and Smad3. In some embodiments, a GDF small molecule antagonist, or combination of small molecule antagonists, inhibits at least Cryptic 1B, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK4, ALK5, ALK7, Cripto, Cryptic, Smad2, and Smad3. In some embodiments, a GDF small molecule antagonist, or combination of small molecule antagonists, inhibits at least ActRIIA, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIB, ALK4, ALK5, ALK7, Cripto, Cryptic 1B, Cryptic, Smad2, and Smad3. In some embodiments, a GDF small molecule antagonist, or combination of small molecule antagonists, inhibits at least ActRIIB, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ALK4, ALK5, ALK7, Cripto, Cryptic 1B, Cryptic, Smad2, and Smad3. In some embodiments, a GDF small molecule antagonist, or combination of small molecule antagonists, inhibits at least ALK4, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK5, ALK7, Cripto, Cryptic 1B, Cryptic, Smad2, and Smad3. In some embodiments, a GDF small molecule antagonist, or combination of small molecule antagonists, inhibits at least ALK5, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK4, ALK7, Cripto, Cryptic 1B, Cryptic, Smad2, and Smad3. In some embodiments, a GDF small molecule antagonist, or combination of small molecule antagonists, inhibits at least ALK7, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK5, ALK4, Cripto, Cryptic 1B, Cryptic, Smad2, and Smad3. In some embodiments, a GDF small molecule antagonist, or combination of small molecule antagonists, inhibits at least Smad2, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK5, ALK4, ALK7, Cripto, Cryptic 1B, Cryptic, and Smad3. In some embodiments, a GDF small molecule antagonist, or combination of small molecule antagonists, inhibits at least Smad3, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK5, ALK4, ALK7, Cripto, Cryptic 1B, Cryptic, and Smad2. In some embodiments, a GDF small molecule antagonist, or combination of small molecule antagonists, as disclosed herein does not inhibit or does not substantially inhibit activin B. In some embodiments, a GDF small molecule antagonist, or combination of small molecule antagonists, as disclosed herein does not inhibit or does not substantially inhibit activin A. GDF small molecule antagonists can be direct or indirect inhibitors. For example, an indirect small molecule antagonist, or combination of small molecule antagonists, may inhibit the expression (e.g., transcription, translation, cellular secretion, or combinations thereof) of at least one or more GDF ligands (e.g., activin (e.g., activin A, activin B, activin C, activin E, activin AB, activin AC, activin BC, activin AE, or activin BE), GDF11, GDF1, Nodal, GDF3, and/or GDF8), type I receptors (e.g., ALK4, ALK5, and/or ALK7), type II receptors (e.g., ActRIIA and/or ActRIIB), co-receptors (e.g., Cryptic, Cryptic 1B, and/or Cripto), and/or one or more downstream signaling components (e.g., Smads, such as Smad2 and Smad3). Alternatively, a direct small molecule antagonist, or combination of small molecule antagonists, may directly bind to and inhibit, for example, one or more one or more GDF ligands (e.g., activin (e.g., activin A, activin B, activin C, activin E, activin AB, activin AC, activin BC, activin AE, or activin BE), GDF11, GDF1, Nodal, GDF3, and/or GDF8), type I receptor (e.g., ALK4, ALK5 and/or ALK7), type II receptors (e.g., ActRIIA and/or ActRIIB), co-receptors (e.g., Cryptic, Cryptic 1B, and/or Cripto), and/or one or more downstream signaling components (e.g., Smads, such as Smad2 and Smad3). Combinations of one or more indirect and one or more direct GDF small molecule antagonists may be used in accordance with the methods disclosed herein.

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

7. Polynucleotide Antagonists

In other aspects, an activin and/or GDF antagonist to be used in accordance with the methods and uses disclosed herein is a polynucleotide (activin and/or GDF polynucleotide antagonist), or combination of polynucleotides. A GDF polynucleotide antagonist, or combination of polynucleotide antagonists, may inhibit, for example, one or more GDF ligands (e.g., activin (e.g., activin A, activin B, activin C, activin E, activin AB, activin AC, activin BC, activin AE, or activin BE), GDF11, GDF8, GDF3, GDF1, and/or Nodal), type I receptors (e.g., ALK4, ALK5, and/or ALK7), type II receptors (e.g., ActRIIA and/or ActRIIB), co-receptors (e.g., Cryptic, Cryptic 1B, and/or Cripto), and/or one or more downstream signaling components (e.g., Smads, such as Smad2 and Smad3). In some embodiments, a GDF polynucleotide antagonist, or combination of polynucleotide antagonists, inhibits signaling mediated by one or more GDF ligands, for example, as determined in a cell-based assay such as those described herein. As described herein, GDF polynucleotide antagonists may be used, alone or in combination with one or more supportive therapies or active agents, to treat, or reduce the progression rate, frequency, and/or severity of kidney diseases, particularly treating, preventing or reducing the progression rate, frequency and/or severity of one or more kidney disease-associated complications (e.g., kidney tissue damage, fibrosis, and/or inflammation).

In some embodiments, a GDF polynucleotide antagonist, or combination of polynucleotide antagonists, inhibits at least GDF11, optionally further inhibiting one or more of GDF8, activin (e.g., activin A, activin B, activin C, activin E, activin AB, activin AC, activin BC, activin AE and/or activin BE), GDF3, GDF1, Nodal, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least GDF8, optionally further inhibiting one or more of GDF11, activin (e.g., activin A, activin B, activin C, activin E, activin AB, activin AC, activin BC, activin AE and/or activin BE), GDF3, GDF1, Nodal, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least activin (activin A, activin B, activin C, activin E, activin AB, activin AC, activin BC, activin AE and/or activin BE), optionally further inhibiting one or more of GDF8, GDF11, GDF3, GDF1, Nodal, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least activin A, optionally further inhibiting one or more of additional activin (e.g., activin B, activin C, activin E, activin AB, activin AC, activin BC, activin AE and/or activin BE), GDF8, GDF11, GDF3, GDF1, Nodal, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least activin B, optionally further inhibiting one or more of additional activin (activin A, activin C, activin E, activin AB, activin AC, activin BC, activin AE and/or activin BE), GDF8, GDF11, GDF3, GDF1, Nodal, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least GDF1, optionally further inhibiting one or more of GDF8, activin (e.g., activin A, activin B, activin C, activin E, activin AB, activin AC, activin BC, activin AE and/or activin BE), GDF3, GDF11, Nodal, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least Nodal, optionally further inhibiting one or more of GDF8, activin (e.g., activin A, activin B, activin C, activin E, activin AB, activin AC, activin BC, activin AE and/or activin BE), GDF3, GDF11, GDF1, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least GDF3, optionally further inhibiting one or more of GDF8, activin (e.g., activin A, activin B, activin C, activin E, activin AB, activin AC, activin BC, activin AE and/or activin BE), GDF1, GDF11, Nodal, ActRIIA, ActRIIB, ALK4, ALK5, ALK7, Cripto, Cryptic, Cryptic 1B, Smad2, and Smad3. In some embodiments, a GDF polynucleotide antagonist, or combination of polynucleotide antagonists, inhibits at least Cripto, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK4, ALK5, ALK7, Cryptic, Cryptic 1B, Smad2, and Smad3. In some embodiments, a GDF polynucleotide antagonist, or combination of polynucleotide antagonists, inhibits at least Cryptic, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK4, ALK5, ALK7, Cripto, Cryptic 1B, Smad2, and Smad3. In some embodiments, a GDF polynucleotide antagonist, or combination of polynucleotide antagonists, inhibits at least Cryptic 1B, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ActRIIB, ALK4, ALK5, ALK7, Cryptic, Cripto, Smad2, and Smad3. In some embodiments, a GDF polynucleotide antagonist, or combination of polynucleotide antagonists, inhibits at least ActRIIA, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIB, ALK4, ALK5, ALK7, Cryptic, Cryptic 1B, Cripto, Smad2, and Smad3. In some embodiments, a GDF polynucleotide antagonist, or combination of polynucleotide antagonists, inhibits at least ActRIIB, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIA, ALK4, ALK5, ALK7, Cryptic, Cryptic 1B, Cripto, Smad2, and Smad3. In some embodiments, a GDF polynucleotide antagonist, or combination of polynucleotide antagonists, inhibits at least ALK4, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIB, ActRIIA, ALK5, ALK7, Cryptic, Cryptic 1B, Cripto, Smad2, and Smad3. In some embodiments, a GDF polynucleotide antagonist, or combination of polynucleotide antagonists, inhibits at least ALK5, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIB, ActRIIA, ALK4, ALK7, Cryptic, Cryptic 1B, Cripto, Smad2, and Smad3. In some embodiments, a GDF polynucleotide antagonist, or combination of polynucleotide antagonists, inhibits at least ALK7, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIB, ActRIIA, ALK5, ALK4, Cryptic, Cryptic 1B, Cripto, Smad2, and Smad3. In some embodiments, a GDF polynucleotide antagonist, or combination of polynucleotide antagonists, inhibits at least Smad2, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIB, ActRIIA, ALK5, ALK4, ALK7, Cryptic, Cryptic 1B, Cripto, and Smad3. In some embodiments, a GDF polynucleotide antagonist, or combination of polynucleotide antagonists, inhibits at least Smad3, optionally further inhibiting one or more of GDF8, activin (e.g., activin A, activin B, activin C, activin E, activin AB, activin AC, activin BC, activin AE and/or activin BE), GDF11, GDF3, GDF1, Nodal, ActRIIB, ActRIIA, ALK5, ALK4, ALK7, Cryptic, Cryptic 1B, Cripto, and Smad2. In some embodiments, a GDF polynucleotide antagonist, or combination of polynucleotide antagonists, as disclosed herein does not inhibit or does not substantially inhibit activin B. In some embodiments, a GDF polynucleotide antagonist, or combination of polynucleotide antagonists, as disclosed herein does not inhibit or does not substantially inhibit activin A.

In some embodiments, the polynucleotide antagonists of the disclosure may be an antisense nucleic acid, an RNAi molecule (e.g., small interfering RNA (siRNA), small-hairpin RNA (shRNA), microRNA (miRNA)), an aptamer and/or a ribozyme. The nucleic acid and amino acid sequences of human GDF11, GDF8, activin (activin A, activin B, activin C, and activin E), GDF1, Nodal, GDF3, ActRIIA, ActRIIB, Cryptic, Cryptic 1B, Cripto, ALK4, ALK5, ALK7, Smad2, and Smad3 are known in the art. In addition, many different methods of generating polynucleotide antagonists are well known in the art. Therefore polynucleotide antagonists for use in accordance with this disclosure may be routinely made by the skilled person in the art based on the knowledge in the art and teachings provided herein.

Antisense technology can be used to control gene expression through antisense DNA or RNA, or through triple-helix formation. Antisense techniques are discussed, for example, in Okano (1991) *J. Neurochem.* 56:560; Oligodeoxynucleotides as Antisense Inhibitors of Gene Expression, CRC Press, Boca Raton, Fla. (1988). Triple-helix formation is discussed in, for instance, Cooney et al. (1988) Science 241:456; and Dervan et al., (1991) *Science* 251:1300. The methods are based on binding of a polynucleotide to a complementary DNA or RNA. In some embodiments, the antisense nucleic acids comprise a single-stranded RNA or DNA sequence that is complementary to at least a portion of an RNA transcript of a gene disclosed herein. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well (see, e.g., Wagner, R., (1994) *Nature* 372:333-335). Thus, oligonucleotides complementary to either the 5'- or 3'-non-translated, non-coding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-, 3'- or coding region of an mRNA of the disclosure, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In one embodiment, the antisense nucleic acid of the present disclosure is produced intracellularly by transcription from an exogenous sequence. For example, a vector or a portion thereof is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) *Nature* 290:304-310], the promoter contained in the 3' long-terminal repeat of Rous sarcoma virus [see, e.g., Yamamoto et al. (1980) *Cell* 22:787-797], the herpes thymidine promoter [see, e.g., Wagner et al. (1981) *Proc. Natl. Acad. Sci. U.S.A.* 78:1441-1445], and the regulatory sequences of the metallothionein gene [see, e.g., Brinster, et al. (1982) *Nature* 296:39-42].

In some embodiments, the polynucleotide antagonists are interfering RNA (RNAi) molecules that target the expression of one or more of: GDF11, GDF8, activin (activin A, activin B, activin C, and activin E), GDF1, GDF3, ActRIIA, ActRIIB, Cryptic, Cryptic 1B, Cripto, ALK4, ALK5, ALK7, Smad2, and Smad3 RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g., at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. (*Genes & Dev.* (2002) 16:948-958, 2002) have used small RNA molecules folded into hairpins as a means to affect RNAi. Accordingly, such short-hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure, which are subsequently processed into processed miRNA after further processing through the RISC.

Molecules that mediate RNAi, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule. The generation and therapeutic use of aptamers are well established in the art (see, e.g., U.S. Pat. No. 5,475,096). Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096; 5,580,737; 5,567,588; 5,707, 796; 5,763,177; 6,011,577; and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield nucleic acid ligands which bind with high affinity and specificity to the target molecule.

Typically, such binding molecules are separately administered to the animal [see, e.g., O'Connor (1991) *J. Neurochem.* 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

8. Follistatin and FLRG Antagonists

In other aspects, an activin and/or GDF antagonist is a follistatin or FLRG polypeptide. As described herein, follistatin and/or FLRG polypeptides may be used to treat or reduce the progression rate, frequency, and/or severity of kidney disease, particularly treating, preventing or reducing the progression rate, frequency, and/or severity of one or more kidney disease-associated complications (e.g., kidney tissue damage, fibrosis, and/or inflammation).

The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. In certain preferred embodiments, follistatin polypeptides of the disclosure bind to and/or inhibit activin activity, particularly activin A. Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 150 and 151, the follistatin N-terminal domain, FSD2, and to a lesser extent FSD1 represent exemplary domains within follistatin that are important for activin binding. In addition, methods for making and testing libraries of polypeptides are described above in the context of ActRII polypeptides, and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the processed follistatin polypeptide or shorter isoforms or other variants of the human follistatin precursor polypeptide as described, for example, in WO2005/025601.

Follistatin is a single-chain polypeptide that can have a range of molecular weights from 31 to 49 kDa based on alternative mRNA splicing and variable glycosylation of the protein. Alternatively spliced mRNAs from the follistatin gene encode isoforms of 288 amino acids (i.e., FST288, SEQ ID NO: 150) and 315 amino acids (i.e., FST315, SEQ ID NO: 151), and the latter can be processed proteolytically to yield yet another isoform, follistatin 303 (FST303). Analysis of the amino acid sequence of native human follistatin polypeptide has revealed that it comprises five domains: a signal sequence (amino acids 1-29 of SEQ ID NO: 150), an N-terminal domain ($FST_{ND}$) (amino acids 30-94 of SEQ ID NO: 150), follistatin domain-1 ($FST_{FD1}$) (amino acids 95-164 of SEQ ID NO: 150), follistatin domain-2 ($FST_{FD2}$) (amino acids (168-239 of SEQ ID NO:1), and follistatin domain-3 ($FST_{FD3}$) (amino acids 245-316 of SEQ ID NO: 150). See Shimanski et al (1988) *Proc Natl Acad Sci USA* 85:4218-4222.

The human follistatin-288 (FST288) precursor has the amino acid sequence of SEQ ID NO: 150 (NCBI Reference Sequence NP_006341; Uniprot P19883-2), with the signal peptide indicated by dotted underline, the N-terminal domain ($FST_{ND}$) indicated by dashed underline, and the follistatin domains 1-3 ($FST_{FD1}$, $FST_{FD2}$, $FST_{FD3}$) indicated by solid underline.

The Processed human follistatin variant FST288 has the amino acid sequence of SEQ ID NO: 152, with the N-terminal domain indicated by dashed underline and the follistatin domains 1-3 indicated by solid underline. Moreover, it will be appreciated that any of the initial amino acids G or N, prior to the first cysteine may be removed by processing or intentionally eliminated without any consequence, and polypeptides comprising such slightly smaller polypeptides are further included.

The human follistatin-315 (FST315) precursor has the amino acid sequence of SEQ ID NO: 151 (NCBI Reference Sequence NP_037541.1; Uniprot P19883), with the signal peptide indicated by dotted underline, the N-terminal domain ($FST_{ND}$) indicated by dashed underline, and the follistatin domains 1-3 ($FST_{FD1}$, $FST_{FD2}$, $FST_{FD3}$) indicated by solid underline. The last 27 residues which represent the C-terminal extension distinguish this follistatin isoform from the shorter follistatin isoform FST288.

Processed human FST315 has the amino acid sequence of SEQ ID NO: 153, with the N-terminal domain indicated by dashed underline and the follistatin domains 1-3 indicated by solid underline. Moreover, it will be appreciated that any of the initial amino acids G or N, prior to the first cysteine may be removed by processing or intentionally eliminated without any consequence, and polypeptides comprising such slightly shorter polypeptides are further included.

Follistatin-related polypeptides of the disclosure may include any naturally occurring domain of a follistatin protein as well as variants thereof (e.g., mutants, fragments, and peptidomimetic forms) that retain a useful activity. For example, it is well-known that FST315 and FST288 have high affinity for myostatin, activins (activin A and activin B), and GDF11 and that the follistatin domains (e.g., $FST_{ND}$, $FST_{FD1}$, $FST_{FD2}$, and $FST_{FD3}$) are thought to be involved in the binding of such TGFβ ligands. However, there is evidence that each of these four domains has a different affinity for these TGF-β ligands. For example, a recent study has demonstrated that polypeptide constructs comprising only the N-terminal domain and two $FST_{FD1}$ domains in tandem retained high affinity for myostatin, demonstrated little or no affinity for activins, and promoted systemic muscle growth when introduced into a mouse by gene expression (Nakatani et al (2008) *FASEB* 22:478-487). Accordingly, the present disclosure encompasses, in part, variant follistatin proteins that demonstrate selective binding and/or inhibition of a given TGFβ ligand relative to a naturally occurring FST protein (e.g., maintaining high-affinity for myostain while having a significantly reduced affinity for activin).

An $FST_{FD1}$ sequence may be advantageously maintained in structural context by expression as a polypeptide further comprising the $FST_{ND}$ domain. Accordingly, the disclosure includes polypeptides comprising the $FST_{ND}$-$FST_{FD1}$ sequence, as set forth in SEQ ID NO: 154, and, for example, one or more heterologous polypeptides, and moreover, it will be appreciated that any of the initial amino acids G or N, prior to the first cysteine may be removed by processing or intentionally eliminated without any consequence, and polypeptides comprising such slightly shorter polypeptides are further included.

As demonstrated by Nakatani et al., a $FST_{ND}$-$FST_{FD1}$-$FST_{FD1}$ construct is sufficient to confer systemic muscle growth when genetically expressed in a mouse, and accordingly the disclosure includes polypeptides comprising the amino acid sequence of SEQ ID NO: 155 and, for example, one or more heterologous polypeptides.

While the $FST_{FD1}$ sequence confers myostatin and GDF11 binding, it has been demonstrated that activins, particularly activin A but also activin B, are also negative regulators of muscle, and therefore a follistatin polypeptide that inhibits both the myostatin/GDF11 ligand group and the activin A/activin B ligand group may provide a more potent muscle effect. Given that $FST_{FD2}$ confers activin A and B binding, the disclosure provides polypeptides comprising $FST_{FD1}$-$FST_{FD2}$ (SEQ ID NO: 156) and $FST_{FD1}$-$FST_{FD2}$-$FST_{FD3}$ (SEQ ID NO: 157), as well as constructs comprising $FST_{ND}$-$FST_{FD1}$-$FST_{FD2}$ (SEQ ID NO: 158) and, for example, one or more heterologous polypeptides.

A follistatin polypeptide of 291 amino acids (representing a truncation of the naturally occurring FST315) may have advantageous properties in certain embodiments. Accordingly, unprocessed (SEQ ID NO: 159) and processed FST291 (SEQ ID NO: 160) polypeptides are included in the disclosure and may be combined with heterologous proteins. Moreover, it will be appreciated that any of the initial amino acids G or N, prior to the first cysteine may be removed by processing or intentionally eliminated without any consequence, and polypeptides comprising such slightly shorter polypeptides are further included.

Follistatin proteins herein may be referred to as FST. If followed by a number, such as FST288, this indicates that the protein is the 288-amino-acid isoform of follistatin. If presented as FST288-Fc, this indicates that an Fc domain is fused to the C-terminus of FST288, which may or may not include an intervening linker. The Fc in this instance may be any immunoglobulin Fc portion as that term is defined herein. If presented as FST288-G1Fc, this indicates that the Fc portion of human IgG1 is fused at the C-terminal of FST288. Unless indicated to the contrary, a protein described with this nomenclature will represent a human follistatin protein.

In other aspects, an agent for use in accordance with the methods disclosed herein is a follistatin-like related gene (FLRG), also known as follistatin-related protein 3 (FSTL3). The term "FLRG polypeptide" includes polypeptides comprising any naturally occurring polypeptide of FLRG as well as any variants thereof (including mutants, fragments, fusions, and peptidomimetic forms) that retain a useful activity. In certain preferred embodiments, FLRG polypeptides of the disclosure bind to and/or inhibit activin activity, particularly activin A. Variants of FLRG polypeptides that retain activin binding properties can be identified using routine methods to assay FLRG and activin interactions (see, e.g., U.S. Pat. No. 6,537,966). In addition, methods for making and testing libraries of polypeptides are described above in the context of ActRII polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

Closely related to the native follistatin isoforms encoded by FSTN is a naturally occurring protein encoded by the FSTL3 gene and known alternatively as follistatin-related gene (FLRG), follistatin-like 3 (FSTL3), or follistatin-related protein (FSRP) (Schneyer et al (2001)*Mol Cell Endocrinol* 180:33-38). Like follistatin, FLRG binds to myostatin, activins, and GDF11 with high affinity and thereby inhibits their bioactivity in vivo (Sidis et al (2006) *Endocrinology* 147:3586-3597). Unlike follistatin, FLRG does not possess a heparin-binding sequence, cannot bind to cell-surface proteoglycans, and therefore is a less potent inhibitor of activin than is FST288 in the immediate vicinity of the cell surface. In contrast to follistatin, FLRG also circulates in the blood bound to processed myostatin, and thus resembles myostatin propeptide in this regard (Hill et al (2002) *J Biol Chem* 277:40735-40741). Unlike follistatin, FLRG deficiency in mice is not lethal, although it does cause a variety of metabolic phenotypes (Mukherjee et al (2007) *Proc Natl Acad Sci USA* 104:1348-1353).

The overall structure of FLRG closely resembles that of follistatin. Native human FLRG precursor is a single-chain polypeptide which comprises four domains: a signal sequence (amino acids 1-26 of SEQ ID NO: 161), an N-terminal domain ($FLRG_{ND}$) (amino acids 38-96 of SEQ ID NO: 161, which interacts differently with myostatin compared with activin A (Cash et al (2012) *J Biol Chem* 287:1043-1053)), and two follistatin domains referred to herein as $FLRG_{FD1}$ (amino acids 99-167 of SEQ ID NO: 161) and $FLRG_{FD2}$ (amino acids 171-243 of SEQ ID NO: 161).

The term "FLRG polypeptide" is used to refer to polypeptides comprising any naturally occurring polypeptide of FLRG as well as any variants thereof (including mutants, fragments, fusions, and peptidomimetic forms) that retain a useful activity. In certain preferred embodiments, FLRG polypeptides of the disclosure bind to and/or inhibit activity of myostatin, GDF11, or activin, particularly activin A (e.g., ligand-mediated activation of ActRIIA and/or ActRIIB Smad2/3 signaling). Variants of FLRG polypeptides that retain ligand binding properties can be identified using routine methods to assay interactions between FLRG and ligands (see, e.g., U.S. Pat. No. 6,537,966). In addition, methods for making and testing libraries of polypeptides are described herein and such methods also pertain to making and testing variants of FLRG.

For example, FLRG polypeptides include polypeptides comprising an amino acid sequence derived from the sequence of any known FLRG having a sequence at least about 80% identical to the sequence of a FLRG polypeptide (for example, SEQ ID NOs: 161-164), and optionally at least 85%, 90%, 95%, 97%, 99% or greater identity to any of SEQ ID NOs: 161-164. The term "FLRG fusion polypeptide" may refer to fusion proteins that comprise any of the polypeptides mentioned above along with a heterologous (non-FLRG) portion. An amino acid sequence is understood to be heterologous to FLRG if it is not uniquely found in human FLRG, represented by SEQ ID NO: 161. Many examples of heterologous portions are provided herein, and such heterologous portions may be immediately adjacent, by amino acid sequence, to the FLRG polypeptide portion of a fusion protein, or separated by intervening amino acid sequence, such as a linker or other sequence.

The human FLRG precursor has the following amino acid sequence (SEQ ID NO: 161) (amino acids 1-263 of NCBI Reference Sequence NP_005851.1), with the signal peptide indicated by dotted underline, the N-terminal domain ($FLRG_{ND}$) indicated by dashed underline, and the two follistatin domains ($FST_{FD1}$, $FST_{FD2}$) indicated by solid underline.

Processed human FLRG comprises the following amino acid sequence (SEQ ID NO: 162) (amino acids 38-263 of NCBI Reference Sequence NP_005851.1) with the N-terminal domain indicated by dashed underline and the two follistatin domains indicated by solid underline. Moreover, it will be appreciated that any of the amino acids (positions 27-37 of SEQ ID NO: 161) prior to the first cysteine (position 38 in SEQ ID NO: 161) may be included without substantial consequence, and polypeptides comprising such slightly longer polypeptides are included.

A $FLRG_{FD}$ sequence may be advantageously maintained in structural context by expression as a polypeptide further comprising the $FLRG_{ND}$ domain. Accordingly, the disclosure includes polypeptides comprising the $FLRG_{ND}$-$FLRG_{FD1}$ sequence (SEQ ID NO: 163) and the $FLRG_{ND}$-$FLRG_{FD1}$-$FLRG_{FD2}$ sequence (SEQ ID NO: 164), as set forth below, and, for example, one or more heterologous polypeptides. Moreover, it will be appreciated that any of the initial amino acids G or N, prior to the first cysteine may be removed by processing or intentionally eliminated without any consequence, and polypeptides comprising such slightly shorter polypeptides are further included.

If presented as FLRG-Fc, this indicates that an Fc domain is fused to the C-terminus of FLRG, which may or may not include an intervening linker. The Fc in this instance may be any immunoglobulin Fc portion as that term is defined herein. If presented as FLRG-G1Fc, this indicates that the Fc portion of IgG1 is fused at the C-terminus of FLRG. Unless indicated to the contrary, a protein described with this nomenclature will represent a human FLRG protein.

In certain embodiments, functional variants or modified forms of the follistatin polypeptides and FLRG polypeptides include fusion proteins having at least a portion of the follistatin polypeptide or FLRG polypeptide and one or more fusion domains, such as, for example, domains that facilitate isolation, detection, stabilization or multimerization of the polypeptide. Suitable fusion domains are discussed in detail above with reference to the ActRII polypeptides. In some embodiment, an antagonist agent of the disclosure is a fusion protein comprising an activin-binding portion of a follistatin polypeptide fused to an Fc domain. In another embodiment, an antagonist agent of the disclosure is a fusion protein comprising an activin binding portion of an FLRG polypeptide fused to an Fc domain.

9. WFIKKN1 and WFIKKN2

In addition to FSTN and FSTL3, two other genes have been identified whose protein products contain a follistatin domain motif and function as extracellular inhibitors of myostatin and GDF11. In humans, these closely related genes are named WFIKKN1 and WFIKKN2 based on their shared domain structure which includes a whey acidic protein domain, a follistatin-Kazal domain, an immunoglobulin domain, two tandem domains related to Kunitz-type protease inhibitor modules, and a netrin domain (Trexler et al (2001) *Proc Natl Acad Sci USA* 98:3705-3709; Trexler et al (2002) *Biol Chem* 383:223-228). WFIKKN2 is also known as WFIKKN-related protein (WFIKKNRP), and murine counterparts of these proteins are named GDF-associated serum protein-2 (Gasp2) and Gasp1, respectively, based on their ligand-binding ability (Hill et al (2003) *Mol Endocrinol* 17:1144-1154).

Native WFIKKN1 (GASP2) and WFIKKN2 (GASP1) proteins possess overlapping activity profiles that are nonetheless distinct from each other and from follistatin or FLRG. WFIKKNs bind with high affinity to myostatin, GDF11, and in some cases to myostatin propeptide, with binding to processed ligand mediated primarily by the follistatin domain (WFIKKN1$_{FD}$, WFIKKN2$_{FD}$) and propeptide binding mediated primarily by the netrin domain (Hill et al., 2003; Kondas et al (2008) *J Biol Chem* 283: 23677-23684). In contrast to follistatin and FLRG, neither WFIKKN1 nor WFIKKN2 bind activin (Szláma et al (2010) *FEBS J* 277:5040-5050). WFIKKN proteins inhibit myostatin and GDF11 signaling by blocking their access to activin type II receptors (Lee et al (2013) *Proc Natl Acad Sci USA* 110:E3713-E3722). Due to the presence of several protease inhibitory modules in both WFIKKNs, it is likely that they also regulate the action of multiple types of proteases. The tissue expression patterns of WFIKKN1 differ prenatally and postnatally from that of WFIKKN2, thus supporting the view that the two proteins serve distinct roles (Trexler et al (2002) *Biol Chem* 383:223-228).

Additional lines of evidence implicate WFIKKNs in the regulation of skeletal muscle mass. Mice with homozygous deletion of WFIKKN1 or WFIKKN2 display phenotypes consistent with overactivity of myostatin and GDF11, including a reduction in muscle weight, a shift in fiber type from fast glycolytic type IIb fibers to fast oxidative type IIa fibers, and impaired muscle regeneration (Lee et al (2013) *Proc Natl Acad Sci USA* 110:E3713-E3722). Conversely, broad overexpression of WFIKKN2 in mice leads mainly to a hypermuscular phenotype (Monestier et al (2012) *BMC Genomics* 13:541-551). Although both WFIKKN proteins bind to myostatin, WFIKKIN1 and WFIKKN2 may interact differently with myostatin propeptide and thus may differentially block the activation of ActRIIA or ActRIIB by semilatent myostatin, which is the native complex between myotatin and a single myostatin propeptide chain (Szláma et al (2013) *FEBS J* 280:3822-3839). Taken together, follistatin-related fusion proteins comprising a WFIKKN1 or WFIKKN2 polypeptide as disclosed herein would be predicted to help in treatment of alleviation of one or more symptoms related to kidney diseases (such as kidney tissue damage, fibrosis, and/or inflammation) in vivo without causing potentially undesirable effects associated with inhibition of endogenous activins.

The term "WFIKKN1 polypeptide" is used to refer to polypeptides comprising any naturally occurring polypeptide of WFIKKN1 as well as any variants thereof (including mutants, fragments, fusions, and peptidomimetic forms) that retain a useful activity. In certain preferred embodiments, WFIKKN1 polypeptides of the disclosure bind to and/or inhibit activity of myostatin, myostatin propeptide, complexes between myostatin and its propeptide, GDF11, and potentially activins (e.g., ligand-mediated activation of ActRIIA and/or ActRIIB Smad2/3 signaling). Variants of WFIKKN1 polypeptides that retain ligand binding properties can be identified using routine methods to assay interactions between WFIKKN1 and ligands (see, e.g., Kondas et al 2008; Szláma et al 2013). In addition, methods for making and testing libraries of polypeptides are described herein and such methods also pertain to making and testing variants of WFIKKN1.

For example, WFIKKN1 polypeptides include polypeptides comprising an amino acid sequence derived from the sequence of any known WFIKKN1 polypeptide having a sequence at least about 80% identical to the sequence of a WFIKKN1 polypeptide (for example, SEQ ID NOs: 165-167), and optionally at least 85%, 90%, 95%, 97%, 99% or greater identity to any of SEQ ID NOs: 165-167. The term "WFIKKN1 fusion polypeptide" may refer to fusion proteins that comprise any of the polypeptides mentioned above along with a heterologous (non-WFIKKN1) portion. An amino acid sequence is understood to be heterologous to WFIKKN1 if it is not uniquely found in human WFIKKN1, represented by SEQ ID NO: 165. Many examples of heterologous portions are provided herein, and such heterologous portions may be immediately adjacent, by amino acid sequence, to the WFIKKN1 polypeptide portion of a fusion protein, or separated by intervening amino acid sequence, such as a linker or other sequence.

The human WFIKKN1 precursor has the amino acid sequence of SEQ ID NO: 165 (NCBI Ref Seq NP_444514.1), with the signal peptide indicated by dotted underline and the follistatin domain (WFIKKN1$_{FD}$) indicated by solid underline.

Processed human WFIKKN1 has the amino acid sequence of SEQ ID NO: 166, with the follistatin domain indicated by solid underline. Moreover, it will be appreciated that any of the 13 amino acids prior to the first cysteine may be removed by processing or intentionally eliminated without substantial consequence, and polypeptides comprising such slightly smaller polypeptides are further included.

In certain aspects, the disclosure includes polypeptides comprising the WFIKKN1$_{FD}$ domain as set forth below (SEQ ID NO: 167), and, for example, one or more heterologous polypeptides.

If presented as WFIKKN1-Fc, this indicates that an Fc portion is fused to the C-terminus of WFIKKN1, which may or may not include an intervening linker. The Fc in this instance may be any immunoglobulin Fc portion as that term is defined herein. If presented as WFIKKN1-G1Fc, this indicates that the Fc portion of IgG1 is fused at the C-terminus of WFIKKN1. Unless indicated to the contrary, a protein described with this nomenclature will represent a human WFIKKN1 protein.

The term "WFIKKN2 polypeptide" includes polypeptides comprising any naturally occurring polypeptide of WFIKKN2 as well as any variants thereof (including mutants, fragments, fusions, and peptidomimetic forms) that retain a useful activity. In certain preferred embodiments, WFIKKN2 polypeptides of the disclosure bind to and/or inhibit activity of myostatin, myostatin propeptide, complexes between myostatin and its propeptide, GDF11, and potentially activins (e.g., ligand-mediated activation of ActRIIA and/or ActRIIB Smad2/3 signaling). Variants of WFIKKN2 polypeptides that retain ligand binding properties can be identified using routine methods to assay interactions between WFIKKN2 and ligands (see, e.g., Kondas et al (2008) *J Biol Chem* 283:23677-23684; Szláma et al (2013) *FEBS J* 280:3822-3839). In addition, methods for making and testing libraries of polypeptides are described herein and such methods also pertain to making and testing variants of WFIKKN2.

For example, WFIKKN2 polypeptides include polypeptides comprising an amino acid sequence derived from the sequence of any known WFIKKN2 polypeptide having a sequence at least about 80% identical to the sequence of a WFIKKN2 polypeptide (for example, SEQ ID NOs: 168-172), and optionally at least 85%, 90%, 95%, 97%, 99% or greater identity to any of SEQ ID NOs: 168-172. The term "WFIKKN2 fusion polypeptide" may refer to fusion proteins that comprise any of the polypeptides mentioned above along with a heterologous (non-WFIKKN2) portion. An amino acid sequence is understood to be heterologous to WFIKKN2 if it is not uniquely found in human WFIKKN2, represented by SEQ ID NO: 168. Many examples of heterologous portions are provided herein, and such heterologous portions may be immediately adjacent, by amino acid sequence, to the WFIKKN2 polypeptide portion of a fusion protein, or separated by intervening amino acid sequence, such as a linker or other sequence.

The human WFIKKN2 precursor has the amino acid sequence of SEQ ID NO: 168 (NCBI Ref Seq NP_783165.1), with the signal peptide indicated by dotted underline and the follistatin domain (WFIKKN2$_{FD}$) indicated by solid underline.

Processed human WFIKKN2 has the amino acid sequence of SEQ ID NO: 169, with the follistatin domain indicated by single underline. Moreover, it will be appreciated that any of the 11 amino acids prior to the first cysteine may be removed by processing or intentionally eliminated without substantial consequence, and polypeptides comprising such slightly smaller polypeptides are further included.

In certain aspects, the disclosure includes polypeptides comprising the WFIKKN2$_{FD}$ domain as set forth in SEQ ID NO: 170, and, for example, one or more heterologous polypeptides.

The murine WFIKKN2 (GASP1) precursor has the following amino acid sequence of SEQ ID NO: 171 (NCBI Ref Seq NP_861540.2), with the signal peptide indicated by dotted underline and the follistatin domain (WFIKKN2$_{FD}$) indicated by solid underline.

Processed murine WFIKKN2 has the following amino acid sequence of SEQ ID NO: 172, with the follistatin domain indicated by single underline. Moreover, it will be appreciated that any of the 11 amino acids prior to the first cysteine may be removed by processing or intentionally eliminated without substantial consequence, and polypeptides comprising such slightly smaller polypeptides are further included.

If presented as WFIKKN2-Fc, this indicates that an Fc portion is fused to the C-terminus of WFIKKN2, which may or may not include an intervening linker. The Fc in this instance may be any immunoglobulin Fc portion as that term is defined herein. If presented as WFIKKN2-G1Fc, this indicates that the Fc portion of IgG1 is fused at the C-terminus of WFIKKN2. Unless indicated to the contrary, a protein described with this nomenclature will represent a human WFIKKN2 protein.

10. Lefty A and B

The Lefty A and B proteins are known to regulate Nodal and other proteins that signal through the ALK7 pathway. Accordingly, in other aspects, an ALK7 antagonist is a Lefty A or Lefty B polypeptide, which may be used alone or in combination with one or more additional supportive therapies and/or active agents as disclosed herein to achieve a desired effect (e.g., treat kidney disease and/or a metabolic condition or disorder).

The term "Lefty A polypeptide" includes polypeptides comprising any naturally occurring polypeptide of Lefty A as well as any variants thereof (including mutants, fragments, fusions, and peptidomimetic forms) that retain a useful activity, and further includes any functional monomer or multimer of Lefty A. In certain preferred embodiments, Lefty A polypeptides of the disclosure bind to and/or inhibit nodal activity. In addition, methods for making and testing libraries of polypeptides are described above in the context of ActRII and ALK7 polypeptides, and such methods also pertain to making and testing variants of Lefty A. Lefty A polypeptides include polypeptides derived from the sequence of any known Lefty A having a sequence at least about 80% identical to the sequence of a Lefty A polypeptide, and optionally at least 85%, 90%, 95%, 96%, 97%, 98%, 99% or greater identity. Examples of Lefty A polypeptides include the processed Lefty A polypeptide or shorter isoforms or other variants of the human Lefty A precursor polypeptide (SEQ ID NO: 173; GenBank Id: AAD48145.1).

The term "Lefty B polypeptide" includes polypeptides comprising any naturally occurring polypeptide of Lefty B as well as any variants thereof (including mutants, fragments, fusions, and peptidomimetic forms) that retain a useful activity, and further includes any functional monomer or multimer of Lefty B. In certain preferred embodiments, Lefty B polypeptides of the disclosure inhibit nodal activity. In addition, methods for making and testing libraries of polypeptides are described above in the context of ActRII and ALK7 polypeptides, and such methods also pertain to making and testing variants of Lefty B. Lefty B polypeptides include polypeptides derived from the sequence of any known Lefty B having a sequence at least about 80% identical to the sequence of a Lefty B polypeptide, and optionally at least 85%, 90%, 95%, 96%, 97%, 98%, 99% or greater identity. Examples of Lefty B polypeptides include the processed Lefty B polypeptide or shorter isoforms or other variants of the human Lefty B precursor polypeptide (SEQ ID NO: 174; GenBank Id: AAD48144.1).

In certain embodiments, functional variants or modified forms of the Lefty A polypeptides and Lefty B polypeptides include fusion proteins having at least a portion of the Lefty A polypeptide or Lefty polypeptide and one or more fusion domains, such as, for example, domains that facilitate isolation, detection, stabilization or multimerization of the polypeptide. Suitable fusion domains are discussed in detail above with reference to the ActRII and ALK7 polypeptides. In some embodiments, an antagonist agent of the disclosure is a fusion protein comprising a nodal-binding portion of a Lefty A and/or Lefty B polypeptide fused to an Fc domain.

11. DAN-Related Proteins

Members of the DAN family of proteins are known to regulate ligands that signal through the ALK7 pathway. Accordingly, in other aspects, an ALK7 antagonist is a DAN-related protein (e.g., Cerberus and Coco), which may be used alone or in combination with one or more additional supportive therapies and/or active agents as disclosed herein to achieve a desired effect (e.g., treat patients having kidney disease and/or a metabolic disorder).

The term "Cerberus polypeptide" includes polypeptides comprising any naturally occurring polypeptide of Cerberus as well as any variants thereof (including mutants, fragments, fusions, and peptidomimetic forms) that retain a useful activity, and further includes any functional monomer or multimer of Cerberus. In certain preferred embodiments, Cerberus polypeptides of the disclosure bind to and/or inhibit nodal activity. In addition, methods for making and testing libraries of polypeptides are described above in the context of ActRII and ALK7 polypeptides, and such methods also pertain to making and testing variants of Cerberus. Cerberus polypeptides include polypeptides derived from the sequence of any known Cerberus having a sequence at least about 80% identical to the sequence of a Cerberus polypeptide, and optionally at least 85%, 90%, 95%, 96%, 97%, 98%, 99% or greater identity. Examples of Cerberus polypeptides include the processed Cerberus polypeptide or shorter isoforms or other variants of the human Cerberus precursor polypeptide (SEQ ID NO: 175; GenBank Id: NP_005445.1).

The term "Coco polypeptide," also known as DAN domain BMP antagonist family member 5, SP1, CER2, CRL2, CERL2, DANTE, GREM3, and CKTSF1B3, includes polypeptides comprising any naturally occurring polypeptide of Coco as well as any variants thereof (including mutants, fragments, fusions, and peptidomimetic forms) that retain a useful activity, and further includes any functional monomer or multimer of Coco. In certain preferred embodiments, Coco polypeptides of the disclosure bind to and/or inhibit nodal activity. In addition, methods for making and testing libraries of polypeptides are described above in the context of ActRII and ALK7 polypeptides, and such methods also pertain to making and testing variants of Coco. Coco polypeptides include polypeptides derived from the sequence of any known Coco having a sequence at least about 80% identical to the sequence of a Coco polypeptide, and optionally at least 85%, 90%, 95%, 96%, 97%, 98%, 99% or greater identity. Examples of Coco polypeptides include the processed Coco polypeptide or shorter isoforms or other variants of the human Coco precursor polypeptide (SEQ ID NO: 176; GenBank Id: NP_689867.1).

In certain embodiments, functional variants or modified forms of the Cerberus polypeptides and Coco polypeptides include fusion proteins having at least a portion of the Cerberus polypeptide and/or Coco polypeptide and one or more fusion domains, such as, for example, domains that facilitate isolation, detection, stabilization or multimerization of the polypeptide. Suitable fusion domains are discussed in detail above with reference to the ActRII and ALK7 polypeptides. In some embodiments, an antagonist agent of the disclosure is a fusion protein comprising a nodal-binding portion of a Cerberus and/or Coco polypeptide fused to an Fc domain.

12. Screening Assays

In certain aspects, the present disclosure relates to the use of the subject activin and/or GDF antagonists (e.g., inhibitors, or combinations of inhibitors, of one or more of: activin (e.g., activin A, activin B, activin AB, activin C, activin AC, activin BC, activin E, activin AE, and/or activin BE), GDF8, GDF11, GDF3, GDF1, Nodal, ActRIIA, ActRIIB, ALK4, ALK5, ALK7, Cryptic, Cryptic 1B, Smad 2, and Smad3) to identify compounds (agents) which may be used to treat or reduce the progression rate, frequency, and/or severity of kidney diseases, particularly treating, preventing, or reducing the progression rate, frequency, and/or severity of one or more kidney-disease-associated complications (e.g., kidney tissue damage, fibrosis, and/or inflammation).

There are numerous approaches to screening for therapeutic agents for treating kidney diseases by targeting signaling (e.g., Smad signaling) of one or more GDF ligands. In certain embodiments, high-throughput screening of compounds can be carried out to identify agents that perturb GDF ligand-mediated effects on a selected cell line. In certain embodiments, the assay is carried out to screen and identify compounds that specifically inhibit or reduce binding of a GDF ligand (e.g., activin (e.g., activin A, activin B, activin AB, activin C, activin AC, activin BC, activin E, activin AE, and/or activin BE), GDF8, GDF11, GDF3, GDF1, Nodal, etc.) to its binding partner, such as a type II receptor (e.g., ActRIIA and/or ActRIIB), a co-receptor (e.g., Cripto, Cryptic, and/or Cryptic 1B), or a type I receptor (e.g., ALK4, ALK5, and/or ALK7). Alternatively, the assay can be used to identify compounds that enhance binding of a GDF ligand to its binding partner such as a type II receptor. In a further embodiment, the compounds can be identified by their ability to interact with a type II receptor.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps.

Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatable crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target induced by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a GDF ligand (e.g., activin (e.g., activin A, activin B, activin AB, activin C, activin AC, activin BC, activin E, activin AE, and/or activin BE), GDF8, GDF11, GDF3, GDF1, Nodal, etc.) and its binding partner, such as an a type II receptor (e.g., ActRIIA and/or ActRIIB), a co-receptor (e.g., Cripto, Cryptic, and/or Cryptic 1), or a type I receptor (e.g., ALK4, ALK5, and/or ALK7).

Merely to illustrate, in an exemplary screening assay of the present disclosure, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added to a composition containing an ActRIIB ligand (e.g., GDF11). Detection and quantification of ActRIIB/ActRIIB-ligand complexes provides a means for determining the compound's efficacy at inhibiting (or potentiating) complex formation between the ActRIIB polypeptide and its binding protein. The efficacy of the compound can be assessed by generating dose-response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between GDF ligand and its binding protein may be detected by a variety of techniques. For instance, modulation of the formation of complexes can be quantitated using, for example, detectably labeled proteins such as radiolabeled (e.g., $^{32}P$, $^{3}S$, $^{14}C$ or $^{3}H$), fluorescently labeled (e.g., FITC), or enzymatically labeled ActRIIB polypeptide and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between a GDF ligand and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between a GDF ligand and its binding partner. See, e.g., U.S. Pat. No. 5,283,317; Zervos et al. (1993) *Cell* 72:223-232; Madura et al. (1993) *J Biol Chem* 268:12046-12054; Bartel et al. (1993) *Biotechniques* 14:920-924; and Iwabuchi et al. (1993) *Oncogene* 8:1693-1696). In a certain embodiments, the present disclosure contemplates the use of reverse two-hybrid systems to identify compounds (e.g., small molecules or peptides) that dissociate interactions between a GDF ligand and its binding protein (see, e.g., Vidal and Legrain, (1999) *Nucleic Acids Res* 27:919-29; Vidal and Legrain, (1999) *Trends Biotechnol* 17:374-81; and U.S. Pat. Nos. 5,525,490; 5,955,280; and 5,965,368).

In certain embodiments, the subject compounds are identified by their ability to interact with a GDF ligand. The interaction between the compound and the GDF ligand may be covalent or non-covalent. For example, such interaction can be identified at the protein level using in vitro biochemical methods, including photo-crosslinking, radiolabeled ligand binding, and affinity chromatography (see, e.g., Jakoby W B et al. (1974) Methods in Enzymology 46:1). In certain cases, the compounds may be screened in a mechanism-based assay, such as an assay to detect compounds which bind to a GDFP ligand. This may include a solid-phase or fluid-phase binding event. Alternatively, the gene encoding GDF ligand can be transfected with a reporter system (e.g., 0-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

13. Therapeutic Uses

In part, the present disclosure relates to methods of treating kidney disease comprising administering to a patient in need thereof an effective amount of an activin and/or GDF antagonist (e.g., an antagonist of one or more of activin (e.g., activin A, activin B, activin AB, activin C, activin AC, activin BC, activin E, activin AE, and/or activin BE), GDF8, GDF11, GDF3, GDF1, Nodal, ActRIIA, ActRIIB, ALK4, ALK5, ALK7, Cryptic, Cryptic 1B, Smad 2, and Smad 3). In some embodiments, the disclosure contemplates methods of treating one or more complications of a kidney disease (e.g., any kidney disease-related symptoms, such as tissue damage, fibrosis, and/or inflammation) comprising administering to a patient in need thereof an effective amount of an activin and/or GDF antagonist. In some embodiments, the disclosure contemplates methods of preventing one or more complications of a kidney disease, comprising administering to a patient in need thereof an effective amount of an activin and/or GDF antagonist. In some embodiments, the disclosure contemplates methods of reducing the progression rate of a kidney disease, comprising administering to a patient in need thereof an effective amount of an activin and/or GDF antagonist. In some embodiments, the disclosure contemplates methods of reducing the progression rate of one or more complications of a kidney disease, comprising administering to a patient in need thereof an effective amount of an activin and/or GDF antagonist. In some embodiments, the disclosure contemplates methods of reducing the frequency of kidney-disease-related disease events, comprising administering to a patient in need thereof an effective amount of an activin and/or GDF antagonist. In some embodiments, the disclosure contemplates methods of reducing the frequency of one or more complications of a kidney disease, comprising administering to a patient in need thereof an effective amount of an activin and/or GDF antagonist. In some embodiments, the disclosure contemplates methods of reducing the severity of a kidney disease, comprising administering to a patient in need thereof an effective amount of an activin and/or GDF antagonist. In some embodiments, the disclosure contemplates methods of reducing the severity of one or more complications of a kidney disease, comprising administering to a patient in need thereof an effective amount of an activin and/or GDF antagonist. Optionally, methods disclosed herein for treating or reducing the progression rate, frequency, and/or severity of a kidney disease and kidney-disease-related disease events, particularly treating, preventing, or reducing the progression rate, frequency, and/or severity of one or more complications of a kidney disease, may further comprise administering to the patient one or more supportive therapies or additional active agents for treating a kidney disease. For example, the patient also may be administered one or more supportive therapies or active agents to treat or alleviate one or more symptoms, such as high blood pressure (e.g., using angiotensin-converting enzyme (ACE) inhibitors or angiotensin II receptor blockers or a water pill (diuretic), optionally with a low-salt diet), high cholesterol levels (e.g., using statins), anemia (e.g., using hormone erythropoietin, optionally with iron supplement), swelling (e.g., using diuretics), lack of fluids in blood (e.g., with intravenous (IV) fluid supplement), lack of calcium or bone failure (e.g, with calcium and/or vitamin D supplement, or a phosphate binder to lower the blood phosphate level and to protect calcification of blood vessels), high blood potassium level (e.g., using calcium, glucose or sodium polystyrene sulfonate (Kayexalate, Kionex) to lower potassium levels), toxin accumulation (e.g., by hemodialysis and/or peritoneal dialysis), etc. In addition, kidney transplant may be also used as an additional therapy. Some exemplary medications for kidney diseases are Lasix® (furosemide), Demadex® (torsemide), Edecrin® (ethacrynic acid), and sodium edecrin.

As used herein, a therapeutic that "prevents" a disorder or condition refers to a compound that, in a statistical sample, reduces the occurrence of the disorder or condition in the treated sample relative to an untreated control sample, delays the onset or reduces the frequency of disorder-related events, or reduces the severity of one or more symptoms of the disorder or condition relative to the untreated control sample.

The term "treating" as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering an activin and/or GDF antagonist in an effective amount. An effective amount of an agent refers to an amount effective, at dosages and for periods of time necessary, to achieve the desired therapeutic or prophylactic result. A therapeutically effective amount of an agent of the present disclosure may vary according to factors such as the disease state, age, sex, and weight of the individual, and the ability of the agent to elicit a desired response in the individual. A prophylactically effective amount refers to an amount effective, at dosages and for periods of time necessary, to achieve the desired prophylactic result.

The terms "subject," an "individual," or a "patient" are interchangeable throughout the specification and generally refer to mammals. Mammals include, but are not limited to, domesticated animals (e.g., cows, sheep, cats, dogs, and horses), primates (e.g., humans and non-human primates such as monkeys), rabbits, and rodents (e.g., mice and rats).

In general, treatment or prevention of a kidney-related disease or condition as described in the present disclosure is achieved by administering an activin and/or GDF antagonist, or combinations of such antagonists, of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

The kidneys maintain many features of the blood, including volume, pH balance, electrolyte concentrations, and blood pressure, as well as bearing responsibility for toxin and waste filtration. These functions depend upon the intricate structure of the kidney nephrons, constant flow of blood through the various capillaries of the kidney, and the regulation of the kidney by signals from the rest of the body, including endocrine hormones. Problems with kidney function manifest by direct mechanisms (e.g., genetic defects, infection, or toxin exposure) and by indirect mechanisms progressively proceeding from long term stressors like hypertrophy and hyperfiltration (themselves often a result of more direct insults to kidney function). Due to the central role of the kidney in blood maintenance and waste secretion, kidney-associated disease manifestations are many and varied; they can be reviewed in Harrison's Principles of Internal Medicine, $18^{th}$ edition, McGraw Hill, N.Y., Part 13, Chp 277-289.

As described herein, an activin and/or GDF antagonist had various beneficial effects in a kidney disease model. In particular, treatment with an ALK7:ActRIIB heteromultimer reduced kidney tissue damage, inflammation, and fibrosis in subjects having unilateral ureteral obstruction (UUO). These data indicate that an activin and/or GDF antagonist may be used to treat or prevent kidney disease, particularly treating or preventing various complications (manifestations) of kidney disease including, for example, kidney tissue damage, inflammation, and/or fibrosis.

Therefore, methods of this invention can be applied to various kidney-associated diseases or conditions. As used herein, "kidney-associated disease or condition" can refer to any disease, disorder, or condition that affects the kidneys or the renal system. Examples of kidney-associated diseases or conditions include, but are not limited to, chronic kidney diseases (or failure), acute kidney diseases (or failure), primary kidney diseases, non-diabetic kidney diseases, glomerulonephritis, interstitial nephritis, diabetic kidney diseases, diabetic chronic kidney disease, diabetic nephropathy, glomerulosclerosis, rapid progressive glomerulonephritis, renal fibrosis, Alport syndrome, IDDM nephritis, mesangial proliferative glomerulonephritis, membranoproliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, polycystic kidney disease (e.g., autosomal dominant (adult) polycystic kidney disease and autosomal recessive (childhood) polycystic kidney disease), acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, acute interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate (GFR), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non-IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schonlein disease, a postinfectious glomerulonephritis, a bacterial endocarditis, a microscopic polyangitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis nodosa, a calcineurin-inhibitor induced-vascular disease, an acute cellular vascular allograft rejection, an acute humoral allograft rejection, early renal function decline (ERFD), end stage renal disease (ESRD), renal vein thrombosis, acute tubular necrosis, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, normocytic normochromic anemia, renal anemia, diabetic chronic kidney disease, IgG4-related disease, von Hippel-Lindau syndrome, tuberous sclerosis, nephronophthisis, medullary cystic kidney disease, renal cell carcinoma, adenocarcinoma, nephroblastoma, lymphoma, leukemia, hyposialylation disorder, chronic cyclosporine nephropathy, renal reperfusion injury, renal dysplasia, azotemia, bilateral arterial occlusion, acute uric acid nephropathy, hypovolemia, acute bilateral obstructive uropathy, hypercalcemic nephropathy, hemolytic uremic syndrome, acute urinary retention, malignant nephrosclerosis, postpartum glomerulosclerosis, scleroderma, non-Goodpasture's anti-GBM disease, microscopic polyarteritis nodosa, allergic granulomatosis, acute radiation nephritis, post-streptococcal glomerulonephritis, Waldenstrom's macroglobulinemia, analgesic nephropathy, arteriovenous fistula, arteriovenous graft, dialysis, ectopic kidney, medullary sponge kidney, renal osteodystrophy, solitary kidney, hydronephrosis, microalbuminuria, uremia, haematuria, hyperlipidemia, hypoalbuminaemia, lipiduria, acidosis, edema, tubulointerstitial renal fibrosis, hypertensive sclerosis, juxtaglomerular cell tumor, Fraser syndrome, Horseshoe kidney, renal tubular dysgenesis, hypokalemia, hypomagnesemia, hypercalcemia, hypophosphatemia, uromodulin-associated kidney disease, Nail-patella syndrome, lithium nephrotoxity, TNF-alpha nephrotoxicity, honeybee resin related renal failure, sugarcane harvesting acute renal failure, complete LCAT deficiency, Fraley syndrome, Page kidney, reflux nephropathy, Bardet-Biedl syndrome, collagenofibrotic glomerulopathy, Dent disease, Denys-Drash syndrome, congenital nephrotic syndrome, immunotactoid glomerulopathy, fibronextin glomerulopathy, Galloway Mowat syndrome, lipoprotein glomerulopathy, MesoAmerican nephropathy, beta-thalassemia renal disease, haemolytic uraemic syndrome, Henoch-Schonlein-Purpura disease, retroperitoneal fibrosis, polyarteritis nodose, cardiorenal syndrome, medullary kidney disease, renal artery stenosis, uromodulin kidney disease, and hyperkalemia.

In some embodiments, an activin and/or GDF antagonist, or combinations of such antagonists, of the present disclosure may be used to treat or prevent chronic kidney disease, optionally in combination with one or more supportive therapies for treating chronic kidney disease. In some embodiments, an activin and/or GDF antagonist, or combinations of such antagonists, of the present disclosure may be used to treat or prevent one or more complications (symptoms or manifestations) of chronic kidney disease (e.g., tissue damage, inflammation, and/or fibrosis), optionally in combination with one or more supportive therapies for treating chronic kidney disease. In some embodiments, an activin and/or GDF antagonist, or combinations of such antagonists, of the present disclosure may be used to treat or prevent end-stage kidney failure, optionally in combination with one or more supportive therapies for treating end-stage kidney disease. Chronic kidney disease (CKD), also known as chronic renal disease, is a progressive loss in renal function over a period of months or years. The symptoms of worsening kidney function may include feeling generally unwell and experiencing a reduced appetite. Often, chronic kidney disease is diagnosed as a result of screening of people known to be at risk of kidney problems, such as those with high blood pressure or diabetes and those with a blood relative with CKD. This disease may also be identified when it leads to one of its recognized complications, such as cardiovascular disease, anemia, or pericarditis. Recent professional guidelines classify the severity of CKD in five stages, with stage 1 being the mildest and usually causing few symptoms and stage 5 being a severe illness with poor life expectancy if untreated. Stage 5 CKD is often called end-stage kidney disease, end-stage renal disease, or end-stage kidney failure, and is largely synonymous with the now outdated terms chronic renal failure or chronic kidney failure; and usually means the patient requires renal replacement therapy, which may involve a form of dialysis, but ideally constitutes a kidney transplant. CKD is initially without specific symptoms and is generally only detected as an increase in serum creatinine or protein in the urine. As the kidney function decreases, various symptoms may manifest as described below. Blood pressure may be increased due to fluid overload and production of vasoactive hormones created by the kidney via the renin-angiotensin system, increasing one's risk of developing hypertension and/or suffering from congestive heart failure. Urea may accumulate, leading to azotemia and ultimately uremia (symptoms ranging from lethargy to pericarditis and encephalopathy). Due to its high systemic circulation, urea is excreted in eccrine sweat at high concentrations and crystallizes on skin as the sweat evaporates ("uremic frost"). Potassium may accumulate in the blood (hyperkalemia with a range of symptoms including malaise and potentially fatal cardiac arrhythmias). Hyperkalemia usually does not develop until the glomerular filtration rate falls to less than 20-25 ml/min/1.73 $m^2$, at which point the kidneys have decreased ability to excrete potassium. Hyperkalemia in CKD can be exacerbated by acidemia (which leads to extracellular shift of potassium) and from lack of insulin. Erythropoietin synthesis may be decreased causing anemia. Fluid volume overload symptoms may occur, ranging from mild edema to life-threatening pulmonary edema. Hyperphosphatemia, due to reduced phosphate excretion, may occur generally following the decrease in glomerular filtration. Hyperphosphatemia is associated with increased cardiovascular risk, being a direct stimulus to vascular calcification. Hypocalcemia may manifest, which is generally caused by stimulation of fibroblast growth factor-23. Osteocytes are responsible for the increased production of FGF23, which is a potent inhibitor of the enzyme 1-alpha-hydroxylase (responsible for the conversion of 25-hydroxycholecalciferol into 1,25-dihydroxyvitamin D3). Later, this progresses to secondary hyperparathyroidism, renal osteodystrophy, and vascular calcification that further impairs cardiac function. Metabolic acidosis (due to accumulation of sulfates, phosphates, uric acid etc.) may occur and cause altered enzyme activity by excess acid acting on enzymes; and also increased excitability of cardiac and neuronal membranes by the promotion of hyperkalemia due to excess acid (acidemia). Acidosis is also due to decreased capacity to generate enough ammonia from the cells of the proximal tubule. Iron deficiency anemia, which increases in prevalence as kidney function decreases, is especially prevalent in those requiring haemodialysis. It is multifactoral in cause, but includes increased inflammation, reduction in erythropoietin, and hyperuricemia leading to bone marrow suppression. People with CKD suffer from accelerated atherosclerosis and are more likely to develop cardiovascular disease than the general population. Patients afflicted with CKD and cardiovascular disease tend to have significantly worse prognoses than those suffering only from the latter.

In another embodiment, an activin and/or GDF antagonist, or combinations of such antagonists, may be used in patients with chronic kidney disease mineral bone disorder (CKD-MBD), a broad syndrome of interrelated skeletal, cardiovascular, and mineral-metabolic disorders arising from kidney disease. CKD-MBD encompasses various skeletal pathologies often referred to as renal osteodystrophy (ROD), which is a preferred embodiment for treatment with, an activin and/or GDF antagonist, or combinations of such antagonists. Depending on the relative contribution of different pathogenic factors, ROD is manifested as diverse pathologic patterns of bone remodeling (Hruska et al., 2008, Chronic kidney disease mineral bone disorder (CKD-MBD); in Rosen et al. (ed) Primer on the Metabolic Bone Diseases and Disorders of Mineral Metabolism, 7th ed. American Society for Bone and Mineral Research, Washington D.C., pp 343-349). At one end of the spectrum is ROD with uremic osteodystrophy and low bone turnover, characterized by a low number of active remodeling sites, profoundly suppressed bone formation, and low bone resorption. At the other extreme is ROD with hyperparathyroidism, high bone turnover, and osteitis fibrosa. Given that an activin and/or GDF antagonist, or combinations of such antagonists, may exert both anabolic and antiresorptive effects, these agents may be useful in patients across the ROD pathology spectrum.

In certain embodiments, the present disclosure provides methods for managing a patient that has been treated with, or is a candidate to be treated with, one or more one or more activin and/or GDF antagonists of the disclosure by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more activin and/or GDF antagonists may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more activin and/or GDF antagonists, then onset of administration of the one or more activin and/or GDF antagonists of the disclosure may be delayed until the hematologic parameters have returned to a normal or acceptable level either naturally or via therapeutic intervention. For example, if a candidate patient is hypertensive or pre-hypertensive, then the patient may be treated with a blood-pressure-lowering agent in order to reduce the patient's blood pressure. Any blood-pressure-lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more antagonists of the disclosure may be delayed until the levels have returned to a normal or acceptable level.

In certain embodiments, if one or more hematologic parameters are outside the normal range or on the high side of normal in a patient who is a candidate to be treated with one or more activin and/or GDF antagonists, then the onset of administration may not be delayed. However, the dosage amount or frequency of dosing of the one or more activin and/or GDF antagonists of the disclosure may be set at an amount that would reduce the risk of an unacceptable increase in the hematologic parameters arising upon administration of the one or more activin and/or GDF antagonists of the disclosure. Alternatively, a therapeutic regimen may be developed for the patient that combines one or more activin and/or GDF antagonists with a therapeutic agent that addresses the undesirable level of the hematologic parameter. For example, if the patient has elevated blood pressure, then a therapeutic regimen may be designed involving administration of one or more activin and/or GDF antagonist agents and a blood-pressure-lowering agent. For a patient having lower than desired iron stores, a therapeutic regimen may be developed involving one or more activin and/or GDF antagonists of the disclosure and iron supplementation.

In one embodiment, baseline parameter(s) for one or more hematologic parameters may be established for a patient who is a candidate to be treated with one or more activin and/or GDF antagonists of the disclosure and an appropriate dosing regimen established for that patient based on the baseline value(s). Alternatively, established baseline parameters based on a patient's medical history could be used to inform an appropriate activin and/or GDF antagonist dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more activin and/or GDF antagonists of the disclosure may also be used as the relevant comparative values for monitoring any changes to the hematologic parameters during treatment with the one or more activin and/or GDF antagonists of the disclosure.

In certain embodiments, one or more hematologic parameters are measured in patients who are being treated with one or more activin and/or GDF antagonists. The hematologic parameters may be used to monitor the patient during treatment and permit adjustment or termination of the dosing with the one or more activin and/or GDF antagonists of the disclosure or additional dosing with another therapeutic agent. For example, if administration of one or more activin and/or GDF antagonists results in an increase in blood pressure, red blood cell level, or hemoglobin level, or a reduction in iron stores, then the dose of the one or more antagonists of the disclosure may be reduced in amount or frequency in order to decrease the effects of the one or more activin and/or GDF antagonists of the disclosure on the one or more hematologic parameters. If administration of one or more activin and/or GDF antagonists results in a change in one or more hematologic parameters that is adverse to the patient, then the dosing of the one or more activin and/or GDF antagonists of the disclosure may be terminated either temporarily, until the hematologic parameter(s) return to an acceptable level, or permanently. Similarly, if one or more hematologic parameters are not brought within an acceptable range after reducing the dose or frequency of administration of the one or more activin and/or GDF antagonists of the disclosure, then the dosing may be terminated. As an alternative, or in addition, to reducing or terminating the dosing with the one or more activin and/or GDF antagonists of the disclosure, the patient may be dosed with an additional therapeutic agent that addresses the undesirable level in the hematologic parameter(s), such as, for example, a blood-pressure-lowering agent or an iron supplement. For example, if a patient being treated with one or more activin and/or GDF antagonists has elevated blood pressure, then dosing with the one or more activin and/or GDF antagonists of the disclosure may continue at the same level and a blood-pressure-lowering agent is added to the treatment regimen, dosing with the one or more activin and/or GDF antagonist of the disclosure may be reduced (e.g., in amount and/or frequency) and a blood-pressure-lowering agent is added to the treatment regimen, or dosing with the one or more activin and/or GDF antagonist of the disclosure may be terminated and the patient may be treated with a blood-pressure-lowering agent.

14. Pharmaceutical Compositions

The therapeutic agents described herein (e.g., activin and/or GDF antagonists) may be formulated into pharmaceutical compositions. Pharmaceutical compositions for use in accordance with the present disclosure may be formulated in conventional manner using one or more physiologically acceptable carriers or excipients.

In certain embodiments, the therapeutic methods of the disclosure include administering the composition systemically, or locally as an implant or device. When administered, the therapeutic composition for use in this disclosure may be in any physiologically acceptable form, such as in a substantially pyrogen-free, or pyrogen-free, physiologically acceptable form. Therapeutically useful agents other than the activin and/or GDF antagonists, which may also optionally be included in the composition as described above, may be administered simultaneously or sequentially with the subject compounds in the methods disclosed herein.

Typically, protein therapeutic agents disclosed herein will be administered parenterally, and particularly intravenously or subcutaneously. Pharmaceutical compositions suitable for parenteral administration may comprise one or more activin and/or GDF antagonists in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more therapeutic compounds (e.g., activin and/or GDF antagonists) to a target tissue site, providing a structure for the developing tissue and optimally capable of being resorbed into the body. For example, the matrix may provide slow release of the activin and/or GDF antagonist. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In certain embodiments, the methods of the invention may be formulated for intranasal administration. Nasal administration of the present invention may comprise the use of a nasal spray which uses water or salt solutions as the liquid carrier with one or more therapeutic compounds (e.g., activin and/or GDF antagonists) being dispersed or dissolved in the water in a therapeutically effective amount.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the disclosure (e.g., activin and/or GDF antagonists). The various factors include, but are not limited to, the patient's age, sex, and diet, the severity of the disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of the ESS or hematologic parameters.

In certain embodiments, the present invention also provides gene therapy for the in vivo production of activin and/or GDF antagonists. Such therapy would achieve its therapeutic effect by introduction of the activin and/or GDF antagonist polynucleotide sequences into cells or tissues having the disorders as listed above. Delivery of activin and/or GDF antagonist polynucleotide sequences can be achieved using a recombinant expression vector such as a chimeric virus or a colloidal dispersion system. Preferred for therapeutic delivery of activin and/or GDF antagonist polynucleotide sequences is the use of targeted liposomes.

Various viral vectors which can be utilized for gene therapy as taught herein include adenovirus, herpes virus, vaccinia, or, preferably, an RNA virus such as a retrovirus.

Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the activin and/or GDF antagonist. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for activin and/or GDF antagonist polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., *Trends Biochem. Sci.*, 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

15. Kits

In certain embodiments, the disclosure also provides a pharmaceutical package or kit comprising one or more containers filled with at least one activin and/or GDF antagonist of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

EXEMPLIFICATION

The invention now being generally described, it will be more readily understood by reference to the following examples, which are included merely for purposes of illustration of certain embodiments of the present invention, and are not intended to limit the invention.

Example 1: ActRIIa-Fc Fusion Proteins

A soluble ActRIIA fusion protein was constructed that has the extracellular domain of human ActRIIa fused to a human or mouse Fc domain with a minimal linker in between. The constructs are referred to as ActRIIA-hFc (SEQ ID NO: 177) and ActRIIA-mFc, respectively.

The ActRIIA-hFc and ActRIIA-mFc proteins were expressed in CHO cell lines. Different leader sequences (e.g., the Honey bee mellitin (HBML) leader (SEQ ID NO: 214), the Tissue plasminogen activator (TPA) leader (SEQ ID NO: 215), or the native leader (SEQ ID NO: 216)) may be used. An exemplary ActRIIA-hFc construct comprises the TPA leader and has the unprocessed amino acid sequence as set forth in SEQ ID NO: 178, encodable by a polynucleotide having the nucleic acid sequence of SEQ ID NO: 179.

Both ActRIIA-hFc and ActRIIA-mFc were remarkably amenable to recombinant expression. The exemplary ActRIIA-hFc protein was purified as a single, well-defined peak of protein. N-terminal sequencing revealed a single sequence of -ILGRSETQE (SEQ ID NO: 50). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIA-hFc protein was purified to a purity of >98% as determined by size exclusion chromatography and >95% as determined by SDS PAGE. As shown in FIG. 7, the fusion protein purifies as a single, well-defined peak as visualized by sizing column (FIG. 7A) and Coomassie stained SDS-PAGE (FIG. 7B).

ActRIIA-hFc and ActRIIA-mFc showed a high affinity for ligands. GDF-11 or activin A were immobilized on a Biacore™ CM5 chip using standard amine-coupling procedure (FIG. 8). ActRIIA-hFc and ActRIIA-mFc proteins were loaded onto the system, and binding was measured. ActRIIA-hFc bound to activin with a dissociation constant ($K_D$) of $5 \times 10^{-12}$ and bound to GDF11 with a $K_D$ of $9.96 \times 10^{-9}$. ActRIIA-mFc behaved similarly.

The ActRIIA-hFc was very stable in pharmacokinetic studies. Rats were dosed with 1 mg/kg, 3 mg/kg, or 10 mg/kg of ActRIIA-hFc protein, and plasma levels of the protein were measured at 24, 48, 72, 144 and 168 hours. In a separate study, rats were dosed at 1 mg/kg, 10 mg/kg, or 30 mg/kg. In rats, ActRIIA-hFc had an 11-14 day serum half-life, and circulating levels of the drug were quite high after two weeks (11 µg/ml, 110 µg/ml, or 304 µg/ml for initial administrations of 1 mg/kg, 10 mg/kg, or 30 mg/kg, respectively.) In cynomolgus monkeys, the plasma half-life was substantially greater than 14 days, and circulating levels of the drug were 25 g/ml, 304 µg/ml, or 1440 µg/ml for initial administrations of 1 mg/kg, 10 mg/kg, or 30 mg/kg, respectively.

Example 2: Alternative ActRIIA-Fc Proteins

A variety of ActRIIA variants that may be used to construct Fc-fusion proteins according to the methods described herein are described in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIA). The amino acid sequence for such a construct is presented in SEQ ID NO: 180.

Example 3. Effects of an Exemplary ActRIIa-Fc Homodimer on Kidney Fibrosis, Inflammation, and Kidney Injury The effects of the ActRIIa-Fc homodimers on kidney disease were assessed in a mouse unilateral ureteral obstruction model, using similar methods to those mentioned in previous Examples and herein in the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with ActRIIa-Fc homodimer significantly suppressed the expression of fibrotic (Col1a1, Col3a1, PAI-1, Fibronectin, CTGF, and a-SMA, shown in FIG. 17) and inflammatory (IL-1B and TNF-alpha, shown in FIG. 18) genes, inhibited the upregulation of TGF β1 and activin A (FIG. 19, top two panels), and reduced kidney injury (downregulation of NGAL, shown in FIG. 19, lower panel).

Example 4: Generation of ActRIIB-Fc Fusion Proteins

Applicants constructed a soluble ActRIIB fusion protein that has the extracellular domain of human ActRIIB fused to a human or mouse Fc domain with a minimal linker in between. The constructs are referred to as ActRIIB(20-134)-hFc (comprising the human ActRIIB extracellular domain (residues 20-134 of the native ActRIIB having the sequence of SEQ ID NO: 1) fused to a human Fc domain) and ActRIIB-mFc, respectively.

The ActRIIB(20-134)-hFc (SEQ ID NO: 181) and ActRIIB-mFc proteins were expressed in CHO cell lines. Three different leader sequences may be added to these sequences, such as: (i) the Honey bee mellitin (HBML) leader (SEQ ID NO: 214), ii) the Tissue plasminogen activator (TPA) leader (SEQ ID NO: 215), and (iii) the Native leader (SEQ ID NO: 216). An exemplary ActRIIB (20-134)-hFc fusion protein with the TPA leader sequence has an unprocessed amino acid sequence of SEQ ID NO: 182, which is encodable by a polynucleotide having the nucleic acid sequence of SEQ ID NO: 183.

N-terminal sequencing of the CHO-cell-produced material revealed a major sequence of -GRGEAE (SEQ ID NO: 51). Notably, other constructs reported in the literature begin with an -SGR . . . sequence. Such reported constructs are also incorporated in the ActRIIB and its fusion proteins disclosed herein.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Applicants further generated an ActRIIB(25-131)-hFc fusion protein, which comprises the human ActRIIB extracellular domain with N-terminal and C-terminal truncations (residues 25-131 of the native ActRIIB having the sequence of SEQ ID NO: 1) fused N-terminally with a TPA leader sequence substituted for the native ActRIIB leader and C-terminally with a human Fc domain via a minimal linker (three glycine residues) (SEQ ID NO: 184). A polynucleotide encoding this fusion protein is shown in SEQ ID NO: 185. Applicants modified the codons and found a variant nucleic acid (SEQ ID NO: 186) encoding the ActRIIB(25-131)-hFc protein that provided substantial improvement in the expression levels of initial transformants. The processed ActRIIB(25-131)-hFc protein has an amino acid sequence of SEQ ID NO: 187 (N-terminus confirmed by N-terminal sequencing).

The expressed molecule was purified using a series of column chromatography steps, including for example, three or more of the following, in any order: Protein A chromatography, Q sepharose chromatography, phenylsepharose chromatography, size exclusion chromatography and cation exchange chromatography. The purification could be completed with viral filtration and buffer exchange.

Affinities of several ligands for ActRIIB(25-131)-hFc and its full-length counterpart ActRIIB(20-134)-hFc were evaluated in vitro with a Biacore™ instrument, and the results are summarized in the Table 3 below. Kd values were obtained by steady-state affinity fit due to very rapid association and dissociation of the complex, which prevented accurate determination of $k_{on}$ and $k_{off}$. ActRIIB(25-131)-hFc bound, for example, activin A, activin B, and GDF11 with high affinity.

TABLE 3

| Ligand Selectivity of ActRIIB-hFc Variants | | | |
|---|---|---|---|
| Fusion Construct | Activin A (Kd, $e^{-11}$) | Activin B (Kd, $e^{-11}$) | GDF11 (Kd, $e^{-11}$) |
| ActRIIB(20-134)-hFc | 1.6 | 1.2 | 3.6 |
| ActRIIB(25-131)-hFc | 1.8 | 1.2 | 3.1 |

Another exemplary ActRIIB-hFc fusion protein has the amino acid sequence of SEQ ID NO: 188, comprising an ActRIIB-derived portion (SEQ ID NO: 189, containing a L79D substitution of the corresponding ActRIIB extracellular domain sequence) fused to a human Fc domain. Either the ActRIIB-derived portion or the full-length of the ActRIIB-hFc fusion protein may be used as a monomer or as a non-Fc fusion protein as a monomer, dimer, or greater-order complex.

The ActRIIB(L79D, 20-134)-hFc fusion protein was expressed in CHO cell lines. Three different leader sequences may be used for the expression: (i) the Honey bee melittin (HBML) leader (SEQ ID NO: 214), (ii) the tissue plasminogen activator (TPA) leader (SEQ ID NO: 215), and (iii) the native leader (SEQ ID NO: 216). An exemplary ActRIIB(L79D, 20-134)-hFc fusion protein contains the TPA leader and has the unprocessed amino acid sequence of SEQ ID NO: 190. A polynucleotide encoding such exemplary fusion protein has the nucleic acid sequence of SEQ ID NO: 191.

Example 5. Effects of an Exemplary ActRIIB(20-134)-Fc Homodimer on Kidney Fibrosis, Inflammation, and Kidney Injury The effects of the ActRIIB(20-134)-Fc homodimer on kidney disease were assessed in a mouse unilateral ureteral obstruction model, with similar methods mentioned in previous Examples and herein in the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with ActRIIB(20-

134)-Fc homodimer significantly suppressed the expression of fibrotic (Col1a1, Col3a1, PAI-1, Fibronectin, CTGF, and a-SMA, shown in FIG. 20) and inflammatory (IL-1B and TNF-alpha, shown in FIG. 21) genes, inhibited the upregulation of TGF R 1 and activin A (FIG. 22, top two panels), and reduced kidney injury (downregulation of NGAL, shown in FIG. 22, lower panel).

Example 6: Generation of a Fusion Protein with Truncated ActRIIB Extracellular Domain As illustrated in Example 4, an ActRIIB(L79D, 20-134)-hFc fusion protein (SEQ ID NO: 190) was generated by N-terminal fusion of TPA leader to the ActRIIB extracellular domain (residues 20-134 in SEQ ID NO: 1) containing a leucine-to-aspartate substitution (at residue 79 in SEQ ID NO: 1) and C-terminal fusion of human Fc domain with minimal linker (three glycine residues). Further, a similar fusion protein with a truncated ActRIIB extracellular domain, referred to as ActRIIB(L79D, 25-131)-hFc (SEQ ID NO: 192), was generated by N-terminal fusion of TPA leader to truncated extracellular domain (residues 25-131 in SEQ ID NO: 1) containing a leucine-to-aspartate substitution (at residue 79 in SEQ ID NO: 1) and C-terminal fusion of human Fc domain with minimal linker (three glycine residues). The sequence of the cell purified form of ActRIIB (L79D, 25-131)-hFc is presented in SEQ ID NO: 193. One nucleotide sequence encoding this fusion protein is shown in SEQ ID NO: 194, while an alternative polynucleotide sequence encoding exactly the same fusion protein is shown in SEQ ID NO: 195.

The affinity of these and other ActRIIB-hFc proteins for several ligands was evaluated in vitro with a Biacore™ instrument. Results are summarized in the Table 4 below. $K_d$ values were obtained by steady-state affinity fit due to the very rapid association and dissociation of the complex, which prevented accurate determination of $k_{on}$ and $k_{off}$.

TABLE 4

Ligand Selectivity of ActRIIB-hFc Variants

| Fusion Construct | Activin A ($K_d$, $e^{-11}$) | Activin B ($K_d$, $e^{-11}$) | GDF11 ($K_d$, $e^{-11}$) |
|---|---|---|---|
| ActRIIB(20-134)-hFc | 1.6 | 1.2 | 3.6 |
| ActRIIB(L79D, 20-134)-hFc | 1350.0 | 78.8 | 12.3 |
| ActRIIB(25-131)-hFc | 1.8 | 1.2 | 3.1 |
| ActRIIB(L79D, 25-131)-hFc | 2290.0 | 62.1 | 7.4 |

The fusion protein with a truncated extracellular domain, ActRIIB(L79D, 25-131)-hFc, equaled or surpassed the ligand selectivity for Activin B and GDF11 displayed by the longer variant, ActRIIB(L79D, 20-134)-hFc, with pronounced loss of activin A binding, partial loss of activin B binding, and nearly full retention of GDF11 binding compared to ActRIIB-hFc counterparts lacking the L79D substitution. Note that different truncation variants without the L79D substitution (i.e., ActRIIB(25-131)-hFc vs. ActRIIB (20-134)-hFc) had similar binding selectivity toward the ligands displayed here. ActRIIB(L79D, 25-131)-hFc also retains strong to intermediate binding to the Smad2/3 signaling ligand GDF8 and the Smad1/5/8 ligands BMP6 and BMP10.

Example 7. Effects of an Exemplary ActRIIB(L79D, 25-131)-hFc Homodimer on Kidney Fibrosis, Inflammation, and Kidney Injury The effects of the ActRIIB(L79D, 25-131)-hFc homodimer on kidney disease were assessed in a mouse unilateral ureteral obstruction model, using similar methods to those mentioned in previous Examples and herein in the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the ActRIIB (L79D, 25-131)-hFc homodimer did not suppress the expression of fibrotic (Col1a1, Col3a1, PAI-1, Fibronectin, CTGF, and a-SMA, shown in FIG. 44) or inflammatory (IL-1B and TNF-alpha, shown in FIG. 45) genes. The treatment did not inhibit the upregulation of TGF R 1 (FIG. 46) and activin A (FIG. 47) or reduce kidney injury (downregulation of NGAL, shown in FIG. 48), either.

Example 8. Generation of an ALK4:ActRTIB Heterodimer

Applicants constructed a soluble ALK4-Fc:ActRIIB-Fc heteromeric complex comprising the extracellular domains of human ActRIIB and human ALK4, which are each separately fused to an Fc domain with a linker positioned between the extracellular domain and the Fc domain. The individual constructs are referred to as ActRIIB-Fc fusion polypeptide and ALK4-Fc fusion polypeptide, respectively, and the sequences for each are provided below. In this and other Examples, it is noted that the ActRIIB portion of the fusion protein used for forming dimers may comprise any part of natural or mutated ActRIIB sequences. For example, the ActRIIB portion may comprise a full-length extracellular domain of nature ActRIIB (e.g., an ActRIIB(20-134) sequence), an extracellular domain with truncations (e.g., an ActRIIB(25-131) sequence), extensions, or mutations (e.g., an ActRIIB(L79D, 25-131) or an ActRIIB(L79D, 20-134) sequence), unless specified otherwise.

A methodology for promoting formation of ALK4-Fc: ActRIIB-Fc heteromeric complexes, as opposed to ActRIIB-Fc or ALK4-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

Figure 9:
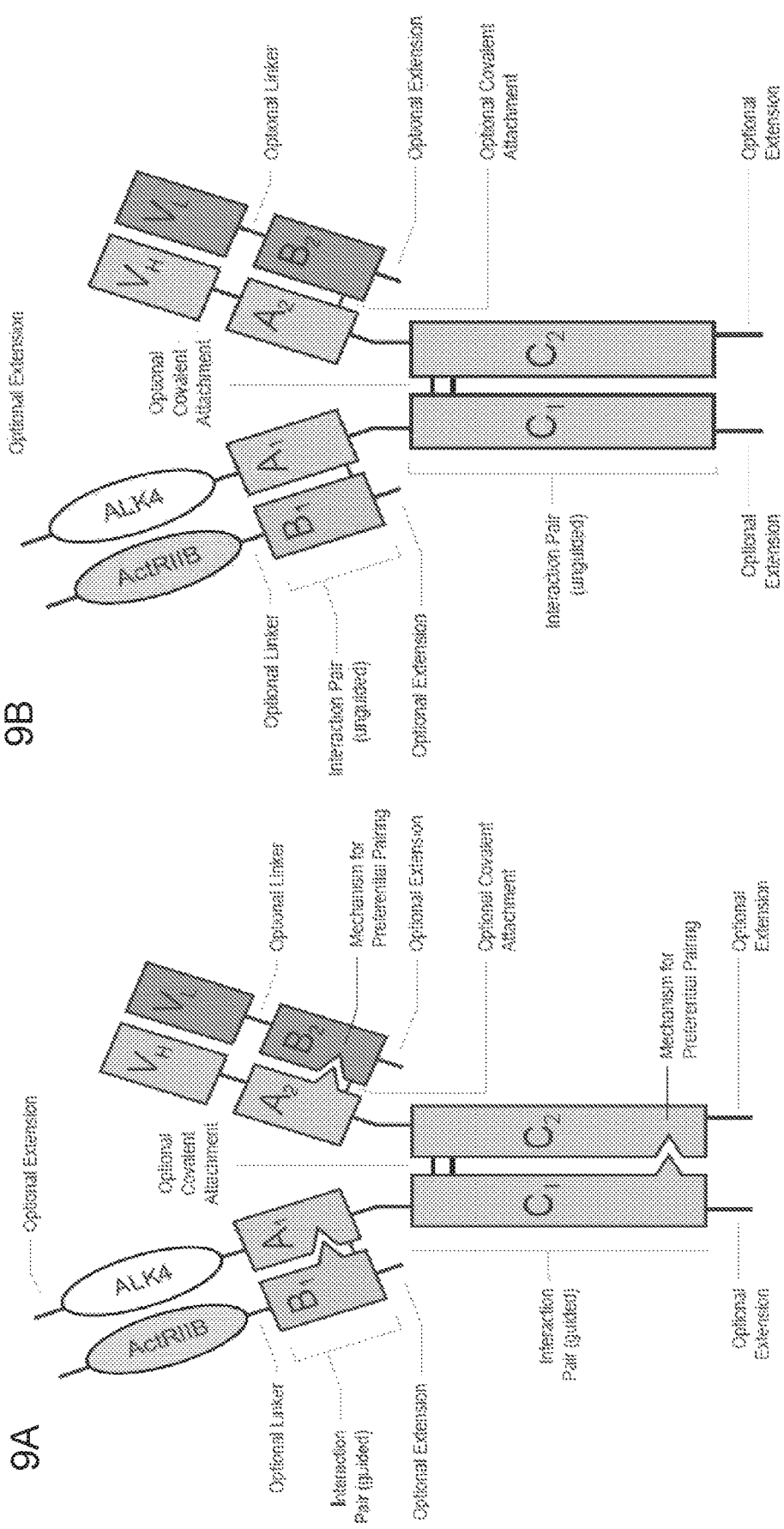

In addition to the structures shown in FIGS. 5A to 5D and FIGS. 6A to 6G, ALK4:ActRIIB heterodimers may be formed in other multimeric structures, such as those in FIGS. 9 and 11. Possible monomers for the multimeric complex include the various fusion proteins exemplified in FIG. 10.

In one approach, illustrated in the ActRIIB-Fc (SEQ ID NO: 199 or 201) and ALK4-Fc (SEQ ID NO: 202 or 204) polypeptide sequences, one Fc domain is altered to introduce cationic amino acids at the interaction face, while the other Fc domain is altered to introduce anionic amino acids at the interaction face. ActRIIB-Fc fusion polypeptide and ALK4-Fc fusion polypeptide each employ the tissue plasminogen activator (TPA) leader (SEQ ID NO: 215).

SEQ ID NO: 199 contains a leader (signal) sequence and linker. To promote formation of ALK4-Fc:ActRIIB-Fc heterodimer rather than ActRIIB-Fc:ActRIIB-Fc or ALK4-Fc: ALK4-Fc homodimeric complexes, two amino acid substitutions (replacing acidic amino acids with lysine) can be introduced into the Fc domain of the ActRIIB fusion protein, in SEQ ID NO: 199. The corresponding processed protein (i.e., no leader sequence) has the amino acid sequence of SEQ ID NO: 201. The amino acid sequences of SEQ ID NO: 199 or 201 may optionally be provided with lysine (K)

removed from the C-terminus. A polynucleotide encoding SEQ ID NO: 199 has a nucleic acid sequence of SEQ ID NO: 200.

The corresponding ALK4-Fc fusion polypeptide having the amino acid sequence of SEQ ID NO: 202. To guide heterodimer formation with the ActRIIB-Fc fusion polypeptide of SEQ ID NOs: 199 and 201 above, two amino acid substitutions (replacing lysines with aspartic acids) can be introduced into the Fc domain of the ALK4-Fc fusion polypeptide in SEQ ID NO: 202. The corresponding processed protein (i.e., without the leader sequence) has the amino acid sequence of SEQ ID NO: 204. The amino acid sequences of SEQ ID NOs: 202 and 204 may optionally be provided with lysine (K) added at the C-terminus. One polynucleotide encoding SEQ ID NO: 202 has a nucleic acid sequence of SEQ ID NO: 203.

The ActRIIB-Fc (SEQ ID NO: 199 or 201, or the corresponding sequences having the lysine (K) removed from the C terminus) and ALK4-Fc proteins (SEQ ID NO: 202 or 204, or the corresponding sequences having a lysine (K) added to the C terminus) may be co-expressed and purified from a CHO cell line, to give rise to a heteromeric complex comprising ALK4-Fc:ActRIIB-Fc.

In another approach to promote the formation of heteromultimer complexes using asymmetric Fc fusion proteins, the Fc domains are altered to introduce complementary hydrophobic interactions and an additional intermolecular disulfide bond as illustrated in the ActRIIB-Fc and ALK4-Fc polypeptide sequences of SEQ ID NOs: 205 or 206 and 207 or 208, respectively. The ActRIIB-Fc fusion polypeptide and ALK4-Fc fusion polypeptide each employ the tissue plasminogen activator (TPA) leader (SEQ ID NO: 215).

An ActRIIB-Fc polypeptide sequence set forth in SEQ ID NO: 205 contains a leader (signal) sequence and linker. To promote formation of the ALK4-Fc:ActRIIB-Fc heterodimer rather than homodimeric complexes, two amino acid substitutions (replacing a serine with a cysteine and a threonine with a tryptophan) can be introduced into the Fc domain of the fusion protein above. The corresponding processed protein (i.e., without the leader sequence) has the amino acid sequence of SEQ ID NO: 206. The amino acid sequences of SEQ ID NOs: 205 and 206 may optionally be provided with lysine (K) removed from the C-terminus.

An ALK4-Fc polypeptide sequence set forth in SEQ ID NO: 207 contains a leader sequence and linker. To guide heterodimer formation with the ActRIIB-Fc fusion polypeptide of SEQ ID NOs: 205 or 206 above, four amino acid substitutions can be introduced into the Fc domain of the ALK4 fusion polypeptide in SEQ ID NO: 207. The corresponding processed protein (i.e., without the leader sequence) has the amino acid sequence of SEQ ID NO: 208. The amino acid sequences of SEQ ID NOs: 207 and 208 may optionally be provided with lysine (K) removed from the C-terminus.

ActRIIB-Fc (SEQ ID NO: 205 or 206, or the corresponding sequences having the lysine (K) removed from the C terminus) and ALK4-Fc proteins (SEQ ID NO: 207 or 208, or the corresponding sequences having the lysine (K) removed from the C terminus) may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 9. Ligand Binding Profile of ALK4-Fc:ActRIIB-Fc Heterodimer Compared to ActRIIB-Fc Homodimer and ALK4-Fc Homodimer A Biacore™-based binding assay was used to compare ligand binding selectivity of an exemplary ALK4-Fc:ActRIIB-Fc heterodimeric complex as described above with the binding selectivity of ActRIIB-Fc and ALK4-Fc homodimer complexes. The ALK4-Fc:ActRIIB-Fc heterodimer, ActRIIB-Fc homodimer, and ALK4-Fc homodimer were independently captured onto the system using an anti-Fc antibody. Ligands were injected and allowed to flow over the captured receptor protein. Results are summarized in the Table 5 below, in which ligand off-rates ($k_d$) most indicative of effective ligand traps are denoted by gray shading.

TABLE 5

Ligand binding profile of ALK4-Fc:ActRIIB-Fc:heterodimer compared to ActRIIB-Fc homodimer and ALK4-Fc homodimer

| Ligand | ActRIIB-Fc homodimer | | | ALK4-Fc homodimer | | | ALK4-Fc:ActRIIB-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $2.3 \times 10^{-4}$ | 19 | $5.8 \times 10^5$ | $1.2 \times 10^{-2}$ | 20000 | $1.3 \times 10^7$ | $1.5 \times 10^{-4}$ | 12 |
| Activin B | $5.1 \times 10^6$ | $1.0 \times 10^{-4}$ | 20 | | No binding | | $7.1 \times 10^6$ | $4.0 \times 10^{-5}$ | 6 |
| BMP6 | $3.2 \times 10^7$ | $6.8 \times 10^{-3}$ | 190 | | — | | $2.0 \times 10^6$ | $5.5 \times 10^{-3}$ | 2700 |
| BMP9 | $1.4 \times 10^7$ | $1.1 \times 10^{-3}$ | 77 | | — | | | Transient* | 3400 |
| BMP10 | $2.3 \times 10^7$ | $2.6 \times 10^{-4}$ | 11 | | — | | $5.6 \times 10^7$ | $4.1 \times 10^{-3}$ | 74 |
| GDF3 | $1.4 \times 10^6$ | $2.2 \times 10^{-3}$ | 1500 | | — | | $3.4 \times 10^6$ | $1.7 \times 10^{-2}$ | 4900 |
| GDF8 | $8.3 \times 10^5$ | $2.3 \times 10^{-4}$ | 280 | $1.3 \times 10^5$ | $1.9 \times 10^{-3}$ | 15000† | $3.9 \times 10^5$ | $2.1 \times 10^{-4}$ | 550 |
| GDF11 | $5.0 \times 10^7$ | $1.1 \times 10^{-4}$ | 2 | $5.0 \times 10^6$ | $4.8 \times 10^{-3}$ | 270† | $3.8 \times 10^7$ | $1.1 \times 10^{-4}$ | 3 |

*Indeterminate due to transient nature of interaction
†Very low signal
— Not tested These comparative binding data demonstrate that ALK4-Fc:ActRIIB-Fc heterodimer has an altered binding profile/selectivity relative to either ActRIIB-Fc or ALK4-Fc homodimers. ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. In particular, BMP9 displays low or no observable affinity for ALK4-Fc:ActRIIB-Fc heterodimer, whereas this ligand binds strongly to ALK4-Fc:ActRIIB-Fc heterodimer. Like the ActRIIB-Fc homodimer, the heterodimer retains intermediate-level binding to BMP6. See FIG. 12.

In addition, an A-204 Reporter Gene Assay was used to evaluate the effects of ALK4-Fc:ActRIIB-Fc heterodimer and ActRIIB-Fc:ActRIIB-Fc homodimer on signaling by activin A, activin B, GDF11, GDF8, BMP10, and BMP9. Cell line: Human Rhabdomyosarcoma (derived from muscle). Reporter vector: pGL3(CAGA)12 (as described in Dennler et al., 1998, EMBO 17: 3091-3100). The CAGA12 motif is present in TGF-beta responsive genes (PAI-1 gene), so this vector is of general use for factors signaling through Smad2 and 3. An exemplary A-204 Reporter Gene Assay is outlined below.

Day 1: Split A-204 cells into 48-well plate.
Day 2: A-204 cells transfected with 10 ug pGL3(CAGA) 12 or pGL3(CAGA)12(10 ug)+pRLCMV (1 ug) and Fugene.
Day 3: Add factors (diluted into medium+0.1% BSA). Inhibitors need to be preincubated with Factors for about one hr before adding to cells. About six hrs later, cells are rinsed with PBS and then lysed.

Following the above steps, applicant performed a Luciferase assay.

Both the ALK4-Fc:ActRIIB-Fc heterodimer and ActRIIB-Fc:ActRIIB-Fc homodimer were determined to be potent inhibitors of activin A, activin B, GDF11, and GDF8 in this assay. In particular, as can be seen in the comparative homodimer/heterodimer $IC_{50}$ data illustrated in FIG. 13, ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. This data is consistent with the above-discussed binding data in which it was observed that both the ALK4-Fc:ActRIIB-Fc heterodimer and ActRIIB-Fc:ActRIIB-Fc homodimer display strong binding to activin A, activin B, GDF8, and GDF11, but BMP10 and BMP9 have significantly reduced affinity for the ALK4-Fc:ActRIIB-Fc heterodimer compared to the ActRIIB-Fc:ActRIIB-Fc homodimer.

Together, these data therefore demonstrate that ALK4-Fc:ActRIIB-Fc heterodimer is a more selective antagonist of activin B, activin A, GDF8, and GDF11 compared to ActRIIB-Fc homodimer. Accordingly, an ALK4-Fc:ActRIIB-Fc heterodimer will be more useful than an ActRIIB-Fc homodimer in certain applications where such selective antagonism is advantageous. Examples include therapeutic applications where it is desirable to retain antagonism of one or more of activin A, activin B, activin AB, GDF8, and GDF11 but minimize antagonism of one or more of BMP9, BMP10, GDF3, and BMP6.

Example 10. Effects of an Exemplary ALK4:ActRIIB Heteromultimer on Kidney Fibrosis, Inflammation, and Kidney Injury The effects of the ALK4-Fc:ActRIIB-Fc heterodimer described in Example 7 on kidney disease was assessed in a mouse unilateral ureteral obstruction model. See, e.g., Klahr and Morrissey (2002) Am J Physiol Renal Physiol 283: F861-F875.

Twenty-four C57BL/6 male mice 12 weeks of age underwent left unilateral ureteral ligation twice at the level of the lower pole of kidney. After 3 days, eight mice were euthanized and kidneys from individual animals were harvested to assess kidney injury. The remaining mice were randomized into two groups: i) eight mice were injected subcutaneously with the ALK4-Fc:ActRIIB-Fc heterodimer at a dose of 10 mg/kg at day 3, day 7, day 10, and day 14 after surgery and a ii) eight mice were injected subcutaneously with vehicle control, phosphate buffered saline (PBS), at day 3, day 7, day 10, and day 14 after surgery. Both groups were sacrificed at day 17 in accordance with the relevant Animal Care Guidelines. Half kidneys from individual animals were collected for histology analysis (H&E, and Masson's Trichrome stain), from both the UUO kidney and contralateral kidney, and ¼ kidneys were used for RNA extraction (RNeasy Midi Kit, Qiagen, IL).

Gene expression analysis on UUO kidney samples was performed to assess levels of various genes. QRT-PCR was performed on a CFX Connect™ Real-time PCR detection system (Bio-Rad, CA) to evaluate the expression of various fibrotic genes (Col1a1, Fibronectin, PAI-1, CTGF, and a-SMA), inflammatory genes (TNF-alpha, and MCP1), cytokines (TGFβ1, TGFβ2, TGFβ3, and activin A), and kidney injury genes (NGAL). See FIGS. 14A to 14C. Treatment of mice with ALK4-Fc:ActRIIB-Fc heterodimer significantly suppressed the expression of fibrotic and inflammatory genes, inhibited the upregulation of TGFβ 1/2/3 and reduced kidney injury. Histology data confirmed that ALK4-Fc:ActRIIB-Fc heterodimer treatment significantly inhibited kidney fibrosis and reduced kidney injury in the UUO model.

Together, these data demonstrate that ALK4:ActRIIB heteromultimer treatment suppresses kidney fibrosis and inflammation and reduces kidney injury. Moreover, these data indicate that other ALK4:ActRIIB antagonists may be useful in the treatment or preventing of kidney disease including, for example, antagonists of ALK4 and/or ActRIIB-binding ligands, antagonists of ALK4 and/or ActRIIB receptors, antagonists of ALK4 and/or ActRIIB downstream signaling mediators (e.g., Smads), and antagonists of TGFβ superfamily co-receptors associated with ALK4 and/or ActRIIB.

Example 11. Generation of an ActRIIB-Fc:ALK7-Fc Heterodimer

Applicants constructed a soluble ActRIIB-Fc:ALK7-Fc heteromeric complex comprising the extracellular domains of human ActRIIB and human ALK7, which are each fused to an Fc domain with a linker positioned between the extracellular domain and the Fc domain. The individual constructs are referred to as ActRIIB-Fc and ALK7-Fc, respectively.

A methodology for promoting formation of ActRIIB-Fc:ALK7-Fc heteromeric complexes, as opposed to the ActRIIB-Fc or ALK7-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB-Fc (SEQ ID NO: 199) and ALK7-Fc polypeptide sequences disclosed below, respectively, one Fc domain is altered to introduce cationic amino acids at the interaction face, while the other Fc domain is altered to introduce anionic amino acids at the interaction face. The ActRIIB-Fc fusion polypeptide and ALK7-Fc fusion polypeptide each employ the tissue plasminogen activator (TPA) leader (SEQ ID NO: 215).

The leader (signal) sequence and linker in SEQ ID NO: 199. To promote formation of the ActRIIB-Fc:ALK7-Fc heterodimer rather than either of the possible homodimeric complexes, two amino acid substitutions (replacing acidic amino acids with lysine) can be introduced into the Fc domain of the ActRIIB fusion protein. The corresponding processed (i.e., no leader sequence) ActRIIB-Fc fusion polypeptide has the amino acid sequence of SEQ ID NO: 201. Both SEQ ID NOs: 199 and 201 may optionally be provided with lysine (K) removed from the C-terminus. A polynucleotide encoding SEQ ID NO: 199 has a nucleic acid sequence of SEQ ID NO: 200.

An exemplary guided form of ALK7-Fc fusion protein is given in SEQ ID NO: 209. The sequence contains a signal sequence and linker sequence. To promote formation of the ActRIIB-Fc:ALK7-Fc heterodimer rather than homodimeric complexes, two amino acid substitutions (replacing lysines with aspartic acids) can be introduced into the Fc domain of the fusion protein. The corresponding processed (i.e., no leader sequence) ALK7-Fc fusion polypeptide has the amino acid sequence of SEQ ID NO: 211. Both SEQ ID NOs: 209 and 211 may optionally be provided with a lysine added at the C-terminus. A polynucleotide encoding SEQ ID NO: 209 has a nucleic acid sequence of SEQ ID NO: 210.

The ActRIIB-Fc (SEQ ID NO: 199 or 201, or the corresponding sequences having the lysine (K) removed from the C-terminus) and ALK7-Fc (SEQ ID NO: 209 or 211, or the corresponding sequences having a lysine (K) added at the C-terminus) proteins may be co-expressed and purified from a CHO cell line to give rise to a heteromeric complex comprising ActRIIB-Fc:ALK7-Fc.

In another approach to promote the formation of heteromultimer complexes using asymmetric Fc fusion proteins, the Fc domains are altered to introduce complementary hydrophobic interactions and an additional intermolecular disulfide bond in the Fc domains of the ActRIIB-Fc and ALK7-Fc polypeptides. For example, in a mutated ActRIIB-Fc polypeptide (SEQ ID NO: 205), the leader sequence and linker. To promote formation of the ActRIIB-Fc:ALK7-Fc heterodimer rather than either of the possible homodimeric complexes, two amino acid substitutions (replacing a serine with a cysteine and a threonine with a tryptophan) can be introduced into the Fc domain of the fusion protein. The corresponding processed (i.e., no leader sequence) ActRIIB-Fc fusion polypeptide has the amino acid sequence of SEQ ID NO: 206. Both SEQ ID NOs: 205 and 206 may optionally be provided with lysine removed from the C-terminus.

An exemplary mutated form (for guided dimerization) of ALK7-Fc fusion protein is given in SEQ ID NO: 212. To guide heterodimer formation with the ActRIIB-Fc fusion polypeptide of SEQ ID NO: 205 or 206 above, four amino acid substitutions can be introduced into the Fc domain of the ALK7 fusion polypeptide. The corresponding processed (i.e., no leader sequence) ALK7-Fc fusion polypeptide has the amino acid sequence of SEQ ID NO: 213. Both SEQ ID NOs: 212 and 213 may optionally be provided with the lysine removed from the C-terminus.

The ActRIIB-Fc (SEQ ID NO: 205 or 206, or the corresponding sequences having the lysine (K) removed from the C-terminus) and ALK7-Fc (SEQ ID NO: 212 or 213, or the corresponding sequences having the lysine (K) removed from the C-terminus) proteins may be co-expressed and purified from a CHO cell line, to give rise to a heteromeric complex comprising ActRIIB-Fc:ALK7-Fc.

Purification of various ActRIIB-Fc:ALK7-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 12. Ligand Binding Profile of ActRIIB-Fc:ALK7-Fc Heterodimer Compared to ActRIIB-Fc Homodimer and ALK7-Fc Homodimer A Biacore™-based binding assay was used to compare ligand binding selectivity of an exemplary ActRIIB-Fc:ALK7-Fc heterodimeric complex with that of ActRIIB-Fc and ALK7-Fc homodimeric complexes. Exemplary dimers such as an ActRIIB-Fc:ALK7-Fc heterodimer, an ActRIIB-Fc homodimer, and an ALK7-Fc homodimer were independently captured onto the system using an anti-Fc antibody. Ligands were injected and allowed to flow over the captured receptor protein. Results are summarized in the Table 6 below, in which ligand off-rates ($k_d$) most indicative of effective ligand traps are denoted by gray shading.

TABLE 6

Ligand binding profile of ActRIIB-Fc:ALK7-Fc heterodimer compared to ActRIIB-Fc homodimer and ALK7-Fc homodimer

| | ActRIIB-Fc homodimer | | | ALK7-Fc homodimer | | | ActRIIB-Fc:ALK7-Fc heterodimer | | |
|---|---|---|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) | ka (1/Ms) | $k_d$ (1/s) | $K_D$ (pM) |
| activin A | $1.3 \times 10^7$ | $1.4 \times 10^{-4}$ | 11 | No binding | | | $4.4 \times 10^7$ | $1.9 \times 10^{-3}$ | 43 |
| activin B | $1.5 \times 10^7$ | $1.6 \times 10^{-4}$ | 8 | No binding | | | $1.2 \times 10^7$ | $2.0 \times 10^{-4}$ | 17 |
| activin C | No binding | | | No binding | | | $3.5 \times 10^5$ | $2.4 \times 10^{-3}$ | 6900 |
| activin AC | $2.0 \times 10^7$ | $3.1 \times 10^{-3}$ | 160 | No binding | | | $2.6 \times 10^6$ | $5.7 \times 10^{-4}$ | 220 |
| BMP5 | $2.6 \times 10^7$ | $7.5 \times 10^{-2}$ | 2900 | No binding | | | $1.5 \times 10^5$ | $8.5 \times 10^{-3}$ | 57000 |
| BMP6 | $2.4 \times 10^7$ | $3.9 \times 10^{-3}$ | 160 | No binding | | | $1.2 \times 10^6$ | $6.3 \times 10^{-3}$ | 5300 |
| BMP9 | $1.2 \times 10^8$ | $1.2 \times 10^{-3}$ | 10 | No binding | | | Transient* | | >1400 |
| BMP10 | $5.9 \times 10^6$ | $1.5 \times 10^{-4}$ | 25 | No binding | | | $1.5 \times 10^7$ | $2.8 \times 10^{-3}$ | 190 |
| GDF3 | $1.4 \times 10^6$ | $2.2 \times 10^{-3}$ | 1500 | No binding | | | $2.3 \times 10^6$ | $1.0 \times 10^{-2}$ | 4500 |
| GDF8 | $3.5 \times 10^6$ | $2.4 \times 10^{-4}$ | 69 | No binding | | | $3.7 \times 10^6$ | $1.0 \times 10^{-3}$ | 270 |
| GDF11 | $9.6 \times 10^7$ | $1.5 \times 10^{-4}$ | 2 | No binding | | | $9.5 \times 10^7$ | $7.5 \times 10^{-4}$ | 8 |

*Indeterminate due to transient nature of interaction
— Not tested

These comparative binding data demonstrate that the ActRIIB-Fc:ALK7-Fc heterodimer has an altered binding profile/selectivity relative to either the ActRIIB-Fc homodimer or ALK7-Fc homodimer. Interestingly, four of the five ligands with the strongest binding to ActRIIB-Fc homodimer (activin A, BMP10, GDF8, and GDF11) exhibit reduced binding to the ActRIIB-Fc:ALK7-Fc heterodimer, the exception being activin B which retains tight binding to the heterodimer. Similarly, three of the four ligands with intermediate binding to ActRIIB-Fc homodimer (GDF3, BMP6, and particularly BMP9) exhibit reduced binding to the ActRIIB-Fc:ALK7-Fc heterodimer, whereas binding to activin AC is increased to become the second strongest ligand interaction with the heterodimer overall. Finally, activin C and BMP5 unexpectedly bind the ActRIIB-Fc:ALK7 heterodimer with intermediate strength despite no binding (activin C) or weak binding (BMP5) to ActRIIB-Fc homodimer. The net result is that the ActRIIB-Fc:ALK7-Fc heterodimer possesses a ligand-binding profile distinctly different from that of either ActRIIB-Fc homodimer or ALK7-Fc homodimer, which binds none of the foregoing ligands. See FIG. 15.

These results therefore demonstrate that the ActRIIB-Fc:ALK7-Fc heterodimer is a more selective antagonist of activin B and activin AC compared to ActRIIB-Fc homodimer. Moreover, ActRIIB-Fc:ALK7-Fc heterodimer exhibits the unusual property of robust binding to activin C. Accordingly, an ActRIIB-Fc:ALK7-Fc heterodimer will be more useful than an ActRIIB-Fc homodimer in certain applications where such selective antagonism is advantageous. Examples include therapeutic applications where it is desirable to retain antagonism of activin B or activin AC but decrease antagonism of one or more of activin A, GDF3, GDF8, GDF11, BMP9, or BMP10. Also included are therapeutic, diagnostic, or analytic applications in which it is desirable to antagonize activin C or, based on the similarity between activin C and activin E, activin E.

Example 13. Effects of an Exemplary ALK7:ActRIIB Heteromultimer on Kidney Fibrosis, Inflammation, and Kidney Injury The effects of the ALK7-Fc:ActRIIB-Fc heterodimer described in Example 11 on kidney disease was assessed in a mouse unilateral ureteral obstruction model. See, e.g., Klahr and Morrissey (2002) *Am J Physiol Renal Physiol* 283: F861-F875.

Twenty-four C57BL/6 male mice 12 weeks of age underwent left unilateral ureteral ligation twice at the level of the lower pole of kidney. After 3 days, eight mice were euthanized and kidneys from individual animals were harvested to assess kidney injury. The remaining mice were randomized into two groups: i) eight mice were injected subcutaneously with the ALK7-Fc:ActRIIB-Fc heterodimer at a dose of 10 mg/kg at day 3, day 7, day 10, and day 14 after surgery and a ii) eight mice were injected subcutaneously with vehicle control, phosphate buffered saline (PBS), at day 3, day 7, day 10, and day 14 after surgery. Both groups were sacrificed at day 17 in accordance with the relevant Animal Care Guidelines. Half kidneys from individual animals were collected for histology analysis (H&E, and Masson's Trichrome stain), from both the UUO kidney and contralateral kidney, and 1/4 kidneys were used for RNA extraction (RNeasy Midi Kit, Qiagen, IL).

Gene expression analysis on UUO kidney samples was performed to assess levels of various genes. QRT-PCR was performed on a CFX Connect™ Real-time PCR detection system (Bio-Rad, CA) to evaluate the expression of various fibrotic genes (Col1a1, Col3a1, Fibronectin, PAI-1, CTGF, and a-SMA), inflammatory genes (TNF-alpha, and MCP1), cytokines (TGFβ 1, TGFβ2, TGFβ3, and activin A), kidney injury genes (NGAL), Hypoxia-inducible factor 1-alpha (HIF1a), and activin A receptor (ActRIIA). See FIGS. 16A to 16C. Treatment of mice with ALK7-Fc:ActRIIB-Fc heterodimer significantly suppressed the expression of fibrotic and inflammatory genes, inhibited the upregulation of TGFβ 1/2/3, activin A, and ActRIIa, and reduced kidney injury. Histology data confirmed that ALK7-Fc:ActRIIB-Fc heterodimer treatment significantly inhibited kidney fibrosis and reduced kidney injury in the UUO model.

Together, these data demonstrate that ALK7:ActRIIB heteromultimer treatment suppresses kidney fibrosis and inflammation and reduces kidney injury. Moreover, these data indicate that other ALK7:ActRIIB antagonists may be useful in the treatment or preventing of kidney disease including, for example, antagonists of ALK7 and/or ActRIIB-binding ligands (e.g., ligand antibodies and other ligand traps such as follistatin, Cerberus and Lefty), antagonists of ALK7 and/or ActRIIB receptors, antagonists of ALK7 and/or ActRIIB downstream signaling mediators (e.g., Smads), and antagonists of TGFβ superfamily co-receptors (e.g., antagonists of Crypto or Cryptic).

Example 14. Effects of an Exemplary Anti-TGF Beta Pan Antibody on Kidney Fibrosis, Inflammation, and Kidney Injury The effects of an anti-TGF-beta 1/2/3 pan antibody (i.e., binds to isoforms 1, 2, and 3 of TGF-beta) on kidney disease were assessed in a mouse unilateral ureteral obstruction model, with the same methods in these Examples and the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the pan antibody significantly suppressed the expression of fibrotic (Col1a1, Col3a1, PAI-1, Fibronectin, CTGF, and a-SMA, shown in FIG. 23) and slightly decreased inflammatory (TNF-alpha, shown in FIG. 24) genes, and inhibited the upregulation of TGF R 1/2/3 and activin A (FIG. 25). However, different from the ActRIIA-Fc homodimer and the ActRIIB-Fc homodimer, the pan antibody did not reduce kidney injury (no downregulation of NGAL, shown in FIG. 25).

Example 15. Effects of an Exemplary Anti-Activin a Antibody on Kidney Fibrosis, Inflammation, and Kidney Injury The effects of an anti-activin A antibody on kidney disease were assessed in a mouse unilateral ureteral obstruction model, using the same methods in these Examples and the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the anti-activin A antibody significantly suppressed the expression of fibrotic (Col1a1, Col3a1, PAI-1, Fibronectin, CTGF, and a-SMA, shown in FIG. 26) and inflammatory (IL-1B and TNF-alpha, shown in FIG. 27) genes, inhibited the upregulation of TGF β1/2/3 and activin A (FIG. 28), and reduced kidney injury (downregulation of NGAL, shown in FIG. 28).

Example 16. Effects of an Exemplary Anti-Activin A/B Antibody on Kidney Fibrosis, Inflammation, and Reduces Kidney Injury The effects of an anti-activin A/B antibody on kidney disease were assessed in a mouse unilateral ureteral obstruction model, using the same methods in these Examples and the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the anti-activin A/B antibody significantly suppressed the expression of fibrotic (Col1a1, Col3a1, PAI-1, Fibronectin, CTGF, and a-SMA, shown in FIG. 29) and inflammatory (IL-1B and TNF-alpha, shown in FIG. 30) genes, inhibited the upregulation of TGF β1/2/3 and activin A (FIG. 31), and reduced kidney injury (downregulation of NGAL, shown in FIG. 31).

Example 17. Effects of an Exemplary Anti-Activin B Antibody Treatment on Kidney Fibrosis, Inflammation, and Kidney Injury The effects of an anti-activin B antibody on kidney disease were assessed in a mouse unilateral ureteral obstruction model, using the same methods in these Examples and the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the anti-activin B antibody did not significantly suppress the expression of fibrotic (Col1a1, Col3a1, PAI-1, Fibronectin, CTGF, and a-SMA, shown in FIG. 32) or inflammatory (IL-1B and TNF-alpha, shown in FIG. 33) genes. The treatment did not significantly inhibit the upregulation of TGF β1/2/3 and activin A (FIG. 34) or reduce kidney injury (downregulation of NGAL, shown in FIG. 34), either.

Example 18. Effects of an Exemplary Anti-ActRIIA Antibody on Kidney Fibrosis, Inflammation, and Kidney Injury The effects of an anti-ActRIIA antibody on kidney disease were assessed in a mouse unilateral ureteral obstruction model, using the same methods in these Examples and the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the anti-ActRIIA antibody significantly suppressed the expression of fibrotic (Col1a1, Col3a1, PAI-1, Fibronectin, CTGF, and a-SMA, shown in FIG. 35) and inflammatory (TNF-alpha, shown in FIG. 36) genes, inhibited the upregulation of TGF β1/2/3 and activin A (FIG. 37), and reduced kidney injury (downregulation of NGAL, shown in FIG. 37).

Example 19. Effects of an Exemplary Anti-ActRIIA/IIB Antibody on Kidney Fibrosis, Inflammation, and Kidney Injury The effects of an anti-ActRIIA/IIB antibody on kidney disease were assessed in a mouse unilateral ureteral obstruction model, using the same methods to those mentioned in these Examples and herein in the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the anti-ActRIIA/IIB antibody significantly suppressed the expression of fibrotic (Col1a1, Col3a1, PAI-1, Fibronectin, CTGF, and a-SMA, shown in FIG. 38) and inflammatory (TNF-alpha, shown in FIG. 39) genes, inhibited the upregulation of TGF β1/2/3 and activin A (FIG. 40), and reduced kidney injury (downregulation of NGAL, shown in FIG. 40).

Example 20. Effects of an Exemplary Anti-ActRIIB Antibody on Kidney Fibrosis, Inflammation, and Kidney Injury The effects of an anti-ActRIIB antibody on kidney disease were assessed in a mouse unilateral ureteral obstruction model, using the same methods in these Examples and the instant description.

QRT-PCR was performed on a CFX Connect™ Real-time PCR detection system (Bio-Rad, CA) to evaluate the expression of various fibrotic and inflammatory genes and kidney injury genes (NGAL). Treatment of mice with the anti-ActRIIB antibody did not suppress the expression of fibrotic (Col1a1, Col3a1, PAI-1, Fibronectin, CTGF, and a-SMA, shown in FIG. 41) or inflammatory (TNF-alpha, shown in FIG. 42) genes. The treatment did not inhibit the upregulation of TGF β1/2/3 and activin A (FIG. 43) or reduce kidney injury (downregulation of NGAL, shown in FIG. 43), either.

Example 21. Ligand Binding Profile of ALK4-Fc:ActRIIA-Fc Heterodimer Compared to ActRIIA-Fc Homodimer and ALK4-Fc Homodimer Similarly, ActRIIA polypeptides (e.g., its extracellular domain) may be fused to, e.g., a human IgG Fc domain for further dimerization with itself (i.e., homodimers) or other polypeptides (i.e., heterodimers). In this and other Examples, it is noted that the ActRIIA portion of the fusion protein used for forming dimers may comprise any part of natural or mutated ActRIIA sequences disclosed herein or known in the art. For example, the ActRIIA portion may comprise a full-length extracellular domain of nature ActRIIA, an extracellular domain with truncations, extensions, or mutations, unless specified otherwise.

A Biacore™-based binding assay was used to compare ligand binding selectivity of an exemplary ALK4-Fc:ActRIIA-Fc heterodimeric complex with that of ActRIIA-Fc and ALK4-Fc homodimer complexes, using the same methods in these Examples and the instant description.

As shown in FIG. 49, these comparative binding data demonstrate that ALK4-Fc:ActRIIA-Fc heterodimer has an altered binding profile/selectivity relative to either ActRIIA-Fc or ALK4-Fc homodimers. ALK4-Fc:ActRIIA-Fc heterodimer displays enhanced binding to activin AC and activin A compared with either homodimer, retains strong binding to Activin AB as observed with ActRIIA-Fc homodimer, and exhibits substantially reduced binding to activin B, BMP10, and BMP7.

Example 22. Effects of an Exemplary ALK4-Fc:ActRIIA-Fc Heterodimer on Kidney Fibrosis, Inflammation, and Kidney Injury The effects of an ALK4-Fc:ActRIIA-Fc heterodimer on kidney disease were assessed in a mouse unilateral ureteral obstruction model, using the same methods in these Examples and the instant description.

Treatment of mice with the ALK4-Fc:ActRIIA-Fc heterodimer significantly suppressed the expression of fibrotic (Col1a1, Col3a1, PAI-1, Fibronectin, CTGF, and a-SMA, shown in FIG. 50) and inflammatory (TNF-alpha, shown in FIG. 51) genes, inhibited the upregulation of TGF β1/2/3 and activin A (FIG. 52), and reduced kidney injury (down-regulation of NGAL, shown in FIG. 52).

Example 23. Ligand Binding Profile of ALK4-Fc:BMPRII-Fc Heterodimer Compared to BMPRII-Fc Homodimer and ALK4-Fc Homodimer A Biacore™-based binding assay was used to compare ligand binding selectivity of an exemplary ALK4-Fc:BMPRII-Fc heterodimeric complex with that of BMPRII-Fc and ALK4-Fc homodimer complexes, using the same methods in these Examples and the instant description.

As shown in FIG. 53, these comparative binding data demonstrate that ALK4-Fc:BMPRII-Fc heterodimer has an altered binding profile/selectivity relative to either BMPRII-Fc or ALK4-Fc homodimers. ALK4-Fc:BMPRII-Fc heterodimer displays enhanced binding to activin A, activin B and activin AB compared with either homodimer, retains intermediate binding to BMP10 as observed with BMPRII-Fc homodimer, and exhibits substantially reduced binding to BMP9 and BMP15.

Example 24. General Methods

Unless specified otherwise, materials and methods used in the above Examples are exemplified as below:
Generation of Human Fusion Proteins Constructed fusion proteins are initially expressed by transient transfection in COS cells. In brief, COS cells (ATCC®) are transfected overnight with plasmids encoding target fusion proteins using FuGENE® 6 transfection reagent (Promega). The next day, cells are washed with phosphate-buffered saline, and serum-free medium is added. After incubation for 72 h, the COS-conditioned medium is harvested, filtered, and loaded on a MabSelect SuRe column (GE Healthcare, UK). Fusion proteins are eluted with 0.1 M glycine (pH 3.0), and the eluted fractions are immediately neutralized by addition 1 M Tris (pH 8.0) in a 1:10 ratio. Proteins are quantitated using a NanoDrop™ spectrophotometer (Thermo Fisher Scientific, Waltham, MA).

CHO cells are transfected by standard methods with plasmid encoding the target fusion proteins and containing a ubiquitous chromatin opening element (UCOE) to facilitate protein expression. See, e.g., *Cytotechnology* (2002) 38:43-46. Pools are selected in methotrexate (MTX) at concentrations of 10 nM, 20 nM, and 50 nM. The 50 nM MTX pool yields the highest expression level, so a dilution clone is obtained from this pool and adapted to serum-free suspension growth to generate conditioned media for purification.
Purification of Fusion Protein Derived from CHO Cells Human fusion proteins expressed in CHO cells are purified as follows for subsequent characterization by surface plasmon resonance and reporter gene assays. Conditioned medium containing the target fusion protein is concentrated, filtered, and loaded on a MAb SelectSuRe column previously equilibrated with PBS. Resin is then washed with PBS, and the protein is eluted with 0.1M glycine pH 3.5. Fractions containing protein are neutralized with 5% (v/v) 1M Tris pH 8.0. The elution pool is loaded on a Q Sepharose FF 10 mL column (GE Healthcare) previously equilibrated with buffers A (50 mM Tris pH 8.0) and B (50 mM Tris, 1M NaCl pH 8.0). A wash is performed at 10% B (100 mM NaCl), followed by elution at 20% B (200 mM NaCl). Protein is further processed over HiLoad™ 26/60 Superdex (GE Healthcare) equilibrated in PBS containing 50 mM arginine (pH 7.22). Fractions are evaluated by analytical size-exclusion chromatography, and those containing over 90% monomer are pooled, concentrated, and characterized. Purity of samples is evaluated by analytical size-exclusion chromatography and SDS-PAGE with Coomassie staining.
Ligand Binding Profiles of Fusion Proteins Surface plasmon resonance is used to investigate and characterize the binding between the fusion proteins and their binding partners. In an initial qualitative screen, recombinant fusion proteins are covalently immobilized on a BIACORE™ CM5 chip, and more than 30 ligands generated in-house or obtained from R&D Systems are injected individually over the captured fusion proteins to characterize their degree of binding at room temperature. Based on the results of this screen, Applicants subject selected ligands to quantitative characterization of binding to human fusion proteins at physiologic temperature. For one condition, fusion proteins are expressed in CHO cells, purified as described in Example 1, captured on a BIACORE™ chip with anti-Fc antibody, and tested by surface plasmon resonance with the following ligands at 37° C.
Inhibition of Ligand Binding to Fusion Proteins Via Cell-Based Assays Reporter gene assays are used to determine the ability of human fusion proteins to inhibit cell signaling (e.g., TGF-beta/Smad signaling). These assays are based on human cell lines transfected with a pGL3 BRE (comprising a TGF-beta/Smad response element) reporter plasmid as well as a *Renilla* reporter plasmid (pRLCMV) to control for transfection efficiency. TGF-beta response elements together with a promoter are present in the promoter of the pGL3 BRE reporter plasmid, so this vector is of general use for factors signaling through Smad proteins.

On the first day of the assay, cells are distributed in 48-well plates at 8.5×10⁴ cells per well or 12.5×10⁴ cells per well, respectively. On the second day, a solution containing 10 μg pGL3 BRE, 100ng pRLCMV, 30 μl Fugene HD (Roche *Applied Science*, DE), and 970 μl OptiMEM™ (Invitrogen) is preincubated for 30 min, then added to assay buffer consisting of either Eagle's minimum essential medium, or McCoy's 5A medium, supplemented with 0.1% BSA. The mixture is applied to the plated cells (500 μl/well) for incubation overnight at 37° C.

On the third day, medium is removed, and cells are incubated overnight at 37° C. with a mixture of ligands and inhibitors prepared as described below. Fusion proteins are serially diluted in 200 μl volumes of assay buffer using a 48-well plate. An equal volume of assay buffer containing the test ligand is added to obtain a final ligand concentration equal to the EC50 determined previously. Test solutions are incubated at 37° C. for 30 minutes, then 250 μl of the mixture is added to all wells. Each concentration of test article is determined in duplicate. After incubation with test solutions overnight, cells are rinsed with phosphate-buffered saline, then lysed with passive lysis buffer (Promega E1941) and stored overnight at −70° C. On the fourth and final day, plates are warmed to room temperature with gentle shaking. Cell lysates are transferred in duplicate to a chemiluminescence plate (96-well) and analyzed in a luminometer with reagents from a Dual-Luciferase Reporter Assay system (Promega E1980) to determine normalized luciferase activity.

These assays are used to evaluate the ability of fusion proteins to inhibit cell signaling mediated by TGF-beta/Smad that Applicants identified by surface plasmon resonance as high-affinity binders. The fusion protein used in these assays is expressed in CHO cells and purified as described above.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method of reducing kidney fibrosis, kidney inflammation, and/or kidney injury in a subject in need thereof, comprising administering to the subject an activin and/or growth and differentiation factor (GDF) antagonist, wherein the antagonist comprises an activin receptor type IIA (ActRIIA) polypeptide and an activin receptor-like kinase 4 (ALK4) polypeptide.

2. The method of claim 1, wherein the antagonist is a multimeric polypeptide complex.

3. The method of claim 2, wherein the ActRIIA polypeptide comprises the extracellular domain of ActRIIA.

4. The method of claim 2, wherein the antagonist is a dimer.

5. The method of claim 4 wherein the ALK4 polypeptide comprises the extracellular domain of ALK4.

6. The method of claim 4, wherein the ActRIIA polypeptide comprises the extracellular domain of ActRIIA, and the ALK4 polypeptide comprises the extracellular domain of ALK4.

7. The method of claim 1, wherein the antagonist is a fusion protein.

8. The method of claim 1, wherein the antagonist is an ActRIIA-Fc-ALK4-Fc heterodimer comprising an ActRIIA-Fc polypeptide and an ALK4-Fc polypeptide, wherein the ActRIIA-Fc-ALK4-Fc heterodimer has increased binding activity to Activin A and Activin AC, and decreased binding activity to Activin B, BMP7, and BMP10 relative to an ActRIIA-Fc homodimer.

9. The method of claim 8, wherein the ALK4-Fc polypeptide comprises an amino acid sequence selected from SEQ ID NO: 204, SEQ ID NO: 208, and SEQ ID NO: 208 without its terminal lysine.

10. The method of claim 8, wherein the ActRIIA-Fc polypeptide comprises an amino acid sequence selected from SEQ ID NO: 177, SEQ ID NO: 180, SEQ ID NO: 177 without its terminal lysine, and SEQ ID NO: 180 without its terminal lysine.

11. The method of claim 1, wherein the subject in need thereof has one or more of chronic kidney diseases (or failure), acute kidney diseases (or failure), primary kidney diseases, non-diabetic kidney diseases, glomerulonephritis, interstitial nephritis, diabetic kidney diseases, diabetic chronic kidney disease, diabetic nephropathy, glomerulosclerosis, rapid progressive glomerulonephritis, renal fibrosis, Alport syndrome, IDDM nephritis, mesangial proliferative glomerulonephritis, membranoproliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, polycystic kidney disease (e.g., autosomal dominant (adult) polycystic kidney disease and autosomal recessive (childhood) polycystic kidney disease), acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, acute interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate (GFR), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non-IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schonlein disease, a postinfectious glomerulonephritis, a bacterial endocarditis, a microscopic polyangitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis nodosa, a calcineurin-inhibitor induced-vascular disease, an acute cellular vascular allograft rejection, an acute humoral allograft rejection, early renal function decline (ERFD), end stage renal disease (ESRD), renal vein thrombosis, acute tubular necrosis, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, normocytic normochromic anemia, renal anemia, diabetic chronic kidney disease, IgG4-related disease, von Hippel-Lindau syndrome, tuberous sclerosis, nephronophthisis, medullary cystic kidney disease, renal cell carcinoma, adenocarcinoma, nephroblastoma, lymphoma, leukemia, hyposialylation disorder, chronic cyclosporine nephropathy, renal reperfusion injury, renal dysplasia, azotemia, bilateral arterial occlusion, acute uric acid nephropathy, hypovolemia, acute bilateral obstructive uropathy, hypercalcemic nephropathy, hemolytic uremic syndrome, acute urinary retention, malignant nephrosclerosis, postpartum glomerulosclerosis, scleroderma, non-Goodpasture's anti-GBM disease, microscopic polyarteritis nodosa, allergic granulomatosis, acute radiation nephritis, post-streptococcal glomerulonephritis, Waldenstrom's macroglobulinemia, analgesic nephropathy, arteriovenous fistula, arteriovenous graft, dialysis, ectopic kidney, medullary sponge kidney, renal osteodystrophy, solitary kidney, hydronephrosis, microalbuminuria, uremia, haematuria, hyperlipidemia, hypoalbuminaemia, lipiduria, acidosis, edema, tubulointerstitial renal fibrosis, hypertensive sclerosis, juxtaglomerular cell tumor, Fraser syndrome, Horseshoe kidney, renal tubular dysgenesis, hypokalemia, hypomagnesemia, hypercalcemia, hypophosphatemia, uromodulin-associated kidney disease, Nail-patella syndrome, lithium nephrotoxity, TNF-alpha nephrotoxicity, honeybee resin related renal failure, sugarcane harvesting acute renal failure, complete LCAT deficiency, Fraley syndrome, Page kidney, reflux nephropathy, Bardet-Biedl syndrome, collagenofibrotic glomerulopathy, Dent disease, Denys-Drash syndrome, congenital nephrotic syndrome, immunotactoid glomerulopathy, fibronextin glomerulopathy, Galloway Mowat syndrome, lipoprotein glomerulopathy, MesoAmerican nephropathy, beta-thalassemia renal disease, haemolytic uraemic syndrome, Henoch-Schonlein-Purpura disease, retroperitoneal fibrosis, polyarteritis nodose, cardiorenal syndrome, medullary kidney disease, renal artery stenosis, uromodulin kidney disease, and hyperkalemia.

12. The method of claim 1, wherein the subject has unilateral ureter obstruction (UUO).

13. The method of claim 1, wherein the ActRIIA polypeptide comprises the amino acid sequence of SEQ ID NO: 12, and wherein the ALK4 polypeptide comprises the amino acid sequence of SEQ ID NO: 58.

14. The method of claim 13, wherein the ActRIIA polypeptide comprises the amino acid sequence of SEQ ID NO: 11.

15. The method of claim 13, wherein the antagonist is a fusion protein comprising an Fc domain having an amino acid sequence selected from SEQ ID NOs: 135-149.

16. The method of claim 15, further comprising one or more linker sequences selected from TGGG (SEQ ID NO: 217), SGGG (SEQ ID NO: 218), TGGGG (SEQ ID NO: 219), SGGGG (SEQ ID NO: 220), GGGGS (SEQ ID NO: 221), GGGG (SEQ ID NO: 222), and GGG (SEQ ID NO: 223).

\* \* \* \* \*